US009504413B2

(12) United States Patent
Simpson et al.

(10) Patent No.: US 9,504,413 B2
(45) Date of Patent: Nov. 29, 2016

(54) DUAL ELECTRODE SYSTEM FOR A CONTINUOUS ANALYTE SENSOR

(71) Applicant: DexCom, Inc., San Diego, CA (US)

(72) Inventors: Peter C. Simpson, Encinitas, CA (US); Mark Brister, Encinitas, CA (US); Matthew Wightlin, San Diego, CA (US); Jack Pryor, San Diego, CA (US)

(73) Assignee: DexCom, Inc., San Diego, CA (US)

( * ) Notice: Subject to any disclaimer, the term of this patent is extended or adjusted under 35 U.S.C. 154(b) by 390 days.

(21) Appl. No.: 13/863,204

(22) Filed: Apr. 15, 2013

(65) Prior Publication Data

US 2013/0231542 A1    Sep. 5, 2013

Related U.S. Application Data

(60) Division of application No. 11/865,572, filed on Oct. 1, 2007, now Pat. No. 8,423,114, which is a continuation-in-part of application No. 11/543,683, filed on Oct. 4, 2006, now Pat. No. 7,366,556.

(51) Int. Cl.
| | |
|---|---|
| *A61B 5/00* | (2006.01) |
| *A61B 5/05* | (2006.01) |
| *A61B 5/1486* | (2006.01) |
| *A61B 5/145* | (2006.01) |
| *C12Q 1/00* | (2006.01) |

(52) U.S. Cl.
CPC ......... *A61B 5/1486* (2013.01); *A61B 5/14532* (2013.01); *A61B 5/14865* (2013.01); *A61B 5/6849* (2013.01); *C12Q 1/006* (2013.01)

(58) Field of Classification Search
CPC .......................... A61B 5/1486; A61B 5/14532
See application file for complete search history.

(56) References Cited

U.S. PATENT DOCUMENTS

| | | | |
|---|---|---|---|
| 1,564,641 | A | 12/1925 | St. James |
| 2,402,306 | A | 6/1946 | Turkel |
| 2,719,797 | A | 10/1955 | Rosenblatt et al. |
| 3,210,578 | A | 10/1965 | Sherer |
| 3,539,455 | A | 11/1970 | Clark |
| 3,652,475 | A | 3/1972 | Wada et al. |
| 3,775,182 | A | 11/1973 | Patton et al. |
| 3,791,871 | A | 2/1974 | Rowley |

(Continued)

FOREIGN PATENT DOCUMENTS

| | | |
|---|---|---|
| DE | 26 58 734 | 6/1978 |
| EP | 0 098 592 | 1/1984 |

(Continued)

OTHER PUBLICATIONS

U.S. Pat. No. 7,530,950, May, 12, 2009, Brister et al. (withdrawn).

(Continued)

*Primary Examiner* — Christian Jang
(74) *Attorney, Agent, or Firm* — Knobbe Martens Olson & Bear, LLP

(57) ABSTRACT

Disclosed herein are systems and methods for a continuous analyte sensor, such as a continuous glucose sensor. One such system utilizes first and second working electrodes to measure additional analyte or non-analyte related signal. Such measurements may provide a background and/or sensitivity measurement(s) for use in processing sensor data and may be used to trigger events such as digital filtering of data or suspending display of data.

38 Claims, 26 Drawing Sheets

(56) References Cited

U.S. PATENT DOCUMENTS

| | | |
|---|---|---|
| 3,826,244 A | 7/1974 | Salcman et al. |
| 3,838,033 A | 9/1974 | Mindt et al. |
| 3,898,984 A | 8/1975 | Mandel et al. |
| 3,933,593 A | 1/1976 | Sternberg |
| 3,943,918 A | 3/1976 | Lewis |
| 3,957,613 A | 5/1976 | Macur |
| 3,982,530 A | 9/1976 | Storch |
| 4,037,563 A | 7/1977 | Pflueger et al. |
| 4,052,754 A | 10/1977 | Homsy |
| 4,067,322 A | 1/1978 | Johnson |
| 4,240,889 A | 12/1980 | Yoda et al. |
| 4,253,469 A | 3/1981 | Aslan |
| 4,255,500 A | 3/1981 | Hooke |
| 4,374,013 A | 2/1983 | Enfors |
| 4,378,016 A | 3/1983 | Loeb |
| 4,402,694 A | 9/1983 | Ash et al. |
| 4,403,847 A | 9/1983 | Chrestensen |
| 4,403,984 A | 9/1983 | Ash et al. |
| 4,419,535 A | 12/1983 | O'hara |
| 4,420,564 A | 12/1983 | Tsuji et al. |
| 4,431,507 A | 2/1984 | Nankai et al. |
| 4,442,841 A | 4/1984 | Uehara et al. |
| 4,494,950 A | 1/1985 | Fischell |
| RE31,916 E | 6/1985 | Oswin et al. |
| 4,554,927 A | 11/1985 | Fussell |
| 4,561,963 A | 12/1985 | Owen et al. |
| 4,571,292 A | 2/1986 | Liu et al. |
| 4,578,215 A | 3/1986 | Bradley |
| 4,583,976 A | 4/1986 | Ferguson |
| 4,650,547 A | 3/1987 | Gough |
| 4,655,880 A | 4/1987 | Liu |
| 4,672,970 A | 6/1987 | Uchida et al. |
| 4,703,756 A | 11/1987 | Gough et al. |
| 4,731,726 A | 3/1988 | Allen |
| 4,750,496 A | 6/1988 | Reinhart et al. |
| 4,752,935 A | 6/1988 | Beck |
| 4,757,022 A | 7/1988 | Shults et al. |
| 4,783,250 A | 11/1988 | Pons et al. |
| 4,805,625 A | 2/1989 | Wyler |
| 4,813,424 A | 3/1989 | Wilkins |
| 4,831,070 A | 5/1989 | McInally et al. |
| 4,852,573 A | 8/1989 | Kennedy |
| 4,858,615 A | 8/1989 | Meinema |
| 4,861,454 A | 8/1989 | Ushizawa et al. |
| 4,871,440 A | 10/1989 | Nagata et al. |
| 4,919,141 A | 4/1990 | Zier et al. |
| 4,953,552 A | 9/1990 | DeMarzo |
| 4,955,861 A | 9/1990 | Enegren et al. |
| 4,958,148 A | 9/1990 | Olson |
| 4,974,929 A | 12/1990 | Curry |
| 4,975,175 A | 12/1990 | Karube et al. |
| 4,988,341 A | 1/1991 | Columbus et al. |
| 4,988,758 A | 1/1991 | Fukuda et al. |
| 5,034,112 A | 7/1991 | Murase et al. |
| 5,050,612 A | 9/1991 | Matsumura |
| 5,068,536 A | 11/1991 | Rosenthal |
| 5,089,112 A | 2/1992 | Skotheim et al. |
| 5,108,819 A | 4/1992 | Heller et al. |
| 5,137,028 A | 8/1992 | Nishimura |
| 5,140,985 A | 8/1992 | Schroeder et al. |
| 5,160,418 A | 11/1992 | Mullen |
| 5,165,407 A | 11/1992 | Wilson et al. |
| 5,198,771 A | 3/1993 | Fidler et al. |
| 5,202,261 A | 4/1993 | Musho et al. |
| 5,243,696 A | 9/1993 | Carr et al. |
| 5,249,576 A | 10/1993 | Goldberger et al. |
| 5,262,305 A | 11/1993 | Heller et al. |
| 5,264,103 A | 11/1993 | Yoshioka et al. |
| 5,264,104 A | 11/1993 | Gregg et al. |
| 5,266,179 A | 11/1993 | Nankai et al. |
| 5,269,891 A | 12/1993 | Colin |
| 5,281,319 A | 1/1994 | Kaneko et al. |
| 5,282,848 A | 2/1994 | Schmitt |
| 5,284,140 A | 2/1994 | Allen et al. |
| 5,298,144 A | 3/1994 | Spokane |
| 5,299,571 A | 4/1994 | Mastrototaro |
| 5,307,263 A | 4/1994 | Brown |
| 5,310,469 A | 5/1994 | Cunningham et al. |
| 5,312,361 A | 5/1994 | Zadini et al. |
| 5,316,008 A | 5/1994 | Suga et al. |
| 5,322,063 A | 6/1994 | Allen et al. |
| 5,324,322 A | 6/1994 | Grill et al. |
| 5,330,634 A | 7/1994 | Wong et al. |
| 5,331,555 A | 7/1994 | Hashimoto et al. |
| 5,337,747 A | 8/1994 | Neftel |
| 5,352,351 A | 10/1994 | White et al. |
| 5,354,449 A | 10/1994 | Band et al. |
| 5,356,786 A | 10/1994 | Heller et al. |
| 5,372,133 A | 12/1994 | Hogen Esch |
| 5,380,422 A | 1/1995 | Negishi et al. |
| 5,384,028 A | 1/1995 | Ito |
| 5,390,671 A | 2/1995 | Lord et al. |
| 5,391,250 A | 2/1995 | Cheney, II et al. |
| 5,411,866 A | 5/1995 | Luong |
| 5,425,717 A | 6/1995 | Mohiuddin |
| 5,429,735 A | 7/1995 | Johnson et al. |
| 5,462,051 A | 10/1995 | Oka et al. |
| 5,462,645 A | 10/1995 | Albery et al. |
| 5,474,552 A | 12/1995 | Palti |
| 5,476,776 A | 12/1995 | Wilkins |
| 5,482,473 A | 1/1996 | Lord et al. |
| 5,486,776 A | 1/1996 | Chiang |
| 5,494,562 A | 2/1996 | Maley et al. |
| 5,496,453 A | 3/1996 | Uenoyama et al. |
| 5,497,772 A | 3/1996 | Schulman et al. |
| 5,502,396 A | 3/1996 | Desarzens et al. |
| 5,507,288 A | 4/1996 | Bocker et al. |
| 5,513,636 A | 5/1996 | Palti |
| 5,518,601 A | 5/1996 | Foos et al. |
| 5,529,676 A | 6/1996 | Maley et al. |
| 5,531,878 A | 7/1996 | Vadgama et al. |
| 5,540,828 A | 7/1996 | Yacynych |
| 5,564,439 A | 10/1996 | Picha |
| 5,568,806 A | 10/1996 | Cheney, II et al. |
| 5,569,186 A | 10/1996 | Lord et al. |
| 5,571,395 A | 11/1996 | Park et al. |
| 5,582,184 A | 12/1996 | Erickson et al. |
| 5,582,697 A | 12/1996 | Ikeda et al. |
| 5,584,813 A | 12/1996 | Livingston et al. |
| 5,586,553 A | 12/1996 | Halili et al. |
| 5,588,560 A | 12/1996 | Benedict et al. |
| 5,593,852 A | 1/1997 | Heller et al. |
| 5,605,152 A | 2/1997 | Slate et al. |
| 5,611,900 A | 3/1997 | Worden |
| 5,624,537 A | 4/1997 | Turner et al. |
| 5,628,890 A | 5/1997 | Carter et al. |
| 5,653,863 A | 8/1997 | Genshaw et al. |
| 5,660,163 A | 8/1997 | Schulman et al. |
| 5,676,820 A | 10/1997 | Wang et al. |
| 5,682,884 A | 11/1997 | Hill |
| 5,683,562 A | 11/1997 | Schaffar et al. |
| 5,686,829 A | 11/1997 | Girault |
| 5,695,623 A | 12/1997 | Michel et al. |
| 5,707,502 A | 1/1998 | McCaffrey et al. |
| 5,711,861 A | 1/1998 | Ward et al. |
| 5,735,273 A | 4/1998 | Kurnik et al. |
| 5,741,634 A | 4/1998 | Nozoe et al. |
| 5,743,262 A | 4/1998 | Lepper, Jr. et al. |
| 5,749,832 A | 5/1998 | Vadgama et al. |
| 5,766,151 A | 6/1998 | Valley et al. |
| 5,776,324 A | 7/1998 | Usala |
| 5,791,344 A | 8/1998 | Schulman et al. |
| 5,795,774 A | 8/1998 | Matsumoto et al. |
| 5,800,420 A | 9/1998 | Gross |
| 5,807,375 A | 9/1998 | Gross et al. |
| 5,822,715 A | 10/1998 | Worthington et al. |
| 5,823,802 A | 10/1998 | Bartley |
| 5,833,603 A | 11/1998 | Kovacs et al. |
| 5,851,197 A | 12/1998 | Marano et al. |
| 5,863,400 A | 1/1999 | Drummond et al. |
| 5,879,373 A | 3/1999 | Roper et al. |
| 5,882,494 A | 3/1999 | Van Antwerp |
| 5,914,026 A | 6/1999 | Blubaugh, Jr. et al. |
| 5,928,130 A | 7/1999 | Schmidt |

(56) References Cited

U.S. PATENT DOCUMENTS

| | | |
|---|---|---|
| 5,931,814 A | 8/1999 | Alex et al. |
| 5,932,175 A | 8/1999 | Knute et al. |
| 5,954,643 A | 9/1999 | Van Antwerp et al. |
| 5,954,954 A | 9/1999 | Houck et al. |
| 5,957,854 A | 9/1999 | Besson et al. |
| 5,961,451 A | 10/1999 | Reber et al. |
| 5,964,993 A | 10/1999 | Blubaugh et al. |
| 5,965,380 A | 10/1999 | Heller et al. |
| 5,972,199 A | 10/1999 | Heller et al. |
| 5,976,085 A | 11/1999 | Kimball et al. |
| 5,985,129 A | 11/1999 | Gough et al. |
| 5,999,848 A | 12/1999 | Gord et al. |
| 6,001,067 A | 12/1999 | Shults et al. |
| 6,011,984 A | 1/2000 | Van Antwerp et al. |
| 6,013,113 A | 1/2000 | Mika |
| 6,036,924 A | 3/2000 | Simons et al. |
| 6,051,389 A | 4/2000 | Ahl et al. |
| 6,059,946 A | 5/2000 | Yukawa et al. |
| 6,066,448 A | 5/2000 | Wohlstadter et al. |
| 6,074,775 A | 6/2000 | Gartstein et al. |
| 6,081,735 A | 6/2000 | Diab et al. |
| 6,081,736 A | 6/2000 | Colvin et al. |
| 6,083,710 A | 7/2000 | Heller et al. |
| 6,088,608 A | 7/2000 | Schulman et al. |
| 6,091,975 A | 7/2000 | Daddona et al. |
| 6,093,156 A | 7/2000 | Cunningham et al. |
| 6,093,172 A | 7/2000 | Funderburk et al. |
| 6,103,033 A | 8/2000 | Say et al. |
| 6,117,290 A | 9/2000 | Say |
| 6,119,028 A | 9/2000 | Schulman et al. |
| 6,120,676 A | 9/2000 | Heller et al. |
| 6,121,009 A | 9/2000 | Heller et al. |
| 6,122,536 A | 9/2000 | Sun et al. |
| 6,134,461 A | 10/2000 | Say et al. |
| 6,144,869 A | 11/2000 | Berner et al. |
| 6,144,871 A | 11/2000 | Saito et al. |
| 6,162,611 A | 12/2000 | Heller et al. |
| 6,169,155 B1 | 1/2001 | Alvarez et al. |
| 6,175,752 B1 | 1/2001 | Say et al. |
| 6,175,753 B1 | 1/2001 | Menkes et al. |
| 6,180,416 B1 | 1/2001 | Kurnik et al. |
| 6,212,416 B1 | 4/2001 | Ward et al. |
| 6,212,417 B1 | 4/2001 | Ikeda et al. |
| 6,214,185 B1 | 4/2001 | Offenbacher et al. |
| 6,219,574 B1 | 4/2001 | Cormier et al. |
| 6,233,471 B1 | 5/2001 | Berner et al. |
| 6,248,067 B1 | 6/2001 | Causey, III et al. |
| 6,259,937 B1 | 7/2001 | Schulman et al. |
| 6,264,825 B1 | 7/2001 | Blackburn et al. |
| 6,268,161 B1 | 7/2001 | Han et al. |
| 6,274,285 B1 | 8/2001 | Gries et al. |
| 6,275,717 B1 | 8/2001 | Gross et al. |
| 6,284,478 B1 | 9/2001 | Heller et al. |
| 6,293,925 B1 | 9/2001 | Safabash et al. |
| 6,294,281 B1 | 9/2001 | Heller |
| 6,299,583 B1 | 10/2001 | Eggers et al. |
| 6,300,002 B1 | 10/2001 | Webb et al. |
| 6,325,979 B1 | 12/2001 | Hahn et al. |
| 6,326,160 B1 | 12/2001 | Dunn et al. |
| 6,329,161 B1 | 12/2001 | Heller et al. |
| 6,343,225 B1 | 1/2002 | Clark, Jr. |
| 6,356,776 B1 | 3/2002 | Berner et al. |
| 6,360,888 B1 | 3/2002 | McIver et al. |
| 6,368,141 B1 | 4/2002 | VanAntwerp et al. |
| 6,368,274 B1 | 4/2002 | Van Antwerp et al. |
| 6,413,393 B1 | 7/2002 | Van Antwerp et al. |
| 6,413,396 B1 | 7/2002 | Yang et al. |
| 6,418,332 B1 | 7/2002 | Mastrototaro et al. |
| 6,424,847 B1 | 7/2002 | Mastrototaro et al. |
| 6,424,861 B2 | 7/2002 | Meredith |
| 6,459,917 B1 | 10/2002 | Gowda et al. |
| 6,461,496 B1 | 10/2002 | Feldman et al. |
| 6,465,066 B1 | 10/2002 | Rule et al. |
| 6,466,810 B1 | 10/2002 | Ward et al. |
| 6,475,372 B1 | 11/2002 | Ohara et al. |
| 6,475,750 B1 | 11/2002 | Han et al. |
| 6,477,395 B2 | 11/2002 | Schulman et al. |
| 6,484,045 B1 | 11/2002 | Holker et al. |
| 6,484,046 B1 | 11/2002 | Say et al. |
| 6,498,043 B1 | 12/2002 | Schulman et al. |
| 6,498,941 B1 | 12/2002 | Jackson |
| 6,510,329 B2 | 1/2003 | Heckel |
| 6,512,939 B1 | 1/2003 | Colvin et al. |
| 6,514,718 B2 | 2/2003 | Heller et al. |
| 6,520,326 B2 | 2/2003 | McIvor et al. |
| 6,542,765 B1 | 4/2003 | Guy et al. |
| 6,546,268 B1 | 4/2003 | Ishikawa et al. |
| 6,547,839 B2 | 4/2003 | Zhang et al. |
| 6,551,494 B1 | 4/2003 | Feldman et al. |
| 6,553,241 B2 | 4/2003 | Mannheimer et al. |
| 6,553,244 B2 | 4/2003 | Lesho et al. |
| 6,558,320 B1 | 5/2003 | Causey |
| 6,558,351 B1 | 5/2003 | Steil et al. |
| 6,560,471 B1 | 5/2003 | Heller et al. |
| 6,561,978 B1 | 5/2003 | Conn et al. |
| 6,565,509 B1 | 5/2003 | Say et al. |
| 6,569,309 B2 | 5/2003 | Otsuka et al. |
| 6,579,690 B1 | 6/2003 | Bonnecaze et al. |
| 6,584,335 B1 | 6/2003 | Haar et al. |
| 6,585,763 B1 | 7/2003 | Keilman et al. |
| 6,587,705 B1 | 7/2003 | Kim et al. |
| 6,594,514 B2 | 7/2003 | Berner et al. |
| 6,595,919 B2 | 7/2003 | Berner et al. |
| 6,607,658 B1 | 8/2003 | Heller et al. |
| 6,612,984 B1 | 9/2003 | Kerr |
| 6,613,379 B2 | 9/2003 | Ward et al. |
| 6,615,078 B1 | 9/2003 | Burson et al. |
| 6,618,934 B1 | 9/2003 | Feldman et al. |
| 6,633,772 B2 | 10/2003 | Ford et al. |
| 6,642,015 B2 | 11/2003 | Vachon et al. |
| 6,653,091 B1 | 11/2003 | Dunn et al. |
| 6,654,625 B1 | 11/2003 | Say et al. |
| 6,673,596 B1 | 1/2004 | Sayler et al. |
| 6,689,265 B2 | 2/2004 | Heller et al. |
| 6,695,860 B1 | 2/2004 | Ward et al. |
| 6,702,972 B1 | 3/2004 | Markle |
| 6,721,587 B2 | 4/2004 | Gough |
| 6,730,200 B1 | 5/2004 | Stewart et al. |
| 6,733,655 B1 | 5/2004 | Davies et al. |
| 6,737,158 B1 | 5/2004 | Thompson |
| 6,743,635 B2 | 6/2004 | Neel et al. |
| 6,793,632 B2 | 9/2004 | Sohrab |
| 6,801,041 B2 | 10/2004 | Karinka et al. |
| 6,802,957 B2 | 10/2004 | Jung et al. |
| 6,809,507 B2 | 10/2004 | Morgan et al. |
| 6,809,653 B1 | 10/2004 | Mann et al. |
| 6,862,465 B2 | 3/2005 | Shults et al. |
| 6,892,085 B2 | 5/2005 | McIvor et al. |
| 6,893,552 B1 | 5/2005 | Wang et al. |
| 6,895,263 B2 | 5/2005 | Shin et al. |
| 6,931,327 B2 | 8/2005 | Goode et al. |
| 6,932,894 B2 | 8/2005 | Mao et al. |
| 6,965,791 B1 | 11/2005 | Hitchcock et al. |
| 6,972,080 B1 | 12/2005 | Tomioka et al. |
| 7,003,336 B2 | 2/2006 | Holker et al. |
| 7,003,341 B2 | 2/2006 | Say et al. |
| 7,060,059 B2 | 6/2006 | Keith et al. |
| 7,070,580 B2 | 7/2006 | Nielsen |
| 7,074,307 B2 | 7/2006 | Simpson et al. |
| 7,078,582 B2 | 7/2006 | Stebbings et al. |
| 7,098,803 B2 | 8/2006 | Mann et al. |
| 7,108,778 B2 | 9/2006 | Simpson et al. |
| 7,115,884 B1 | 10/2006 | Walt et al. |
| 7,153,265 B2 | 12/2006 | Vachon |
| 7,171,252 B1 | 1/2007 | Scarantino et al. |
| 7,190,988 B2 | 3/2007 | Say et al. |
| 7,192,450 B2 | 3/2007 | Brauker et al. |
| 7,207,974 B2 | 4/2007 | Safabash et al. |
| 7,267,665 B2 | 9/2007 | Steil et al. |
| 7,276,029 B2 | 10/2007 | Goode et al. |
| 7,310,544 B2 | 12/2007 | Brister et al. |
| 7,344,499 B1 | 3/2008 | Prausnitz et al. |
| 7,366,556 B2 | 4/2008 | Brister et al. |
| 7,381,184 B2 | 6/2008 | Funderburk et al. |

(56) References Cited

U.S. PATENT DOCUMENTS

| | | |
|---|---|---|
| 7,399,277 B2 | 7/2008 | Saidara et al. |
| 7,417,164 B2 | 8/2008 | Suri |
| 7,424,318 B2 | 9/2008 | Brister et al. |
| 7,460,898 B2 | 12/2008 | Brister et al. |
| 7,467,003 B2 | 12/2008 | Brister et al. |
| 7,471,972 B2 | 12/2008 | Rhodes et al. |
| 7,494,465 B2 | 2/2009 | Brister et al. |
| 7,497,827 B2 | 3/2009 | Brister et al. |
| 7,525,298 B2 | 4/2009 | Morgan et al. |
| 7,637,868 B2 | 12/2009 | Saint et al. |
| 7,640,048 B2 | 12/2009 | Dobbles et al. |
| 7,654,956 B2 | 2/2010 | Brister et al. |
| 7,831,287 B2 | 11/2010 | Brister et al. |
| 7,896,809 B2 | 3/2011 | Simpson et al. |
| 7,917,186 B2 | 3/2011 | Kamath et al. |
| RE43,039 E | 12/2011 | Brister et al. |
| 8,160,671 B2 | 4/2012 | Kamath et al. |
| 8,249,684 B2 | 8/2012 | Kamath et al. |
| 8,287,453 B2 | 10/2012 | Li et al. |
| 8,386,004 B2 | 2/2013 | Kamath et al. |
| 8,423,114 B2 | 4/2013 | Simpson et al. |
| 8,428,678 B2 | 4/2013 | Kamath et al. |
| 8,483,793 B2 | 7/2013 | Simpson et al. |
| 2001/0016682 A1 | 8/2001 | Berner et al. |
| 2002/0016535 A1 | 2/2002 | Martin et al. |
| 2002/0019022 A1 | 2/2002 | Dunn et al. |
| 2002/0023852 A1 | 2/2002 | McIvor et al. |
| 2002/0042090 A1 | 4/2002 | Heller et al. |
| 2002/0042561 A1 | 4/2002 | Schulman et al. |
| 2002/0043471 A1 | 4/2002 | Ikeda et al. |
| 2002/0045808 A1 | 4/2002 | Ford et al. |
| 2002/0055673 A1 | 5/2002 | Van Antwerp et al. |
| 2002/0065453 A1 | 5/2002 | Lesho et al. |
| 2002/0084196 A1 | 7/2002 | Liamos et al. |
| 2002/0099997 A1 | 7/2002 | Piret |
| 2002/0119711 A1 | 8/2002 | Van Antwerp et al. |
| 2002/0161288 A1 | 10/2002 | Shin et al. |
| 2002/0169369 A1 | 11/2002 | Ward et al. |
| 2002/0177763 A1 | 11/2002 | Burns et al. |
| 2002/0177764 A1 | 11/2002 | Sohrab et al. |
| 2002/0188185 A1 | 12/2002 | Sohrab |
| 2003/0003524 A1 | 1/2003 | Taniike et al. |
| 2003/0004457 A1 | 1/2003 | Andersson |
| 2003/0006669 A1 | 1/2003 | Pei et al. |
| 2003/0032874 A1 | 2/2003 | Rhodes et al. |
| 2003/0036773 A1 | 2/2003 | Whitehurst et al. |
| 2003/0050546 A1 | 3/2003 | Desai et al. |
| 2003/0065254 A1 | 4/2003 | Schulman et al. |
| 2003/0076082 A1 | 4/2003 | Morgan et al. |
| 2003/0097082 A1 | 5/2003 | Purdy et al. |
| 2003/0100040 A1 | 5/2003 | Bonnecaze et al. |
| 2003/0114836 A1 | 6/2003 | Estes et al. |
| 2003/0125612 A1 | 7/2003 | Fox et al. |
| 2003/0130616 A1 | 7/2003 | Steil et al. |
| 2003/0134347 A1 | 7/2003 | Heller et al. |
| 2003/0138674 A1 | 7/2003 | Zeikus et al. |
| 2003/0181794 A1 | 9/2003 | Rini et al. |
| 2003/0187338 A1 | 10/2003 | Say et al. |
| 2003/0188427 A1 | 10/2003 | Say et al. |
| 2003/0199744 A1 | 10/2003 | Buse et al. |
| 2003/0203498 A1 | 10/2003 | Neel et al. |
| 2003/0211625 A1 | 11/2003 | Cohan |
| 2003/0225437 A1 | 12/2003 | Ferguson |
| 2003/0228681 A1 | 12/2003 | Ritts et al. |
| 2003/0235817 A1 | 12/2003 | Bartkowiak et al. |
| 2004/0023253 A1 | 2/2004 | Kunwar et al. |
| 2004/0023317 A1 | 2/2004 | Motamedi et al. |
| 2004/0074785 A1 | 4/2004 | Holker |
| 2004/0078219 A1 | 4/2004 | Kaylor |
| 2004/0106859 A1 | 6/2004 | Say et al. |
| 2004/0133131 A1 | 7/2004 | Kuhn et al. |
| 2004/0133164 A1 | 7/2004 | Funderburk et al. |
| 2004/0167801 A1 | 8/2004 | Say et al. |
| 2004/0173472 A1 | 9/2004 | Jung et al. |
| 2004/0186365 A1 | 9/2004 | Jin et al. |
| 2004/0204687 A1 | 10/2004 | Mogensen |
| 2004/0236200 A1 | 11/2004 | Say et al. |
| 2004/0236251 A1 | 11/2004 | Roe et al. |
| 2004/0242982 A1 | 12/2004 | Sakata et al. |
| 2004/0248282 A1 | 12/2004 | Sobha et al. |
| 2004/0254433 A1 | 12/2004 | Bandis |
| 2005/0006122 A1 | 1/2005 | Burnette |
| 2005/0027180 A1 | 2/2005 | Goode et al. |
| 2005/0027181 A1 | 2/2005 | Goode et al. |
| 2005/0027182 A1 | 2/2005 | Siddiqui et al. |
| 2005/0027463 A1 | 2/2005 | Goode et al. |
| 2005/0031689 A1 | 2/2005 | Shults et al. |
| 2005/0033132 A1 | 2/2005 | Shults et al. |
| 2005/0038332 A1 | 2/2005 | Saidara et al. |
| 2005/0043598 A1 | 2/2005 | Goode et al. |
| 2005/0051427 A1 | 3/2005 | Brauker et al. |
| 2005/0054909 A1 | 3/2005 | Petisce et al. |
| 2005/0056551 A1 | 3/2005 | White et al. |
| 2005/0056552 A1 | 3/2005 | Simpson et al. |
| 2005/0059871 A1 | 3/2005 | Gough et al. |
| 2005/0090607 A1 | 4/2005 | Tapsak et al. |
| 2005/0103625 A1 | 5/2005 | Rhodes et al. |
| 2005/0115832 A1 | 6/2005 | Simpson et al. |
| 2005/0121322 A1 | 6/2005 | Say |
| 2005/0133368 A1 | 6/2005 | Davies et al. |
| 2005/0139489 A1 | 6/2005 | Davies et al. |
| 2005/0143635 A1 | 6/2005 | Kamath et al. |
| 2005/0143675 A1 | 6/2005 | Neel et al. |
| 2005/0176136 A1 | 8/2005 | Burd et al. |
| 2005/0177036 A1 | 8/2005 | Shults et al. |
| 2005/0181012 A1 | 8/2005 | Saint et al. |
| 2005/0183954 A1 | 8/2005 | Hitchcock et al. |
| 2005/0192557 A1 | 9/2005 | Brauker et al. |
| 2005/0195930 A1 | 9/2005 | Spital et al. |
| 2005/0215871 A1 | 9/2005 | Feldman et al. |
| 2005/0242479 A1 | 11/2005 | Petisce et al. |
| 2005/0245795 A1 | 11/2005 | Goode et al. |
| 2005/0245799 A1 | 11/2005 | Brauker et al. |
| 2005/0258037 A1 | 11/2005 | Hajizadeh et al. |
| 2005/0261563 A1 | 11/2005 | Zhou et al. |
| 2005/0272989 A1 | 12/2005 | Shah et al. |
| 2006/0015020 A1 | 1/2006 | Neale et al. |
| 2006/0015024 A1 | 1/2006 | Brister et al. |
| 2006/0016700 A1 | 1/2006 | Brister et al. |
| 2006/0020186 A1 | 1/2006 | Brister et al. |
| 2006/0020187 A1 | 1/2006 | Brister et al. |
| 2006/0020189 A1 | 1/2006 | Brister et al. |
| 2006/0020191 A1 | 1/2006 | Brister et al. |
| 2006/0020192 A1 | 1/2006 | Brister et al. |
| 2006/0036139 A1 | 2/2006 | Brister et al. |
| 2006/0036141 A1 | 2/2006 | Kamath et al. |
| 2006/0036142 A1 | 2/2006 | Brister et al. |
| 2006/0036143 A1 | 2/2006 | Brister et al. |
| 2006/0036144 A1 | 2/2006 | Brister et al. |
| 2006/0036145 A1 | 2/2006 | Brister et al. |
| 2006/0155180 A1 | 7/2006 | Brister et al. |
| 2006/0173444 A1 | 8/2006 | Choy et al. |
| 2006/0183984 A1 | 8/2006 | Dobbles et al. |
| 2006/0183985 A1 | 8/2006 | Brister et al. |
| 2006/0189856 A1 | 8/2006 | Petisce et al. |
| 2006/0189863 A1 | 8/2006 | Peyser et al. |
| 2006/0195029 A1 | 8/2006 | Shults et al. |
| 2006/0200020 A1 | 9/2006 | Brister et al. |
| 2006/0222566 A1 | 10/2006 | Brauker et al. |
| 2006/0229512 A1 | 10/2006 | Petisce et al. |
| 2006/0235285 A1 | 10/2006 | Brister et al. |
| 2006/0258761 A1 | 11/2006 | Boock et al. |
| 2006/0270922 A1 | 11/2006 | Brauker et al. |
| 2006/0270923 A1 | 11/2006 | Brauker et al. |
| 2007/0017805 A1 | 1/2007 | Hodges et al. |
| 2007/0027384 A1 | 2/2007 | Brister et al. |
| 2007/0027385 A1 | 2/2007 | Brister et al. |
| 2007/0032717 A1 | 2/2007 | Brister et al. |
| 2007/0045902 A1 | 3/2007 | Brauker et al. |
| 2007/0088208 A1 | 4/2007 | Yasuzawa et al. |
| 2007/0093704 A1 | 4/2007 | Brister et al. |
| 2007/0173709 A1 | 7/2007 | Petisce et al. |
| 2007/0173710 A1 | 7/2007 | Petisce et al. |
| 2007/0173711 A1 | 7/2007 | Shah et al. |

(56) References Cited

U.S. PATENT DOCUMENTS

| | | |
|---|---|---|
| 2007/0197889 A1 | 8/2007 | Brister et al. |
| 2007/0200254 A1 | 8/2007 | Curry |
| 2007/0202672 A1 | 8/2007 | Curry |
| 2007/0203966 A1 | 8/2007 | Brauker et al. |
| 2007/0208246 A1 | 9/2007 | Brauker et al. |
| 2007/0213611 A1* | 9/2007 | Simpson et al. .............. 600/365 |
| 2007/0232879 A1 | 10/2007 | Brister et al. |
| 2007/0235331 A1 | 10/2007 | Simpson et al. |
| 2007/0259217 A1 | 11/2007 | Logan |
| 2008/0021666 A1 | 1/2008 | Goode et al. |
| 2008/0154101 A1 | 6/2008 | Jain et al. |
| 2008/0187655 A1 | 8/2008 | Markle et al. |
| 2008/0188722 A1 | 8/2008 | Markle et al. |
| 2008/0188725 A1 | 8/2008 | Markle et al. |
| 2008/0188731 A1 | 8/2008 | Brister et al. |
| 2008/0194935 A1 | 8/2008 | Brister et al. |
| 2008/0194938 A1 | 8/2008 | Brister et al. |
| 2008/0208025 A1 | 8/2008 | Shults et al. |
| 2008/0214915 A1 | 9/2008 | Brister et al. |
| 2008/0214918 A1 | 9/2008 | Brister et al. |
| 2008/0242961 A1 | 10/2008 | Brister et al. |
| 2008/0275313 A1 | 11/2008 | Brister et al. |
| 2008/0296155 A1 | 12/2008 | Shults et al. |
| 2008/0305009 A1 | 12/2008 | Gamsey et al. |
| 2008/0305506 A1 | 12/2008 | Suri |
| 2009/0018418 A1 | 1/2009 | Markle et al. |
| 2009/0018426 A1 | 1/2009 | Markle et al. |
| 2009/0045055 A1 | 2/2009 | Rhodes et al. |
| 2009/0061528 A1 | 3/2009 | Suri |
| 2009/0076356 A1 | 3/2009 | Simpson |
| 2009/0076360 A1 | 3/2009 | Brister et al. |
| 2009/0081803 A1 | 3/2009 | Gamsey et al. |
| 2009/0099434 A1 | 4/2009 | Liu et al. |
| 2009/0099436 A1 | 4/2009 | Brister et al. |
| 2009/0124879 A1 | 5/2009 | Brister et al. |
| 2009/0143660 A1 | 6/2009 | Brister et al. |
| 2009/0177143 A1 | 7/2009 | Markle et al. |
| 2009/0182217 A1 | 7/2009 | Li et al. |
| 2009/0192751 A1 | 7/2009 | Kamath et al. |
| 2009/0242399 A1 | 10/2009 | Kamath et al. |
| 2009/0242425 A1 | 10/2009 | Kamath et al. |
| 2009/0264719 A1 | 10/2009 | Markle et al. |
| 2010/0081908 A1 | 4/2010 | Dobbles et al. |
| 2010/0185070 A1 | 7/2010 | Brister et al. |
| 2010/0185071 A1 | 7/2010 | Simpson et al. |
| 2010/0198035 A1 | 8/2010 | Kamath et al. |
| 2010/0286496 A1 | 11/2010 | Simpson et al. |
| 2010/0331648 A1 | 12/2010 | Kamath et al. |
| 2010/0331655 A1 | 12/2010 | Kamath et al. |
| 2011/0046467 A1 | 2/2011 | Simpson et al. |
| 2011/0319739 A1 | 12/2011 | Kamath et al. |
| 2012/0226121 A1 | 9/2012 | Kamath et al. |

FOREIGN PATENT DOCUMENTS

| | | |
|---|---|---|
| EP | 0 127 958 | 12/1984 |
| EP | 0 284 518 | 9/1988 |
| EP | 0 286 118 | 10/1988 |
| EP | 0 320 109 | 6/1989 |
| EP | 0 353 328 | 2/1990 |
| EP | 0 390 390 | 10/1990 |
| EP | 0 476 980 | 3/1992 |
| EP | 0 563 795 | 10/1993 |
| EP | 0 690 134 | 1/1996 |
| EP | 0 838 230 | 4/1998 |
| EP | 1 077 634 | 2/2001 |
| EP | 0 958 495 | 11/2002 |
| EP | 1785085 A1 | 5/2007 |
| FR | 2656423 | 6/1991 |
| FR | 2760962 | 9/1998 |
| GB | 1 556 969 | 12/1979 |
| GB | 2149918 | 6/1985 |
| JP | 02002913 | 1/1990 |
| JP | 3-293556 | 12/1991 |
| WO | WO 87/63242 | 10/1987 |
| WO | WO 89/02720 | 4/1989 |
| WO | WO 91/09302 | 6/1991 |
| WO | WO 92/13271 | 8/1992 |
| WO | WO 93/05701 | 4/1993 |
| WO | WO 93/14693 | 8/1993 |
| WO | WO 93/23744 | 11/1993 |
| WO | WO 93/25898 | 12/1993 |
| WO | WO 94/22367 | 10/1994 |
| WO | WO 95-02357 | 1/1995 |
| WO | WO 96/14026 | 5/1996 |
| WO | WO 96/25089 | 8/1996 |
| WO | WO 97/01986 | 1/1997 |
| WO | WO 97/06727 | 2/1997 |
| WO | WO 97-17884 | 5/1997 |
| WO | WO 98/19159 | 5/1998 |
| WO | WO 98/24358 | 6/1998 |
| WO | WO 98/38906 | 9/1998 |
| WO | WO 99/56613 | 4/1999 |
| WO | WO 99/58051 | 11/1999 |
| WO | WO 99/58709 | 11/1999 |
| WO | WO 00/19887 | 4/2000 |
| WO | WO 00/32098 | 6/2000 |
| WO | WO 00/33065 | 6/2000 |
| WO | WO 00/49940 | 8/2000 |
| WO | WO 00/59373 | 10/2000 |
| WO | WO 00/74753 | 12/2000 |
| WO | WO 00/79258 | 12/2000 |
| WO | WO 01/20019 | 3/2001 |
| WO | WO 01/58348 | 8/2001 |
| WO | WO 01-73109 | 10/2001 |
| WO | WO 01/88524 | 11/2001 |
| WO | WO 01/88534 | 11/2001 |
| WO | WO 03-000127 | 1/2003 |
| WO | WO 03/011131 | 2/2003 |
| WO | WO 03/012422 | 2/2003 |
| WO | WO 03/032411 | 4/2003 |
| WO | WO 03/082091 | 9/2003 |
| WO | WO 2005/012873 | 2/2005 |
| WO | WO 2005/026689 | 3/2005 |
| WO | WO 2005-045414 | 5/2005 |
| WO | WO 2005/057168 | 6/2005 |
| WO | WO 2005/122296 | 12/2005 |
| WO | WO 2006/017358 | 2/2006 |
| WO | WO 2006/105146 | 10/2006 |
| WO | WO 2006-127694 | 11/2006 |
| WO | WO 03/011131 | 2/2013 |

OTHER PUBLICATIONS

Aalders et al. 1991. Development of a wearable glucose sensor; studies in healthy volunteers and in diabetic patients. The International Journal of Artificial Organs 14(2):102-108.

Abe et al. 1992. Characterization of glucose microsensors for intracellular measurements. Anal. Chem. 64(18):2160-2163.

Abel et al. 1984. Experience with an implantable glucose sensor as a prerequisite of an artificial beta cell, Biomed. Biochim. Acta 43(5):577-584.

Abel et al. 2002. Biosensors for in vivo glucose measurement: can we cross the experimental stage. Biosens Bioelectron 17:1059-1070.

Alcock & Turner. 1994. Continuous Analyte Monitoring to Aid Clinical Practice. IEEE Engineering in Med. & Biol. Mag. 13:319-325.

American Heritage Dictionary, 4th Edition. 2000. Houghton Mifflin Company, p. 82.

Amin et al. 2003. Hypoglycemia prevalence in prepubertal children with type 1 diabetes on standard insulin regimen: Use of continuous glucose monitoring system. Diabetes Care 26(3):662-667.

Answers.com. "xenogenic." The American Heritage Stedman's Medical Dictionary. Houghton Mifflin Company, 2002. Answers. com Nov. 7, 2006 http://www. Answers.com/topic/xenogenic.

Armour et al. Dec. 1990. Application of Chronic Intravascular Blood Glucose Sensor in Dogs. Diabetes 39:1519-1526.

Assolant-Vinet et al. 1986. New Immoblized Enzyme Membranes for Tailor-Made Biosensors, Anal Letters 19(7&8): 875-885.

(56) References Cited

OTHER PUBLICATIONS

Atanasov et al. 1997. Implantation of a refillable glucose monitoring-telemetry device. Biosens Bioelectron 12:669-680.
Atanasov, et al. 1994. Biosensor for continuous glucose monitoring. Biotechnology and Bioengineering 43:262-266.
Aussedat et al. 1997. A user-friendly method for calibrating a subcutaneous glucose sensor-based hypoglycaemic alarm. Biosensors & Bioelectronics 12(11):1061-1071.
Bailey et al. 2007. Reduction in hemoglobin A1c with real-time continuous glucose monitoring: results from a 12-week observational study. Diabetes Technology & Therapeutics 9(3):203-210.
Bani Amer, M. M. 2002. An accurate amperometric glucose sensor based glucometer with eliminated cross-sensitivity. J Med Eng Technol 26(5):208-213.
Bard et al. 1980. Electrochemical Methods. John Wiley & Sons, pp. 173-175.
Bardeletti et al. 1986. A Reliable L-Lactate Electrode with a New Membrane for Enzyme Immobilization for Amperometric Assay of Lactate. Analyt Chim Acta, 187: 47-54.
Beach et al. 1999. Subminiature implantable potentiostat and modified commercial telemetry device for remote glucose monitoring. IEEE Transactions on Instrumentation and Measurement 48(6):1239-1245.
Bellucci et al. Jan. 1986. Electrochemical behaviour of graphite-epoxy composite materials (GECM) in aqueous salt solutions, Journal of Applied Electrochemistry, 16(1):15-22.
Bertrand et al. 1981 Multipurpose Electrode with Different Enzyme Systems Bound to Collagen Films. Anal Chim Acta 126: 23-34.
Bessman et al., Progress toward a glucose sensor for the artificial pancreas, Proceedings of a Workshop on Ion-Selective Microelectrodes, Jun. 4-5, 1973, Boston, MA, 189-197.
Biermann et al. 2008. How would patients behave if they were continually informed of their blood glucose levels? A simulation study using a "virtual" patient. Diab. Thechnol. & Therapeut., 10:178-187.
Bindra et al. 1991. Design and In Vitro Studies of a Needle-Type Glucose Senso for Subcutaneous Monitoring. Anal. Chem 63:1692-96.
Bisenberger et al. 1995. A triple-step potential waveform at enzyme multisensors with thick-film gold electrodes for detection of glucose and sucrose. Sensors and Actuators, B 28:181-189.
Bland et al. 1990. A note on the use of the intraclass correlation coefficient in the evaluation of agreement between two methods of measurement. Comput. Biol. Med. 20(5):337-340.
Bobbioni-Harsch et al. 1993. Lifespan of subcutaneous glucose sensors and their performances during dynamic glycaemia changes in rats, J. Biomed. Eng. 15:457-463.
Bode et al. 1999. Continuous glucose monitoring used to adjust diabetes therapy improves glycosylated hemoglobin: A pilot study. Diabetes Research and Clinical Practice 46:183-190.
Bode et al. 2000. Using the continuous glucose monitoring system to improve the management of type 1 diabetes. Diabetes Technology & Therapeutics, 2(Suppl 1):S43-48.
Bode, B. W. 2000. Clinical utility of the continuous glucose monitoring system. Diabetes Technol Ther, 2(Suppl 1):S35-41.
Boedeker Plastics, Inc. 2009. Polyethylene Specifications Data Sheet, http://www.boedeker.com/polye_p.htm [Aug. 19, 2009 3:36:33 PM].
Boland et al. 2001. Limitations of conventional methods of self-monitoring of blood glucose. Diabetes Care 24(11):1858-1862.
Bowman, L.; Meindl, J. D. 1986. The packaging of implantable integrated sensors. IEEE Trans Biomed Eng BME33(2):248-255.
Brauker et al. Jun. 27, 1996. Local Inflammatory Response Around Diffusion Chambers Containing Xenografts Transplantation 61(12):1671-1677.
Braunwald, 2008. Biomarkers in heart failure. N. Engl. J. Med., 358: 2148-2159.
Bremer et al. 2001. Benchmark data from the literature for evaluation of new glucose sensing technologies. Diabetes Technology & Therapeutics 3(3):409-418.

Brooks, et al. "Development of an on-line glucose sensor for fermentation monitoring," Biosensors, 3:45-56 (1987/1988).
Bruckel et al. 1989. In vivo measurement of subcutaneous glucose concentrations with an enzymatic glucose sensor and a wick method. Klin Wochenschr 67:491-495.
Cai et al. 2004. A wireless, remote query glucose biosensor based on a pH-sensitive polymer. Anal Chem 76(4):4038-4043.
Campanella et al. 1993. Biosensor for direct determination of glucose and lactate in undiluted biological fluids. Biosensors & Bioelectronics 8:307-314.
Candas et al (1994). "An adaptive plasma glucose controller basedon on a nonlinear insulin/glucose model." IEEE Transactions on Biomedical Engineering, 41(2): 116-124.
Cass et al. "Ferrocene-mediated enzyme electrodes for amperometric determination of glucose," Anal. Chem., 36:667-71 (1984).
Cassidy et al., Apr. 1993. Novel electrochemical device for the detection of cholesterol or glucose, Analyst, 118:415-418.
Chase et al. 2001. Continuous subcutaneous glucose monitoring in children with type 1 diabetes. Pediatrics 107:222-226.
Chia et al. 2004. Glucose sensors: toward closed loop insulin delivery. Endocrinol Metab Clin North Am 33:175-95.
Choleau, et al. 2002. Calibration of a subcutaneous amperometric glucose sensor implanted for 7 days in diabetic patients. Part 1. Effect of measurement uncertainties on the determination of sensor sensitivity and background current . Biosensors and Bioelectronics 17:641-646.
Choleau, et al. 2002. Calibration of a subcutaneous amperometric glucose sensor implanted for 7 days in diabetic patients. Part 2. Superiority of the one-point calibration method. Biosensors and Bioelectronics 17:647-654.
Ciba® Irgacure® 2959 Photoinitiator, Product Description. Apr. 2, 1998. Ciba Specialty Chemicals Inc., Basel, Switzerland. 3 pages.
Claremont et al. 1986. Subcutaneous implantation of a ferrocene-mediated glucose sensor in pigs. Diabetologia 29:817-821.
Claremont et al. Jul. 1986. Potentially-implntable, ferrocene-mediated glucose sensor. J. Biomed. Eng. 8:272-274.
Clark et al. 1987. Configurational cyclic voltammetry: increasing the specificity and reliablity of implanted electrodes, IEEE/Ninth Annual Conference of the Engineering in Medicine and Biology Society, pp. 0782-0783.
Clark et al. 1988. Long-term stability of electroenzymatic glucose sensors implanted in mice. Trans Am Soc Artif Intern Organs 34:259-265.
Clark et al., 1981. One-minute electrochemical enzymic assay for cholesterol in biological materials, Clin. Chem. 27(12):1978-1982.
CLSI. Performance metrics for continuous interstitial glucose monitoring; approved guideline, CLSI document POCT05-A. Wayne, PA: Clinical and Laboratory Standards Institute: 2008 28(33), 72 pp.
Colangelo et al. 1967. Corrosion rate measurements in vivo, Journal of Biomedical Materials Research, 1:405-414.
Colowick et al. 1976. Methods in Enzymlology, vol. XLIV, Immobilized Enzymes. New York: Academic Press.
Coulet et al. (1981) Enzymes immobilized on collagen membranes: A tool for fundamental research and enzyme engineering. J Chromatography 215: 65-72.
Coulet, P.R. 1992. Polymeric membranes and coupled enzymes in the design of biosensors. J Membr Science 68: 217-228.
Cox et al. 1985. Accuracy of perceiving blood glucose in IDDM. Diabetes Care 8(6):529-536.
Csoregi et al., 1994. Design, characterization, and one-point in vivo calibration of a subcutaneously implanted glucose electrode. Anal Chem. 66(19):3131-3138.
Danielsson et al. 1988. Enzyme thermistors, Methods in Enzymology, 137:181-197.
Dassau et al., In silico evaluation platform for artifical pancreatic β-cell development—a dynamic simulator for closed loop control with hardware-in-the-loop, Diabetes Technology & Therapeutics, 11(3):1-8, 2009.
Davies, et al. 1992. Polymer membranes in clinical sensor applications. I. An overview of membrane function, Biomaterials, 13(14):971-978.

(56) References Cited

OTHER PUBLICATIONS

Davis et al. 1983. Bioelectrochemical fuel cell and sensor based on a quinoprotein, alcohol dehydrogenase. Enzyme Microb. Technol., vol. 5, September, 383-388.
Direct 30/30® Blood Glucose Sensor, (Markwell Medical) Catalog, © 1990, ELCO Diagnostics Company. 1 page.
Dixon et al. 2002. Characterization in vitro and in vivo of the oxygen dependence of an enzyme/polymer biosensor for monitoring brain glucose. Journal of Neuroscience Methods 119:135-142.
DuPont Dimension AR®. 1998. The chemistry analyzer that makes the most of your time, money and effort. Catalog. Dade International, Chemistry Systems. Newark, DE. 18 pages.
Durliat et al. 1976. Spectrophotometric and electrochemical determinations of L(+)-lactate in blood by use of lactate dehydrogenase from yeast, Clin. Chem. 22(11):1802-1805.
Edwards Lifesciences. Accuracy for your and your patients. Marketing materials, 4 pp. 2002.
El Degheidy et al. 1986. Optimization of an implantable coated wire glucose sensor. J. Biomed Eng. 8:121-129.
Electronic File History of Reexamination Control No. 90/011671, filed May 5, 2011 containing Office Action(s) mailed May 13, 2011 and 3rd Party submissions dated May 5, 2011 as of Jun. 3, 2011.
Electronic File History of Reissue U.S. Appl. No. 12/839,260, filed Jul. 19, 2010 containing Office Action(s) dated Aug. 9, 2010, Feb. 28, 2011 and Applicant Response(s) filed Jul. 19, 2010, Apr. 1, 2011 as of Jun. 2, 2011.
El-Khatib et al. 2007. Adaptive closed-loop control provides blood-glucose regulation using dual subcutaneous insulin and glucagon infusion in diabetic swine, Journal of Diabetes Science and Technology, 1(2):181-192.
El-Sa'ad et al. 1990. Moisture Absorption by Epoxy Resins: the Reverse Thermal Effect. Journal of Materials Science 25:3577-3582.
Ernst, et al. 2002. Reliable glucose monitoring through the use of microsystem technology. Anal. Bioanal. Chem. 373:758-761.
Fahy et al., An analysis: hyperglycemic intensive care patients need continuous glocuse monitoring—easier said than done, Journal of Diabetese Science and Technology, 2(2):201-204, Mar. 2008.
Fare, et al. 1998. Functional characterization of a conducting polymer-based immunoassay system. Biosensors & Bioelectronics 13(3-4):459-470.
Feldman, B.; Brazg, R.; Schwartz, S.; Weinstein, R. 2003. A continuous glucose sensor based on wired enzyme technology—results from a 3-day trial in patients with type 1 diabetes. Diabetes Technol Ther 5(5):769-779.
Fischer et al. 1987. Assessment of subcutaneous glucose concentration: validation of the wick technique as a reference for implanted electrochemical sensors in normal and diabetic dogs, Diabetologia 30:940-945.
Fischer et al. 1989. Oxygen Tension at the Subcutaneous Implantation Site of Glucose Sensors. Biomed. Biochem 11/12:965-972.
Fischer et al. 1995. Hypoglycaemia-warning by means of subcutaneous electrochemical glucose sensors: an animal study, Horm. Metab. Rese. 27:53.
Freedman et al. 1991. Statistics, Second Edition, W.W. Norton & Company, p. 74.
Frohnauer et al. 2001. Graphical human insulin time-activity profiles using standardized definitions. Diabetes Technology & Therapeutics 3(3):419-429.
Frost et al. 2002. Implantable chemical sensors for real-time clinical monitoring: Progress and challenges. Current Opinion in Chemical Biology 6:633-641.
Gabbay et al. 2008. Optical coherence tomography-based continuous noninvasive glucose monitoring in patients with diabetes. Diab. Thechnol. & Therapeut., 10:188-193.
Ganesan et al., Gold layer-based dual crosslinking procedure of glucose oxidase with ferrocene monocarboxylic acid provides a stable biosensor, Analytical Biochemistry 343:188-191, 2005.

Ganesh et al., Evaluation of the VIA® blood chemistry monitor for glucose in healthy and diabetic volunteers, Journal of Diabetese Science and Technology, 2(2):182-193, Mar. 2008.
Garg et al. 2004. Improved Glucose Excursions Using an Implantable Real-Time continuous Glucose Sensor in Adults with Type I Diabetes. Diabetes Care 27:734-738.
Gerritsen et al. 1999. Performance of subcutaneously implanted glucose sensors for continuous monitoring. The Netherlands Journal of Medicine 54:167-179.
Gerritsen, M. 2000. Problems associated with subcutaneously implanted glucose sensors. Diabetes Care 23(2):143-145.
Gilligan, B. C.; Shults, M.; Rhodes, R. K.; Jacobs, P. G.; Brauker, J. H.; Pintar, T. J.; Updike, S. J. 2004, Feasibility of continuous long-term glucose monitoring from a subcutaneous glucose sensor in humans. Diabetes Technol Ther 6:378-386.
Gilligan, et al. 1994. Evaluation of a subcutaneous glucose sensor out to 3 months in a dog model. Diabetes Care 17(8):882-887.
Godsland, et al. 2001. Maximizing the Success Rate of Minimal Model Insulin Sensitivity Measurement in Humans: The Importance of Basal Glucose Levels. The Biochemical Society and the Medical Research Society, 1-9.
Gouda et al., Jul. 4, 2003. Thermal inactiviation of glucose oxidase, The Journal of Biological Chemistry, 278(27):24324-24333.
Gough et al. 2000. Immobilized glucose oxidase in implantable glucose sensor technology. Diabetes Technology & Therapeutics 2(3):377-380.
Gough et al. 2003. Frequency characterization of blood glucose dynamics. Annals of Biomedical Engineering 31:91-97.
Gross et al. 2000. Efficacy and reliability of the continuous glucose monitoring system. Diabetes Technology & Therapeutics, 2(Suppl 1):S19-26.
Gross et al. 2000. Performance evaluation of the MiniMed® continuous glucose monitoring system during patient home use. Diabetes Technology & Therapeutics 2(1):49-56.
Guerci et al., Clinical performance of CGMS in type 1 diabetic patents treated by continuous subcutaneous insulin infusion using insulin analogs, Diabetes Care, 26:582-589, 2003.
Hall et al. 1998. Electrochemical oxidation of hydrogen peroxide at platinum electrodes. Part I: An adsorption-controlled mechanism. Electrochimica Acta, 43(5-6):579-588.
Hall et al. 1998. Electrochemical oxidation of hydrogen peroxide at platinum electrodes. Part II: Effect of potential. Electrochimica Acta 43(14-15):2015-2024.
Hall et al. 1999. Electrochemical oxidation of hydrogen peroxide at platinum electrodes. Part III: Effect of temperature. Electrochimica Acta, 44:2455-2462.
Hall et al. 1999. Electrochemical oxidation of hydrogen peroxide at platinum electrodes. Part IV: Phosphate buffer dependence. Electrochimica Acta, 44:4573-4582.
Hall et al. 2000. Electrochemical oxidation of hydrogen peroxide at platinum electrodes. Part V: Inhibition by chloride. Electrochimica Acta, 45:3573-3579.
Hamilton Syringe Selection Guide. 2006. Syringe Selection. www.hamiltoncompany.com.
Harrison, et al. 1988. Characterization of perfluorosulfonic acid polymer coated enzyme electrodes and a miniaturized integrated potentiostat for glucose analysis in whole blood. Anal. Chem. 60:2002-2007.
Hashiguchi et al. (1994). "Development of a miniaturized glucose monitoring system by combining a needle-type glucose sensor with microdialysis sampling method: Long-term subcutaneous tissue glucose monitoring in ambulatory diabetic patients," Diabetes Care, 17(5): 387-396.
Heller, "Electrical wiring of redox enzymes," Acc. Chem. Res., 23:128-134 (1990).
Heller, A. 1992. Electrical Connection of Enzyme Redox Centers to Electrodes. J. Phys. Chem. 96:3579-3587.
Heller, A. 1999. Implanted electrochemical glucose sensors for the management of diabetes. Annu Rev Biomed Eng 1:153-175.
Heller, A. 2003. Plugging metal connectors into enzymes. Nat Biotechnol 21:631-2.
Hicks, 1985. In Situ Monitoring, Clinical Chemistry, 31(12):1931-1935.

(56) References Cited

OTHER PUBLICATIONS

Hitchman, M. L. 1978. Measurement of Dissolved Oxygen. In Elving et al. (Eds.). Chemical Analysis, vol. 49, Chap. 3, pp. 34-49, 59-123. New York: John Wiley & Sons.

Hoel, Paul G. 1976. Elementary Statistics, Fourth Edition. John Wiley & Sons, Inc.. pp. 113-114.

Hrapovic et al. 2003. Picoamperometric detection of glucose at ultrasmall platinum-based biosensors: preparation and characterization. Anal Chem 75:3308-3315.

http://www.merriam-webster.com/dictionary, definition for "aberrant," Aug. 19, 2008, p. 1.

Hu, et al. 1993. A needle-type enzyme-based lactate sensor for in vivo monitoring, Analytica Chimica Acta, 281:503-511.

Huang et al. Aug. 1975. Electrochemical Generation of Oxygen. 1: The Effects of Anions and Cations on Hydrogen Chemisorption and Anodic Oxide Film Formation on Platinum Electrode. 2: The Effects of Anions and Cations on Oxygen Generation on Platinum Electrode. U.S. Department of Commerce/NTIS, pp. 1-116.

Huang et al., Sep. 1997, A 0.5mW Passive Telemetry IC for Biomedical Applications, Proceedings of the 23rd European Solid-State Circuits Conference (ESSCIRC '97), pp. 172-175, Southampton, UK.

Hunter et al. Mar. 31, 2000. Minimally Invasive Glucose Sensor and Insulin Delivery System. MIT Home Automation and Healthcare Consortium. Progress Report No. 2-5. 17 pages.

Ishikawa et al. 1998. Initial evaluation of a 290-mm diameter subcutaneous glucose sensor: Glucose monitoring with a biocompatible, flexible-wire, enzyme-based amperometric microsensor in diabetic and nondiabetic humans. Journal of Diabetes and Its Complications, 12:295-301.

Jaffari et al. 1995. Recent advances in amperometric glucose biosensors for in vivo monitoring, Physiol. Meas. 16: 1-15.

Jensen et al. 1997. Fast wave forms for pulsed electrochemical detection of glucose by incorporation of reductive desorption of oxidation products. Analytical Chemistry 69(9):1776-1781.

Jeong, et al. 2003. In vivo calibration of the subcutaneous amperometric glucose sensors using a non-enzyme electrode. Biosensors and Bioelectronics 19:313-319.

Jeutter, D. C. 1982. A transcutaneous implanted battery recharging and biotelemeter power switching system. IEEE Trans Biomed Eng 29:314-321.

Jobst et al., Thin-Film Microbiosensors for Glucose-Lactate Monitoring, Anal Chem. (1996) 68(18):3173-3179.

Johnson (1991). "Reproducible electrodeposition of biomolecules for the fabrication of miniature electroenzymatic biosensors," Sensors and Actuators B, 5:85-89.

Johnson, et al. 1992. In vivo evaluation of an electroenzymatic glucose sensor implanted in subcutaneous tissue. Biosensors & Bioelectronics 7:709-714.

Jovanovic, L. 2000. The role of continuous glucose monitoring in gestational diabetes mellitus. Diabetes Technology & Therapeutics, 2 Suppl 1, S67-71.

Kacaniklic May-Jun. 1994. Electroanalysis, 6(5-6):381-390.

Kamath et al. Calibration of a continuous glucose monitor: effect of glucose rate of change, Eighth Annual Diabetes Technology Meeting, Nov. 13-15, 2008, p. A88.

Kang et al. 2003. In vitro and short-term in vivo characteristics of a Kel-F thin film modified glucose sensor. Anal Sci 19:1481-1486.

Kaufman et al. 2001. A pilot study of the continuous glucose monitoring system. Diabetes Care 24(12):2030-2034.

Kaufman. 2000. Role of the continuous glucose monitoring system in pediatric patients. Diabetes Technology & Therapeutics 2(1):S-49-S-52.

Kawagoe et al. 1991. Enzyme-modified organic conducting salt microelectrode, Anal. Chem. 63:2961-2965.

Keedy et al. 1991. Determination of urate in undiluted whole blood by enzyme electrode. Biosensors & Bioelectronics, 6: 491-499.

Kerner et al. 1988. A potentially implantable enzyme electrode for amperometric measurement of glucose, Horm Metab Res Suppl. 20:8-13.

Kerner, et al. "The function of a hydrogen peroxide-detecting electroenzymatic glucose electrode is markedly impaired in human sub-cutaneous tissue and plasma," Biosensors & Bioelectronics, 8:473-482 (1993).

Klueh et al. 2003. Use of Vascular Endothelia Cell Growth Factor Gene Transfer to Enhance Implantable Sensor Function in Vivo, Biosensor Function and Vegf-Gene Transfer, pp. 1072-1086.

Ko, Wen H. 1985. Implantable Sensors for Closed-Loop Prosthetic Systems, Futura Pub. Co., Inc., Mt. Kisco, NY, Chapter 15:197-210.

Kondo et al. 1982. A miniature glucose sensor, implantable in the blood stream. Diabetes Care. 5(3):218-221.

Koschinsky et al. 2001. Sensors for glucose monitoring: Technical and clinical aspects. Diabetes Metab. Res. Rev. 17:113-123.

Koschinsky, et al. 1998. New approach to technical and clinical evaluation of devices for self-monitoring of blood glucose. Diabetes Care 11(8): 619-619.

Kost et al. 1985. Glucose-sensitive membranes containing glucose oxidase: activitiy, swelling, and permeability studies, Journal of Biomedical Materials Research 19:1117-1133.

Koudelka et al. 1989. In vivo response of microfabricated glucose sensors to glycemia changes in normal rats. Biomed Biochim Acta 48(11-12):953-956.

Koudelka et al. 1991. In-vivo behaviour of hypodermically implanted microfabricated glucose sensors. Biosensors & Bioelectronics 6:31-36.

Kraver et al. 2001. A mixed-signal sensor interface microinstrument. Sensors and Actuators A 91:266-277.

Kruger et al. 2000. Psychological motivation and patient education: A role for continuous glucose monitoring. Diabetes Technology & Therapeutics, 2(Suppl 1):S93-97.

Kulys et al., 1994. Carbon-paste biosensors array for long-term glucose measurement, Biosensors& Beioelectronics, 9:491-500.

Kunjan et al., Automated blood sampling and glocuse sensing in critical care settings, Journal of Diabetes Science and Technology 2(3):194-200, Mar. 2008.

Kurtz et al. 2005. Recommendations for blood pressure measurement in humans and experimental animals, Part 2: Blood pressure measurement in experimental animals, A statement for professionals from the subcommittee of professional and public education of the American Heart Association Council on High Blood Pressure Research. Hypertension 45:299-310.

Ladd et al., Structure Determination by X-ray Crystallography, 3rd ed. Plenum, 1996, Ch. 1, pp. xxi-xxiv and 1-58.

Lehmann et al. May 1994. Retrospective valication of a physiological model of glucose-iunsulin interaaction in tyhpe 1 diabetes mellitus, Med. Eng. Phys. 16:193-202.

Lerner et al. 1984. An implantable electrochemical glucose sensor. Ann. N. Y. Acad. Sci. 428:263-278.

Lewandowski et al. 1988. Evaluation of a miniature blood glucose sensor. Trans Am Soc Artif Intern Organs 34:255-258.

Leypoldt et al. 1984. Model of a two-substrate enzyme electrode for glucose. Anal. Chem. 56:2896-2904.

Linke et al. 1994. Amperometric biosensor for in vivo glucose sensing based on glucose oxidase immobilized in a redox hydrogel. Biosensors & Bioelectronics 9:151-158.

Lowe, 1984. Biosensors, Trends in Biotechnology, 2(3):59-65.

Luong et al. 2004. Solubilization of Multiwall Carbon Nanotubes by 3-Aminopropyltriethoxysilane Towards the Fabrication of Electrochemical Biosensors with Promoted Electron Transfer. Electronanalysis 16(1-2):132-139.

Lyandres et al. (2008). Progress toward an in vivo surface-enhanced raman spectroscopy glucose sensor. Diabetes Technology & Therapeutics, 10(4): 257-265.

Maidan et al. 1992. Elimination of Electrooxidizable Interferent-Produced Currents in Amperometric Biosensors, Analytical Chemistry, 64:2889-2896.

Makale et al. 2003. Tissue window chamber system for validation of implanted oxygen sensors. Am. J. Physiol. Heart Circ. Physiol. 284:H2288-2294.

Malin et al. 1999. Noninvasive Prediction of Glucose by Near-Infrared Diffuse Reflectance Spectroscopy. Clinical Chemistry 45:9, 1651-1658.

(56) References Cited

OTHER PUBLICATIONS

Maran et al. 2002. Continuous subcutaneous glucose monitoring in diabetic patients: A multicenter analysis. Diabetes Care 25(2):347-352.

March, W. F. 2002. Dealing with the delay. Diabetes Technol Ther 4(1):49-50.

Marena et al. 1993. The artifical endocrine pancreas in clinical practice and research. Panminerva Medica 35(2):67-74.

Mascini et al. 1989. Glucose electrochemical probe with extended linearity for whole blood. J Pharm Biomed Anal 7(12): 1507-1512.

Mastrototaro, et al. "An electroenzymatic glucose sensor fabricated on a flexible substrate," Sensors and Actuators B, 5:139-44 (1991).

Matsumoto et al. 1998. A micro-planar amperometeric glucose sensor unsusceptible to interference species. Sensors and Actuators B 49:68-72.

Matsumoto, et al. 2001. A long-term lifetime amperometric glucose sensor with a perfluorocarbon polymer coating. Biosens Bioelectron 16:271-276.

McGrath et al. 1995. The use of differential measurements with a glucose biosensor for interference compensation during glucose determinations by flow injection analysis. Biosens Bioelectron 10:937-943.

McKean, et al. Jul. 7, 1988. A Telemetry Instrumentation System for Chronically Implanted Glucose and Oxygen Sensors. Transactions on Biomedical Engineering 35:526-532.

Memoli et al. 2002. A comparison between different immobilised glucoseoxidase-based electrodes. J Pharm Biomed Anal 29:1045-1052.

Moatti-Sirat et al. 1992. Evaluating in vitro and in vivo the interference of ascorbate and acetaminophen on glucose detection by a needle-type glucose sensor, Biosensors & Bioelectronics 7:345-352.

Moatti-Sirat et al., Reduction of acetaminophen interference in glucose sensors by a composite Nafion membrane: demonstration in rats and man, Diabetologia 37(6):610-616, Jun. 1994.

Moatti-Sirat et al. 1992. Towards continuous glucose monitoring: in vivo evaluation of a miniaturized glucose sensor implanted for several days in rat subcutaneous tissue. Diabetologia 35:224-230.

Morff et al. 1990. Microfabrication of reproducible, economical, electroenzymatic glucose sensors, Annual International Conference of the IEEE Engineering in Medicine and Biology Society, 12(2):0483-0484.

Moussy et al. 1993. Performance of subcutaneously implanted needle-type glucose sensors employing a novel trilayer coating, Anal Chem. 85: 2072-2077.

Moussy, Francis (Nov. 2002) Implantable Glucose Sensor: Progress and Problems, Sensors, 1:270-273.

Murphy, et al. 1992. Polymer membranes in clinical sensor applications. II. The design and fabrication of permselective hydrogels for electrochemical devices, Biomaterials, 13(14):979-990.

Ohara, et al. Dec. 1993. Glucose electrodes based on cross-linked bis(2,2'-bipyridine)chloroosmium(+/2+) complexed poly(1-vinylimidazole) films, Analytical Chemistry, 65:3512-3517.

Ohara et al. 1994. "Wired" enzyme electrodes for amperometric determination of glucose or lactate in the presence of interfering substances. Anal Chem 66:2451-2457.

Palmisano, et al. 2000. Simultaneous monitoring of glucose and lactate by an interference and cross-talk free dual electrode amperometric biosensor based on electropolymerized thin films. Biosensors & Bioelectronics 15:531-539.

Peguin et al. 1989. Pyruvate Oxidase and Oxaloacetate Decarbozylase Enzyme Electrodes—Simultaneous Determination of Transaminases with a Two-electrode-based Analyzer, Anal Chim Acta 222: 83-93.

Pickup, et al. "Implantable glucose sensors: choosing the appropriate sensor strategy," Biosensors, 3:335-346 (1987/88).

Pickup, et al. "In vivo molecular sensing in diabetes mellitus: an implantable glucose sensor with direct electron transfer," Diabetologia, 32:213-217 (1989).

Pishko et al. "Amperometric glucose microelectrodes prepared through immobilization of glucose oxidase in redox hydrogels," Anal. Chem., 63:2268-72 (1991).

Poitout, et al. 1991. In Vitro and In Vivo Evaluation in Dogs of a Miniaturized Glucose Sensor, ASAIO Transactions, 37:M298-M300.

Postlethwaite, et al. 1996. Interdigitated array electrode as an alternative to the rotated ring-disk electrode for determination of the reaction products of dioxygen reduction. Analytical Chemistry 68:2951-2958.

Reach et al. 1992. Can continuous glucose monitoring be used for the treatment of diabetes? Analytical Chemistry 64(5):381-386.

Rebrin, et al. "Automated feedback control of subcutaneous glucose concentration in diabetic dogs," Diabetologia, 32:573-76 (1989).

Rhodes, et al. 1994. Prediction of pocket-portable and implantable glucose enzyme electrode performance from combined species permeability and digital simulation analysis. Analytical Chemistry 66(9):1520-1529.

Sakakida et al. 1993. Ferrocene-Mediated Needle Type Glucose Sensor Covered with Newly Designed Biocompatible Membran, Sensors and Actuators B 13-14:319-322.

Samuels, M.P. 2004. The effects of flight and altitude. Arch Dis Child. 89: 448-455.

Schaffar, Bernhard P.H. (Dec. 2001). Thick film biosensors for metabolites in undiluted whole blood and plasma samples, Anal Bioanal Chem. 372: 254-260.

Shaw, et al. "In vitro testing of a simply constructed, highly stable glucose sensor suitable for implantation in diabetic patients," Biosensors & Bioelectronics, 6:401-406 (1991).

Shichiri et al. 1986. Telemetry Glucose Monitoring Device with Needle-Type Glucose Sensor: A Useful Tool for Blood Glucose Monitoring in Diabetic Individuals. Diabetes Care, Inc. 9(3):298-301.

Shichiri et al. 1983. Glycaemic Control in Pancreatectomized Dogs with a Wearable Artificial Endocrine Pancreas. Diabetologia 24:179-184.

Shichiri et al. 1985. Needle-type Glucose Sensor for Wearable Artificial Endocrine Pancreas in Implantable Sensors 197-210.

Shichiri et al., 1989. Membrane Design for Extending the Long-Life of an Implantable Glucose Sensor. Diab. Nutr. Metab. 2:309-313.

Shults et al. 1994. A telemetry-instrumentation system for monitoring multiple subcutaneously implanted glucose sensors. IEEE Transactions on Biomedical Engineering 41(10):937-942.

Sokol et al. 1980, Immobilized-enzyme rate-determination method for glucose analysis, Clin. Chem. 26(1):89-92.

Sternberg et al. 1988. Study and Development of Multilayer Needle-type Enzyme-based Glucose Microsensors. Biosensors 4:27-40.

Takatsu et al. 1987. Solid State Biosensors Using Thin-Film Electrodes. Sens Actuators 11: 309-317.

Thome et al. 1995. Can the decrease in subcutaneous glucose concentration precede the decrease in blood glucose level? Proposition for a push-pull kinetics hypothesis, Horm. Metab. Res. 27:53.

Thomé-Duret et al. 1996. Modification of the sensitivity of glucose sensor implanted into subcutaneous tissue. Diabetes Metabolism, 22:174-178.

Thompson et al., In Vivo Probes: Problems and Perspectives, Department of Chemistry, University of Toronto, Canada, pp. 255-261, 1986.

Tierney et al. 2000. Effect of acetaminophen on the accuracy of glucose measurements obtained with the GlucoWatch biographer. Diabetes Technol Ther 2(2):199-207.

Turner and Pickup, "Diabetes mellitus: biosensors for research and management," Biosensors, 1:85-115 (1985).

Turner, A.P.F. 1988. Amperometric biosensor based on mediator-modified electrodes. Methods in Enzymology 137:90-103.

U.S. Appl. No. 09/447,227, filed Nov. 22, 1999.

Updike et al. 1979. Continuous glucose monitor based on an immobilized enzyme electrode detector. J Lab Clin Med, 93(4):518-527.

Updike et al. 1997. Principles of long-term fully implanted sensors with emphasis on radiotelemetric monitoring of blood glucose form

(56) References Cited

OTHER PUBLICATIONS inside a subcutaneous foreign body capsule (FBC). In Fraser, ed., Biosensors in the Body. New York. John Wiley & Sons, pp. 117-137.

Updike, et al. 1982. Implanting the glucose enzyme electrode: Problems, progress, and alternative solutions. Diabetes Care 5(3):207-212.

Velho et al. 1989. Strategies for calibrating a subcutaneous glucose sensor. Biomed Biochim Acta 48(11/12):957-964.

von Woedtke et al. 1989. In situ calibration of implanted electrochemical glucose sensors. Biomed Biochim. Acta 48(11/12):943-952.

Wagner, et al. 1998. Continuous amperometric monitoring of glucose in a brittle diabetic chimpanzee with a miniature subcutaneous electrode. Proc. Natl. Acad. Sci. A, 95:6379-6382.

Ward et al. 1999. Assessment of chronically implanted subcutaneous glucose sensors in dogs: The effect of surrounding fluid masses. ASAIO Journal, 45:555-561.

Ward et al. 2004. A wire-based dual-analyte sensor for Glucose and Lactate: In Vitro and In Vivo Evaluation, Diab Tech Therapeut. 6(3): 389-401.

Ward, et al. 2000. Rise in background current over time in a subcutaneous glucose sensor in the rabbit: Relevance to calibration and accuracy. Biosensors & Bioelectronics 15:53-61.

Ward et al. 2000. Understanding Spontaneous Output Fluctuations of an Amperometric Glucose Sensor: Effect of Inhalation Anesthesia and e of a Nonenzyme Containing Electrode. ASAIO Journal 540-546.

Wilkins, et al. 1995. Integrated implantable device for long-term glucose monitoring. Biosens. Bioelectron 10:485-494.

Wilson, et al. 1992. Progress toward the development of an implantable sensor for glucose. Clin. Chem. 38(9):1613-1617.

Yang et al (1996). "A glucose biosensor based on an oxygen electrode: In-vitro performances in a model buffer solution and in blood plasma," Biomedical Instrumentation & Technology, 30:55-61.

Yang et al. 1995. Glucose Biosensors with enzyme entrapped in polymer coating, Biomed Instrum Technol. 29(2): 125-133.

Zhang et al (1993). Electrochemical oxidation of $H_2O_2$ on Pt and Pt + Ir electrodes in physiological buffer and its applicability to $H_2O_2$-based biosensors. J. Electroanal. Chem., 345:253-271.

Zhang, et al. 1994. Elimination of the acetaminophen interference in an implantable glucose sensor. Analytical Chemistry 66(7):1183-1188.

Zhu et al. (1994). "Fabrication and characterization of glucose sensors based on a microarray $H_2O_2$ electrode." Biosensors & Bioelectronics, 9: 295-300.

ISR and WO dated Aug. 8, 2008 for PCT/US2007/007612, filed Mar. 27, 2007.

IPRP dated Oct. 23, 2008 for PCT/US2007/007612, filed Mar. 27, 2007.

ISR and WO dated Jun. 20, 2007 for PCT/US2006/038820, filed Oct. 4, 2006.

IPRP for PCT/US06/38820 filed Oct. 4, 2006.

ISR and WO for PCT/US07/080228, filed Oct. 2, 2007.

ISR and WO PCT/US04/40476 filed Dec. 3, 2004.

IPRP for PCT/US04/40476 filed Dec. 3, 2004.

EPO Supplementary European Search Report for App. No. 04812899.5, dated May 8, 2008.

EPO Office Action in European App. No. 04812899.5, dated Oct. 8, 2008.

EPO Office Action in European App. No. 04812899.5, dated May 5, 2009.

EPO Communication dated Oct. 13, 2010 in EP Application No. 10168369.6 filed Dec. 3, 2004.

EPO Communication dated Oct. 14, 2010 in EP Application No. 10168368.8 filed Dec. 3, 2004.

EPO Communication dated Oct. 14, 2010 in EP Application No. 10168371.2 filed Dec. 3, 2004.

EPO communication dated Oct. 8, 2010 in EP Application No. 07853741.2 filed Oct. 2, 2007.

Abbott Diabetes Care Inc. Grounds of Opposition dated Mar. 30, 2011 against EP 1711790, issued Sep. 8, 2010.

EPO Notice of Opposition dated May 11, 2011 by Abbott Diabetes Care, Inc. against EP Patent No. 1711790, issued Oct. 18, 2006.

Roche Diagnostics GmbH Grounds of Opposition dated Jun. 6, 2011 against EP 1711790, issued Sep. 8, 2010.

EPO Notice of Opposition dated Jun. 20, 2011 by Roche Diagnostics GmbH against EP Patent No. 1711790, issued Oct. 18, 2006.

Burmeister et al., Self-Referencing Ceramic-Based Multisite Microelectrodes for the Detection and Elimination of Interferences from the Measurement of L-Glutamate and Other Analytes. Anal Chem. (2001) 73: 1037-1042.

Burmeister et al., Anal. Chem. 73(5):1037-1042 (2001): Self-Referencing Ceramic-Based Multisite Microelectrodes for the Detection and Elimination of Interferences from the Me.

\* cited by examiner

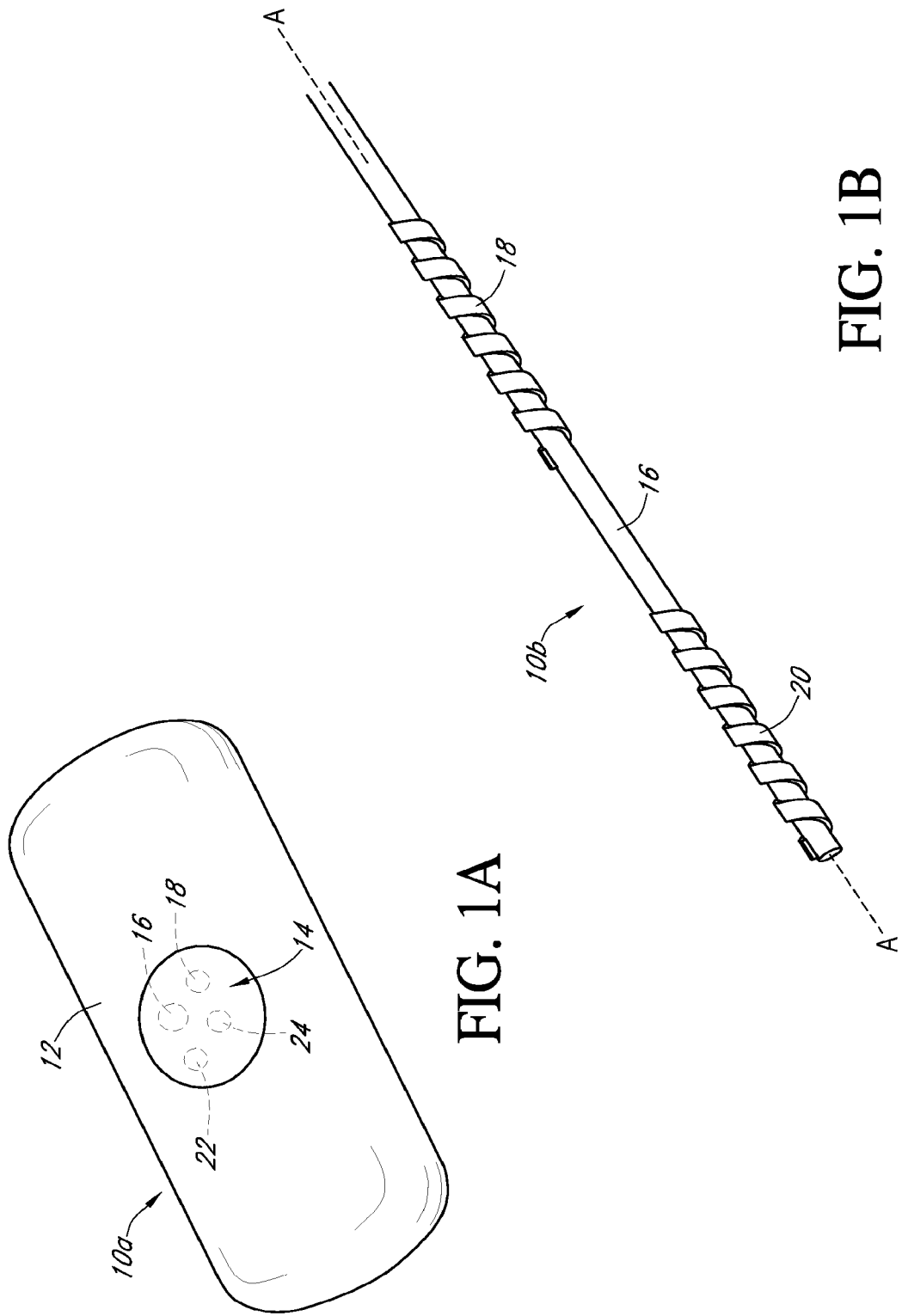

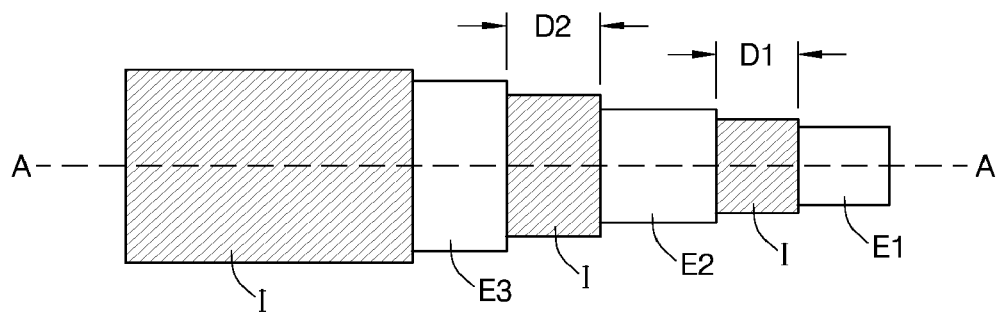
FIG. 7A$_1$
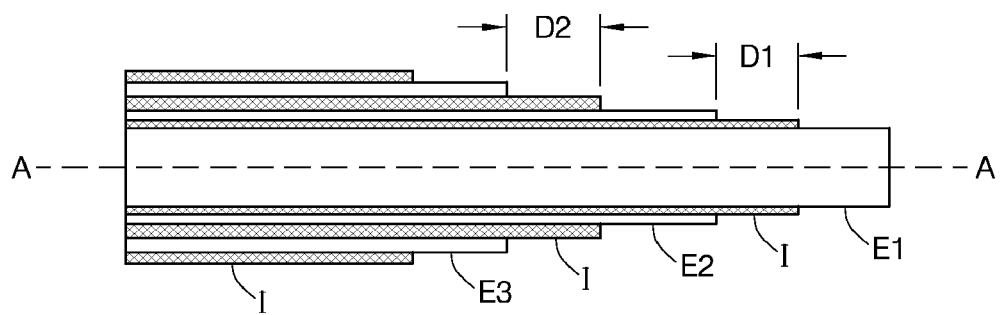
FIG. 7A$_2$

DUAL ELECTRODE SYSTEM FOR A CONTINUOUS ANALYTE SENSOR

INCORPORATION BY REFERENCE TO RELATED APPLICATIONS

Any and all priority claims identified in the Application Data Sheet, or any correction thereto, are hereby incorporated by reference under 37 CFR 1.57. This application is a divisional of U.S. application Ser. No. 11/865,572 filed Oct. 1, 2007, which is a continuation-in-part of U.S. application Ser. No. 11/543,683 filed Oct. 4, 2006, now U.S. Pat. No. 7,366,556, the disclosures of which are hereby expressly incorporated by reference in their entirety and are hereby expressly made a portion of this application.

FIELD OF THE INVENTION

The present invention relates generally to systems and methods for measuring an analyte concentration in a host.

BACKGROUND OF THE INVENTION

Diabetes mellitus is a disorder in which the pancreas cannot create sufficient insulin (Type I or insulin dependent) and/or in which insulin is not effective (Type 2 or non-insulin dependent). In the diabetic state, the victim suffers from high blood sugar, which may cause an array of physiological derangements (for example, kidney failure, skin ulcers, or bleeding into the vitreous of the eye) associated with the deterioration of small blood vessels. A hypoglycemic reaction (low blood sugar) may be induced by an inadvertent overdose of insulin, or after a normal dose of insulin or glucose-lowering agent accompanied by extraordinary exercise or insufficient food intake.

Conventionally, a diabetic person carries a self-monitoring blood glucose (SMBG) monitor, which typically comprises uncomfortable finger pricking methods. Due to the lack of comfort and convenience, a diabetic will normally only measure his or her glucose level two to four times per day. Unfortunately, these time intervals are so far spread apart that the diabetic will likely find out too late, sometimes incurring dangerous side effects, of a hyper- or hypo-glycemic condition. In fact, it is not only unlikely that a diabetic will take a timely SMBG value, but the diabetic will not know if their blood glucose value is going up (higher) or down (lower) based on conventional methods, inhibiting their ability to make educated insulin therapy decisions.

SUMMARY OF THE INVENTION

A variety of continuous glucose sensors have been developed for detecting and/or quantifying glucose concentration in a host. These sensors have typically required one or more blood glucose measurements, or the like, from which to calibrate the continuous glucose sensor to calculate the relationship between the current output of the sensor and blood glucose measurements, to provide meaningful values to a patient or doctor. Unfortunately, continuous glucose sensors are conventionally also sensitive to non-glucose related changes in the baseline current and sensitivity over time, for example, due to changes in a host's metabolism, maturation of the tissue at the biointerface of the sensor, interfering species which cause a measurable increase or decrease in the signal, or the like. Therefore, in addition to initial calibration, continuous glucose sensors should be responsive to baseline and/or sensitivity changes over time, which requires recalibration of the sensor. Consequently, users of continuous glucose sensors have typically been required to obtain numerous blood glucose measurements daily and/or weekly in order to maintain calibration of the sensor over time.

In a first aspect, a continuous glucose sensor is provided, the sensor comprising a first working electrode comprising a first electroactive surface disposed beneath an active enzymatic portion of a sensor membrane, wherein the first working electrode is configured to generate a first signal having a first noise component related to a noise-causing species; and a second working electrode comprising a second electroactive surface disposed beneath an inactive-enzymatic or a non-enzymatic portion of the sensor membrane, wherein the second working electrode is configured to generate a second signal having a second noise component related to the noise-causing species; wherein the first electroactive surface and the second electroactive surface are each dimensioned to integrate at least one signal generated by a plurality of local point sources that produce the noise-causing species, such that the first noise component and the second noise component are substantially equivalent.

In an embodiment of the first aspect, at least one dimension of each of the first electroactive surface and second electroactive surface is greater than a sum of diameters of about 10 average human cells.

In an embodiment of the first aspect, at least one dimension of each of the first electroactive surface and second electroactive surface is greater than about 500 µm.

In an embodiment of the first aspect, each of the first electroactive surface and second electroactive surface is configured and arranged to integrate noise detected about a circumference of the sensor.

In an embodiment of the first aspect, the noise-causing species comprises at least one member selected from the group consisting of externally produced $H_2O_2$, urea, lactic acid, phosphates, citrates, peroxides, amino acids, amino acid precursors, amino acid break-down products, nitric oxide, NO-donors, NO-precursors, reactive oxygen species, compounds having electroactive acidic, amine or sulfhydryl groups, acetaminophen, ascorbic acid, dopamine, ephedrine, ibuprofen, L-dopa, methyldopa, salicylate, tetracycline, tolazamide, tolbutamide, and triglycerides.

In an embodiment of the first aspect, the noise-causing species is non-constant.

In an embodiment of the first aspect, the first electroactive surface and second electroactive surface are spaced at a distance that allows noise caused by a local point source that produces noise-causing species to be measured equivalently at the first electroactive surface and the second electroactive surface.

In an embodiment of the first aspect, the first electroactive surface and second electroactive surface are spaced at a distance less than a crosstalk diffusion distance of a measured species.

In an embodiment of the first aspect, the measured species comprises $H_2O_2$ produced in the active enzymatic portion of the sensor membrane.

In an embodiment of the first aspect, the sensor further comprises a physical diffusion barrier configured and arranged to physically block crosstalk from the active enzymatic portion of the sensor membrane to the second electroactive surface by at least 50%.

In an embodiment of the first aspect, the physical diffusion barrier is configured and arranged to physically block an amount of the measured species diffusing from the active enzymatic portion of the membrane to the second electroactive surface, such that there is substantially no signal associated with crosstalk measured at the second working electrode.

In an embodiment of the first aspect, the sensor further comprises a physical diffusion barrier comprising a discontinuous portion of a membrane disposed between the first electroactive surface and the second electroactive surface.

In an embodiment of the first aspect, the physical diffusion barrier comprises a first barrier layer formed on the first working electrode and a second barrier layer formed on the second working electrode, wherein the first barrier layer and the second barrier layer are each independently formed.

In an embodiment of the first aspect, the physical diffusion barrier comprises a first resistance domain formed on the first working electrode and a second resistance domain formed on the second working electrode, and the sensor membrane further comprises a third resistance domain disposed continuously over the first and second resistance domains, wherein the first resistance domain and the second resistance domain are configured and arranged to attenuate diffusion of the measurable species from the active enzymatic portion of the sensor to the second electroactive surface by at least 2-fold, and the third resistance domain is configured such that a sensitivity of each of the first signal and the second signal is substantially equivalent.

In an embodiment of the first aspect, the physical diffusion barrier is configured and arranged to attenuate the diffusion of the measured species by at least 10-fold.

In an embodiment of the first aspect, the sensitivities of the first signal and the second signals are within 20% of each other.

In a second aspect, a continuous glucose sensor configured for insertion into a host and for detecting glucose in the host is provided, the sensor comprising a first working electrode comprising a first electroactive surface disposed beneath an active enzymatic portion of a sensor membrane, wherein the first working electrode is configured to generate a first signal having a first noise component related to a noise-causing species; a second working electrode comprising a second electroactive surface disposed beneath an inactive-enzymatic or a non-enzymatic portion of the sensor membrane, wherein the second working electrode is configured to generate a second signal having a second noise component related to the noise-causing species; and a physical diffusion barrier; wherein the first electroactive surface and the second electroactive surface are spaced at a distance that allows noise caused by a local point source that produces noise-causing species to be measured substantially equivalently at the first electroactive surface and the second electroactive surface.

In an embodiment of the second aspect, the sensor membrane has a thickness, and wherein the distance between the first electroactive surface and the second electroactive surface is less than about twice the thickness of the sensor membrane.

In an embodiment of the second aspect, the thickness of the sensor membrane is less than about 80 microns.

In an embodiment of the second aspect, the distance between the first electroactive surface and the second electroactive surface is less than or equal to about a crosstalk diffusion distance of a measurable species.

In an embodiment of the second aspect, the measurable species comprises $H_2O_2$ produced in the active enzymatic portion of the sensor membrane.

In an embodiment of the second aspect, the noise-causing species comprises at least one member selected from the group consisting of externally produced $H_2O_2$, urea, lactic acid, phosphates, citrates, peroxides, amino acids, amino acid precursors, amino acid break-down products, nitric oxide, NO-donors, NO-precursors, reactive oxygen species, compounds having electroactive acidic, amine or sulfhydryl groups, acetaminophen, ascorbic acid, dopamine, ephedrine, ibuprofen, L-dopa, methyldopa, salicylate, tetracycline, tolazamide, tolbutamide, and triglycerides.

In an embodiment of the second aspect, the active enzymatic portion of the membrane is configured to produce a measurable species, and wherein the physical diffusion barrier is configured and arranged to physically block at least some diffusion of the measurable species from the active enzymatic portion of the membrane to the second electroactive surface.

In an embodiment of the second aspect, the physical diffusion barrier is configured and arranged to physically block at least 50% of the measurable species diffusing from the active enzymatic portion of the membrane to the second electroactive surface, such that there is substantially no signal associated with crosstalk measured at the second working electrode.

In an embodiment of the second aspect, the measurable species comprises $H_2O_2$ produced in the active enzymatic portion of the sensor membrane.

In an embodiment of the second aspect, the physical diffusion barrier comprises a discontinuous portion of the membrane disposed between the first electroactive surface and the second electroactive surface.

In an embodiment of the second aspect, the physical diffusion barrier comprises a first barrier layer formed on the first electrode and a second barrier layer formed on the second electrode, wherein each of the first barrier layer and the second barrier layer is independently formed.

In an embodiment of the second aspect, the physical diffusion barrier comprises a first resistance domain formed on the first electrode and a second resistance domain formed on the second electrode, and wherein the first resistance domain and the second resistance domain are configured and arranged to attenuate diffusion of the measurable species from the active enzymatic portion of the membrane to the second electroactive surface by at least 2-fold.

In an embodiment of the second aspect, the physical diffusion barrier is configured and arranged to attenuate the diffusion of the measurable species by at least 10-fold.

In an embodiment of the second aspect, the sensor membrane further comprises a third resistance domain disposed continuously over the first electroactive surface and the second electroactive surface, wherein the third resistance domain is configured such that a sensitivity of each of the first signal and the second signal is substantially equivalent.

In an embodiment of the second aspect, the sensor further comprises an insulator configured to insulate the first working electrode from the second working electrode, wherein the sensor membrane is the insulator.

In an embodiment of the second aspect, the first electroactive surface and the second electroactive surface are each dimensioned to integrate noise caused by a plurality of local point sources that produce noise-causing species in vivo.

In an embodiment of the second aspect, the first electroactive surface and the second electroactive surface are each sized in at least one dimension such that each of the first noise component and second noise component can be integrated across the dimension.

In an embodiment of the second aspect, the dimension is greater than a sum of diameters of about 10 average human cells.

In an embodiment of the second aspect, each of the first electroactive surface and the second electroactive surface is dimensioned such that each of the first noise component and the second noise component is substantially equivalent.

In a third aspect, a sensor configured and arranged for insertion into a host and for continuously detecting glucose in the host is provided, the sensor comprising a first working electrode configured to generate a first signal having a first noise component related to a noise-causing species, the first working electrode having a first electroactive surface having a first surface area; and a second working electrode configured to generate a second signal having a second noise component related to the noise-causing species, the second working electrode having a second electroactive surface having a second surface area; wherein the first working electrode and the second working electrode are configured and arranged to integrate the first noise component and the second noise component about a circumference of the sensor.

In an embodiment of the third aspect, the noise-causing species comprises at least one member selected from the group consisting of externally produced $H_2O_2$, urea, lactic acid, phosphates, citrates, peroxides, amino acids, amino acid precursors, amino acid break-down products, nitric oxide, NO-donors, NO-precursors, reactive oxygen species, compounds having electroactive acidic, amine or sulfhydryl groups, acetaminophen, ascorbic acid, dopamine, ephedrine, ibuprofen, L-dopa, methyldopa, salicylate, tetracycline, tolazamide, tolbutamide, and triglycerides.

In an embodiment of the third aspect, the noise-causing species is non-constant.

In an embodiment of the third aspect, the first surface area and the second surface area are each dimensioned to integrate noise caused by a plurality of local point sources that produce noise-causing species in vivo.

In an embodiment of the third aspect, the first surface area and the second surface area are each sized in at least one dimension such that each of the first noise component and the second noise component can be integrated across the dimension.

In an embodiment of the third aspect, the dimension is greater than a sum of diameters of about 10 average human cells.

In an embodiment of the third aspect, the dimension is greater than about 500 μm.

In an embodiment of the third aspect, the first surface area and the second surface area are each dimensioned such that each of the first noise component and the second noise component is substantially equivalent.

In an embodiment of the third aspect, the first surface area and the second surface area are each dimensioned such that each of the first noise component and the second noise component is equivalent to ±10%.

In an embodiment of the third aspect, the first electroactive surface and the second electroactive surface are spaced a distance that allows noise caused by a local point source that produces noise-causing species to be measured equivalently at the first electroactive surface and the second electroactive surface.

In an embodiment of the third aspect, the first electroactive surface is disposed beneath an active enzymatic portion of a sensor membrane and the second electroactive surface is disposed beneath at least one of an inactive enzymatic or a non-enzymatic portion of the sensor membrane, and wherein the first electroactive surface and the second electroactive surface are spaced a distance less than about a crosstalk distance of a measurable species produced in the active enzymatic portion of the sensor membrane.

In an embodiment of the third aspect, the measurable species comprises $H_2O_2$.

In an embodiment of the third aspect, the crosstalk distance comprises a maximum distance the measurable species can diffuse from the active enzymatic portion of the sensor membrane to the second electroactive surface, and thereby cause a measurable signal on the second working electrode.

In an embodiment of the third aspect, the sensor further comprises a physical diffusion barrier.

In an embodiment of the third aspect, the physical diffusion barrier comprises a first barrier layer formed on the first working electrode and a second barrier layer formed on the second working electrode, wherein each of the first barrier layer and the second barrier layer is independently formed.

In an embodiment of the third aspect, the physical diffusion barrier comprises a first resistance domain formed on the first working electrode and a second resistance domain formed on the second working electrode, and wherein the first resistance domain and the second resistance domain are configured and arranged to attenuate diffusion of the measurable species from the active enzymatic portion of the membrane to the second electroactive surface by at least 2-fold.

In an embodiment of the third aspect, the physical diffusion barrier is configured and arranged to attenuate the diffusion of the measurable species by at least 10-fold.

In an embodiment of the third aspect, the sensor membrane further comprises a third resistance domain disposed continuously over the first resistance domain and the second resistance domain, wherein the third resistance domain is configured such that a sensitivity of each of the first signal and the second signal is substantially equivalent.

In an embodiment of the third aspect, the sensor further comprises an insulator configured to insulate the first working electrode from the second working electrode, wherein the sensor membrane is the insulator.

In a fourth aspect, a continuous glucose sensor configured and arranged for insertion into a host and for detecting glucose in the host is provided, the sensor comprising a first working electrode comprising a first electroactive surface disposed beneath an active enzymatic portion of a sensor membrane, wherein the first electroactive surface is configured to measure a measurable species; a second working electrode comprising a second electroactive surface disposed beneath at least one of an inactive enzymatic portion of the sensor membrane and a non-enzymatic portion of the sensor membrane, wherein the second electroactive surface is configured to measure said measurable species, and wherein the first electroactive surface and the second electroactive surface are spaced within a crosstalk distance of the measurable species; and a physical diffusion barrier disposed between the first working electrode and the second working electrode, wherein the physical diffusion barrier is configured and arranged such that there is substantially no signal associated with crosstalk.

In an embodiment of the fourth aspect, the noise-causing species comprises at least one member selected from the group consisting of externally produced $H_2O_2$, urea, lactic acid, phosphates, citrates, peroxides, amino acids, amino acid precursors, amino acid break-down products, nitric oxide, NO-donors, NO-precursors, reactive oxygen species, compounds having electroactive acidic, amine or sulfhydryl groups, acetaminophen, ascorbic acid, dopamine, ephedrine, ibuprofen, L-dopa, methyldopa, salicylate, tetracycline, tolazamide, tolbutamide, and triglycerides.

In an embodiment of the fourth aspect, the noise-causing species is non-constant.

In an embodiment of the fourth aspect, the measurable species is $H_2O_2$ produced in an active enzymatic portion of a sensor membrane.

In an embodiment of the fourth aspect, the crosstalk distance is a maximum distance the measurable species can diffuse between the active enzymatic portion of the membrane and the second working electrode, and be detected as crosstalk.

In an embodiment of the fourth aspect, the first electroactive surface has a first area and the second electroactive surface has a second area; wherein the first area and the second area are dimensioned such that the first noise component and the second noise component are substantially equivalent.

In an embodiment of the fourth aspect, at least one dimension of each of the first area and the second area is greater than a sum of diameters of about 10 average human cells.

In an embodiment of the fourth aspect, at least one dimension of each of the first area and the second area is greater than about 500 µm.

In an embodiment of the fourth aspect, the first area and the second area are each configured and arranged to integrate noise caused by a plurality of local point sources that produce noise-causing species in vivo.

In an embodiment of the fourth aspect, the first area and the second area are each configured and arranged to integrate noise detected about a circumference of the sensor.

In an embodiment of the fourth aspect, the physical diffusion barrier comprises a discontinuous portion of the membrane disposed between the first electroactive surface and the second electroactive surface.

In an embodiment of the fourth aspect, the physical diffusion barrier comprises a first barrier layer formed on the first working electrode and a second barrier layer formed on the second working electrode, wherein the first barrier layer and the second barrier layer are independently formed.

In an embodiment of the fourth aspect, the physical diffusion barrier comprises a first resistance domain formed on the first working electrode and a second resistance domain formed on the second working electrode, and wherein the first resistance domain and the second resistance domain are configured and arranged to attenuate diffusion of the measurable species from the active enzymatic portion of the membrane to the second electroactive surface by at least 2-fold.

In an embodiment of the fourth aspect, the physical diffusion barrier is configured and arranged to attenuate the diffusion of the measurable species by at least 10-fold.

In an embodiment of the fourth aspect, the sensor membrane further comprises a third resistance domain disposed continuously over the first resistance domain and the second resistance domain, wherein the third resistance domain is configured such that a sensitivity of each of the first signal and the second signal is substantially equivalent.

In an embodiment of the fourth aspect, the sensor further comprises an insulator configured to insulate the first working electrode from the second working electrode, wherein the sensor membrane is the insulator.

In an embodiment of the fourth aspect, the first electroactive surface and the second electroactive surface are spaced a distance that allows noise caused by a local point source that produces noise-causing species to be measured equivalently at the first electroactive surface and the second electroactive surface.

In a fifth aspect, a continuous glucose sensor configured and arranged for insertion into a host for and detecting glucose in the host is provided, the sensor comprising a first working electrode comprising a first resistance domain, wherein the first working electrode is configured to generate a first signal having a first noise component related to a noise-causing species; a second working electrode comprising a second resistance domain, wherein the second working electrode is configured to generate a second signal having a second noise component related to the noise-causing species; and a third resistance domain disposed continuously over the first resistance domain and the second resistance domain.

In an embodiment of the fifth aspect, the noise-causing species comprises at least one member selected from the group consisting of externally produced $H_2O_2$, urea, lactic acid, phosphates, citrates, peroxides, amino acids, amino acid precursors, amino acid break-down products, nitric oxide, NO-donors, NO-precursors, reactive oxygen species, compounds having electroactive acidic, amine or sulfhydryl groups, acetaminophen, ascorbic acid, dopamine, ephedrine, ibuprofen, L-dopa, methyldopa, salicylate, tetracycline, tolazamide, tolbutamide, and triglycerides.

In an embodiment of the fifth aspect, the noise-causing species is non-constant.

In an embodiment of the fifth aspect, the first signal comprises a first sensitivity and the second signal comprises a second sensitivity, and wherein the third resistance domain is configured such that the first sensitivity and the second sensitivity are substantially equivalent.

In an embodiment of the fifth aspect, the first sensitivity and the second sensitivity are equivalent to ±10%.

In an embodiment of the fifth aspect, each of the first resistance domain and the second resistance domain is independently formed on the first working electrode and the second working electrode, respectively.

In an embodiment of the fifth aspect, the first working electrode comprises a first electroactive surface and a first membrane portion disposed thereon, the first membrane portion comprising an active enzymatic enzyme domain and the first resistance domain, and wherein the second working electrode comprises a second electroactive surface and a second membrane portion disposed thereon, the second membrane portion comprising at least one of an inactive enzymatic portion or a non-enzymatic portion and the second resistance domain.

In an embodiment of the fifth aspect, the active enzymatic enzyme domain is configured to generate a measurable species.

In an embodiment of the fifth aspect, the measurable species comprises $H_2O_2$ produced in the active enzymatic portion of the sensor membrane.

In an embodiment of the fifth aspect, the sensor further comprises a physical diffusion barrier, wherein physical diffusion barrier comprises the first resistance domain and the second resistance domain.

In an embodiment of the fifth aspect, the physical diffusion barrier is configured and arranged to attenuate diffusion of the measurable species from the active enzymatic enzyme domain to the second electroactive surface by at least 2-fold.

In an embodiment of the fifth aspect, the diffusion is attenuated by at least 10-fold.

In an embodiment of the fifth aspect, the physical diffusion barrier is configured and arranged to physically block some crosstalk from the active enzymatic enzyme domain to the second electroactive surface.

In an embodiment of the fifth aspect, the physical diffusion barrier is configured and arranged to physically block an amount of a measurable species diffusing from the active enzymatic enzyme domain to the second electroactive surface, such that there is substantially no signal associated with crosstalk measured at the second working electrode.

In an embodiment of the fifth aspect, the physical diffusion barrier comprises a first barrier layer formed on the first working electrode and a second barrier layer formed on the second working electrode, wherein each of the first barrier layer and the second barrier layer is independently formed.

In an embodiment of the fifth aspect, the first electroactive surface and the second electroactive surface are spaced closer together than a crosstalk distance.

In an embodiment of the fifth aspect, the crosstalk distance comprises a distance less than a maximum distance the measurable species can diffuse, and generate a signal associated with crosstalk.

In an embodiment of the fifth aspect, the first electroactive surface and the second electroactive surface are spaced a distance that allows noise caused by a local point source that produces noise-causing species to be measured equivalently at the first and second electroactive surfaces.

In an embodiment of the fifth aspect, each of the first electroactive surface and the second electroactive surface is configured and arranged to integrate the signal caused by a plurality of local point sources that produce noise-causing species in vivo, such that the first noise component and the second noise component are substantially equivalent.

In an embodiment of the fifth aspect, the first electroactive surface and the second electroactive surface are configured and arranged to integrate signals detected about a circumference of the sensor.

In an embodiment of the fifth aspect, the first electroactive surface and the second electroactive surface are each sized in at least one dimension such that the first noise component and the second noise component can be integrated across the dimension.

In an embodiment of the fifth aspect, the dimension of each of the first electroactive surface and the second electroactive surface is greater than a sum of diameters of about 10 average human cells.

In an embodiment of the fifth aspect, the dimension of each of the first electroactive surface and the second electroactive surface is greater than about 500 μm.

BRIEF DESCRIPTION OF THE DRAWINGS

FIG. 1A is a perspective view of a continuous analyte sensor, including an implantable body with a membrane system disposed thereon FIG. 1B is an expanded view of an alternative embodiment of a continuous analyte sensor, illustrating the in vivo portion of the sensor.

FIG. 7A1 is a schematic of one embodiment of a coaxial sensor having axis A-A.

FIG. 7A2 is a cross-section of the sensor shown in FIG. 7A1.

DETAILED DESCRIPTION OF THE PREFERRED EMBODIMENT

Figure 2A:
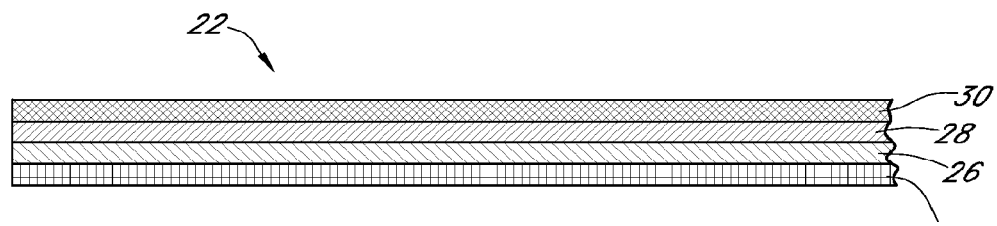
FIG. 2A is a schematic view of a membrane system in one embodiment, configured for deposition over the electroactive surfaces of the analyte sensor of FIG. 1A.

The following description and examples illustrate some exemplary embodiments of the disclosed invention in detail. Those of skill in the art will recognize that there are numerous variations and modifications of this invention that are encompassed by its scope. Accordingly, the description of a certain exemplary embodiment should not be deemed to limit the scope of the present invention.

DEFINITIONS

In order to facilitate an understanding of the disclosed invention, a number of terms are defined below.

The term "analyte" as used herein is a broad term, and is to be given its ordinary and customary meaning to a person of ordinary skill in the art (and it is not to be limited to a special or customized meaning), and refers without limitation to a substance or chemical constituent in a biological fluid (for example, blood, interstitial fluid, cerebral spinal fluid, lymph fluid or urine) that can be analyzed. Analytes may include naturally occurring substances, artificial substances, metabolites, and/or reaction products. In some embodiments, the analyte for measurement by the sensor heads, devices, and methods disclosed herein is glucose. However, other analytes are contemplated as well, including but not limited to acarboxyprothrombin; acylcarnitine; adenine phosphoribosyl transferase; adenosine deaminase; albumin; alpha-fetoprotein; amino acid profiles (arginine (Krebs cycle), histidine/urocanic acid, homocysteine, phenylalanine/tyrosine, tryptophan); andrenostenedione; antipyrine; arabinitol enantiomers; arginase; benzoylecgonine (cocaine); biotimidase; biopterin; c-reactive protein; carnitine; carnosinase; CD4; ceruloplasmin; chenodeoxycholic acid; chloroquine; cholesterol; cholinesterase; conjugated 1-β hydroxy-cholic acid; cortisol; creatine kinase; creatine kinase MM isoenzyme; cyclosporin A; d-penicillamine; de-ethylchloroquine; dehydroepiandrosterone sulfate; DNA (acetylator polymorphism, alcohol dehydrogenase, alpha 1-antitrypsin, cystic fibrosis, Duchenne/Becker muscular dystrophy, analyte-6-phosphate dehydrogenase, hemoglobinopathies, A,S,C,E, D-Punjab, beta-thalassemia, hepatitis B virus, HCMV, HIV-1, HTLV-1, Leber hereditary optic neuropathy, MCAD, RNA, PKU, *Plasmodium vivax*, sexual differentiation, 21-deoxycortisol); desbutylhalofantrine; dihydropteridine reductase; diptheria/tetanus antitoxin; erythrocyte arginase; erythrocyte protoporphyrin; esterase D; fatty acids/acylglycines; free β-human chorionic gonadotropin; free erythrocyte porphyrin; free thyroxine (FT4); free tri-iodothyronine (FT3); fumarylacetoacetase; galactose/gal-1-phosphate; galactose-1-phosphate uridyltransferase; gentamicin; analyte-6-phosphate dehydrogenase; glutathione; glutathione perioxidase; glycocholic acid; glycosylated hemoglobin; halofantrine; hemoglobin variants; hexosaminidase A; human erythrocyte carbonic anhydrase I; 17 alpha-hydroxyprogesterone; hypoxanthine phosphoribosyl transferase; immunoreactive trypsin; lactate; lead; lipoproteins ((a), B/A-1, β); lysozyme; mefloquine; netilmicin; phenobarbitone; phenyloin; phytanic/pristanic acid; progesterone; prolactin; prolidase; purine nucleoside phosphorylase; quinine; reverse tri-iodothyronine (rT3); selenium; serum pancreatic lipase; sissomicin; somatomedin C; specific antibodies (adenovirus, anti-nuclear antibody, anti-zeta antibody, arbovirus, Aujeszky's disease virus, dengue virus, *Dracunculus medinensis, Echinococcus granulosus, Entamoeba histolytica,* enterovirus, *Giardia duodenalisa, Helicobacter pylori,* hepatitis B virus, herpes virus, HIV-1, IgE (atopic disease), influenza virus, *Leishmania donovani, leptospira,* measles/mumps/rubella, *Mycobacterium leprae, Mycoplasma pneumoniae,* Myoglobin, *Onchocerca volvulus,* parainfluenza virus, *Plasmodium falciparum,* poliovirus,

*Pseudomonas aeruginosa*, respiratory syncytial virus, *rickettsia* (scrub typhus), *Schistosoma mansoni, Toxoplasma gondii, Trepenoma pallidium, Trypanosoma cruzi/rangeli*, vesicular stomatis virus, *Wuchereria bancrofti*, yellow fever virus); specific antigens (hepatitis B virus, HIV-1); succinylacetone; sulfadoxine; theophylline; thyrotropin (TSH); thyroxine (T4); thyroxine-binding globulin; trace elements; transferrin; UDP-galactose-4-epimerase; urea; uroporphyrinogen I synthase; vitamin A; white blood cells; and zinc protoporphyrin. Salts, sugar, protein, fat, vitamins, and hormones naturally occurring in blood or interstitial fluids may also constitute analytes in certain embodiments. The analyte may be naturally present in the biological fluid, for example, a metabolic product, a hormone, an antigen, an antibody, and the like. Alternatively, the analyte may be introduced into the body, for example, a contrast agent for imaging, a radioisotope, a chemical agent, a fluorocarbon-based synthetic blood, or a drug or pharmaceutical composition, including but not limited to insulin; ethanol; *cannabis* (marijuana, tetrahydrocannabinol, hashish); inhalants (nitrous oxide, amyl nitrite, butyl nitrite, chlorohydrocarbons, hydrocarbons); cocaine (crack cocaine); stimulants (amphetamines, methamphetamines, Ritalin, Cylert, Preludin, Didrex, PreState, Voranil, Sandrex, Plegine); depressants (barbiturates, methaqualone, tranquilizers such as Valium, Librium, Miltown, Serax, Equanil, Tranxene); hallucinogens (phencyclidine, lysergic acid, mescaline, peyote, psilocybin); narcotics (heroin, codeine, morphine, opium, meperidine, Percocet, Percodan, Tussionex, Fentanyl, Darvon, Talwin, Lomotil); designer drugs (analogs of fentanyl, meperidine, amphetamines, methamphetamines, and phencyclidine, for example, Ecstasy); anabolic steroids; and nicotine. The metabolic products of drugs and pharmaceutical compositions are also contemplated analytes. Analytes such as neurochemicals and other chemicals generated within the body may also be analyzed, such as, for example, ascorbic acid, uric acid, dopamine, noradrenaline, 3-methoxytyramine (3MT), 3,4-Dihydroxyphenylacetic acid (DOPAC), Homovanillic acid (HVA), 5-Hydroxytryptamine (5HT), and 5-Hydroxyindoleacetic acid (FHIAA).

The term "continuous glucose sensor" as used herein is a broad term, and is to be given its ordinary and customary meaning to a person of ordinary skill in the art (and it is not to be limited to a special or customized meaning), and refers without limitation to a device that continuously or continually measures glucose concentration, for example, at time intervals ranging from fractions of a second up to, for example, 1, 2, or 5 minutes, or longer. It should be understood that continuous glucose sensors can continually measure glucose concentration without requiring user initiation and/or interaction for each measurement, such as described with reference to U.S. Pat. No. 6,001,067, for example.

The phrase "continuous glucose sensing" as used herein is a broad term, and is to be given its ordinary and customary meaning to a person of ordinary skill in the art (and it is not to be limited to a special or customized meaning), and refers without limitation to the period in which monitoring of plasma glucose concentration is continuously or continually performed, for example, at time intervals ranging from fractions of a second up to, for example, 1, 2, or 5 minutes, or longer.

The term "biological sample" as used herein is a broad term, and is to be given its ordinary and customary meaning to a person of ordinary skill in the art (and it is not to be limited to a special or customized meaning), and refers without limitation to a sample of a host body, for example, blood, interstitial fluid, spinal fluid, saliva, urine, tears, sweat, tissue, and the like.

The term "host" as used herein is a broad term, and is to be given its ordinary and customary meaning to a person of ordinary skill in the art (and it is not to be limited to a special or customized meaning), and refers without limitation to plants or animals, for example humans.

The term "biointerface membrane" as used herein is a broad term, and is to be given its ordinary and customary meaning to a person of ordinary skill in the art (and it is not to be limited to a special or customized meaning), and refers without limitation to a permeable or semi-permeable membrane that can include one or more domains and is typically constructed of materials of a few microns thickness or more, which can be placed over the sensing region to keep host cells (for example, macrophages) from gaining proximity to, and thereby damaging the membrane system or forming a barrier cell layer and interfering with the transport of glucose across the tissue-device interface.

The term "membrane system" as used herein is a broad term, and is to be given its ordinary and customary meaning to a person of ordinary skill in the art (and it is not to be limited to a special or customized meaning), and refers without limitation to a permeable or semi-permeable membrane that can be comprised of one or more domains and is typically constructed of materials of a few microns thickness or more, which may be permeable to oxygen and are optionally permeable to glucose. In one example, the membrane system comprises an immobilized glucose oxidase enzyme, which enables an electrochemical reaction to occur to measure a concentration of glucose.

The term "domain" as used herein is a broad term, and is to be given its ordinary and customary meaning to a person of ordinary skill in the art (and it is not to be limited to a special or customized meaning), and refers without limitation to regions of a membrane that can be layers, uniform or non-uniform gradients (for example, anisotropic), functional aspects of a material, or provided as portions of the membrane.

The term "copolymer" as used herein is a broad term, and is to be given its ordinary and customary meaning to a person of ordinary skill in the art (and it is not to be limited to a special or customized meaning), and refers without limitation to polymers having two or more different repeat units and includes copolymers, terpolymers, tetrapolymers, and the like.

The term "sensing region" as used herein is a broad term, and is to be given its ordinary and customary meaning to a person of ordinary skill in the art (and it is not to be limited to a special or customized meaning), and refers without limitation to the region of a monitoring device responsible for the detection of a particular analyte. In one embodiment, the sensing region generally comprises a non-conductive body, at least one electrode, a reference electrode and a optionally a counter electrode passing through and secured within the body forming an electrochemically reactive surface at one location on the body and an electronic connection at another location on the body, and a membrane system affixed to the body and covering the electrochemically reactive surface. In another embodiment, the sensing region generally comprises a non-conductive body, a working electrode (anode), a reference electrode (optionally can be remote from the sensing region), an insulator disposed therebetween, and a multi-domain membrane affixed to the body and covering the electrochemically reactive surfaces of the working and optionally reference electrodes.

The term "electrochemically reactive surface" as used herein is a broad term, and is to be given its ordinary and customary meaning to a person of ordinary skill in the art (and it is not to be limited to a special or customized meaning), and refers without limitation to the surface of an electrode where an electrochemical reaction takes place. In one embodiment, a working electrode measures hydrogen peroxide creating a measurable electronic current.

The term "electrochemical cell" as used herein is a broad term, and is to be given its ordinary and customary meaning to a person of ordinary skill in the art (and it is not to be limited to a special or customized meaning), and refers without limitation to a device in which chemical energy is converted to electrical energy. Such a cell typically consists of two or more electrodes held apart from each other and in contact with an electrolyte solution. Connection of the electrodes to a source of direct electric current renders one of them negatively charged and the other positively charged. Positive ions in the electrolyte migrate to the negative electrode (cathode) and there combine with one or more electrons, losing part or all of their charge and becoming new ions having lower charge or neutral atoms or molecules; at the same time, negative ions migrate to the positive electrode (anode) and transfer one or more electrons to it, also becoming new ions or neutral particles. The overall effect of the two processes is the transfer of electrons from the negative ions to the positive ions, a chemical reaction.

The term "electrode" as used herein is a broad term, and is to be given its ordinary and customary meaning to a person of ordinary skill in the art (and it is not to be limited to a special or customized meaning), and refers without limitation to a conductor through which electricity enters or leaves something such as a battery or a piece of electrical equipment. In one embodiment, the electrodes are the metallic portions of a sensor (e.g., electrochemically reactive surfaces) that are exposed to the extracellular milieu, for detecting the analyte. In some embodiments, the term electrode includes the conductive wires or traces that electrically connect the electrochemically reactive surface to connectors (for connecting the sensor to electronics) or to the electronics.

The term "enzyme" as used herein is a broad term, and is to be given its ordinary and customary meaning to a person of ordinary skill in the art (and it is not to be limited to a special or customized meaning), and refers without limitation to a protein or protein-based molecule that speeds up a chemical reaction occurring in a living thing. Enzymes may act as catalysts for a single reaction, converting a reactant (also called an analyte herein) into a specific product. In one exemplary embodiment of a glucose oxidase-based glucose sensor, an enzyme, glucose oxidase (GOX) is provided to react with glucose (the analyte) and oxygen to form hydrogen peroxide.

The term "co-analyte" as used herein is a broad term, and is to be given its ordinary and customary meaning to a person of ordinary skill in the art (and it is not to be limited to a special or customized meaning), and refers without limitation to a molecule required in an enzymatic reaction to react with the analyte and the enzyme to form the specific product being measured. In one exemplary embodiment of a glucose sensor, an enzyme, glucose oxidase (GOX) is provided to react with glucose and oxygen (the co-analyte) to form hydrogen peroxide.

The term "constant analyte" as used herein is a broad term, and is to be given its ordinary and customary meaning to a person of ordinary skill in the art (and it is not to be limited to a special or customized meaning), and refers without limitation to an analyte that remains relatively constant over a time period, for example over an hour to a day as compared to other variable analytes. For example, in a person with diabetes, oxygen and urea may be relatively constant analytes in particular tissue compartments relative to glucose, which is known to oscillate between about 40 and 400 mg/dL during a 24-hour cycle. Although analytes such as oxygen and urea are known to oscillate to a lesser degree, for example due to physiological processes in a host, they are substantially constant, relative to glucose, and can be digitally filtered, for example low pass filtered, to minimize or eliminate any relatively low amplitude oscillations. Constant analytes other than oxygen and urea are also contemplated.

The term "proximal" as used herein is a broad term, and is to be given its ordinary and customary meaning to a person of ordinary skill in the art (and it is not to be limited to a special or customized meaning), and refers without limitation to near to a point of reference such as an origin or a point of attachment. For example, in some embodiments of a membrane system that covers an electrochemically reactive surface, the electrolyte domain is located more proximal to the electrochemically reactive surface than the resistance domain.

The term "distal" as used herein is a broad term, and is to be given its ordinary and customary meaning to a person of ordinary skill in the art (and it is not to be limited to a special or customized meaning), and refers without limitation to spaced relatively far from a point of reference, such as an origin or a point of attachment. For example, in some embodiments of a membrane system that covers an electrochemically reactive surface, a resistance domain is located more distal to the electrochemically reactive surfaces than the electrolyte domain.

The term "substantially" as used herein is a broad term, and is to be given its ordinary and customary meaning to a person of ordinary skill in the art (and it is not to be limited to a special or customized meaning), and refers without limitation to a sufficient amount that provides a desired function. For example, the interference domain of the preferred embodiments is configured to resist a sufficient amount of interfering species such that tracking of glucose levels can be achieved, which may include an amount greater than 50 percent, an amount greater than 60 percent, an amount greater than 70 percent, an amount greater than 80 percent, or an amount greater than 90 percent of interfering species.

The term "computer" as used herein is a broad term, and is to be given its ordinary and customary meaning to a person of ordinary skill in the art (and it is not to be limited to a special or customized meaning), and refers without limitation to machine that can be programmed to manipulate data.

The term "modem" as used herein is a broad term, and is to be given its ordinary and customary meaning to a person of ordinary skill in the art (and it is not to be limited to a special or customized meaning), and refers without limitation to an electronic device for converting between serial data from a computer and an audio signal suitable for transmission over a telecommunications connection to another modem.

The terms "processor module" and "microprocessor" as used herein are broad terms, and are to be given their ordinary and customary meaning to a person of ordinary skill in the art (and they are not to be limited to a special or customized meaning), and refer without limitation to a computer system, state machine, processor, or the like designed to perform arithmetic and logic operations using logic circuitry that responds to and processes the basic instructions that drive a computer.

The term "ROM" as used herein is a broad term, and is to be given its ordinary and customary meaning to a person of ordinary skill in the art (and it is not to be limited to a special or customized meaning), and refers without limitation to read-only memory, which is a type of data storage device manufactured with fixed contents. ROM is broad enough to include EEPROM, for example, which is electrically erasable programmable read-only memory (ROM).

The term "RAM" as used herein is a broad term, and is to be given its ordinary and customary meaning to a person of ordinary skill in the art (and it is not to be limited to a special or customized meaning), and refers without limitation to a data storage device for which the order of access to different locations does not affect the speed of access. RAM is broad enough to include SRAM, for example, which is static random access memory that retains data bits in its memory as long as power is being supplied.

The term "A/D Converter" as used herein is a broad term, and is to be given its ordinary and customary meaning to a person of ordinary skill in the art (and it is not to be limited to a special or customized meaning), and refers without limitation to hardware and/or software that converts analog electrical signals into corresponding digital signals.

The term "RF transceiver" as used herein is a broad term, and is to be given its ordinary and customary meaning to a person of ordinary skill in the art (and it is not to be limited to a special or customized meaning), and refers without limitation to a radio frequency transmitter and/or receiver for transmitting and/or receiving signals.

The terms "raw data stream" and "data stream" as used herein are broad terms, and are to be given their ordinary and customary meaning to a person of ordinary skill in the art (and they are not to be limited to a special or customized meaning), and refer without limitation to an analog or digital signal directly related to the analyte concentration measured by the analyte sensor. In one example, the raw data stream is digital data in "counts" converted by an A/D converter from an analog signal (for example, voltage or amps) representative of an analyte concentration. The terms broadly encompass a plurality of time spaced data points from a substantially continuous analyte sensor, which comprises individual measurements taken at time intervals ranging from fractions of a second up to, for example, 1, 2, or 5 minutes or longer. In some embodiments, raw data includes one or more values (e.g., digital value) representative of the current flow integrated over time (e.g., integrated value), for example, using a charge counting device, or the like.

The term "counts" as used herein is a broad term, and is to be given its ordinary and customary meaning to a person of ordinary skill in the art (and it is not to be limited to a special or customized meaning), and refers without limitation to a unit of measurement of a digital signal. In one example, a raw data stream measured in counts is directly related to a voltage (for example, converted by an A/D converter), which is directly related to current from a working electrode.

The term "electronic circuitry" as used herein is a broad term, and is to be given its ordinary and customary meaning to a person of ordinary skill in the art (and it is not to be limited to a special or customized meaning), and refers without limitation to the components (for example, hardware and/or software) of a device configured to process data. In the case of an analyte sensor, the data includes biological information obtained by a sensor regarding the concentration of the analyte in a biological fluid. U.S. Pat. Nos. 4,757,022, 5,497,772 and 4,787,398, which are hereby incorporated by reference in their entirety, describe suitable electronic circuits that can be utilized with devices of certain embodiments.

The term "potentiostat" as used herein is a broad term, and is to be given its ordinary and customary meaning to a person of ordinary skill in the art (and it is not to be limited to a special or customized meaning), and refers without limitation to an electrical system that applies a potential between the working and reference electrodes of a two- or three-electrode cell at a preset value and measures the current flow through the working electrode. Typically, the potentiostat forces whatever current is necessary to flow between the working and reference or counter electrodes to keep the desired potential, as long as the needed cell voltage and current do not exceed the compliance limits of the potentiostat.

The terms "operably connected" and "operably linked" as used herein are broad terms, and are to be given their ordinary and customary meaning to a person of ordinary skill in the art (and they are not to be limited to a special or customized meaning), and refer without limitation to one or more components being linked to another component(s) in a manner that allows transmission of signals between the components. For example, one or more electrodes can be used to detect the amount of glucose in a sample and convert that information into a signal; the signal can then be transmitted to an electronic circuit. In this case, the electrode is "operably linked" to the electronic circuit. These terms are broad enough to include wired and wireless connectivity.

The term "smoothing" and "filtering" as used herein are broad terms, and are to be given their ordinary and customary meaning to a person of ordinary skill in the art (and they are not to be limited to a special or customized meaning), and refer without limitation to modification of a set of data to make it smoother and more continuous and remove or diminish outlying points, for example, by performing a moving average of the raw data stream.

The term "algorithm" as used herein is a broad term, and is to be given its ordinary and customary meaning to a person of ordinary skill in the art (and it is not to be limited to a special or customized meaning), and refers without limitation to the computational processes (for example, programs) involved in transforming information from one state to another, for example using computer processing.

The term "regression" as used herein is a broad term, and is to be given its ordinary and customary meaning to a person of ordinary skill in the art (and it is not to be limited to a special or customized meaning), and refers without limitation to finding a line in which a set of data has a minimal measurement (for example, deviation) from that line. Regression can be linear, non-linear, first order, second order, and so forth. One example of regression is least squares regression.

The term "pulsed amperometric detection" as used herein is a broad term, and is to be given its ordinary and customary meaning to a person of ordinary skill in the art (and it is not to be limited to a special or customized meaning), and refers without limitation to an electrochemical flow cell and a controller, which applies the potentials and monitors current generated by the electrochemical reactions. The cell can include one or multiple working electrodes at different applied potentials. Multiple electrodes can be arranged so that they face the chromatographic flow independently (parallel configuration), or sequentially (series configuration).

The term "calibration" as used herein is a broad term, and is to be given its ordinary and customary meaning to a person of ordinary skill in the art (and it is not to be limited to a special or customized meaning), and refers without limitation to the relationship and/or the process of determining the relationship between the sensor data and corresponding reference data, which may be used to convert sensor data into meaningful values substantially equivalent to the reference. In some embodiments, namely in continuous analyte sensors, calibration may be updated or recalibrated over time if changes in the relationship between the sensor and reference data occur, for example due to changes in sensitivity, baseline, transport, metabolism, or the like.

The term "sensor analyte values" and "sensor data" as used herein are broad terms, and are to be given their ordinary and customary meaning to a person of ordinary skill in the art (and they are not to be limited to a special or customized meaning), and refer without limitation to data received from a continuous analyte sensor, including one or more time-spaced sensor data points.

The term "reference analyte values" and "reference data" as used herein are broad terms, and are to be given their ordinary and customary meaning to a person of ordinary skill in the art (and they are not to be limited to a special or customized meaning), and refer without limitation to data from a reference analyte monitor, such as a blood glucose meter, or the like, including one or more reference data points. In some embodiments, the reference glucose values are obtained from a self-monitored blood glucose (SMBG) test (for example, from a finger or forearm blood test) or an YSI (Yellow Springs Instruments) test, for example.

The term "matched data pairs" as used herein is a broad term, and is to be given its ordinary and customary meaning to a person of ordinary skill in the art (and it is not to be limited to a special or customized meaning), and refers without limitation to reference data (for example, one or more reference analyte data points) matched with substantially time corresponding sensor data (for example, one or more sensor data points).

The terms "interferants" and "interfering species" as used herein are broad terms, and are to be given their ordinary and customary meaning to a person of ordinary skill in the art (and they are not to be limited to a special or customized meaning), and refer without limitation to effects and/or species that interfere with the measurement of an analyte of interest in a sensor to produce a signal that does not accurately represent the analyte measurement. In one example of an electrochemical sensor, interfering species are compounds with an oxidation potential that overlaps with the analyte to be measured, producing a false positive signal. In another example of an electrochemical sensor, interfering species are substantially non-constant compounds (e.g., the concentration of an interfering species fluctuates over time). In yet another example of an electrochemical sensor, an interferent is a "noise-causing species" that causes noise on the sensor. Interfering species include but are not limited to compounds with electroactive acidic, amine or sulfhydryl groups, urea, lactic acid, phosphates, citrates, peroxides, amino acids, amino acid precursors or break-down products, nitric oxide (NO), NO-donors, NO-precursors, acetaminophen, ascorbic acid, bilirubin, cholesterol, creatinine, dopamine, ephedrine, ibuprofen, L-dopa, methyl dopa, salicylate, tetracycline, tolazamide, tolbutamide, triglycerides, and uric acid electroactive species produced during cell metabolism and/or wound healing, electroactive species that arise during body pH changes and the like.

The term "bifunctional" as used herein is a broad term, and is to be given its ordinary and customary meaning to a person of ordinary skill in the art (and it is not to be limited to a special or customized meaning), and refers without limitation to having or serving two functions. For example, in a needle-type analyte sensor, a metal wire is bifunctional because it provides structural support and acts as an electrical conductor.

The term "function" as used herein is a broad term, and is to be given its ordinary and customary meaning to a person of ordinary skill in the art (and it is not to be limited to a special or customized meaning), and refers without limitation to an action or use for which something is suited or designed.

The term "electrical conductor" as used herein is a broad term, and is to be given its ordinary and customary meaning to a person of ordinary skill in the art (and is not to be limited to a special or customized meaning) and refers without limitation to materials that contain movable charges of electricity. When an electric potential difference is impressed across separate points on a conductor, the mobile charges within the conductor are forced to move, and an electric current between those points appears in accordance with Ohm's law.

Accordingly, the term "electrical conductance" as used herein is a broad term, and is to be given its ordinary and customary meaning to a person of ordinary skill in the art (and is not to be limited to a special or customized meaning) and refers without limitation to the propensity of a material to behave as an electrical conductor. In some embodiments, the term refers to a sufficient amount of electrical conductance (e.g., material property) to provide a necessary function (electrical conduction).

The terms "insulative properties," "electrical insulator" and "insulator" as used herein are broad terms, and are to be given their ordinary and customary meaning to a person of ordinary skill in the art (and is not to be limited to a special or customized meaning) and refers without limitation to the tendency of materials that lack mobile charges to prevent movement of electrical charges between two points. In one exemplary embodiment, an electrically insulative material may be placed between two electrically conductive materials, to prevent movement of electricity between the two electrically conductive materials. In some embodiments, the terms refer to a sufficient amount of insulative property (e.g., of a material) to provide a necessary function (electrical insulation). The terms "insulator" and "non-conductive material" can be used interchangeably herein.

The term "structural support" as used herein is a broad term, and is to be given its ordinary and customary meaning to a person of ordinary skill in the art (and is not to be limited to a special or customized meaning) and refers without limitation to the tendency of a material to keep the sensor's structure stable or in place. For example, structural support can include "weight bearing" as well as the tendency to hold the parts or components of a whole structure together. A variety of materials can provide "structural support" to the sensor.

The term "diffusion barrier" as used herein is a broad term, and is to be given its ordinary and customary meaning to a person of ordinary skill in the art (and is not to be limited to a special or customized meaning) and refers without limitation to something that obstructs the random movement of compounds, species, atoms, molecules, or ions from one site in a medium to another. In some embodiments, a diffusion barrier is structural, such as a wall that separates two working electrodes and substantially prevents diffusion of a species from one electrode to the other. In some embodiments, a diffusion barrier is spatial, such as separating working electrodes by a distance sufficiently large enough to substantially prevent a species at a first electrode from affecting a second electrode. In other embodiments, a diffusion barrier can be temporal, such as by turning the first and second working electrodes on and off, such that a reaction at a first electrode will not substantially affect the function of the second electrode.

The terms "integral," "integrally," "integrally formed," integrally incorporated," "unitary" and "composite" as used herein are broad terms, and are to be given their ordinary and customary meaning to a person of ordinary skill in the art (and they are not to be limited to a special or customized meaning), and refer without limitation to the condition of being composed of essential parts or elements that together make a whole. The parts are essential for completeness of the whole. In one exemplary embodiment, at least a portion (e.g., the in vivo portion) of the sensor is formed from at least one platinum wire at least partially covered with an insulative coating, which is at least partially helically wound with at least one additional wire, the exposed electroactive portions of which are covered by a membrane system (see description of FIG. 1B or 9B); in this exemplary embodiment, each element of the sensor is formed as an integral part of the sensor (e.g., both functionally and structurally).

The term "coaxial" as used herein is a broad term, and is to be given its ordinary and customary meaning to a person of ordinary skill in the art (and it is not to be limited to a special or customized meaning), and refers without limitation to having a common axis, having coincident axes or mounted on concentric shafts.

The term "twisted" as used herein is a broad term, and is to be given its ordinary and customary meaning to a person of ordinary skill in the art (and it is not to be limited to a special or customized meaning), and refers without limitation to united by having one part or end turned in the opposite direction to the other, such as, but not limited to the twisted strands of fiber in a string, yarn, or cable.

The term "helix" as used herein is a broad term, and is to be given its ordinary and customary meaning to a person of ordinary skill in the art (and it is not to be limited to a special or customized meaning), and refers without limitation to a spiral or coil, or something in the form of a spiral or coil (e.g. a corkscrew or a coiled spring). In one example, a helix is a mathematical curve that lies on a cylinder or cone and makes a constant angle with the straight lines lying in the cylinder or cone. A "double helix" is a pair of parallel helices intertwined about a common axis, such as but not limited to that in the structure of DNA.

The term "in vivo portion" as used herein is a broad term, and is to be given its ordinary and customary meaning to a person of ordinary skill in the art (and it is not to be limited to a special or customized meaning), and refers without limitation to a portion of a device that is to be implanted or inserted into the host. In one exemplary embodiment, an in vivo portion of a transcutaneous sensor is a portion of the sensor that is inserted through the host's skin and resides within the host.

The terms "background," "baseline," and "noise" as used herein are broad terms, and are to be given their ordinary and customary meaning to a person of ordinary skill in the art (and is not to be limited to a special or customized meaning), and refer without limitation to a component of an analyte sensor signal that is not related to the analyte concentration. In one example of a glucose sensor, the background is composed substantially of signal contribution due to factors other than glucose (for example, interfering species, non-reaction-related hydrogen peroxide, or other electroactive species with an oxidation potential that overlaps with hydrogen peroxide). In some embodiments wherein a calibration is defined by solving for the equation y=mx+b, the value of b represents the background of the signal. In general, the background (noise) comprises components related to constant and non-constant factors.

The term "constant noise" and "constant background" as used herein are broad terms, and are to be given their ordinary and customary meaning to a person of ordinary skill in the art (and it is not to be limited to a special or customized meaning), and refer without limitation to the component of the background signal that remains relatively constant over time. For example, certain electroactive compounds found in the human body are relatively constant factors (e.g., baseline of the host's physiology) and do not significantly adversely affect accuracy of the calibration of the glucose concentration (e.g., they can be relatively constantly eliminated using the equation y=mx+b). In some circumstances, constant background noise can slowly drift over time (e.g., increases or decreases), however this drift need not adversely affect the accuracy of a sensor, for example, because a sensor can be calibrated and re-calibrated and/or the drift measured and compensated for.

The term "non-constant noise" or non-constant background" as used herein are broad terms, and are to be given their ordinary and customary meaning to a person of ordinary skill in the art (and it is not to be limited to a special or customized meaning), and refer without limitation to a component of the background signal that is relatively non-constant, for example, transient and/or intermittent. For example, certain electroactive compounds, are relatively non-constant (e.g., intermittent interferents due to the host's ingestion, metabolism, wound healing, and other mechanical, chemical and/or biochemical factors), which create intermittent (e.g., non-constant) "noise" on the sensor signal that can be difficult to "calibrate out" using a standard calibration equations (e.g., because the background of the signal does not remain constant).

The terms "inactive enzyme" or "inactivated enzyme" as used herein are broad terms, and are to be given their ordinary and customary meaning to a person of ordinary skill in the art (and it is not to be limited to a special or customized meaning), and refer without limitation to an enzyme (e.g., glucose oxidase, GOx) that has been rendered inactive (e.g., "killed" or "dead") and has no enzymatic activity. Enzymes can be inactivated using a variety of techniques known in the art, such as but not limited to heating, freeze-thaw, denaturing in organic solvent, acids or bases, cross-linking, genetically changing enzymatically critical amino acids, and the like. In some embodiments, a solution containing active enzyme can be applied to the sensor, and the applied enzyme subsequently inactivated by heating or treatment with an inactivating solvent.

The term "non-enzymatic" as used herein is a broad term, and is to be given their ordinary and customary meaning to a person of ordinary skill in the art (and it is not to be limited to a special or customized meaning), and refers without limitation to a lack of enzyme activity. In some embodiments, a "non-enzymatic" membrane portion contains no enzyme; while in other embodiments, the "non-enzymatic" membrane portion contains inactive enzyme. In some embodiments, an enzyme solution containing inactive enzyme or no enzyme is applied. In one example of an electrochemical sensor, a non-enzymatic or inactive enzymatic portion of the membrane includes an enzyme domain formed of enzyme domain materials, as described elsewhere herein, and either inactivated enzyme or no enzyme.

The term "GOx" as used herein is a broad term, and is to be given their ordinary and customary meaning to a person of ordinary skill in the art (and it is not to be limited to a special or customized meaning), and refers without limitation to the enzyme Glucose Oxidase (e.g., GOx is an abbreviation).

The term "equivalent," as used herein is a broad term, and is to be given their ordinary and customary meaning to a person of ordinary skill in the art (and it is not to be limited to a special or customized meaning), and refers without limitation to the state of being substantially equal or well matched; having the same or similar quantity, value, amplitude or measure as another. In some embodiments, equivalent amounts are within 20% of each other (e.g., a number plus or minus 10%). In some embodiments, equivalent amounts are within 10% of each other (e.g., a number plus or minus 5%).

The term "measured/measurable species," as used herein is a broad term, and is to be given their ordinary and customary meaning to a person of ordinary skill in the art (and it is not to be limited to a special or customized meaning), and refers without limitation to a compound that can be or is detected by an analyte sensor, the amount of which is indicative of the amount of analyte present. The identity of the measure/measurable species is dependent upon what substance (e.g., glucose, urea, creatinine, cholesterol, phosphate) the biosensor in question is configured to detect. In one example, in the case of a diffusion-based glucose biosensor including glucose oxidase (GOx), the measured/measurable species is $H_2O_2$, which is produced by the reaction of glucose with the GOx, and is subsequently detected/measured at a working electrode.

The term "crosstalk" as used herein is a broad term, and is to be given their ordinary and customary meaning to a person of ordinary skill in the art (and it is not to be limited to a special or customized meaning), and refers without limitation to the presence of (e.g., detection of) an unwanted signal via an accidental coupling. In one exemplary circumstance, crosstalk can occur on a glucose sensor having two working electrodes when a measured species (e.g., $H_2O_2$) produced at one working electrode diffuses to and is detected by the other working electrode.

The term "crosstalk diffusion distance," as used herein is a broad term, and is to be given their ordinary and customary meaning to a person of ordinary skill in the art (and it is not to be limited to a special or customized meaning), and refers without limitation to, in a dual electrode biosensor, the maximum distance a measured species (e.g., $H_2O_2$ produced in the active enzymatic portion of the membrane) can diffuse from a first working electrode (e.g., having the active enzymatic portion of the membrane) toward/to a second working electrode (e.g., having the non-enzymatic/inactive enzymatic portion of the membrane) and cause a detectable signal on the second working electrode.

The term "physical diffusion barrier," as used herein is a broad term, and is to be given their ordinary and customary meaning to a person of ordinary skill in the art (and it is not to be limited to a special or customized meaning), and refers without limitation to a structure that physically (e.g., other than or in addition to spacing of the electrodes) attenuates diffusion (of a substance/compound/species/molecule) from one side of the barrier to the other. In one example of an electrochemical sensor, a physical diffusion barrier is configured and arranged to attenuate diffusion of $H_2O_2$ from a first portion of the sensor to a second portion of the sensor.

The term "comprising" as used herein is synonymous with "including," "containing," or "characterized by," and is inclusive or open-ended and does not exclude additional, unrecited elements or method steps.

All numbers expressing quantities of ingredients, reaction conditions, and so forth used in the specification and claims are to be understood as being modified in all instances by the term "about." Accordingly, unless indicated to the contrary, the numerical parameters set forth in the specification and attached claims are approximations that can vary depending upon the desired properties sought to be obtained by the present invention. At the very least, and not as an attempt to limit the application of the doctrine of equivalents to the scope of the claims, each numerical parameter should be construed in light of the number of significant digits and ordinary rounding approaches.

Overview

The preferred embodiments provide a continuous analyte sensor that measures a concentration of the analyte of interest or a substance indicative of the concentration or presence of the analyte. In some embodiments, the analyte sensor is an invasive, minimally invasive, or non-invasive device, for example a subcutaneous, transdermal, or intravascular device. In some embodiments, the analyte sensor may analyze a plurality of intermittent biological samples. The analyte sensor may use any method of analyte-measurement, including enzymatic, chemical, physical, electrochemical, spectrophotometric, polarimetric, calorimetric, radiometric, or the like.

In general, analyte sensors provide at least one working electrode and at least one reference electrode, which are configured to measure a signal associated with a concentration of the analyte in the host, such as described in more detail below, and as appreciated by one skilled in the art. The output signal is typically a raw data stream that is used to provide a useful value of the measured analyte concentration in a host to the patient or doctor, for example. However, the analyte sensors of the preferred embodiments may further measure at least one additional signal. For example, in some embodiments, the additional signal is associated with the baseline and/or sensitivity of the analyte sensor, thereby enabling monitoring of baseline and/or sensitivity changes that may occur in a continuous analyte sensor over time.

In general, continuous analyte sensors define a relationship between sensor-generated measurements (for example, current in nA or digital counts after A/D conversion) and a reference measurement (for example, mg/dL or mmol/L) that are meaningful to a user (for example, patient or doctor). In the case of an implantable enzyme-based electrochemical glucose sensor, the sensing mechanism generally depends on phenomena that are linear with glucose concentration, for example: (1) diffusion of glucose through a membrane system (for example, biointerface membrane and membrane system) situated between implantation site and the electrode surface, (2) an enzymatic reaction within the membrane system (for example, membrane system), and (3) diffusion of the $H_2O_2$ to the sensor. Because of this linearity, calibration of the sensor can be understood by solving an equation:

$$y = mx + b$$

where y represents the sensor signal (counts), x represents the estimated glucose concentration (mg/dL), m represents the sensor sensitivity to glucose (counts/mg/dL), and b represents the baseline signal (counts). Because both sensitivity m and baseline (background) b change over time in vivo, calibration has conventionally required at least two independent, matched data pairs ($x_1$, $y_1$; $x_2$, $y_2$) to solve for m and b and thus allow glucose estimation when only the sensor signal, y is available. Matched data pairs can be created by matching reference data (for example, one or more reference glucose data points from a blood glucose meter, or the like) with substantially time corresponding sensor data (for example, one or more glucose sensor data points) to provide one or more matched data pairs, such as described in co-pending U.S. Patent Publication No. US-2005-0027463-A1.

Accordingly, in some embodiments, the sensing region is configured to measure changes in sensitivity of the analyte sensor over time, which can be used to trigger calibration, update calibration, avoid inaccurate calibration (for example, calibration during unstable periods), and/or trigger filtering of the sensor data. Namely, the analyte sensor is configured to measure a signal associated with a non-analyte constant in the host. Preferably, the non-analyte constant signal is measured beneath the membrane system on the sensor. In one example of a glucose sensor, a non-glucose constant that can be measured is oxygen, wherein a measured change in oxygen transport is indicative of a change in the sensitivity of the glucose signal, which can be measured by switching the bias potential of the working electrode, an auxiliary oxygen-measuring electrode, an oxygen sensor, or the like, as described in more detail elsewhere herein.

Alternatively or additionally, in some embodiments, the sensing region is configured to measure changes in the amount of background noise (e.g., baseline) in the signal, which can be used to trigger calibration, update calibration, avoid inaccurate calibration (for example, calibration during unstable periods), and/or trigger filtering of the sensor data. In one example of a glucose sensor, the baseline is composed substantially of signal contribution due to factors other than glucose (for example, interfering species, non-reaction-related hydrogen peroxide, or other electroactive species with an oxidation potential that overlaps with hydrogen peroxide). Namely, the glucose sensor is configured to measure a signal associated with the baseline (all non-glucose related current generated) measured by sensor in the host. In some embodiments, an auxiliary electrode located beneath a non-enzymatic portion of the membrane system is used to measure the baseline signal. In some embodiments, the baseline signal is subtracted from the glucose signal (which includes the baseline) to obtain the signal contribution substantially only due to glucose. Subtraction may be accomplished electronically in the sensor using a differential amplifier, digitally in the receiver, and/or otherwise in the hardware or software of the sensor or receiver as is appreciated by one skilled in the art, and as described in more detail elsewhere herein.

One skilled in the art appreciates that the above-described sensitivity and baseline signal measurements can be combined to benefit from both measurements in a single analyte sensor.

Preferred Sensor Components

In general, sensors of the preferred embodiments describe a variety of sensor configurations, wherein each sensor generally comprises two or more working electrodes, a reference and/or counter electrode, an insulator, and a membrane system. In general, the sensors can be configured to continuously measure an analyte in a biological sample, for example, in subcutaneous tissue, in a host's blood flow, and the like. Although a variety of exemplary embodiments are shown, one skilled in the art appreciates that the concepts and examples here can be combined, reduced, substituted, or otherwise modified in accordance with the teachings of the preferred embodiments and/or the knowledge of one skilled in the art.

Preferably, each exemplary sensor design (e.g., FIGS. 1A, 2A, 7A through 9B, and 11) includes a first working electrode, wherein the working electrode is formed from known materials. In some embodiments, each electrode is formed from a fine wire with a diameter of from about 0.001 or less to about 0.010 inches or more, for example, and is formed from, e.g., a plated insulator, a plated wire, or bulk electrically conductive material. In preferred embodiments, the working electrode comprises a wire formed from a conductive material, such as platinum, platinum-iridium, palladium, graphite, gold, carbon, conductive polymer, alloys, or the like. Although the electrodes can by formed by a variety of manufacturing techniques (bulk metal processing, deposition of metal onto a substrate, and the like), it can be advantageous to form the electrodes from plated wire (e.g., platinum on steel wire) or bulk metal (e.g., platinum wire). It is believed that electrodes formed from bulk metal wire provide superior performance (e.g., in contrast to deposited electrodes), including increased stability of assay, simplified manufacturability, resistance to contamination (e.g., which can be introduced in deposition processes), and improved surface reaction (e.g., due to purity of material) without peeling or delamination.

Preferably, the working electrode is configured to measure the concentration of an analyte. In an enzymatic electrochemical sensor for detecting glucose, for example, the working electrode measures the hydrogen peroxide produced by an enzyme catalyzed reaction of the analyte being detected and creates a measurable electronic current. For example, in the detection of glucose wherein glucose oxidase produces hydrogen peroxide as a byproduct, hydrogen peroxide ($H_2O_2$) reacts with the surface of the working electrode producing two protons ($2H^+$), two electrons ($2e^-$) and one molecule of oxygen ($O_2$), which produces the electronic current being detected.

Preferably, each exemplary sensor design (e.g., FIGS. 1A, 2A, 7A through 9B, and 11) includes at least one additional working electrode configured to measure a baseline (e.g., background noise) signal, to measure another analyte (e.g., oxygen), to generate oxygen, and/or as a transport-measuring electrode, all of which are described in more detail elsewhere herein. In general, the additional working electrode(s) can be formed as described with reference to the first working electrode. In one embodiment, the auxiliary (additional) working electrode is configured to measure a background signal, including constant and non-constant analyte signal components.

Preferably, each exemplary sensor design (e.g., FIGS. 1A, 2A, and 7A through 9B) includes a reference and/or counter electrode. In general, the reference electrode has a configuration similar to that described elsewhere herein with reference to the first working electrode, however may be formed from materials, such as silver, silver/silver chloride, calomel, and the like. In some embodiments, the reference electrode is integrally formed with the one or more working electrodes, however other configurations are also possible (e.g., remotely located on the host's skin, or otherwise in bodily fluid contact). In some exemplary embodiments (e.g., FIGS. 1B and 9B, the reference electrode is helically wound around other component(s) of the sensor system. In some alternative embodiments, the reference electrode is disposed remotely from the sensor, such as but not limited to on the host's skin, as described herein.

Preferably, each exemplary sensor design (e.g., FIGS. 1A, 2A, 7A through 9B, and 11) includes an insulator (e.g., non-conductive material) or similarly functional component. In some embodiments, one or more electrodes are covered with an insulating material, for example, a non-conductive polymer. Dip-coating, spray-coating, vapor-deposition, or other coating or deposition techniques can be used to deposit the insulating material on the electrode(s). In some embodiments, the insulator is a separate component of the system (e.g., see FIG. 7E) and can be formed as is appreciated by one skilled in the art. In one embodiment, the insulating material comprises parylene, which can be an advantageous polymer coating for its strength, lubricity, and electrical insulation properties. Generally, parylene is produced by vapor deposition and polymerization of para-xylylene (or its substituted derivatives). In alternative embodiments, any suitable insulating material can be used, for example, fluorinated polymers, polyethyleneterephthalate, polyurethane, polyimide, other nonconducting polymers, or the like. Glass or ceramic materials can also be employed. Other materials suitable for use include surface energy modified coating systems such as are marketed under the trade names AMC18, AMC148, AMC141, and AMC321 by Advanced Materials Components Express of Bellafonte, Pa.

Preferably, each exemplary sensor design (e.g., FIGS. 1A, 2A, 7A through 9B, and 11) includes exposed electroactive area(s). In embodiments wherein an insulator is disposed over one or more electrodes, a portion of the coated electrode(s) can be stripped or otherwise removed, for example, by hand, excimer lasing, chemical etching, laser ablation, grit-blasting (e.g., with sodium bicarbonate or other suitable grit), and the like, to expose the electroactive surfaces. Alternatively, a portion of the electrode can be masked prior to depositing the insulator in order to maintain an exposed electroactive surface area. In one exemplary embodiment, grit blasting is implemented to expose the electroactive surfaces, preferably utilizing a grit material that is sufficiently hard to ablate the polymer material, while being sufficiently soft so as to minimize or avoid damage to the underlying metal electrode (e.g., a platinum electrode). Although a variety of "grit" materials can be used (e.g., sand, talc, walnut shell, ground plastic, sea salt, and the like), in some preferred embodiments, sodium bicarbonate is an advantageous grit-material because it is sufficiently hard to ablate, a coating (e.g., parylene) without damaging, an underlying conductor (e.g., platinum). One additional advantage of sodium bicarbonate blasting includes its polishing action on the metal as it strips the polymer layer, thereby eliminating a cleaning step that might otherwise be necessary. In some embodiments, the tip (e.g., end) of the sensor is cut to expose electroactive surface areas, without a need for removing insulator material from sides of insulated electrodes. In general, a variety of surfaces and surface areas can be exposed.

Preferably, each exemplary sensor design (e.g., FIGS. 1A, 2A, 7A through 9B, and 11) includes a membrane system. Preferably, a membrane system is deposited over at least a portion of the electroactive surfaces of the sensor (working electrode(s) and optionally reference electrode) and provides protection of the exposed electrode surface from the biological environment, diffusion resistance (limitation) of the analyte if needed, a catalyst for enabling an enzymatic reaction, limitation or blocking of interferents, and/or hydrophilicity at the electrochemically reactive surfaces of the sensor interface. Some examples of suitable membrane systems are described in U.S. Patent Publication No. US-2005-0245799-A1.

Figure 2B:
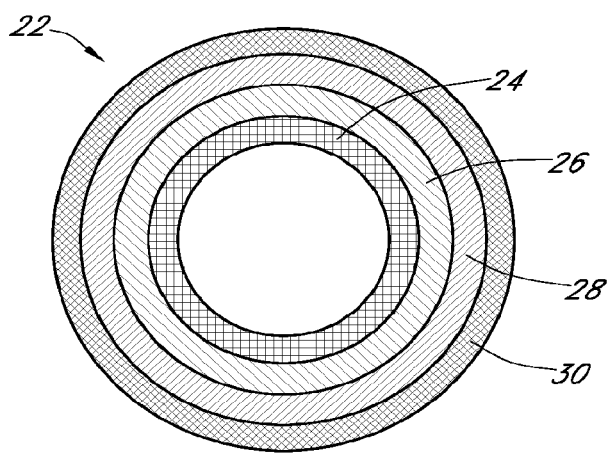
FIG. 2B is a schematic view of a membrane system in an alternative embodiment, configured for deposition over the electroactive surfaces of the analyte sensor of FIG. 1B.

In general, the membrane system includes a plurality of domains, for example, one or more of an electrode domain 24, an optional interference domain 26, an enzyme domain 28 (for example, including glucose oxidase), and a resistance domain 30, as shown in FIGS. 2A and 2B, and can include a high oxygen solubility domain, and/or a bioprotective domain (not shown), such as is described in more detail in U.S. Patent Publication No. US-2005-0245799-A1, and such as is described in more detail below. The membrane system can be deposited on the exposed electroactive surfaces using known thin film techniques (for example, vapor deposition, spraying, electro-depositing, dipping, or the like). In alternative embodiments, however, other vapor deposition processes (e.g., physical and/or chemical vapor deposition processes) can be useful for providing one or more of the insulating and/or membrane layers, including ultrasonic vapor deposition, electrostatic deposition, evaporative deposition, deposition by sputtering, pulsed laser deposition, high velocity oxygen fuel deposition, thermal evaporator deposition, electron beam evaporator deposition, deposition by reactive sputtering molecular beam epitaxy, atmospheric pressure chemical vapor deposition (CVD), atomic layer CVD, hot wire CVD, low-pressure CVD, microwave plasma-assisted CVD, plasma-enhanced CVD, rapid thermal CVD, remote plasma-enhanced CVD, and ultra-high vacuum CVD, for example. However, the membrane system can be disposed over (or deposited on) the electroactive surfaces using any known method, as will be appreciated by one skilled in the art.

In some embodiments, one or more domains of the membrane systems are formed from materials such as silicone, polytetrafluoroethylene, polyethylene-co-tetrafluoroethylene, polyolefin, polyester, polycarbonate, biostable polytetrafluoroethylene, homopolymers, copolymers, terpolymers of polyurethanes, polypropylene (PP), polyvinylchloride (PVC), polyvinylidene fluoride (PVDF), polybutylene terephthalate (PBT), polymethylmethacrylate (PMMA), polyether ether ketone (PEEK), polyurethanes, cellulosic polymers, polysulfones and block copolymers thereof including, for example, di-block, tri-block, alternating, random and graft copolymers. U.S. Patent Publication No. US-2005-0245799-A1 describes biointerface and membrane system configurations and materials that may be applied to the preferred embodiments.

Electrode Domain

In some embodiments, the membrane system comprises an optional electrode domain 24 (FIGS. 2A-2B). The electrode domain is provided to ensure that an electrochemical reaction occurs between the electroactive surfaces of the working electrode and the reference electrode, and thus the electrode domain is preferably situated more proximal to the electroactive surfaces than the interference and/or enzyme domain. Preferably, the electrode domain includes a coating that maintains a layer of water at the electrochemically reactive surfaces of the sensor. In other words, the electrode domain is present to provide an environment between the surfaces of the working electrode and the reference electrode, which facilitates an electrochemical reaction between the electrodes. For example, a humectant in a binder material can be employed as an electrode domain; this allows for the full transport of ions in the aqueous environment. The electrode domain can also assist in stabilizing the operation of the sensor by accelerating electrode start-up and drifting problems caused by inadequate electrolyte. The material that forms the electrode domain can also provide an environment that protects against pH-mediated damage that can result from the formation of a large pH gradient due to the electrochemical activity of the electrodes.

In one embodiment, the electrode domain includes a flexible, water-swellable, hydrogel film having a "dry film" thickness of from about 0.05 micron or less to about 20 microns or more, more preferably from about 0.05, 0.1, 0.15, 0.2, 0.25, 0.3, 0.35, 0.4, 0.45, 0.5, 1, 1.5, 2, 2.5, 3, or 3.5 microns to about 4, 5, 6, 7, 8, 9, 10, 11, 12, 13, 14, 15, 16, 17, 18, 19, or 19.5 microns, and more preferably still from about 2, 2.5 or 3 microns to about 3.5, 4, 4.5, or 5 microns. "Dry film" thickness refers to the thickness of a cured film cast from a coating formulation by standard coating techniques.

In certain embodiments, the electrode domain is formed of a curable mixture of a urethane polymer and a hydrophilic polymer. Particularly preferred coatings are formed of a polyurethane polymer having carboxylate or hydroxyl functional groups and non-ionic hydrophilic polyether segments, wherein the polyurethane polymer is crosslinked with a water-soluble carbodiimide (e.g., 1-ethyl-3-(3-dimethylaminopropyl)carbodiimide (EDC)) in the presence of polyvinylpyrrolidone and cured at a moderate temperature of about 50° C.

In some preferred embodiments, the electrode domain is formed from a hydrophilic polymer such as polyvinylpyrrolidone (PVP). An electrode domain formed from PVP has been shown to reduce break-in time of analyte sensors; for example, a glucose sensor utilizing a cellulosic-based interference domain such as described in more detail below.

Preferably, the electrode domain is deposited by vapor deposition, spray coating, dip coating, or other thin film techniques on the electroactive surfaces of the sensor. In one preferred embodiment, the electrode domain is formed by dip-coating the electroactive surfaces in an electrode layer solution and curing the domain for a time of from about 15 minutes to about 30 minutes at a temperature of from about 40° C. to about 55° C. (and can be accomplished under vacuum (e.g., 20 to 30 mmHg)). In embodiments wherein dip-coating is used to deposit the electrode domain, a preferred insertion rate of from about 1 to about 3 inches per minute into the electrode layer solution, with a preferred dwell time of from about 0.5 to about 2 minutes in the electrode layer solution, and a preferred withdrawal rate of from about 0.25 to about 2 inches per minute from the electrode layer solution provide a functional coating. However, values outside of those set forth above can be acceptable or even desirable in certain embodiments, for example, depending upon solution viscosity and solution surface tension, as is appreciated by one skilled in the art. In one embodiment, the electroactive surfaces of the electrode system are dip-coated one time (one layer) and cured at 50° C. under vacuum for 20 minutes.

Although an independent electrode domain is described herein, in some embodiments sufficient hydrophilicity can be provided in the interference domain and/or enzyme domain (the domain adjacent to the electroactive surfaces) so as to provide for the full transport of ions in the aqueous environment (e.g. without a distinct electrode domain). In these embodiments, an electrode domain is not necessary.

Interference Domain

Interferents are molecules or other species that are reduced or oxidized at the electrochemically reactive surfaces of the sensor, either directly or via an electron transfer agent, to produce a false positive analyte signal. In preferred embodiments, an optional interference domain 26 is provided that substantially restricts, resists, or blocks the flow of one or more interfering species (FIGS. 2A-2B). Some known interfering species for a glucose sensor, as described in more detail above, include acetaminophen, ascorbic acid, bilirubin, cholesterol, creatinine, dopamine, ephedrine, ibuprofen, L-dopa, methyldopa, salicylate, tetracycline, tolazamide, tolbutamide, triglycerides, and uric acid. In general, the interference domain of the preferred embodiments is less permeable to one or more of the interfering species than to the analyte, e.g., glucose.

In one embodiment, the interference domain is formed from one or more cellulosic derivatives. In general, cellulosic derivatives include polymers such as cellulose acetate, cellulose acetate butyrate, 2-hydroxyethyl cellulose, cellulose acetate phthalate, cellulose acetate propionate, cellulose acetate trimellitate, and the like.

In one preferred embodiment, the interference domain is formed from cellulose acetate butyrate. Cellulose acetate butyrate with a molecular weight of about 10,000 daltons to about 75,000 daltons, preferably from about 15,000, 20,000, or 25,000 daltons to about 50,000, 55,000, 60,000, 65,000, or 70,000 daltons, and more preferably about 20,000 daltons is employed. In certain embodiments, however, higher or lower molecular weights can be preferred. Additionally, a casting solution or dispersion of cellulose acetate butyrate at a weight percent of about 15% to about 25%, preferably from about 15%, 16%, 17%, 18%, 19% to about 20%, 21%, 22%, 23%, 24% or 25%, and more preferably about 18% is preferred. Preferably, the casting solution includes a solvent or solvent system, for example an acetone:ethanol solvent system. Higher or lower concentrations can be preferred in certain embodiments. A plurality of layers of cellulose acetate butyrate can be advantageously combined to form the interference domain in some embodiments, for example, three layers can be employed. It can be desirable to employ a mixture of cellulose acetate butyrate components with different molecular weights in a single solution, or to deposit multiple layers of cellulose acetate butyrate from different solutions comprising cellulose acetate butyrate of different molecular weights, different concentrations, and/or different chemistries (e.g., functional groups). It can also be desirable to include additional substances in the casting solutions or dispersions, e.g., functionalizing agents, crosslinking agents, other polymeric substances, substances capable of modifying the hydrophilicity/hydrophobicity of the resulting layer, and the like.

In one alternative embodiment, the interference domain is formed from cellulose acetate. Cellulose acetate with a molecular weight of about 30,000 daltons or less to about 100,000 daltons or more, preferably from about 35,000, 40,000, or 45,000 daltons to about 55,000, 60,000, 65,000, 70,000, 75,000, 80,000, 85,000, 90,000, or 95,000 daltons, and more preferably about 50,000 daltons is preferred. Additionally, a casting solution or dispersion of cellulose acetate at a weight percent of about 3% to about 10%, preferably from about 3.5%, 4.0%, 4.5%, 5.0%, 5.5%, 6.0%, or 6.5% to about 7.5%, 8.0%, 8.5%, 9.0%, or 9.5%, and more preferably about 8% is preferred. In certain embodiments, however, higher or lower molecular weights and/or cellulose acetate weight percentages can be preferred. It can be desirable to employ a mixture of cellulose acetates with molecular weights in a single solution, or to deposit multiple layers of cellulose acetate from different solutions comprising cellulose acetates of different molecular weights, different concentrations, or different chemistries (e.g., functional groups). It can also be desirable to include additional substances in the casting solutions or dispersions such as described in more detail above.

Layer(s) prepared from combinations of cellulose acetate and cellulose acetate butyrate, or combinations of layer(s) of cellulose acetate and layer(s) of cellulose acetate butyrate can also be employed to form the interference domain.

In some alternative embodiments, additional polymers, such as Nafion®, can be used in combination with cellulosic derivatives to provide equivalent and/or enhanced function of the interference domain. As one example, a 5 wt % Nafion® casting solution or dispersion can be used in combination with a 8 wt % cellulose acetate casting solution or dispersion, e.g., by dip coating at least one layer of cellulose acetate and subsequently dip coating at least one layer Nafion® onto a needle-type sensor such as described with reference to the preferred embodiments. Any number of coatings or layers formed in any order may be suitable for forming the interference domain of the preferred embodiments.

In some alternative embodiments, more than one cellulosic derivative can be used to form the interference domain of the preferred embodiments. In general, the formation of the interference domain on a surface utilizes a solvent or solvent system in order to solvate the cellulosic derivative (or other polymer) prior to film formation thereon. In preferred embodiments, acetone and ethanol are used as solvents for cellulose acetate; however one skilled in the art appreciates the numerous solvents that are suitable for use with cellulosic derivatives (and other polymers). Additionally, one skilled in the art appreciates that the preferred relative amounts of solvent can be dependent upon the cellulosic derivative (or other polymer) used, its molecular weight, its method of deposition, its desired thickness, and the like. However, a percent solute of from about 1% to about 25% is preferably used to form the interference domain solution so as to yield an interference domain having the desired properties. The cellulosic derivative (or other polymer) used, its molecular weight, method of deposition, and desired thickness can be adjusted, depending upon one or more other of the parameters, and can be varied accordingly as is appreciated by one skilled in the art.

In some alternative embodiments, other polymer types that can be utilized as a base material for the interference domain including polyurethanes, polymers having pendant ionic groups, and polymers having controlled pore size, for example. In one such alternative embodiment, the interference domain includes a thin, hydrophobic membrane that is non-swellable and restricts diffusion of low molecular weight species. The interference domain is permeable to relatively low molecular weight substances, such as hydrogen peroxide, but restricts the passage of higher molecular weight substances, including glucose and ascorbic acid. Other systems and methods for reducing or eliminating interference species that can be applied to the membrane system of the preferred embodiments are described in U.S. Patent Publication No. US-2005-0115832-A1, U.S. Patent Publication No. US-2005-0176136-A1, U.S. Patent Publication No. US-2005-0161346-A1, and U.S. Patent Publication No. US-2005-0143635-A1. In some alternative embodiments, a distinct interference domain is not included.

In preferred embodiments, the interference domain is deposited directly onto the electroactive surfaces of the sensor for a domain thickness of from about 0.05 micron or less to about 20 microns or more, more preferably from about 0.05, 0.1, 0.15, 0.2, 0.25, 0.3, 0.35, 0.4, 0.45, 0.5, 1, 1.5, 2, 2.5, 3, or 3.5 microns to about 4, 5, 6, 7, 8, 9, 10, 11, 12, 13, 14, 15, 16, 17, 18, 19, or 19.5 microns, and more preferably still from about 1, 1.5 or 2 microns to about 2.5 or 3 microns. Thicker membranes can also be desirable in certain embodiments, but thinner membranes are generally preferred because they have a lower impact on the rate of diffusion of hydrogen peroxide from the enzyme membrane to the electrodes.

In general, the membrane systems of the preferred embodiments can be formed and/or deposited on the exposed electroactive surfaces (e.g., one or more of the working and reference electrodes) using known thin film techniques (for example, casting, spray coating, drawing down, electro-depositing, dip coating, and the like), however casting or other known application techniques can also be utilized. Preferably, the interference domain is deposited by vapor deposition, spray coating, or dip coating. In one exemplary embodiment of a needle-type (transcutaneous) sensor such as described herein, the interference domain is formed by dip coating the sensor into an interference domain solution using an insertion rate of from about 20 inches/min to about 60 inches/min, preferably 40 inches/min, a dwell time of from about 0 minute to about 5 seconds, preferably 0 seconds, and a withdrawal rate of from about 20 inches/minute to about 60 inches/minute, preferably about 40 inches/minute, and curing (drying) the domain from about 1 minute to about 30 minutes, preferably from about 3 minutes to about 15 minutes (and can be accomplished at room temperature or under vacuum (e.g., 20 to 30 mmHg)). In one exemplary embodiment including cellulose acetate butyrate interference domain, a 3-minute cure (i.e., dry) time is preferred between each layer applied. In another exemplary embodiment employing a cellulose acetate interference domain, a 15-minute cure (i.e., dry) time is preferred between each layer applied.

The dip process can be repeated at least one time and up to 10 times or more. The preferred number of repeated dip processes depends upon the cellulosic derivative(s) used, their concentration, conditions during deposition (e.g., dipping) and the desired thickness (e.g., sufficient thickness to provide functional blocking of (or resistance to) certain interferents), and the like. In some embodiments, 1 to 3 microns may be preferred for the interference domain thickness; however, values outside of these can be acceptable or even desirable in certain embodiments, for example, depending upon viscosity and surface tension, as is appreciated by one skilled in the art. In one exemplary embodiment, an interference domain is formed from three layers of cellulose acetate butyrate. In another exemplary embodiment, an interference domain is formed from 10 layers of cellulose acetate. In another exemplary embodiment, an interference domain is formed of one relatively thicker layer of cellulose acetate butyrate. In yet another exemplary embodiment, an interference domain is formed of four relatively thinner layers of cellulose acetate butyrate. In alternative embodiments, the interference domain can be formed using any known method and combination of cellulose acetate and cellulose acetate butyrate, as will be appreciated by one skilled in the art.

In some embodiments, the electroactive surface can be cleaned prior to application of the interference domain. In some embodiments, the interference domain of the preferred embodiments can be useful as a bioprotective or biocompatible domain, namely, a domain that interfaces with host tissue when implanted in an animal (e.g., a human) due to its stability and biocompatibility.

Enzyme Domain

In preferred embodiments, the membrane system further includes an enzyme domain 28 disposed more distally from the electroactive surfaces than the interference domain; however other configurations can be desirable (FIGS.

2A-2B). In the preferred embodiments, the enzyme domain provides an enzyme to catalyze the reaction of the analyte and its co-reactant, as described in more detail below. In the preferred embodiments of a glucose sensor, the enzyme domain includes glucose oxidase; however other oxidases, for example, galactose oxidase or uricase oxidase, can also be used.

For an enzyme-based electrochemical glucose sensor to perform well, the sensor's response is preferably limited by neither enzyme activity nor co-reactant concentration. Because enzymes, including glucose oxidase (GOx), are subject to deactivation as a function of time even in ambient conditions, this behavior is compensated for in forming the enzyme domain. Preferably, the enzyme domain is constructed of aqueous dispersions of colloidal polyurethane polymers including the enzyme. However, in alternative embodiments the enzyme domain is constructed from an oxygen enhancing material, for example, silicone, or fluorocarbon, in order to provide a supply of excess oxygen during transient ischemia. Preferably, the enzyme is immobilized within the domain. See, e.g., U.S. Patent Publication No. US-2005-0054909-A1.

In preferred embodiments, the enzyme domain is deposited onto the interference domain for a domain thickness of from about 0.05 micron or less to about 20 microns or more, more preferably from about 0.05, 0.1, 0.15, 0.2, 0.25, 0.3, 0.35, 0.4, 0.45, 0.5, 1, 1.5, 2, 2.5, 3, or 3.5 microns to about 4, 5, 6, 7, 8, 9, 10, 11, 12, 13, 14, 15, 16, 17, 18, 19, or 19.5 microns, and more preferably still from about 2, 2.5 or 3 microns to about 3.5, 4, 4.5, or 5 microns. However in some embodiments, the enzyme domain can be deposited directly onto the electroactive surfaces. Preferably, the enzyme domain is deposited by spray or dip coating. In one embodiment of needle-type (transcutaneous) sensor such as described herein, the enzyme domain is formed by dip coating the interference domain coated sensor into an enzyme domain solution and curing the domain for from about 15 to about 30 minutes at a temperature of from about 40° C. to about 55° C. (and can be accomplished under vacuum (e.g., 20 to 30 mmHg)). In embodiments wherein dip coating is used to deposit the enzyme domain at room temperature, a preferred insertion rate of from about 0.25 inch per minute to about 3 inches per minute, with a preferred dwell time of from about 0.5 minutes to about 2 minutes, and a preferred withdrawal rate of from about 0.25 inch per minute to about 2 inches per minute provides a functional coating. However, values outside of those set forth above can be acceptable or even desirable in certain embodiments, for example, depending upon viscosity and surface tension, as is appreciated by one skilled in the art. In one embodiment, the enzyme domain is formed by dip coating two times (namely, forming two layers) in an enzyme domain solution and curing at 50° C. under vacuum for 20 minutes. However, in some embodiments, the enzyme domain can be formed by dip coating and/or spray coating one or more layers at a predetermined concentration of the coating solution, insertion rate, dwell time, withdrawal rate, and/or desired thickness.

Resistance Domain

In preferred embodiments, the membrane system includes a resistance domain 30 disposed more distal from the electroactive surfaces than the enzyme domain (FIGS. 2A-2B). In general, the resistance domain is configured and arranged to attenuate flux (e.g., diffusion) of a measured/measurable species (e.g., an analyte and/or co-reactant, such as but not limited to glucose, $H_2O_2$ or other species) therethrough. 'Although the following description is directed to a resistance domain for a glucose sensor, the resistance domain can be modified for other analytes and co-reactants as well.

There exists a molar excess of glucose relative to the amount of oxygen in blood; that is, for every free oxygen molecule in extracellular fluid, there are typically more than 100 glucose molecules present (see Updike et al., Diabetes Care 5:207-21 (1982)). However, an immobilized enzyme-based glucose sensor employing oxygen as co-reactant is preferably supplied with oxygen in non-rate-limiting excess in order for the sensor to respond linearly to changes in glucose concentration, while not responding to changes in oxygen concentration. Specifically, when a glucose-monitoring reaction is oxygen limited, linearity is not achieved above minimal concentrations of glucose. Without a semipermeable membrane situated over the enzyme domain to control the flux of glucose and oxygen, a linear response to glucose levels can be obtained only for glucose concentrations of up to about 40 mg/dL. However, in a clinical setting, a linear response to glucose levels is desirable up to at least about 400 mg/dL.

The resistance domain includes a semipermeable membrane that controls the flux of oxygen and glucose to the underlying enzyme domain, preferably rendering oxygen in a non-rate-limiting excess (e.g., by attenuating glucose flux). As a result, the upper limit of linearity of glucose measurement is extended to a much higher value than that which is achieved without the resistance domain. In one embodiment, the resistance domain exhibits an oxygen to glucose permeability ratio of from about 50:1 or less to about 400:1 or more, preferably about 200:1. As a result, one-dimensional reactant diffusion is adequate to provide excess oxygen at all reasonable glucose and oxygen concentrations found in the subcutaneous matrix (See Rhodes et al., Anal. Chem., 66:1520-1529 (1994)).

In alternative embodiments, a lower ratio of oxygen-to-glucose can be sufficient to provide excess oxygen by using a high oxygen solubility domain (for example, a silicone or fluorocarbon-based material or domain) to enhance the supply/transport of oxygen to the enzyme domain. If more oxygen is supplied to the enzyme, then more glucose can also be supplied to the enzyme without creating an oxygen rate-limiting excess. In alternative embodiments, the resistance domain is formed from a silicone composition, such as is described in U.S. Patent Publication No. US-2005-0090607-A1.

In a preferred embodiment, the resistance domain includes a polyurethane membrane with both hydrophilic and hydrophobic regions to control the diffusion of glucose and oxygen to an analyte sensor, the membrane being fabricated easily and reproducibly from commercially available materials. A suitable hydrophobic polymer component is a polyurethane, or polyetherurethaneurea. Polyurethane is a polymer produced by the condensation reaction of a diisocyanate and a difunctional hydroxyl-containing material. A polyurethaneurea is a polymer produced by the condensation reaction of a diisocyanate and a difunctional amine-containing material. Preferred diisocyanates include aliphatic diisocyanates containing from about 4 to about 8 methylene units. Diisocyanates containing cycloaliphatic moieties can also be useful in the preparation of the polymer and copolymer components of the membranes of preferred embodiments. The material that forms the basis of the hydrophobic matrix of the resistance domain can be any of those known in the art as appropriate for use as membranes in sensor devices and as having sufficient permeability to allow relevant compounds to pass through it, for example, to allow an oxygen molecule to pass through the membrane from the sample under examination in order to reach the active enzyme or electrochemical electrodes. Examples of materials which can be used to make non-polyurethane type membranes include vinyl polymers, polyethers, polyesters, polyamides, inorganic polymers such as polysiloxanes and polycarbosiloxanes, natural polymers such as cellulosic and protein based materials, and mixtures or combinations thereof.

In a preferred embodiment, the hydrophilic polymer component is polyethylene oxide. For example, one useful hydrophobic-hydrophilic copolymer component is a polyurethane polymer that includes about 20% hydrophilic polyethylene oxide. The polyethylene oxide portions of the copolymer are thermodynamically driven to separate from the hydrophobic portions of the copolymer and the hydrophobic polymer component. The 20% polyethylene oxide-based soft segment portion of the copolymer used to form the final blend affects the water pick-up and subsequent glucose permeability of the membrane.

In some embodiments, the resistance domain is formed from a silicone polymer modified to allow analyte (e.g., glucose) transport.

In some embodiments, the resistance domain is formed from a silicone polymer/hydrophobic-hydrophilic polymer blend. In one embodiment, The hydrophobic-hydrophilic polymer for use in the blend may be any suitable hydrophobic-hydrophilic polymer, including but not limited to components such as polyvinylpyrrolidone (PVP), polyhydroxyethyl methacrylate, polyvinylalcohol, polyacrylic acid, polyethers such as polyethylene glycol or polypropylene oxide, and copolymers thereof, including, for example, di-block, tri-block, alternating, random, comb, star, dendritic, and graft copolymers (block copolymers are discussed in U.S. Pat. Nos. 4,803,243 and 4,686,044, which are incorporated herein by reference). In one embodiment, the hydrophobic-hydrophilic polymer is a copolymer of poly (ethylene oxide) (PEO) and poly(propylene oxide) (PPO). Suitable such polymers include, but are not limited to, PEO-PPO diblock copolymers, PPO-PEO-PPO triblock copolymers, PEO-PPO-PEO triblock copolymers, alternating block copolymers of PEO-PPO, random copolymers of ethylene oxide and propylene oxide, and blends thereof. In some embodiments, the copolymers may be optionally substituted with hydroxy substituents. Commercially available examples of PEO and PPO copolymers include the PLURONIC® brand of polymers available from BASF®. In one embodiment, PLURONIC® F-127 is used. Other PLURONIC® polymers include PPO-PEO-PPO triblock copolymers (e.g., PLURONIC® R products). Other suitable commercial polymers include, but are not limited to, SYNPERONICS® products available from UNIQEMA®.

In preferred embodiments, the resistance domain is deposited onto the enzyme domain to yield a domain thickness of from about 0.05 microns or less to about 20 microns or more, more preferably from about 0.05, 0.1, 0.15, 0.2, 0.25, 0.3, 0.35, 0.4, 0.45, 0.5, 1, 1.5, 2, 2.5, 3, or 3.5 microns to about 4, 5, 6, 7, 8, 9, 10, 11, 12, 13, 14, 15, 16, 17, 18, 19, or 19.5 microns, and more preferably still from about 2, 2.5 or 3 microns to about 3.5, 4, 4.5, or 5 microns. Preferably, the resistance domain is deposited onto the enzyme domain by vapor deposition, spray coating, or dip coating. In one preferred embodiment, spray coating is the preferred deposition technique. The spraying process atomizes and mists the solution, and therefore most or all of the solvent is evaporated prior to the coating material settling on the underlying domain, thereby minimizing contact of the solvent with the enzyme.

In a preferred embodiment, the resistance domain is deposited on the enzyme domain by spray coating a solution of from about 1 wt. % to about 5 wt. % polymer and from about 95 wt. % to about 99 wt. % solvent. In spraying a solution of resistance domain material, including a solvent, onto the enzyme domain, it is desirable to mitigate or substantially reduce any contact with enzyme of any solvent in the spray solution that can deactivate the underlying enzyme of the enzyme domain. Tetrahydrofuran (THF) is one solvent that minimally or negligibly affects the enzyme of the enzyme domain upon spraying. Other solvents can also be suitable for use, as is appreciated by one skilled in the art.

Preferably, each exemplary sensor design (e.g., FIGS. 1A, 2A, and 7A through 9B) includes electronic connections, for example, one or more electrical contacts configured to provide secure electrical contact between the sensor and associated electronics. In some embodiments, the electrodes and membrane systems of the preferred embodiments are coaxially formed, namely, the electrodes and/or membrane system all share the same central axis. While not wishing to be bound by theory, it is believed that a coaxial design of the sensor enables a symmetrical design without a preferred bend radius. Namely, in contrast to prior art sensors comprising a substantially planar configuration that can suffer from regular bending about the plane of the sensor, the coaxial design of the preferred embodiments do not have a preferred bend radius and therefore are not subject to regular bending about a particular plane (which can cause fatigue failures and the like). However, non-coaxial sensors can be implemented with the sensor system of the preferred embodiments.

In addition to the above-described advantages, the coaxial sensor design of the preferred embodiments enables the diameter of the connecting end of the sensor (proximal portion) to be substantially the same as that of the sensing end (distal portion) such that a needle is able to insert the sensor into the host and subsequently slide back over the sensor and release the sensor from the needle, without slots or other complex multi-component designs, as described in detail in U.S. Patent Publication No. US-2006-0063142-A1 and U.S. Patent Publication No. US-2007-0197889-A1 which are incorporated in their entirety herein by reference.

Exemplary Continuous Sensor Configurations

Figure 10:
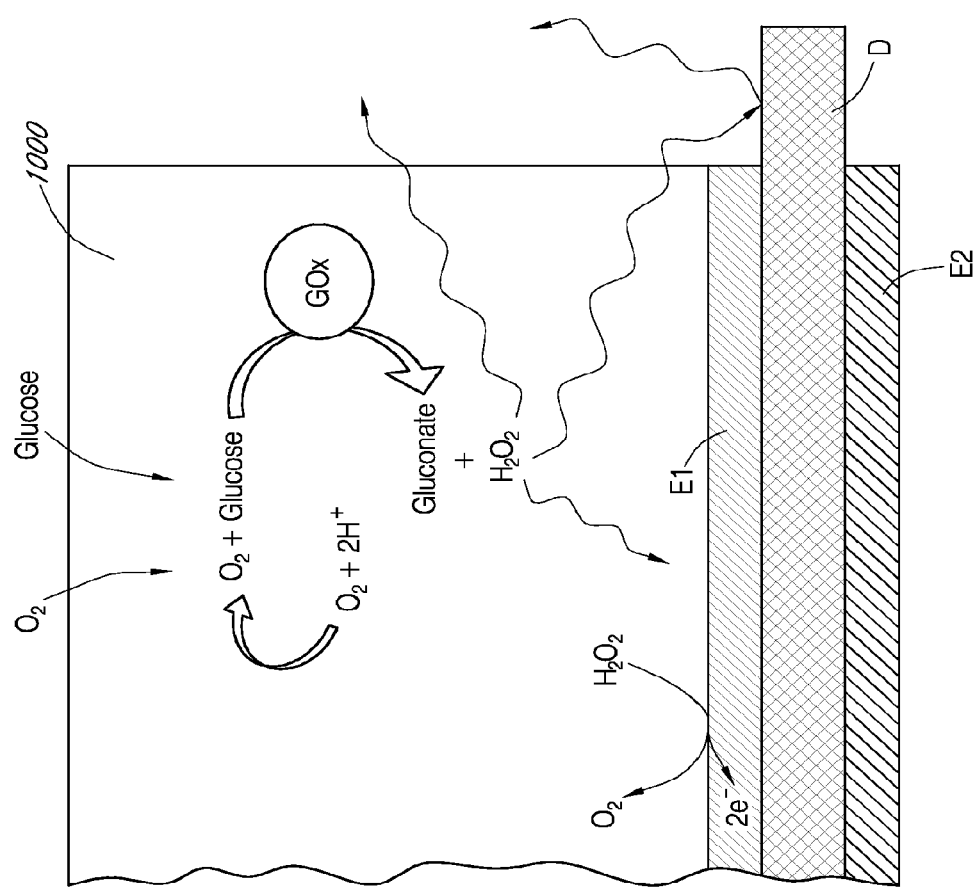
FIG. 10 is a schematic illustrating metabolism of glucose by Glucose Oxidase (GOx) and one embodiment of a diffusion barrier D that substantially prevents the diffusion of $H_2O_2$ produced on a first side of the sensor (e.g., from a first electrode that has active GOx) to a second side of the sensor (e.g., to the second electrode that lacks active GOx).

In some embodiments, the sensor is an enzyme-based electrochemical sensor, wherein the glucose-measuring working electrode 16 (e.g., FIGS. 1A-1B) measures the hydrogen peroxide produced by the enzyme catalyzed reaction of glucose being detected and creates a measurable electronic current (for example, detection of glucose utilizing glucose oxidase produces hydrogen peroxide ($H_2O_2$) as a by product, $H_2O_2$ reacts with the surface of the working electrode producing two protons ($2H^+$), two electrons ($2e^-$) and one molecule of oxygen ($O_2$) which produces the electronic current being detected, see FIG. 10), such as described in more detail elsewhere herein and as is appreciated by one skilled in the art. Preferably, one or more potentiostat is employed to monitor the electrochemical reaction at the electroactive surface of the working electrode (s). The potentiostat applies a constant potential to the working electrode and its associated reference electrode to determine the current produced at the working electrode. The current that is produced at the working electrode (and flows through the circuitry to the counter electrode) is substantially proportional to the amount of $H_2O_2$ that diffuses to the working electrodes. The output signal is typically a raw data stream that is used to provide a useful value of the measured analyte concentration in a host to the patient or doctor, for example.

Some alternative analyte sensors that can benefit from the systems and methods of the preferred embodiments include U.S. Pat. No. 5,711,861 to Ward et al., U.S. Pat. No. 6,642,015 to Vachon et al., U.S. Pat. No. 6,654,625 to Say et al., U.S. Pat. No. 6,565,509 to Say et al., U.S. Pat. No. 6,514,718 to Heller, U.S. Pat. No. 6,465,066 to Essenpreis et al., U.S. Pat. No. 6,214,185 to Offenbacher et al., U.S. Pat. No. 5,310,469 to Cunningham et al., and U.S. Pat. No. 5,683,562 to Shaffer et al., U.S. Pat. No. 6,579,690 to Bonnecaze et al., U.S. Pat. No. 6,484,046 to Say et al., U.S. Pat. No. 6,512,939 to Colvin et al., U.S. Pat. No. 6,424,847 to Mastrototaro et al., U.S. Pat. No. 6,424,847 to Mastrototaro et al, for example. All of the above patents are incorporated in their entirety herein by reference and are not inclusive of all applicable analyte sensors; in general, it should be understood that the disclosed embodiments are applicable to a variety of analyte sensor configurations.

Although some exemplary glucose sensor configurations are described in detail below, it should be understood that the systems and methods described herein can be applied to any device capable of continually or continuously detecting a concentration of analyte of interest and providing an output signal that represents the concentration of that analyte, for example oxygen, lactose, hormones, cholesterol, medicaments, viruses, or the like.

FIG. 1A is a perspective view of an analyte sensor, including an implantable body with a sensing region including a membrane system disposed thereon. In the illustrated embodiment, the analyte sensor 10a includes a body 12 and a sensing region 14 including membrane and electrode systems configured to measure the analyte. In this embodiment, the sensor 10a is preferably wholly implanted into the subcutaneous tissue of a host, such as described in U.S. Patent Publication No. US-2006-0015020-A1; U.S. Patent Publication No. US-2005-0245799-A1; U.S. Patent Publication No. US-2005-0192557-A1; U.S. Patent Publication No. US-2004-0199059-A1; U.S. Patent Publication No. US-2005-0027463-A1; and U.S. Pat. No. 6,001,067 issued Dec. 14, 1999 and entitled "DEVICE AND METHOD FOR DETERMINING ANALYTE LEVELS," each of which are incorporated herein by reference in their entirety.

The body 12 of the sensor 10a can be formed from a variety of materials, including metals, ceramics, plastics, or composites thereof. In one embodiment, the sensor is formed from thermoset molded around the sensor electronics. U.S. Patent Publication No. US-2004-0199059-A1 discloses suitable configurations for the body, and is incorporated by reference in its entirety.

In some embodiments, the sensing region 14 includes a glucose-measuring working electrode 16, an optional auxiliary working electrode 18, a reference electrode 20, and a counter electrode 24. Generally, the sensing region 14 includes means to measure two different signals, 1) a first signal associated with glucose and non-glucose related electroactive compounds having a first oxidation potential, wherein the first signal is measured at the glucose-measuring working electrode disposed beneath an active enzymatic portion of a membrane system, and 2) a second signal associated with the baseline and/or sensitivity of the glucose sensor. In some embodiments, wherein the second signal measures sensitivity, the signal is associated with at least one non-glucose constant data point, for example, wherein the auxiliary working electrode 18 is configured to measure oxygen. In some embodiments, wherein the second signal measures baseline, the signal is associated with non-glucose related electroactive compounds having the first oxidation potential, wherein the second signal is measured at an auxiliary working electrode 18 and is disposed beneath a non-enzymatic portion of the membrane system, such as described in more detail elsewhere herein.

Preferably, a membrane system (see FIG. 2A) is deposited over the electroactive surfaces of the sensor 10a and includes a plurality of domains or layers, such as described in more detail below, with reference to FIGS. 2A and 2B. In general, the membrane system may be disposed over (deposited on) the electroactive surfaces using methods appreciated by one skilled in the art. See U.S. Patent Publication No. US-2006-0015020-A1.

The sensing region 14 comprises electroactive surfaces, which are in contact with an electrolyte phase (not shown), which is a free-flowing fluid phase disposed between the membrane system 22 and the electroactive surfaces. In this embodiment, the counter electrode is provided to balance the current generated by the species being measured at the working electrode. In the case of glucose oxidase based analyte sensors, the species being measured at the working electrode is $H_2O_2$. Glucose oxidase catalyzes the conversion of oxygen and glucose to hydrogen peroxide and gluconate according to the following reaction:

$$Glucose + O_2 \rightarrow Gluconate + H_2O_2$$

The change in $H_2O_2$ can be monitored to determine glucose concentration because for each glucose molecule metabolized, there is a proportional change in the product $H_2O_2$ (see FIG. 10). Oxidation of $H_2O_2$ by the working electrode is balanced by reduction of ambient oxygen, enzyme generated $H_2O_2$, or other reducible species at the counter electrode. The $H_2O_2$ produced from the glucose oxidase reaction further reacts at the surface of the working electrode and produces two protons ($2H^+$), two electrons ($2e^-$), and one oxygen molecule ($O_2$). Preferably, one or more potentiostats are employed to monitor the electrochemical reaction at the electroactive surface of the working electrode(s). The potentiostat applies a constant potential to the working electrode and its associated reference electrode to determine the current produced at the working electrode. The current that is produced at the working electrode (and flows through the circuitry to the counter electrode) is substantially proportional to the amount of $H_2O_2$ that diffuses to the working electrodes. The output signal is typically a raw data stream that is used to provide a useful value of the measured analyte concentration in a host to the patient or doctor, for example.

FIG. 1B is a schematic view of an alternative exemplary embodiment of a continuous analyte sensor 10b, also referred to as an in-dwelling or transcutaneous analyte sensor in some circumstances, particularly illustrating the in vivo portion of the sensor. In this embodiment, the in vivo portion of the sensor 10b is the portion adapted for insertion under the host's skin, in a host's blood stream, or other biological sample, while an ex vivo portion of the sensor (not shown) is the portion that remains above the host's skin after sensor insertion and operably connects to an electronics unit. In the illustrated embodiment, the analyte sensor 10b is coaxial and includes three electrodes: a glucose-measuring working electrode 16, an optional auxiliary working electrode 18, and at least one additional electrode 20, which may function as a counter and/or reference electrode, hereinafter referred to as the reference electrode 20. Generally, the sensor 10*b* may include the ability to measure two different signals, 1) a first signal associated with glucose and non-glucose related electroactive compounds having a first oxidation potential, wherein the first signal is measured at the glucose-measuring working electrode disposed beneath an active enzymatic portion of a membrane system, and 2) a second signal associated with the baseline and/or sensitivity of the glucose sensor, such as described in more detail above with reference to FIG. 1A.

One skilled in the art appreciates that the analyte sensor of FIG. 1B can have a variety of configurations. In one exemplary embodiment, the sensor is generally configured of a first working electrode, a second working electrode, and a reference electrode. In one exemplary configuration, the first working electrode 16 is a central metal wire or plated non-conductive rod/filament/fiber and the second working and reference electrodes (20 and 18, respectively OR 18 and 20, respectively) are coiled around the first working electrode 16. In another exemplary configuration, the first working electrode is a central wire, as depicted in FIG. 1B, the second working electrode is coiled around the first working electrode, and the reference electrode is disposed remotely from the sensor, as described herein. In another exemplary configuration, the first and second working electrodes (20 and 18) are coiled around a supporting rod 16 of insulating material. The reference electrode (not shown) can be disposed remotely from the sensor, as described herein, or disposed on the non-conductive supporting rod 16. In still another exemplary configuration, the first and second working electrodes (20 and 18) are coiled around a reference electrode 16 (not to scale).

Preferably, each electrode is formed from a fine wire, with a diameter in the range of 0.001 to 0.010 inches, for example, and may be formed from plated wire or bulk material, however the electrodes may be deposited on a substrate or other known configurations as is appreciated by one skilled in the art.

In one embodiment, the glucose-measuring working electrode 16 comprises a wire formed from a conductive material, such as platinum, palladium, graphite, gold, carbon, conductive polymer, or the like. Alternatively, the glucose-measuring working electrode 16 can be formed of a non-conductive fiber or rod that is plated with a conductive material. The glucose-measuring working electrode 16 is configured and arranged to measure the concentration of glucose. The glucose-measuring working electrode 16 is covered with an insulating material, for example a non-conductive polymer. Dip-coating, spray-coating, or other coating or deposition techniques can be used to deposit the insulating material on the working electrode, for example. In one preferred embodiment, the insulating material comprises Parylene, which can be an advantageous conformal coating for its strength, lubricity, and electrical insulation properties, however, a variety of other insulating materials can be used, for example, fluorinated polymers, polyethyleneterephthalate, polyurethane, polyimide, or the like.

In this embodiment, the auxiliary working electrode 18 comprises a wire formed from a conductive material, such as described with reference to the glucose-measuring working electrode 16 above. Preferably, the reference electrode 20, which may function as a reference electrode alone, or as a dual reference and counter electrode, is formed from silver, Silver/Silver chloride, or the like.

Preferably, the electrodes are juxtapositioned and/or twisted with or around each other; however other configurations are also possible. In one example, the auxiliary working electrode 18 and reference electrode 20 may be helically wound around the glucose-measuring working electrode 16 as illustrated in FIG. 1B. Alternatively, the auxiliary working electrode 18 and reference electrode 20 may be formed as a double helix around a length of the glucose-measuring working electrode 16. In some embodiments, the working electrode, auxiliary working electrode and reference electrodes may be formed as a triple helix. The assembly of wires may then be optionally coated together with an insulating material, similar to that described above, in order to provide an insulating attachment. Some portion of the coated assembly structure is then stripped, for example using an excimer laser, chemical etching, or the like, to expose the necessary electroactive surfaces. In some alternative embodiments, additional electrodes may be included within the assembly, for example, a three-electrode system (including separate reference and counter electrodes) as is appreciated by one skilled in the art.

FIGS. 2A and 2B are schematic views membrane systems in some embodiments that may be disposed over the electroactive surfaces of an analyte sensors of FIGS. 1A and 1B, respectively, wherein the membrane system includes one or more of the following domains: a resistance domain 30, an enzyme domain 28, an optional interference domain 26, and an electrolyte domain 24, such as described in more detail below. However, it is understood that the membrane system 22 can be modified for use in other sensors, by including only one or more of the domains, additional domains not recited above, or for other sensor configurations. For example, the interference domain can be removed when other methods for removing interferants are utilized, such as an auxiliary electrode for measuring and subtracting out signal due to interferants. As another example, an "oxygen antenna domain" composed of a material that has higher oxygen solubility than aqueous media so that it concentrates oxygen from the biological fluid surrounding the biointerface membrane can be added. The oxygen antenna domain can then act as an oxygen source during times of minimal oxygen availability and has the capacity to provide on demand a higher rate of oxygen delivery to facilitate oxygen transport to the membrane. This enhances function in the enzyme reaction domain and at the counter electrode surface when glucose conversion to hydrogen peroxide in the enzyme domain consumes oxygen from the surrounding domains. Thus, this ability of the oxygen antenna domain to apply a higher flux of oxygen to critical domains when needed improves overall sensor function.

In some embodiments, the membrane system generally provides one or more of the following functions: 1) protection of the exposed electrode surface from the biological environment, 2) diffusion resistance (limitation) of the analyte, 3) a catalyst for enabling an enzymatic reaction, 4) optionally limitation or blocking of interfering species, and 5) hydrophilicity at the electrochemically reactive surfaces of the sensor interface, such as described in U.S. Patent Publication No. US-2005-0245799-A1. In some embodiments, the membrane system additionally includes a cell disruptive domain, a cell impermeable domain, and/or an oxygen domain (not shown), such as described in more detail in U.S. Patent Publication No. US-2005-0245799-A1. However, it is understood that a membrane system modified for other sensors, for example, by including fewer or additional domains is within the scope of the preferred embodiments.

One aspect of the preferred embodiments provides for a sensor (for transcutaneous, wholly implantable, or intravascular short-term or long-term use) having integrally formed parts, such as but not limited to a plurality of electrodes, a membrane system and an enzyme. For example, the parts may be coaxial, juxtapositioned, helical, bundled and/or twisted, plated and/or deposited thereon, extruded, molded, held together by another component, and the like. In another example, the components of the electrode system are integrally formed, (e.g., without additional support, such as a supporting substrate), such that substantially all parts of the system provide essential functions of the sensor (e.g., the sensing mechanism or "in vivo" portion). In a further example, a first electrode can be integrally formed directly on a second electrode (e.g., electrically isolated by an insulator), such as by vapor deposition of a conductive electrode material, screen printing a conductive electrode ink or twisting two electrode wires together in a coiled structure.

Some embodiments provide an analyte sensor that is configured for insertion into a host and for measuring an analyte in the host, wherein the sensor includes a first working electrode disposed beneath an active enzymatic portion of a membrane (e.g., membrane system) on the sensor and a second working electrode disposed beneath an inactive- or non-enzymatic portion of the membrane on the sensor. In these embodiments, the first and second working electrodes integrally form at least a portion of the sensor.

Exemplary Sensor Configurations

FIG. 1B is a schematic view of a sensor in one embodiment. In some preferred embodiments, the sensor is configured to be integrally formed and coaxial. In this exemplary embodiment, one or more electrodes are helically wound around a central core, all of which share axis A-A. The central core 16 can be an electrode (e.g., a wire or metal-plated insulator) or a support made of insulating material. The coiled electrodes 18, 20 are made of conductive material (e.g., plated wire, metal-plated polymer filaments, bulk metal wires, etc.) that is helically wound or twisted about the core 16. Generally, at least the working electrodes are coated with an insulator I of non-conductive or dielectric material.

One skilled in the art will recognize that various electrode combinations are possible. For example, in one embodiment, the core 16 is a first working electrode and can be substantially straight. One of the coiled electrodes (18 or 20) is a second working electrode and the remaining coiled electrode is a reference or counter electrode. In a further embodiment, the reference electrode can be disposed remotely from the sensor, such as on the host's skin or on the exterior of the sensor, for example. Although this exemplary embodiment illustrates an integrally formed coaxial sensor, one skilled in the art appreciates a variety of alternative configurations. In one exemplary embodiment, the arrangement of electrodes is reversed, wherein the first working electrode is helically wound around the second working electrode core 16. In another exemplary embodiment, the reference electrode can form the central core 16 with the first and second working electrodes coiled there around. In some exemplary embodiments, the sensor can have additional working, reference and/or counter electrodes, depending upon the sensor's purpose. Generally, one or more of the electrode wires are coated with an insulating material, to prevent direct contact between the electrodes. Generally, a portion of the insulating material can be removed (e.g., etched, scraped or grit-blasted away) to expose an electroactive surface of the electrode. An enzyme solution can be applied to the exposed electroactive surface, as described herein.

The electrodes each have first and second ends. The electrodes can be of any geometric solid shape, such as but not limited to a cylinder having a circular or oval cross-section, a rectangle (e.g., extruded rectangle), a triangle (e.g., extruded triangle), an X-cross section, a Y-cross section, flower petal-cross sections, star-cross sections, melt-blown fibers loaded with conductive material (e.g., conductive polymers) and the like. The first ends (e.g., an in vivo portion, "front end") of the electrodes are configured for insertion in the host and the second ends (e.g., an ex vivo portion, "back end") are configured for electrical connection to sensor electronics. In some embodiments, the sensor includes sensor electronics that collect data from the sensor and provide the data to the host in various ways. Sensor electronics are discussed in detail elsewhere herein.

Figure 7B:
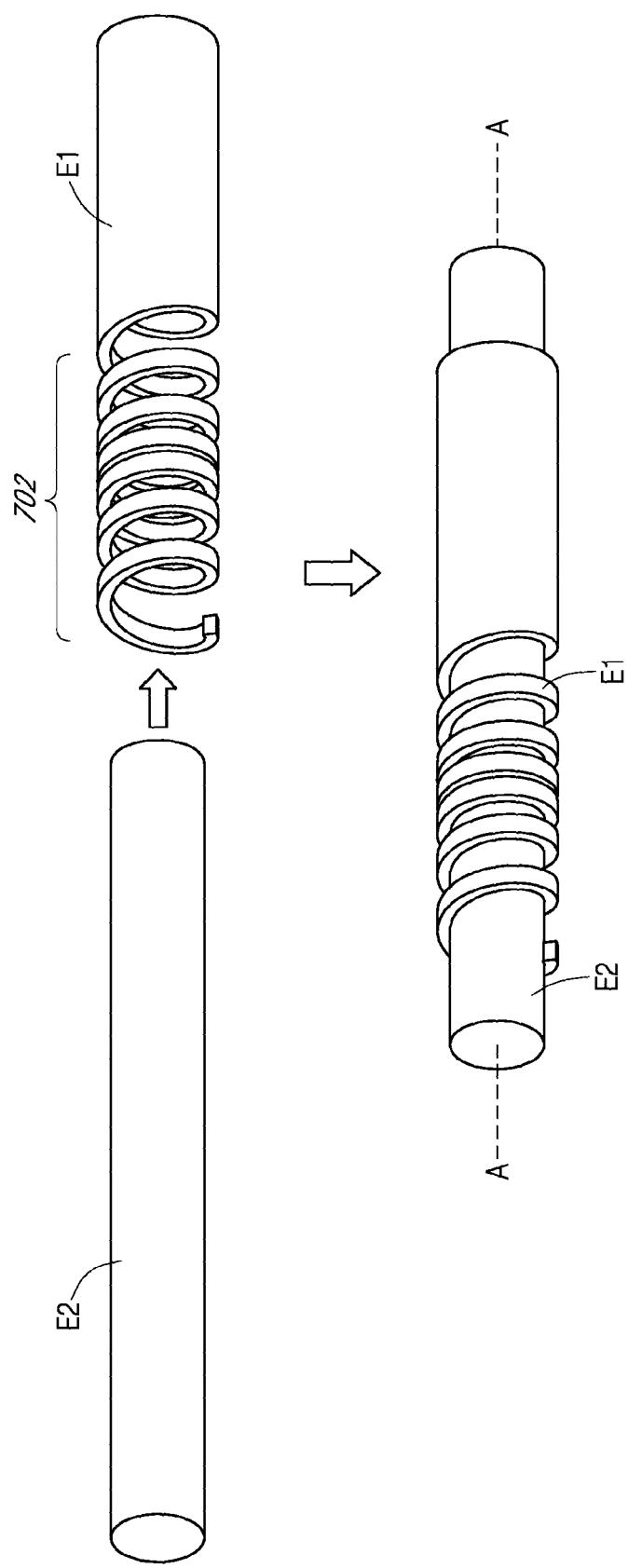
FIG. 7B is a schematic of another embodiment of a coaxial sensor.

FIGS. 7A1 and 7A2 are schematics of an analyte sensor in another embodiment. FIG. 7A1 is a side view and FIG. 7A2 is a side-cutaway view. In some preferred embodiments, the sensor is configured to be integrally formed and coaxial, with an optional stepped end. In this exemplary embodiment, the sensor includes a plurality of electrodes E1, E2, E3 to En, wherein n equals any number of electrode layers. Layers of insulating material I (e.g., non-conductive material) separate the electrode layers. All of the electrode and insulating material layers share axis A-A. The layers can be applied by any technique known in the art, such as but not limited to spraying, dipping, spraying, etc. For example, a bulk metal wire electrode E1 can be dipped into a solution of insulating polymer that is vulcanized to form a layer of non-conductive, electrically insulating material I. A second electrode E2 can be plated (e.g., by electroplating or other plating technique used in the art) on the first insulating layer, followed by application of a second insulating layer I applied in the same manner as the first layer. Additional electrode layers (e.g., E3 to En) and insulating layers can be added to the construct, to create the desired number of electrodes and insulating layers. As an example, multiple sensors can be formed from a long wire (with insulating and electrode layers applied) that can be cut to yield a plurality of sensors of the desired length. After the sensor has been cut to size, it can be polished or otherwise treated to prepare the electrodes for use. In some embodiments, the various electrode and/or insulator layers can be applied by dipping, spraying, printing, vapor deposition, plating, spin coating or any other method known in the art. Although this exemplary embodiment illustrates an integrally formed coaxial sensor, one skilled in the art appreciates a variety of alternative configurations. For example, in some embodiments, the sensor can have two, three, four or more electrodes separated by insulating material I. In another embodiment, the analyte sensor has two or more electrodes, such as but not limited to a first working electrode, an auxiliary working electrode, a reference electrode and/or counter electrode. FIG. 7B is a schematic view of an integrally formed, coaxial sensor in another embodiment. In this exemplary embodiment, a coiled first electrode E1 is manufactured from an electrically conductive tube or cylinder, such as but not limited to a silver Hypotube. A portion of the Hypotube is trimmed or carved into a helix or coil 702. A second electrode E2 that is sized to fit (e.g., with minimal tolerance) within the first electrode E1 mates (e.g., slides into) with the first electrode E1, to form the sensor. In general, the surfaces of the electrodes are coated with an insulator, to prevent direct contact between the electrodes. As described herein, portion of the insulator can be stripped away to expose the electroactive surfaces. Although this exemplary embodiment illustrates one configuration of a coaxial, integrally formed sensor, one skilled in the art appreciates a variety of alternative configurations. For example, in some embodiments, the first electrode E1 is a reference or auxiliary electrode, and the second electrode E2 is a working electrode. However, the first electrode E1 can be a working electrode and the second electrode E2 can be a reference or auxiliary electrode. In some embodiments, additional electrodes are applied to the construct (e.g., after E2 is inserted into E1). One advantage of this configuration is that the silver Hypotube can be cut to increase or decrease the flexibility of the sensor. For example, the spiral cut can space the coils farther apart to increase the sensor's flexibility. Another example of this configuration is that it is easier to construct the sensor in this manner, rather than winding one electrode around another (e.g., as is done for the embodiment shown in FIG. 1B).

Figure 7C:
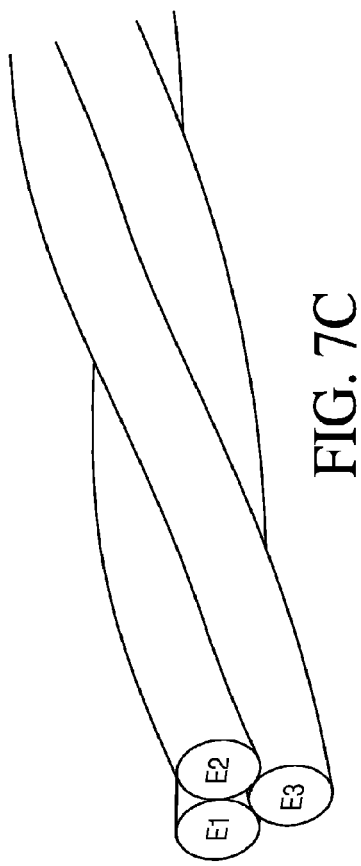
FIG. 7C is a schematic of one embodiment of a sensor having three electrodes.
Figure 7E:
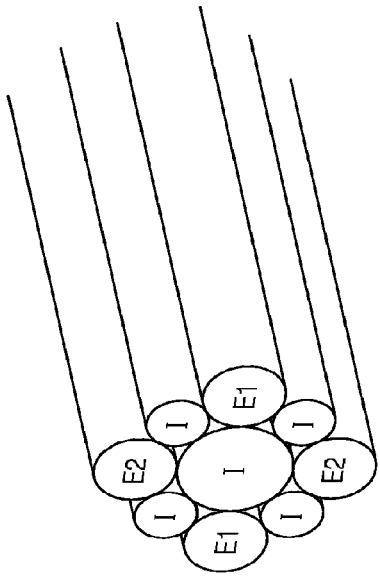
FIG. 7E is a schematic of one embodiment of a sensor having two pairs of electrodes and insulating material.
Figure 7D:
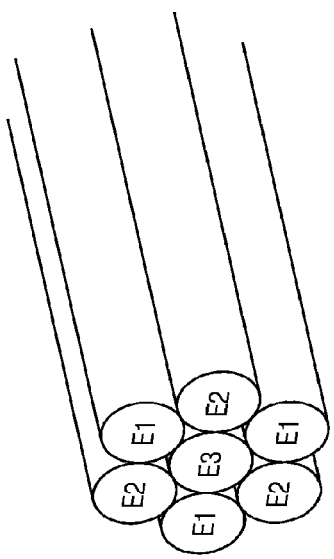
FIG. 7D is a schematic of one embodiment of a sensor having seven electrodes.

FIGS. 7C to 7E are schematics of three embodiments of bundled analyte sensors. In these embodiments, of the sensors are configured to be integrally formed sensors, wherein a plurality (E1, E2, E3, to En) of electrodes are bundled, coiled or twisted to form a portion of the sensor. In some embodiments, the electrodes can be twisted or helically coiled to form a coaxial portion of the sensor, which share the same axis. In one embodiment, the first and second working electrodes are twisted or helically wound together, to form at least a portion of the sensor (e.g., a glucose sensor). For example, the electrodes can be twisted in a double helix. In some embodiments, additional electrodes are provided and twisted, coiled or wound with the first and second electrodes to form a larger super helix, such as a triple helix, a quadruple helix, or the like. For example, three wires (E1, E2, and E3) can be twisted to form a triple helix. In still other embodiments, at least one reference electrode can be disposed remotely from the working electrodes, as described elsewhere herein. In some embodiments, the tip of the sensor can be cut at an angle (90° or other angle) to expose the electrode tips to varying extents, as described herein.

FIG. 7C is a schematic of an exemplary embodiment of a sensor having three bundled electrodes E1, E2, and E3. In some preferred embodiments of the sensor, two or all of the electrodes can be identical. Alternatively, the electrodes can be non-identical. For example, the sensor can have a glucose-sensing electrode, an oxygen-sensing electrode and a reference electrode. Although this exemplary embodiment illustrates a bundled sensor, one skilled in the art appreciates a variety of alternative sensor configurations. For example, only two electrodes can be used or more than three electrodes can be used. In another example, holding one end of the bundled wires in a clamp and twisting the other end of the wires, to form a cable-like structure, can coil the electrodes together. Such a coiled structure can hold the electrodes together without additional structure (e.g., bound by a wire or coating). In another example, non-coiled electrodes can be bundled and held together with a wire or fiber coiled there around, or by applying a coating of insulating material to the electrode bundle. In still another example, the reference electrode can be disposed remotely from the working electrodes, as described elsewhere herein.

FIG. 7D is a schematic view of a sensor in one embodiment. In some preferred embodiments, the sensor is designed to be integrally formed and bundled and/or coaxial. In this exemplary embodiment, the sensor includes seven electrodes, wherein three electrodes of a first type (e.g., 3×E1) and three electrodes of a second type (e.g., 3×E2) are bundled around one electrode of a third type (e.g., E3). Those skilled in the art appreciate a variety of configurations possible with this embodiment. For example, the different types of electrodes can be alternated or not alternated. For example, in FIG. 7D, the two types of electrodes are alternately disposed around E3. However, the two types of electrodes can be grouped around the central structure. As described herein, some or all of the electrodes can be coated with a layer of insulating material, to prevent direct contact between the electrodes. The electrodes can be coiled together, as in a cable, or held together by a wire or fiber wrapping or a coating of insulating material. The sensor can be cut, to expose the electroactive surfaces of the electrodes, or portions of the insulating material coating can be stripped away, as described elsewhere herein. In another example, the sensor can include additional (or fewer) electrodes. In one exemplary embodiment, the E1 and E2 electrodes are bundled around a non-conductive core (e.g., instead of electrode E3), such as an insulated fiber. In another embodiment, different numbers of E1, E2, and E3 electrodes can be used (e.g., two E1 electrodes, two E2 electrodes, and three E3 electrodes). In another embodiment, additional electrode type can be included in the sensor (e.g., an electrode of type E4, E5 or E6, etc.). In still another exemplary embodiment, three glucose-detecting electrodes (e.g., E1) and three reference electrodes (e.g., E2) are bundled and (optionally) coiled around a central auxiliary working electrode (e.g., E3).

FIG. 7E is a schematic of a sensor in another embodiment. In this exemplary embodiment of an integrally formed sensor, two pairs of electrodes (e.g., 2×E1 and 2×E2) are bundled around a core of insulating material I. Fibers or strands of insulating material I also separate the electrodes from each other. Although this exemplary embodiment illustrates an integrally formed sensor, one skilled in the art appreciates a variety of alternative configurations. For example, the pair of E1 electrodes can be working electrodes and the pair of E2 electrodes can be reference and/or auxiliary electrodes. In one exemplary embodiment, the E1 electrodes are both glucose-detecting electrodes, a first E2 electrode is a reference electrode and a second E2 electrode is an auxiliary electrode. In another exemplary embodiment, one E1 electrode includes active GOx and measures a glucose-related signal; the other E1 electrode lacks active GOx and measures a non-glucose-related signal, and the E2 electrodes are reference electrodes. In yet another exemplary embodiment, one E1 electrode detects glucose and the other E1 electrode detects urea, and both E2 electrodes are reference electrodes. One skilled in the art of electrochemical sensors will recognized that the size of the various electrodes can be varied, depending upon their purpose and the current and/or electrical potential used. Electrode size and insulating material size/shape are not constrained by their depiction of relative size in the Figures, which are schematic schematics intended for only illustrative purposes.

Figure 7F:
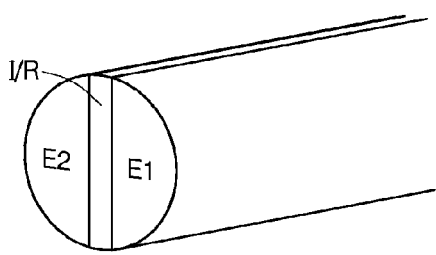
FIG. 7F is a schematic of one embodiment of a sensor having two electrodes separated by a reference electrode or insulating material.

FIG. 7F is a schematic view of a cross-section of an integrally formed sensor in another embodiment. In some preferred embodiments, the sensor is configured to be bifunctional. In this exemplary embodiment, the sensor includes two working electrodes E1/E2 separated by either a reference electrode R or an insulating material I. The electrodes E1, E2 and optionally the reference electrode R are conductive and support the sensor's shape. In addition, the reference electrode R (or the insulating material I) can act as a diffusion barrier (D, described herein) between the working electrodes E1, E2 and support the sensor's structure. Although this exemplary embodiment illustrates one configuration of an integrally formed sensor having bifunctional components, one skilled in the art appreciates a variety of alternative configurations. Namely, FIG. 7F is not to scale and the working electrodes E1, E2 can be relatively larger or smaller in scale, with regard to the reference electrode/insulator R/I separating them. For example, in one embodiment, the working electrodes E1, E2 are separated by a reference electrode that has at least 6-times the surface area of the working electrodes, combined. While the working electrodes E1, E2 and reference electrode/insulator RA are shown and semi-circles and a rectangle, respectively, one skilled in the art recognizes that these components can take on any geometry know in the art, such as but not limited to rectangles, cubes, cylinders, cones, and the like.

Figure 7G:
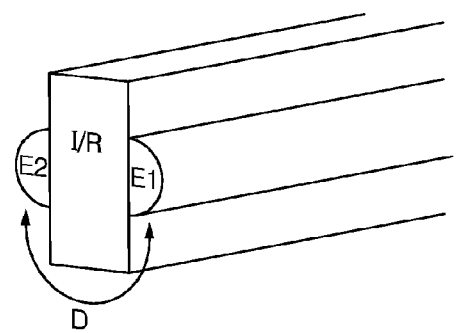
FIG. 7G is a schematic of another embodiment of a sensor having two electrodes separated by a reference electrode or insulating material.

FIG. 7G is a schematic view of a sensor in yet another embodiment. In some preferred embodiments, the sensor is configured to be integrally formed with a diffusion barrier D, as described herein. In this exemplary embodiment, the working electrodes E1, E2 (or one working electrode and one counter electrode) are integrally formed on a substantially larger reference electrode R or an insulator I that substantially prevents diffusion of analyte or other species from one working electrode to another working electrode (e.g., from the enzymatic electrode (e.g., coated with active enzyme) to the non-enzymatic electrode (e.g., no enzyme or inactive enzyme)). Although this exemplary embodiment illustrates an integrally formed sensor having a diffusion barrier, one skilled in the art appreciates a variety of alternative configurations. For example, in one embodiment, the reference electrode is designed to include an exposed electroactive surface area that is at least equal to, greater than, or more than about 2, 3, 4, 5, 6, 7, 8, 9, 10 or more times greater than the surface area of the working electrodes (e.g., combined). In other embodiments, the surface of the reference electrode is about 6 (e.g., about 6 to 20) or more times greater than the working electrodes. In some embodiments, each working electrode detects a separate analyte (e.g., glucose, oxygen, uric acid, nitrogen, pH, and the like). In other embodiments, one of the working electrodes is a counter electrode. In still another exemplary embodiment, an enzyme solution containing active GOx is applied to the E1 electroactive surface, while an enzyme solution containing inactive GOx (or no GOx at all) is applied to the E2 electroactive surface. As described herein, this configuration allows the measurement of two signals. Electrode E1 measures both a signal related to glucose concentration and a signal that is not related to glucose concentration. Electrode E2 measures a signal that is not related to glucose concentration. The sensor electronics, as described herein, can use these data to calculate glucose concentration without signal due to non-glucose-related contributions.

Figure 7H:
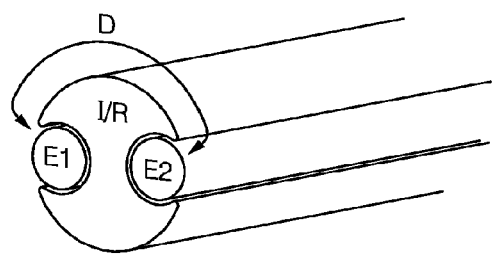
FIG. 7H is a schematic of another embodiment of a sensor having two electrodes separated by a reference electrode or insulating material.

FIG. 7H is a schematic view of a sensor in another embodiment. In some preferred embodiments, the sensor is configured of a geometric solid (e.g., cylindrical) reference electrode R having two or more working electrodes E1, E2 to En disposed within two or more grooves or channels carved in the sides of the reference electrode R (parallel to the axis of the reference electrode R). The grooves are sized such that the electrodes E1, E2 can snuggly fit therein. Additionally, the depth of the grooves can be configured that the electrode placed therein is externally exposed to a greater or lesser degree. For example, the opening to the groove may be wider or narrower. In some embodiments, a portion of an electrode protrudes from the groove in which the electrode has been disposed. In some embodiments, an insulator (e.g., I) takes the place of a reference electrode (which can be disposed elsewhere, such remotely as described in more detail elsewhere herein). The reference electrode/insulator R/I can take any geometric structure known in the art, such as but not limited to cylinders, rectangles, cones, and the like. Similarly, the relative sizes of the working electrodes E1, E2 and the reference electrode/insulator R/I can be varied to achieve a desired signal level, to enable the use of the desired voltage (e.g., to bias the sensor), and the like, as described herein.

In one exemplary embodiment, a diffusion barrier D (described in greater detail below) separates the working electrodes. The diffusion barrier can be spatial, physical, or temporal. For example, the distance around the reference electrode (e.g., from the first working electrode E1 to the second working electrode E2, around a portion of the circumference of the reference electrode R) acts as a spatial diffusion barrier. In one exemplary embodiment, the working electrodes are coated with a layer of insulating material I (e.g., non-conductive material or dielectric) to prevent direct contact between the working electrodes E1, E2 and the reference electrode R. A portion of the insulator I on an exterior surface of each working electrode is etched away, to expose the electrode's electroactive surface. In some embodiments, an enzyme solution (e.g., containing active GOx) is applied to the electroactive surfaces of both electrodes, and dried. Thereafter, the enzyme applied to one of the electroactive surfaces is inactivated. As is known in the art, enzymes can be inactivated by a variety of means, such as heat, treatment with inactivating (e.g., denaturing) solvents, proteolysis, laser irradiation or UV irradiation (e.g., at 254-320 nm). For example, the enzyme coating one of the electroactive surfaces can be inactivated by masking one of the electroactive surfaces/electrodes (e.g., E1, temporarily covered with a UV-blocking material); irradiating the sensor with UV light (e.g., 254-320 nm; a wavelength that inactivates the enzyme, such as by cross-linking amino acid residues) and removing the mask. Accordingly, the GOx on E2 is inactivated by the UV treatment, but the E1 GOx is still active due to the protective mask. In other embodiments, an enzyme solution containing active enzyme is applied to a first electroactive surface (e.g., E1) and an enzyme solution containing either inactivated enzyme or no enzyme is applied to the second electroactive surface (e.g., E2). Accordingly, the enzyme-coated first electroactive surface (e.g., E1) detects analyte-related signal and non-analyte-related signal; while the second electroactive surface (e.g., E2), which lacks active enzyme, detects non-analyte-related signal. As described herein, the sensor electronics can use the data collected from the two working electrodes to calculate the analyte-only signal.

Figure 7I:
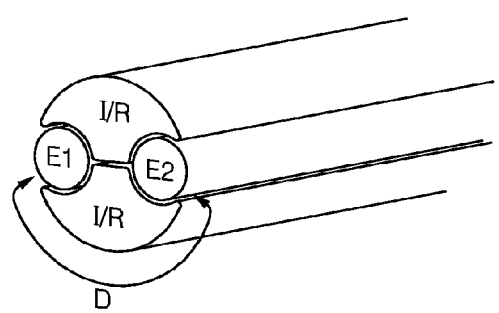
FIG. 7I is a schematic of another embodiment of a sensor having two electrodes separated by reference electrodes or insulating material.

Although this exemplary embodiment illustrates one embodiment of an integrally-formed sensor having a diffusion barrier D, one skilled in the art appreciates a variety of alternative configurations, such as but not limited to the embodiment shown in FIG. 7I. In this exemplary embodiment, the reference electrode is formed of at least two adjacent pieces shaped such that the working electrodes fill at least some space between them. The at least two pieces can be any shape known in the art, as described herein. In some embodiments, the at least two pieces are symmetrical and/or mirror images of each other, but one skilled in the art will recognize that this is not a requirement. In various embodiments, an insulating material can be coated on the working electrodes and/or the reference electrode(s) to prevent contact there between. As described elsewhere herein, the working electrodes can detect the same analyte or separate analytes, or one of the working electrodes may act as a counter electrode (e.g., auxiliary electrode). Although this exemplary embodiment illustrates one example of a sensor having a reference electrode R that is formed of at least two pieces shaped such that the working electrodes fill at least some space between the pieces, one skilled in the art appreciates that a variety of sensor configurations are possible. For example, the reference electrode can be formed of three or more pieces. In other example, the sensor can be configured with more than two working electrodes (e.g., 3, 4, or 5 working electrodes, or more).

Figure 7J:
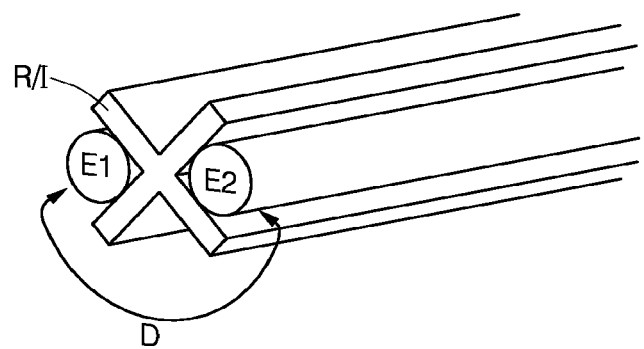
FIG. 7J is a schematic of one embodiment of a sensor having two electrodes separated by a substantially X-shaped reference electrode or insulating material.
Figure 7K:
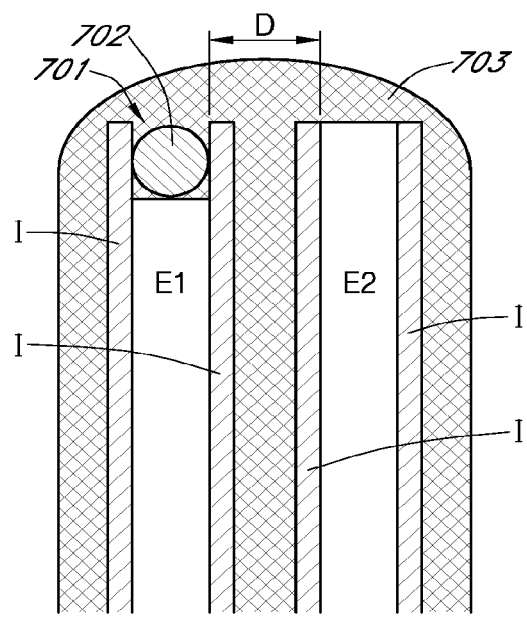
FIG. 7K is a schematic of one embodiment of a sensor having two electrodes coated with insulating material, wherein one electrode has a space for enzyme, the electrodes are separated by a distance D and covered by a membrane system.

FIG. 7J is a schematic view of an integrally formed sensor in yet another embodiment. In this exemplary embodiment, the reference electrode R is formed in any desired extruded geometry, such as an approximate X-shape. Two or more working electrodes E1, E2 are disposed on substantially opposing sides of the reference electrode, with a diffusion barrier D between them. In this embodiment, the diffusion barrier is a physical diffusion barrier, namely the distance between the two working electrodes (e.g., around the reference electrode). In some embodiments, the electrodes are bundled and held together by a wrapping of wire or fiber. In other embodiments, the electrodes are twisted around the lengthwise axis of the extruded X-shaped reference electrode, to form a coaxial sensor. Although this exemplary embodiment illustrates an integrally formed sensor, one skilled in the art appreciates a variety of alternative configurations. For example, furthering some embodiments, three or four working electrodes can be disposed around the reference electrode (e.g., in the indentations between the legs/arms of the X-shaped electrode). In other embodiments, the reference electrode can be Y-shapes, star-shaped, flower-shaped, scalloped, or any other convenient shape with multiple substantially isolated sides. In some embodiments, an insulating material I takes the place of the reference electrode of FIG. 7J, which is remotely located. In an alternative embodiment, a working electrode is replaced with a counter electrode. As described elsewhere herein, the sensor components are bifunctional. Namely, the electrodes and reference electrode provide electrical conduction and the sensor's structure. The reference electrode (or insulating material) provides a physical diffusion barrier D. In addition to providing shape to the sensor, the insulating material acts as insulator by preventing direct electrical contact between the electrodes. Similarly, the materials selected to construct the sensor determine the sensor's flexibility. As described elsewhere, active enzyme is applied to the electroactive surface of at least one working electrode (e.g., E1). In some embodiments, no enzyme (or inactivated enzyme) is applied to the electroactive surface of a second working electrode (e.g., E2). In an alternative embodiment, a second enzyme is applied to the second working electrode (e.g., E2) such that the sensor can measure the signals of two different analytes (e.g., glucose and aureate or oxygen). FIG. 7K is a schematic of a sensor in another embodiment. In some preferred embodiments, the sensor is configured to be integrally formed of two working electrodes. In this exemplary embodiment, the sensor includes two electrodes E1, E2 (e.g., metal wires), wherein each electrode is coated with a non-conductive material I (e.g., and insulator). As is shown in FIG. 7K, the first working electrode E1 formed within the insulator I leaving space for an enzyme. For example, an enzyme solution 702 (e.g., GOx for detecting glucose) is disposed within the space 701. In contrast, the second working electrode E2 extends substantially flush with the insulator I. A membrane system 703 coats the electrodes. A diffusion barrier D separates the working electrodes. In some embodiments, the first and second electrodes are separated by a distance D that substantially prevents diffusion of $H_2O_2$ from the first electrode (e.g., with active enzyme) to the second electrode (e.g., without active enzyme). Although this exemplary embodiment illustrates one integrally formed sensor, one skilled in the art appreciates a variety of alternative configurations. For example, the use of more than two working electrodes and wrapping the construct with a reference electrode wire R or disposing the reference electrode remotely from the sensor.

Figure 7L:
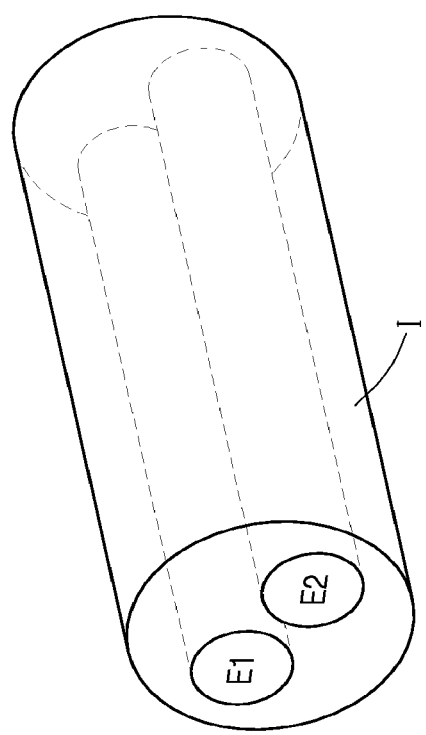
FIG. 7L is a schematic of one embodiment of a sensor having two electrodes embedded in an insulating material.

FIG. 7L is a schematic of a sensor in one embodiment. In some preferred embodiments, the sensor is designed to be integrally formed. In this exemplary embodiment, two electrodes E1, E2 are embedded within an insulator I. The sensor can be formed by embedding conductive wires within a dielectric, curing the dielectric and then cutting sensors of the desired length. The cut end provides the exposed electroactive electrode surfaces and can be polished or otherwise treated. Although this exemplary embodiment illustrates one integrally formed sensor, one skilled in the art appreciates a variety of alternative configurations. For example, additional electrode wires can be embedded in the dielectric material. In another example, a reference electrode (e.g., wire or cylinder) can be coiled or wrapped around the sensor (e.g., on the surface of the insulator). Alternatively, as described elsewhere herein, the reference electrode can be disposed remotely from the working electrodes E1, E2, such as on the host's skin or on another portion of the sensor. One advantage of this configuration is that it is relatively simple to embed electrode wires in a long cylinder of insulating material and then cut the sensors to any desired size and/or shape.

Figure 7M:
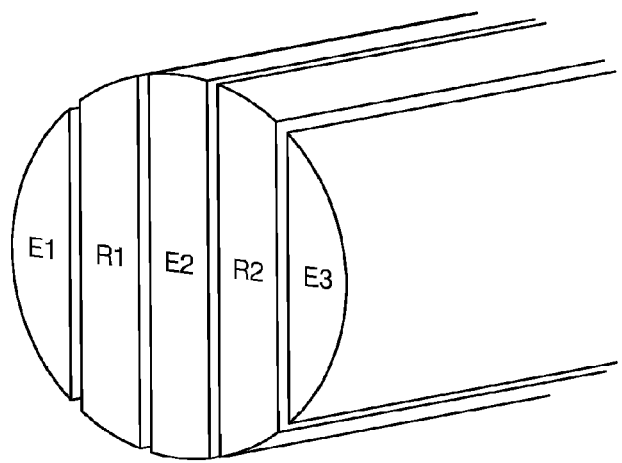
FIG. 7M is a schematic of one embodiment of a sensor having multiple working electrodes and multiple reference electrodes.

FIG. 7M is a schematic cross-sectional view of a sensor having multiple working and reference electrodes, in one embodiment. In some preferred embodiments, the sensor is integrally formed. In this exemplary embodiment, the sensor includes a plurality of working electrodes (e.g., E1, E2, E3) that are layered with a plurality of reference electrodes (e.g., R1, R2, Rn). In some embodiments, the working electrodes are coated with an insulating material to prevent direct contact with adjacent reference electrodes. In some embodiments, the reference electrodes are also coated with insulative material. In some embodiments, layers of insulating material separate the layers. In some embodiments, at least one of the working electrodes is a counter electrode. As described herein, in some embodiments, electroactive surfaces are exposed on one or more electrodes, such as by stripping away a portion of an insulating coating, such as on the sides of the sensor. In other embodiments, an extended electrode structure (e.g., a long sandwich of electrode layers) that is cut to the desired length, and the cut end includes the exposed electroactive surfaces of the electrodes. An enzyme layer can be applied to one or more of the electroactive surfaces, as described herein. Depending upon the desired sensor function, the working electrodes can be configured to detect the same analyte (e.g., all electroactive surfaces coated with GOx glucose) or different analytes (e.g., one working electrode detects glucose, another detects oxygen and the third detects ureate), as described herein. Although this exemplary embodiment illustrates a sensor having a plurality of working and reference electrodes, one skilled in the art appreciates a variety of alternative configurations. For example, in some embodiments, the electrodes can be of various sizes, depending upon their purpose. For example, in one sensor, it may be preferred to use a 3 mm oxygen electrode, a 10 mm glucose electrode and a 4 mm counter electrode, all separated by reference electrodes. In another embodiment, each reference electrode can be functionally paired with a working electrode. For example, the electrodes can be pulsed on and off, such that a first reference electrode R1 is active only when the first working electrode E1 is active, and a second reference electrode R2 is active only when the second working electrode E2 is active. In another embodiment, a flat sensor (e.g., disk-shaped) can be manufactured by sandwiching reference electrodes between working electrodes, cutting the sandwich into a cylinder, and the cutting the cylinder cross-wise (perpendicularly or at an angle) into disks.

Figure 7N:
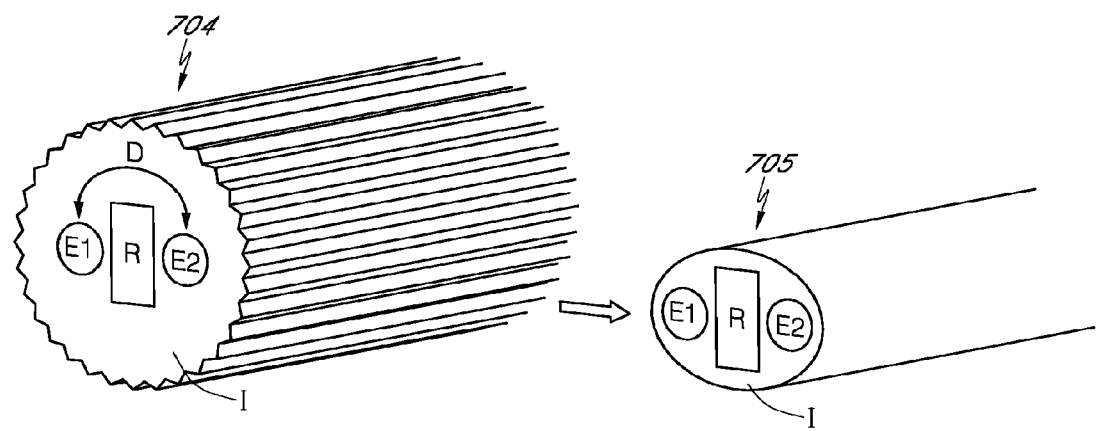
FIG. 7N is a schematic of one step of the manufacture of one embodiment of a sensor having, embedded in insulating material, two working electrodes separated by a reference electrode, wherein the sensor is trimmed to a final size and/or shape.

FIG. 7N is a schematic cross-sectional view of the manufacture of an integrally formed sensor, in one embodiment. In some preferred embodiments, at least two working electrodes (E1, E2) and optionally a reference electrode R are embedded in a quantity 704 of insulating material I. The working electrodes are separated by a diffusion barrier D. After the insulator has been cured (e.g., vulcanized or solidified) the structure is shaped (e.g., carved, scraped or cut etc.) to the final sensor shape 705, such that excess insulation material is removed. In some embodiments, multiple sensors can be formed as an extended structure of electrode wires embedded in insulator, which is subsequently cut to the desired length, wherein the exposed electrode ends (e.g., at the cut surface) become the electroactive surfaces of the electrodes. In other embodiments, portions of the insulator adjacent to the electrodes (e.g., windows) can be removed (e.g., by cutting or scraping, etc.) to expose the electroactive surfaces. Depending upon the sensor's configuration and purpose, an enzyme solution can be applied to one or more of the electroactive surfaces, as described elsewhere herein. Although this exemplary embodiment illustrates one technique of manufacturing a sensor having insulation-embedded electrodes, one skilled in the art appreciates a variety of alternative configurations. For example, a diffusion barrier D, can comprise both the reference electrode R and the insulating material I, or only the reference electrode. In another example, windows exposing the electroactive surfaces can be formed adjacent to each other (e.g., on the same side of the reference electrode) or on opposite sides of the reference electrode. Still, in other embodiments, more working or reference electrodes can be included, and the working and reference electrodes can be of relatively larger or smaller size, depending upon the sensor's configuration and operating requirements (e.g., voltage and/or current requirements).

Figure 8A:
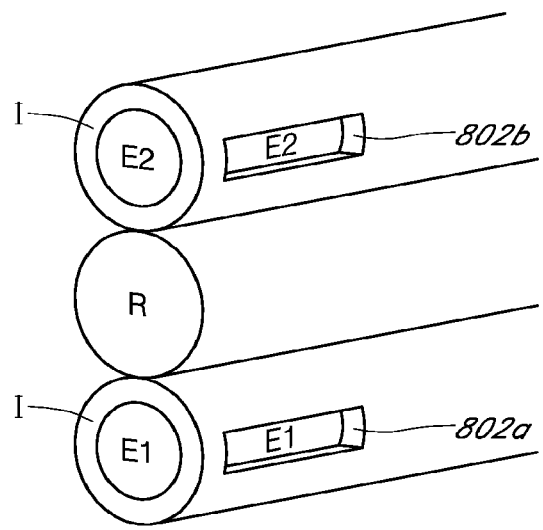
FIG. 8A is a schematic on one embodiment of a sensor having two working electrodes coated with insulating material, and separated by a reference electrode.
Figure 8B:
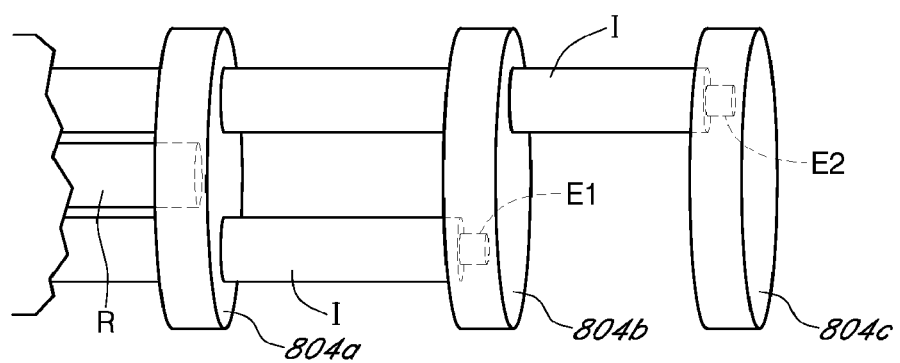
FIG. 8B is a schematic of the second end (e.g., ex vivo terminus) of the sensor of FIG. 8A having a stepped connection to the sensor electronics.

FIGS. 8A and 8B are schematic views of a sensor in yet another embodiment. FIG. 8A is a view of the cross-section and side of an in vivo portion of the sensor. FIG. 8B is a side view of the ex vivo portion of the sensor (e.g., the portion that is connected to the sensor electronics, as described elsewhere herein). Namely, two working electrodes E1, E2 that are coated with insulator I and then disposed on substantially opposing sides of a reference electrode R, such as a silver or silver/silver chloride electrode (see FIG. 8A). The working electrodes are separated by a diffusion barrier D that can include a physical barrier (provided by the reference electrode and/or the insulating material coatings), a spatial barrier (provided by staggering the electroactive surfaces of the working electrodes), or a temporal barrier (provided by oscillating the potentials between the electrodes). In some embodiments, the reference electrode R has a surface area at least 6-times the surface area of the working electrodes. Additionally, the reference electrode substantially can act as a spatial diffusion barrier between the working electrodes due to its larger size (e.g., the distance across the reference electrode, from one working electrode to another).

The electrodes can be held in position by wrapping with wire or a non-conductive fiber, a non-conductive sheath, a biointerface membrane coating, or the like. The electroactive surfaces of the working electrodes are exposed. In some embodiments, the end of the sensor is cut off, to expose the ends of the wires. In other embodiments, the ends of the wires are coated with insulating material; and the electroactive surfaces are exposed by removing a portion of the insulating material (e.g., a window 802 cut into the side of the insulation coating the electrode). In some embodiments, the windows exposing the electroactive surfaces of the electrodes can be staggered (e.g., spaced such that one or more electrodes extends beyond the other one or more electrodes), symmetrically arranged or rotated to any degree; for example, to substantially prevent diffusion of electroactive species from one working electrode (e.g., 802a) to the other working electrode (e.g., 802b), as will be discussed in greater detail elsewhere herein. In various embodiments, the reference electrode is not coated with a nonconductive material. The reference electrode can have a surface area that is at least 6 times the surface area of the exposed working electrode electroactive surfaces. In some embodiments, the reference electrode R surface area is 7-10 times (or larger) than the surface area of the working electrode electroactive surfaces. In still other embodiments, the reference electrode can be only 1-5 times the surface area of working electrode electroactive surfaces (e.g., (E1+E2)× 1=R or (E1+E2)×2=R, etc.).

The ex vivo end of the sensor is connected to the sensor electronics (not shown) by electrical connectors 804a, 804b, 804c. In some embodiments, the ex vivo end of the sensor is stepped. For example, the ex vivo end of the reference electrode R terminates within electrical connector 804a. The ex vivo end of the first working electrode E1 is exposed (e.g., nonconductive material removed therefrom) and terminates a small distance past the reference electrode R, within electrical connector 804b. Similarly, the ex vivo end of the second working electrode E2 is exposed (e.g., nonconductive material removed therefrom) and terminates a small distance past the termination of the first working electrode E1, within electrical connector 804c.

Although this exemplary embodiment illustrates one configuration of an integrally formed sensor, one skilled in the art appreciates a variety of alternative configurations. For example, in some embodiments, a portion of the in vivo portion of the sensor can be twisted and/or stepped. More working, reference, and/or counter electrodes, as well as insulators, can be included. The electrodes can be of relatively larger or smaller size, depending upon the sensor's intended function. In some embodiments, the electroactive surfaces can be staggered. In still other embodiments, the reference electrode can be disposed remotely from the sensor, as described elsewhere herein. For example, the reference electrode shown in FIG. 8A can be replaced with a non-conductive support and the reference electrode disposed on the host's skin.

With reference to the ex vivo portion of the sensor, one skilled in the art appreciates additional alternative configurations. For example, in one embodiment, a portion of the ex vivo portion of the sensor can be twisted or coiled. In some embodiments, the working and reference electrodes can be of various lengths and configurations not shown in FIG. 8B. For example, the reference electrode R can be the longest (e.g., connect to electrical contact 804c) and the first second working electrode E2 can be the shortest (e.g., connect to electrical contact 804a). In other embodiments, the first working electrode E1 may be either the longest electrode (e.g., connect to electrical contact 804c) or the shortest electrode (e.g., connect to electrical contact 804a).

Figure 9A:
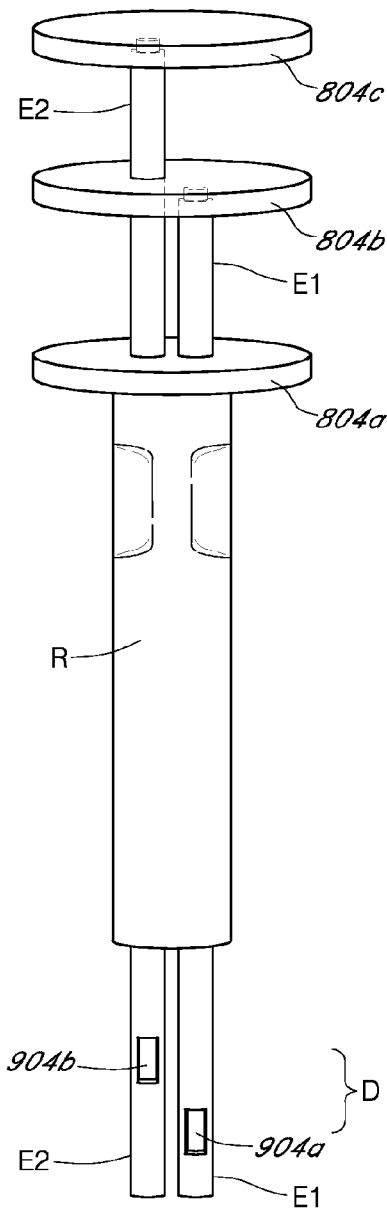
FIG. 9A is a schematic of one embodiment of a sensor having two working electrodes and a substantially cylindrical reference electrode there around, wherein the second end (the end connected to the sensor electronics) of the sensor is stepped.

FIG. 9A is a schematic view that illustrates yet another exemplary embodiment of an integrally formed analyte sensor. Namely, two working electrodes E1, E2 are bundled together and substantially encircled with a cylindrical silver or silver/silver chloride reference electrode R (or the like).

The reference electrode can be crimped at a location 902, to prevent movement of the working electrodes E1, E2 within the reference electrode R cylinder. In alternative embodiments, a reference electrode can be rolled or coiled around the working electrodes E1, E2, to form the reference electrode R. Preferably, the working electrodes are at least partially insulated as described in more detail elsewhere herein; such as by coating with a non-conductive material, such as but not limited to Parylene. One skilled in the art appreciates that a variety of alternative configurations are possible.

Figure 9B:
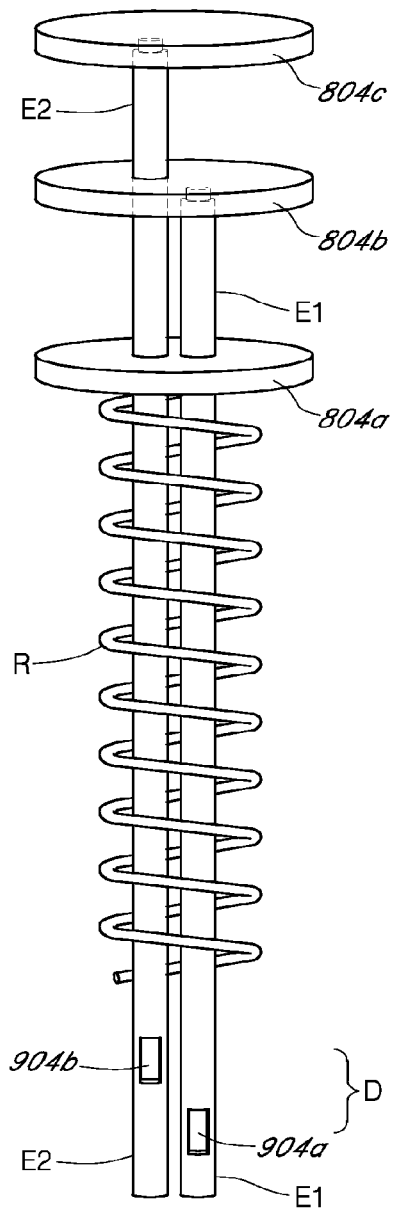
FIG. 9B is a schematic of one embodiment of a sensor having two working electrodes and an electrode coiled there around, wherein the second end (the end connected to the sensor electronics) of the sensor is stepped.

FIG. 9B illustrates another embodiment of an integrally formed analyte sensor. Namely, two working electrodes E1, E2 are bundled together with a silver or silver/silver chloride wire reference electrode R coiled there around. The reference electrode can be coiled tightly, to prevent movement of the working electrodes E1, E2 within the reference electrode R coil.

Referring again to FIGS. 9A to 9B, near the tip of the in vivo portion of the sensor, windows 904a and 904b are formed on the working electrodes E1, E2. Portions of the non-conductive material (e.g., insulator) coating each electrode is removed to form windows 904a and 904b. The electroactive surfaces of the electrodes are exposed via windows 904a and 904b. As described elsewhere herein, the electrode electroactive surfaces exposed through windows 904a and 904b are coated with a membrane system. An active enzyme (e.g., GOx is used if glucose is the analyte) is disposed within or beneath or within the membrane covering one of the windows (e.g., 904a or 904b). The membrane covering the other window can include inactivated enzyme (e.g., GOx inactivated by heat, solvent, UV or laser irradiation, etc., as described herein) or no enzyme. The electrode having active enzyme detects a signal related to the analyte concentration and non-analyte related signal (e.g., due to background, etc.). In contrast, the electrode having inactive enzyme or no enzyme detects substantially only the non-analyte related signal. These signals are transmitted to sensor electronics (discussed elsewhere herein) to calculate an analyte concentration based on only the signal component related to only the analyte (described elsewhere herein).

In general, the windows 904a and 904b are separated or staggered by a distance D, which is selected to be sufficiently large that electroactive species (e.g., $H_2O_2$) do not substantially diffuse from one window to the other (e.g., from 904a to 904b). In an exemplary embodiment of a glucose-oxidase-based sensor, active enzyme is included in the membrane covering window 904a and inactive enzyme is included in the membrane covering window 904b. Distance D is configured to be large enough that $H_2O_2$ cannot diffuse from window 904a to window 904b, which lacks active enzyme (as discussed elsewhere herein). In some embodiments, the distance D is at least about 0.020 inches or less to about 0.120 inches or more. In some embodiments, D is at least about 0.030 to about 0.050 inches. In other embodiments, D is at least about 0.090 to about 0.095 inches. One skilled in the art appreciates alternative embodiments of the diffusion barrier D. Namely, the diffusion barrier D can be spatial (discussed herein with relation to FIGS. 9A and 9B), physical or temporal (see discussion of Diffusion Barriers herein and FIG. 10). In some embodiments, a physical diffusion barrier D, such as but not limited to an extended non-conductive structure placed between the working electrodes (e.g., FIG. 8A), substantially prevents diffusion of $H_2O_2$ from one working electrode (having active enzyme) to another working electrode (having no active enzyme). In other embodiments, a temporal diffusion barrier D is created by pulsing or oscillating the electrical potential, such that only one working electrode is activated at a time.

In various embodiments, one of the windows 904a or 904b comprises an enzyme system configured to detect the analyte of interest (e.g., glucose or oxygen). The other window comprises no active enzyme system (e.g., wherein the enzyme system lacks enzyme or wherein the enzyme has been de-activated). In some embodiments, wherein the "enzyme system lacks enzyme," a layer may be applied, similar to an active enzyme layer, but without the actual enzyme included therein. In some embodiments, wherein "the enzyme has been de-activated" the enzyme can be inactivated (e.g., by heat or solvent) prior to addition to the enzyme system solution or the enzyme can be inactivated after application to the window.

In one exemplary embodiment, an enzyme is applied to both windows 904a and 904b followed by deactivation of the enzyme in one window. For example, one window can be masked (e.g., to protect the enzyme under the mask) and the sensor then irradiated (to deactivate the enzyme in the unmasked window). Alternatively, one of the enzyme-coated windows (e.g., the first window but not the second window) can be sprayed or dipped in an enzyme-deactivating solvent (e.g., treated with a protic acid solution such a hydrochloric acid or sulfuric acid). For example, a window coated with GOx can be dipped in dimethyl acetamide (DMAC), ethanol, or tetrahydrofuran (THF) to deactivate the GOx. In another example, the enzyme-coated window can be dipped into a hot liquid (e.g., water or saline) to deactivate the enzyme with heat.

In these embodiments, the design of the active and inactive enzyme window is at least partially dependent upon the sensor's intended use. In some embodiments, it is preferred to deactivate the enzyme coated on window 904a. In other embodiments, it is preferred to deactivate the enzyme coated on window 904b. For example, in the case of a sensor to be used in a host's blood stream, the choice depends upon whether the sensor will be inserted pointing upstream (e.g., against the blood flow) or pointing downstream (e.g., with the blood flow).

In one exemplary embodiment, an intravascular sensor is inserted into the host's vein pointing upstream (against the blood flow), an enzyme coating on electrode E1 (window 904a) is inactivated (e.g., by dipping in THF and rinsing) and an enzyme coating on electrode E2 (in window 904b) is not inactivated (e.g., by not dipping in THF). Because the enzyme on the first electrode E1 (e.g., in window 904a) is inactive, electroactive species (e.g., $H_2O_2$) will not be substantially generated at window 904a (e.g., the first electrode E1 generates substantially no $H_2O_2$ to effect the second electrode E2). In contrast, the active enzyme on the second electrode E2 (in window 904b) generates $H_2O_2$ which at least partially diffuses down stream (away from the windows) and thus has no effect on the first electrode E1, other features and advantages of spatial diffusion barriers are described in more detail elsewhere herein.

In another exemplary embodiment, an intravascular sensor is inserted into the host's vein pointing downstream (with the blood flow), the enzyme coating on electrode E1 (window 904a) is active and the enzyme coating on electrode E2 (in window 904b) is inactive. Because window 904a is located farther downstream than window 904b, the $H_2O_2$ produced by the enzyme in 904a diffuses downstream (away from window 904b), and therefore does not affect substantially electrode E2. In a preferred embodiment, the enzyme is GOx, and the sensor is configured to detect glucose. Accordingly, $H_2O_2$ produced by the GOx in window 904a does not affect electrode E2, because the sensor is pointing downstream and the blood flow carries away the $H_2O_2$ produced on electrode E1.

FIGS. 9A and 9B illustrate two embodiments of a sensor having a stepped second end (e.g., the back end, distal end or ex vivo end, described with reference to FIG. 8B) that connects the sensor to the sensor electronics. Namely, each electrode terminates within an electrical connector 804 such as but not limited to an elastomeric electrical connector. Additionally, each electrode is of a different length, such that each electrode terminates within one of a plurality of sequential electrical connectors. For example, with reference to FIG. 9A, the reference electrode R is the shortest in length and terminates within the first electrical connector 804. The first working electrode E1 is longer than the reference electrode R, and terminates within the second electrical connector 804. Finally, the second working electrode E2 is the longest electrode and terminates within the third electrical connector 804. One skilled in the art appreciates that other configurations are possible. For example, the first working electrode E1 can be longer than the second working electrode E2. Accordingly, the second working electrode E2 would terminate within the second (e.g., middle) electrical connector 804 and the first working electrode E1 would terminate within the third (e.g., last) electrical connector 804. With reference to FIG. 9B, additional stepped second end configurations are possible. In alternative embodiments, the second ends of the sensor may be separated from each other to connect to non-parallel, non-sequential electrical connectors.

Figure 11:
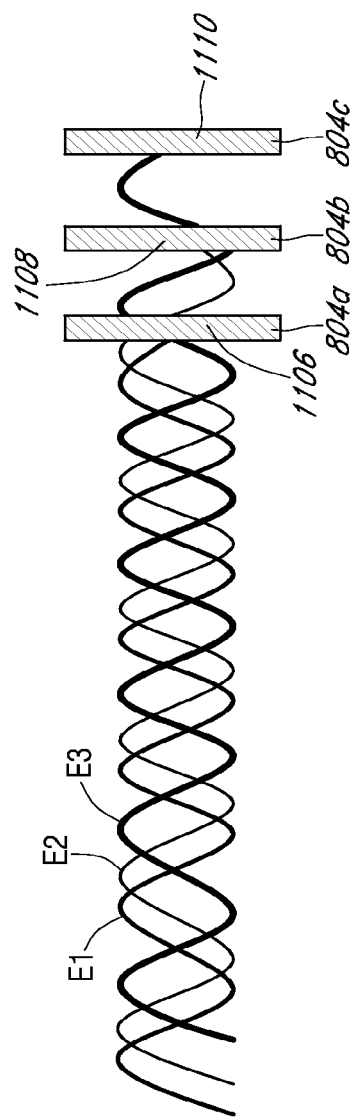
FIG. 11 is a schematic illustrating one embodiment of a triple helical coaxial sensor having a stepped second terminus for engaging the sensor electronics.

FIG. 11 is a schematic view of a sensor in yet another embodiment. In preferred embodiments, the sensor is integrally formed, coaxial, and has a stepped ex vivo end (e.g., back or second end). Electrodes E1, E2 and E3 are twisted to form a helix, such as a triple helix. Additionally, at the back end of the sensor, the electrodes are stepped and each electrode is individually connected to the sensor electronics by an electrical connector 804. At each electrode's second end, the electrode engages an electrical connector 804 that joins the electrode to the sensor electronics. For example, the second end of electrode E1 electrically connects electrical connector 1106. Similarly, the second end of electrode E2 electrically connects electrical connector 1108 and the second end of electrode E3 electrically connects electrical connector 1110. As described elsewhere herein, each sensor component is difunctional, and provides electrical conductance, structural support, a diffusion barrier, or insulation (see description elsewhere herein). Although this exemplary embodiment illustrates an integrally formed, coaxial sensor having a stepped back end, one skilled in the art appreciates a variety of alternative configurations. For example, one of the electrodes E1, E2 or E3 can be a reference electrode, or the reference electrode can be disposed remotely from the sensor, such as but not limited to on the host's skin. In another example, the sensor can have only two electrodes or more than three electrodes.

One skilled in the art recognizes a variety of alternative configurations for the embodiments described herein. For example, in any embodiment of an analyte sensor, the reference electrode (and optionally a counter electrode) can be disposed remotely from the working electrodes. For example, in FIGS. 7A1 through 9B and FIG. 11, the reference electrode R can be replaced with a non-conductive material, such as an insulator I. Depending upon the sensor's configuration and location of use, the reference electrode R can then be inserted into the host in a location near to the sensor, applied to the host's skin, be disposed within a fluid connector, be disposed on the ex-vivo portion of the sensor or even disposed on the exterior of the sensor electronics.

FIG. 7L illustrates an embodiment in which the reference and/or counter electrode is located remotely from the first and second working electrodes E1 and E2, respectively. In one exemplary embodiment, the sensor is a needle-type sensor such as described with reference to FIG. 1B, and the working electrodes E1, E2 are integrally formed together with a substantially X-shaped insulator I and the reference electrode (and/or counter electrode) is placed on the host's skin (e.g., a button, plate, foil or wire, such as under the housing) or implanted transcutaneously in a location separate from the working electrodes.

As another example, in one embodiment of a sensor configured to measure a host's blood, such as described in co-pending U.S. patent application Ser. No. 11/543,396, entitled "ANALYTE SENSOR" and filed on even date herewith, and which is incorporated herein by reference in its entirety; one or more working electrodes can be inserted into the host's blood via a catheter and the reference and/or counter electrode can be placed within the a fluid connector (on the sensor) configured to be in fluid communication with the catheter; in such an example, the reference and/or counter electrode is in contact with fluid flowing through the fluid connector but not in direct contact with the host's blood. In still other embodiments, the reference and/or counter electrodes can be placed exterior to the sensor, in bodily contact for example.

With reference to the analyte sensor embodiments disclosed herein, the surface area of the electroactive portion of the reference (and/or counter) electrode is at least six times the surface area of one or more working electrodes. In other embodiments, the reference (and/or counter) electrode surface is 1, 2, 3, 4, 5, 7, 8, 9 or 10 times the surface area of the working electrodes. In other embodiments, the reference (and/or counter) electrode surface area is 11, 12, 13, 14, 15, 16, 17, 18, 19 or 20 times the surface area of the working electrodes. For example, in a needle-type glucose sensor, similar to the embodiment shown in FIG. 1B, the surface area of the reference electrode (e.g., 18 or 20) includes the exposed surface of the reference electrode, such as but not limited to the electrode surface facing away from the working electrode 16.

In various embodiments, the electrodes can be stacked or grouped similar to that of a leaf spring configuration, wherein layers of electrode and insulator (or individual insulated electrodes) are stacked in offset layers. The offset layers can be held together with bindings of non-conductive material, foil, or wire. As is appreciated by one skilled in the art, the strength, flexibility, and/or other material property of the leaf spring-configured or stacked sensor can be either modified (e.g., increased or decreased), by varying the amount of offset, the amount of binding, thickness of the layers, and/or materials selected and their thicknesses, for example.

In some embodiments, the sensor (e.g., a glucose sensor) is configured for implantation into the host. For example, the sensor may be wholly implanted into the host, such as but not limited to in the host's subcutaneous tissue (e.g., the embodiment shown in FIG. 1A). In other embodiments, the sensor is configured for transcutaneous implantation in the host's tissue. For example, the sensor can have a portion that is inserted through the host's skin and into the underlying tissue, and another portion that remains outside the host's body (e.g., such as described in more detail with reference to FIG. 1B). In still other embodiments, the sensor is configured for indwelling in the host's blood stream. For example, a needle-type sensor can be configured for insertion into a catheter dwelling in a host's vein or artery. In another example, the sensor can be integrally formed on the exterior surface of the catheter, which is configured to dwell within a host's vein or artery. Examples of indwelling sensors can be found in co-pending U.S. patent application Ser. No. 11/543,396 filed on even date herewith and entitled "ANALYTE SENSOR." In various embodiments, the in vivo portion of the sensor can take alternative configurations, such as but not limited to those described in more detail with reference to FIGS. 7A-9B and 11.

In preferred embodiments, the analyte sensor substantially continuously measures the host's analyte concentration. In some embodiments, for example, the sensor can measure the analyte concentration every fraction of a second, about every fraction of a minute or every minute. In other exemplary embodiments, the sensor measures the analyte concentration about every 2, 3, 4, 5, 6, 7, 8, 9, or 10 minutes. In still other embodiments, the sensor measures the analyte concentration every fraction of an hour, such as but not limited to every 15, 30 or 45 minutes. Yet in other embodiments, the sensor measures the analyte concentration about every hour or longer. In some exemplary embodiments, the sensor measures the analyte concentration intermittently or periodically. In one preferred embodiment, the analyte sensor is a glucose sensor and measures the host's glucose concentration about every 4-6 minutes. In a further embodiment, the sensor measures the host's glucose concentration every 5 minutes.

In one exemplary embodiment, the analyte sensor is a glucose sensor having a first working electrode configured to generate a first signal associated with both glucose and non-glucose related electroactive compounds that have a first oxidation potential. Non-glucose related electroactive compounds can be any compound, in the sensor's local environment that has an oxidation potential substantially overlapping with the oxidation potential of $H_2O_2$, for example. While not wishing to be bound by theory, it is believed that the glucose-measuring electrode can measure both the signal directly related to the reaction of glucose with GOx (produces $H_2O_2$ that is oxidized at the working electrode) and signals from unknown compounds that are in the extracellular milieu surrounding the sensor. These unknown compounds can be constant or non-constant (e.g., intermittent or transient) in concentration and/or effect. In some circumstances, it is believed that some of these unknown compounds are related to the host's disease state. For example, it is know that blood chemistry changes dramatically during/after a heart attack (e.g., pH changes, changes in the concentration of various blood components/ protein, and the like). Other compounds that can contribute to the non-glucose related signal are believed to be related to the wound healing process that is initiated by implantation/insertion of the sensor into the host, which is described in more detail with reference to co-pending U.S. patent application Ser. No. 11/503,367 filed Aug. 10, 2006 and entitled "ANALYTE SENSOR," which is incorporated herein by reference in its entirety. For example, transcutaneously inserting a needle-type sensor initiates a cascade of events that includes the release of various reactive molecules by macrophages.

In some embodiments, the glucose sensor includes a second (e.g., auxiliary) working electrode that is configured to generate a second signal associated with non-glucose related electroactive compounds that have the same oxidation potential as the above-described first working electrode (e.g., para supra). In some embodiments, the non-glucose related electroactive species includes at least one of interfering species, non-reaction-related $H_2O_2$, and other electroactive species. For example, interfering species includes any compound that is not directly related to the electrochemical signal generated by the glucose-GOx reaction, such as but not limited to electroactive species in the local environment produces by other bodily processes (e.g., cellular metabolism, wound healing, a disease process, and the like). Non-reaction-related $H_2O_2$ includes $H_2O_2$ from sources other than the glucose-GOx reaction, such as but not limited to $H_2O_2$ released by nearby cells during the course of the cells' metabolism, $H_2O_2$ produced by other enzymatic reactions (e.g., extracellular enzymes around the sensor or such as can be released during the death of nearby cells or such as can be released by activated macrophages), and the like. Other electroactive species includes any compound that has an oxidation potential similar to or overlapping that of $H_2O_2$.

The non-analyte (e.g., non-glucose) signal produced by compounds other than the analyte (e.g., glucose) obscured the signal related to the analyte, contributes to sensor inaccuracy, and is considered background noise. As described in greater detail in the section entitled "Noise Reduction," background noise includes both constant and non-constant components and must be removed to accurately calculate the analyte concentration. While not wishing to be bound by theory, it is believed that the sensor of the preferred embodiments are designed (e.g., with symmetry, coaxial design and/or integral formation) such that the first and second electrodes are influenced by substantially the same external/environmental factors, which enables substantially equivalent measurement of both the constant and non-constant species/noise. This advantageously allows the substantial elimination of noise (including transient biologically related noise that has been previously seen to affect accuracy of sensor signal due to it's transient and unpredictable behavior) on the sensor signal (using electronics described elsewhere herein) to substantially reduce or eliminate signal effects due to noise, including non-constant noise (e.g., unpredictable biological, biochemical species or the like) known to effect the accuracy of conventional continuous sensor signals. Preferably, the sensor includes electronics operably connected to the first and second working electrodes. The electronics are configured to provide the first and second signals that are used to generate glucose concentration data substantially without signal contribution due to non-glucose-related noise. Preferably, the electronics include at least a potentiostat that provides a bias to the electrodes. In some embodiments, sensor electronics are configured to measure the current (or voltage) to provide the first and second signals. The first and second signals are used to determine the glucose concentration substantially without signal contribution due to non-glucose-related noise such as by but not limited to subtraction of the second signal from the first signal or alternative data analysis techniques. In some embodiments, the sensor electronics include a transmitter that transmits the first and second signals to a receiver, where additional data analysis and/or calibration of glucose concentration can be processed. U.S. Patent Publication No. US-2005-0027463-A1, US-2005-0203360-A1 and U.S. Patent Publication No. US-2006-0036142-A1 describe systems and methods for processing sensor analyte data and are incorporated herein by reference in their entirety.

In preferred embodiments, the sensor electronics (e.g., electronic components) are operably connected to the first and second working electrodes. The electronics are configured to calculate at least one analyte sensor data point. For example, the electronics can include a potentiostat, A/D converter, RAM, ROM, transmitter, and the like. In some embodiments, the potentiostat converts the raw data (e.g., raw counts) collected from the sensor to a value familiar to the host and/or medical personnel. For example, the raw counts from a glucose sensor can be converted to milligrams of glucose per deciliter of glucose (e.g., mg/dl). In some embodiments, the electronics are operably connected to the first and second working electrodes and are configured to process the first and second signals to generate a glucose concentration substantially without signal contribution due to non-glucose noise artifacts. The sensor electronics determine the signals from glucose and non-glucose related signal with an overlapping measuring potential (e.g., from a first working electrode) and then non-glucose related signal with an overlapping measuring potential (e.g., from a second electrode). The sensor electronics then use these data to determine a substantially glucose-only concentration, such as but not limited to subtracting the second electrode's signal from the first electrode's signal, to give a signal (e.g., data) representative of substantially glucose-only concentration, for example. In general, the sensor electronics may perform additional operations, such as but not limited to data smoothing and noise analysis.

Bifunctionality

In some embodiments, the components of at least a portion (e.g., the in vivo portion or the sensing portion) of the sensor possess bifunctional properties (e.g., provide at least two functions to the sensor). These properties can include electrical conductance, insulative properties, structural support, and diffusion barrier properties.

In one exemplary embodiment, the analyte sensor is designed with two working electrodes, a membrane system and an insulating material disposed between the working electrodes. An active enzymatic membrane is disposed above the first working electrode, while an inactive- or non-enzymatic membrane is disposed above the second working electrode. Additionally, the working electrodes and the insulating material are configured provide at least two functions to the sensor, including but not limited to electrical conductance, insulative properties, structural support, and diffusion barrier. For example, in one embodiment of a glucose sensor, the two working electrodes support the sensor's structure and provide electrical conductance; the insulating material provides insulation between the two electrodes and provides additional structural support and/or a diffusional barrier.

In some embodiments, a component of the sensor is configured to provide both electrical conductance and structural support. In an exemplary embodiment, the working electrode(s) and reference electrode are generally manufactured of electrically conductive materials, such as but not limited silver or silver/silver chloride, copper, gold, platinum, iridium, platinum-iridium, palladium, graphite, carbon, conductive polymers, alloys, and the like. Accordingly, the electrodes are both conductive and they give the sensor its shape (e.g., are supportive).

Referring to FIG. 1B, all three electrodes 16, 18, and 20 are manufactured from plated insulator, a plated wire, or electrically conductive material, such as but not limited to a metal wire. Accordingly, the three electrodes provide both electrical conductance (to measure glucose concentration) and structural support. Due to the configuration of the electrodes (e.g., the wires are about 0.001 inches in diameter or less, to about 0.01 inches or more), the sensor is needle-like and only about 0.003 inches or less to about 0.015 inches or more.

Similarly, the electrodes of FIG. 7A through FIG. 9 provide electrical conductance, to detect the analyte of interest, as well as structural support for the sensor. For example, the sensors depicted in FIGS. 7A through 7L embodiments that are substantially needle-like. Additionally, these sensors are substantially resilient, and therefore able to flex in response to mechanical pressure and then to regain their original shapes. FIG. 7M depicts a cross-section of another sensor embodiment, which can be a composite (e.g., built up of layers of working and reference electrode materials) needle-like sensor or the composite "wire" can be cut to produce pancake-shaped sensors [describe its bifunctionality without unnecessary characterizations (e.g., not "pancake-shaped"). FIG. 7N through FIG. 9 illustrate additional sensor embodiments, wherein the electrodes provide electrical conductance and support the sensor's needle-like shape.

In some embodiments, the first and second working electrodes are configured to provide both electrical conductance and structural support. For example, in a needle-type sensor, the working electrodes are often manufactured of bulk metal wires (e.g., copper, gold, platinum, iridium, platinum-iridium, palladium, graphite, carbon, conductive polymers, alloys, and the like). The reference electrode, which can function as a reference electrode alone, or as a dual reference and counter electrode, are formed from silver or silver/silver chloride, or the like. The metal wires are conductive (e.g., can conduct electricity) and give the sensor its shape and/or structural support. For example, one electrode metal wire may be coiled around the other electrode metal wire (e.g., FIG. 1B or FIG. 7B). In a further embodiment, the sensor includes a reference electrode that is also configured to provide electrical conductance and structural support (e.g., FIG. 1B, FIGS. 7C to 7E). In general, reference electrodes are made of metal, such as bulk silver or silver/silver chloride wires. Like the two working electrodes, the reference electrode both conducts electricity and supports the structure of the sensor.

In some embodiments, the first and second working electrode and the insulating material are configured provide at least two functions, such as but not limited to electrical conductance, insulative properties, structural support, and diffusion barrier. As described elsewhere herein, the working electrodes are electrical conductors and also provide support for the sensor. The insulating material (e.g., I) acts as an insulator, to prevent electrical communication between certain parts of the various electrodes. The insulating material also provides structural support or substantially prevents diffusion of electroactive species from one working electrode to the other, which is discussed in greater detail elsewhere herein.

In preferred embodiments, the sensor has a diffusion barrier disposed between the first and second working electrodes. The diffusion barrier is configured to substantially block diffusion of the analyte or a co-analyte (e.g., $H_2O_2$) between the first and second working electrodes. For example, a sheet of a polymer through which $H_2O_2$ cannot diffuse can be interposed between the two working electrodes. Diffusion barriers are discussed in greater detail elsewhere herein.

In some embodiments of the preferred embodiments, the analyte sensor includes a reference electrode that is configured to provide electrical conductance and a diffusion barrier. Electrical conductance is an inherent property of the metal used to manufacture the reference electrode. However, the reference electrode can be configured to prevent species (e.g., $H_2O_2$) from diffusing from the first working electrode to the second working electrode. For example, a sufficiently large reference electrode can be placed between the two working electrodes. In some embodiments, the reference electrode projects farther than the two working electrodes. In other embodiments, the reference electrode is so broad that a substantial portion of the $H_2O_2$ produced at the first working electrode cannot diffuse to the second working electrode, and thereby significantly affect the second working electrode's function.

In a further embodiment, the reference electrode is configured to provide a diffusion barrier and structural support. As described elsewhere herein, the reference electrode can be constructed of a sufficient size and/or shape that a substantial portion of the $H_2O_2$ produced at a first working electrode cannot diffuse to the second working electrode and affect the second working electrode's function. Additionally, metal wires are generally resilient and hold their shape, the reference electrode can also provide structural support to the sensor (e.g., help the sensor to hold its shape).

In some embodiments of the analyte sensor described elsewhere herein, the insulating material is configured to provide both electrical insulative properties and structural support. In one exemplary embodiment, portions of the electrodes are coated with a non-conductive polymer. Inherently, the non-conductive polymer electrically insulates the coated electrodes from each other, and thus substantially prevents passage of electricity from one coated wire to another coated wire. Additionally, the non-conductive material (e.g., a non-conductive polymer or insulating material) can stiffen the electrodes and make them resistant to changes in shape (e.g., structural changes).

In some embodiments, a sensor component is configured to provide electrical insulative properties and a diffusion barrier. In one exemplary embodiment, the electrodes are coated with the non-conductive material that substantially prevents direct contact between the electrodes, such that electricity cannot be conducted directly from one electrode to another. Due to the non-conductive coatings on the electrodes, electrical current must travel from one electrode to another through the surrounding aqueous medium (e.g., extracellular fluid, blood, wound fluid, or the like). Any non-conductive material (e.g., insulator) known in the art can be used to insulate the electrodes from each other. In exemplary embodiments, the electrodes can be coated with non-conductive polymer materials (e.g., parylene, PTFE, ETFE, polyurethane, polyethylene, polyimide, silicone and the like) by dipping, painting, spraying, spin coating, or the like.

Non-conductive material (e.g., insulator, as discussed elsewhere herein) applied to or separating the electrodes can be configured to prevent diffusion of electroactive species (e.g., $H_2O_2$) from one working electrode to another working electrode. Diffusion of electroactive species from one working electrode to another can cause a false analyte signal. For example, electroactive species (e.g., $H_2O_2$) that are created at a first working electrode having active enzyme (e.g., GOx) can diffuse to a nearby working electrode (e.g., without active GOx). When the electroactive species arrives at the second working electrode, the second electrode registers a signal (e.g., as if the second working electrode comprised active GOx). The signal registered at the second working electrode due to the diffusion of the $H_2O_2$ is aberrant and can cause improper data processing in the sensor electronics. For example, if the second electrode is configured to measure a substantially non-analyte related signal (e.g., background) the sensor will record a higher non-analyte related signal than is appropriate, possibly resulting in the sensor reporting a lower analyte concentration than actually is present in the host. This is discussed in greater detail elsewhere herein.

In preferred embodiments, the non-conductive material is configured to provide a diffusion barrier and structural support to the sensor. Diffusion barriers are described elsewhere herein. Non-conductive materials can be configured to support the sensor's structure. In some, non-conductive materials with relatively more or less rigidity can be selected. For example, if the electrodes themselves are relatively flexible, it may be preferred to select a relatively rigid non-conductive material, to make the sensor stiffer (e.g., less flexible or bendable). In another example, if the electrodes are sufficiently resilient or rigid, a very flexible non-conductive material may be coated on the electrodes to bind the electrodes together (e.g., keep the electrodes together and thereby hold the sensor's shape).

Referring now to FIGS. 7C to 7J, the non-conductive material can be coated on or wrapped around the grouped or bundled electrodes, to prevent the electrodes from separating and also to prevent the electrodes from directly touching each other. For example, with reference to FIG. 7C, each electrode can be individually coated by a first non-conductive material and then bundled together. Then the bundle of individually insulated electrodes can be coated with a second layer of the first non-conductive material or with a layer or a second non-conductive material. In an embodiment of a sensor having the structure shown in FIG. 7K, each electrode E1, E2 is coated with a non-conductive material/insulator I, and then coated with a second non-conductive material 703 (e.g., instead of a biointerface membrane). Similarly, in FIG. 7L, the non-conductive material I prevents electrodes E1 and E2 from making direct contact with each other as well as giving the needle-like sensor its overall dimensions and shape.

FIG. 7N illustrates one method of configuring a sensor having a non-conductive material I that both provides electrical insulation between the electrodes E1, E2, R and provides structural support to the sensor. Namely, the electrodes are embedded in a non-conductive polymer I, which is subsequently vulcanized (704=before shaping). After vulcanization, the excess non-conductive polymer I is trimmed away (e.g., cutting or scraping, etc.) to produce a sensor having the final desired sensor shape 705=after shaping).

In some embodiments, a component of the sensor is configured to provide both insulative properties and a diffusion barrier. Diffusion barriers are discussed elsewhere herein. In one exemplary embodiment, the working electrodes are separated by a non-conductive material/insulator that is configured such that electroactive species (e.g., $H_2O_2$) cannot diffuse around it (e.g., from a first electrode to a second electrode). For example, with reference to the embodiment shown in FIG. 7H, the electrodes E1, E2 are placed in the groves carved into a cylinder of non-conductive material I. The distance D from E1 to E2 (e.g., around I) is sufficiently great that $H_2O_2$ produced at E1 cannot diffuse to E2 and thereby cause an aberrant signal at E2.

In some preferred embodiments, in addition to two working electrodes and a non-conductive material/insulator, the sensor includes at least a reference or a counter electrode. In preferred embodiments, the reference and/or counter electrode, together with the first and second working electrodes, integrally form at least a portion of the sensor. In some embodiments, the reference and/or counter electrode is located remote from the first and second working electrodes. For example, in some embodiments, such as in the case of a transcutaneous sensor, the reference and/or counter electrodes can be located on the ex vivo portion of the sensor or reside on the host's skin, such as a portion of an adhesive patch. In other embodiments, such as in the case of an intravascular sensor, the reference and/or counter electrode can be located on the host's skin, within or on the fluid connector (e.g., coiled within the ex vivo portion of the device and in contact with fluid within the device, such as but not limited to saline) or on the exterior of the ex vivo portion of the device. In preferred embodiments, the surface area of the reference and/or counter electrode is as least six times the surface area of at least one of the first and second working electrodes. In a further embodiment, the surface area of the reference and/or counter electrode is at least ten times the surface area of at least one of the first and second electrodes.

In preferred embodiments, the sensor is configured for implantation into the host. The sensor can be configured for subcutaneous implantation in the host's tissue (e.g., transcutaneous or wholly implantable). Alternatively, the sensor can be configured for indwelling in the host's blood stream (e.g., inserted through an intravascular catheter or integrally formed on the exterior surface of an intravascular catheter that is inserted into the host's blood stream).

In some embodiments, the sensor is a glucose sensor that has a first working electrode configured to generate a first signal associated with glucose (e.g., the analyte) and non-glucose related electroactive compounds (e.g., physiological baseline, interferents, and non-constant noise) having a first oxidation potential. For example, glucose has a first oxidation potential. The interferents have an oxidation potential that is substantially the same as the glucose oxidation potential (e.g., the first oxidation potential). In a further embodiment, the glucose sensor has a second working electrode that is configured to generate a second signal associated with noise of the glucose sensor. The noise of the glucose sensor is signal contribution due to non-glucose related electroactive compounds (e.g., interferents) that have an oxidation potential that substantially overlaps with the first oxidation potential (e.g., the oxidation potential of glucose, the analyte). In various embodiments, the non-glucose related electroactive species include an interfering species, non-reaction-related hydrogen peroxide, and/or other electroactive species.

In preferred embodiments, the glucose sensor has electronics that are operably connected to the first and second working electrodes and are configured to provide the first and second signals to generate glucose concentration data substantially without signal contribution due to non-glucose-related noise. For example, the sensor electronics analyze the signals from the first and second working electrodes and calculate the portion of the first electrode signal that is due to glucose concentration only. The portion of the first electrode signal that is not due to the glucose concentration can be considered to be background, such as but not limited to noise.

In preferred embodiments, the glucose sensor has a non-conductive material (e.g., insulative material) positioned between the first and second working electrodes. The non-conductive material substantially prevents cross talk between the first and second working electrodes. For example, the electrical signal cannot pass directly from a first insulated electrode to a second insulated electrode. Accordingly, the second insulated electrode cannot aberrantly record an electrical signal due to electrical signal transfer from the first insulated electrode.

In preferred embodiments, the first and second working electrodes and the non-conductive material integrally form at least a portion of the sensor (e.g., a glucose sensor). The first and second working electrodes integrally form a substantial portion of the sensor configured for insertion in the host (e.g., the in vivo portion of the sensor). In a further embodiment, the sensor (e.g., a glucose sensor) includes a reference electrode that, in addition to the first and second working electrodes, integrally forms a substantial portion of the sensor configured for insertion in the host (e.g., the in vivo portion of the sensor). In yet a further embodiment, the sensor (e.g., a glucose sensor) has an insulator (e.g., non-conductive material), wherein the first and second working electrodes and the insulator integrally form a substantial portion of the sensor configured for insertion in the host (e.g., the in vivo portion of the sensor).

In preferred embodiments, the sensor (e.g., a glucose sensor) includes a diffusion barrier configured to substantially block diffusion of the analyte (e.g., glucose) or a co-analyte (e.g., $H_2O_2$) between the first and second working electrodes. For example, as described with reference to FIG. 10, a diffusion barrier D (e.g., spatial, physical and/or temporal) blocks (e.g., attenuates) diffusion of a species (e.g., glucose and/or $H_2O_2$) from the first working electrode E1 to the second working electrode E2. In some embodiments, the diffusion barrier D is a physical diffusion barrier, such as a structure between the working electrodes that blocks glucose and $H_2O_2$ from diffusing from the first working electrode E1 to the second working electrode E2. In other embodiments, the diffusion barrier D is a spatial diffusion barrier, such as a distance between the working electrodes that blocks glucose and $H_2O_2$ from diffusing from the first working electrode E1 to the second working electrode E2. In still other embodiments, the diffusion barrier D is a temporal diffusion barrier, such as a period of time between the activity of the working electrodes such that if glucose or $H_2O_2$ diffuses from the first working electrode E1 to the second working electrode E2, the second working electrode E2 will not substantially be influenced by the $H_2O_2$ from the first working electrode E1.

With reference to FIG. 7H, if the diffusion barrier is spatial, a distance D separates the working electrodes, such that the analyte or co-analyte substantially cannot diffuse from a first electrode E1 to a second electrode E2. In some embodiments, the diffusion barrier is physical and configured from a material that substantially prevents diffusion of the analyte or co-analyte there through. Again referring to FIG. 7H, the insulator I and/or reference electrode R is configured from a material that the analyte or co-analyte cannot substantially pass through. For example, $H_2O_2$ cannot substantially pass through a silver/silver chloride reference electrode. In another example, a parylene insulator can prevent $H_2O_2$ diffusion between electrodes. In some embodiments, wherein the diffusion barrier is temporal, the two electrodes are activated at separate, non-overlapping times (e.g., pulsed). For example, the first electrode E1 can be activated for a period of one second, followed by activating the second electrode E2 three seconds later (e.g., after E1 has been inactivated) for a period of one second.

In additional embodiments, a component of the sensor is configured to provide both a diffusional barrier and a structural support, as discussed elsewhere herein. Namely, the diffusion barrier can be configured of a material that is sufficiently rigid to support the sensor's shape. In some embodiments, the diffusion barrier is an electrode, such as but not limited to the reference and counter electrodes (e.g., FIG. 7G to 7J and FIG. 8A). In other embodiments, the diffusion barrier is an insulating coating (e.g., parylene) on an electrode (e.g., FIG. 7K to 7L) or an insulating structure separating the electrodes (e.g., FIG. 8A and FIG. 10).

One preferred embodiment provides a glucose sensor configured for insertion into a host for measuring a glucose concentration in the host. The sensor includes a first working electrode configured to generate a first signal associated with glucose and non-glucose related electroactive compounds having a first oxidation potential. The sensor also includes a second working electrode configured to generate a second signal associated with noise of the glucose sensor comprising signal contribution due to non-glucose related electroactive compounds that have an oxidation potential that substantially overlaps with the first oxidation potential (e.g., the oxidation potential of $H_2O_2$). Additionally, the glucose sensor includes a non-conductive material located between the first and second working electrodes. Each of the first working electrode, the second working electrode, and the non-conductive material are configured to provide at least two functions selected from the group consisting of: electrical conductance, insulative properties, structural support, and diffusion barrier.

In some embodiments of the glucose sensor, each of the first working electrode and the second working electrode are configured to provide electrical conductance and structural support. For example, the metal plated wire of electrodes conducts electricity and helps maintain the sensor's shape. In a further embodiment, the glucose sensor includes a reference electrode that is configured to provide electrical conductance and structural support. For example, the silver/silver chloride reference electrode is both electrically conductive and supports the sensor's shape. In some embodiments of the glucose sensor includes a reference electrode that is configured to provide electrical conductance and a diffusion barrier. For example, the silver/silver chloride reference electrode can be configured as a large structure or protruding structure, which separates the working electrodes by the distance D (e.g., FIG. 7G). Distance "D" is sufficiently large that glucose and/or $H_2O_2$ cannot substantially diffuse around the reference electrode. Accordingly, $H_2O_2$ produced at a first working electrode does not substantially contribute to signal at a second working electrode. In some embodiments of the glucose sensor includes a reference electrode that is configured to provide a diffusion barrier and structural support. In some embodiments of the glucose sensor, the non-conductive material is configured to provide electrical insulative properties and structural support. For example, non-conductive dielectric materials can insulate an electrode and can be sufficiently rigid to stiffen the sensor. In still other embodiments, the non-conductive material is configured to provide electrical insulative properties and a diffusion barrier. For example, a substantially rigid, non-conductive dielectric can coat the electrodes and provide support, as shown in FIG. 7L. In other embodiments, the non-conductive material is configured to provide diffusion barrier and structural support. For example, a dielectric material can protrude between the electrodes, to act as a diffusion barrier and provide support to the sensor's shape, as shown in FIG. 10.

Noise Reduction

In another aspect, the sensor is configured to reduce noise, including non-constant non-analyte related noise with an overlapping measuring potential with the analyte. A variety of noise can occur when a sensor has been implanted in a host. Generally, implantable sensors measure a signal (e.g., counts) that generally comprises at least two components, the background signal (e.g., background noise) and the analyte signal. The background signal is composed substantially of signal contribution due to factors other than glucose (e.g., interfering species, non-reaction-related hydrogen peroxide, or other electroactive species with an oxidation potential that overlaps with the analyte or co-analyte). The analyte signal (e.g., glucose) is composed substantially of signal contribution due to the analyte. Consequently, because the signal includes these two components, a calibration is performed in order to determine the analyte (e.g., glucose) concentration by solving for the equation y=mx+b, where the value of b represents the background of the signal.

In some circumstances, the background is comprised of both constant (e.g., baseline) and non-constant (e.g., noise) factors. Generally, it is desirable to remove the background signal, to provide a more accurate analyte concentration to the host or health care professional.

The term "baseline" as used herein is a broad term, and is to be given its ordinary and customary meaning to a person of ordinary skill in the art (and is not to be limited to a special or customized meaning), and refers without limitation to a substantially constant signal derived from certain electroactive compounds found in the human body that are relatively constant (e.g., baseline of the host's physiology, non-analyte related). Therefore, baseline does not significantly adversely affect the accuracy of the calibration of the analyte concentration (e.g., baseline can be relatively constantly eliminated using the equation y=mx+b).

In contrast, "noise" as used herein is a broad term, and is to be given its ordinary and customary meaning to a person of ordinary skill in the art (and is not to be limited to a special or customized meaning), and refers without limitation to a substantially intermittent signal caused by relatively non-constant factors (e.g., the presence of intermittent noise-causing compounds that have an oxidation potential that substantially overlaps the oxidation potential of the analyte or co-analyte and arise due to the host's ingestion, metabolism, wound healing, and other mechanical, chemical and/or biochemical factors, also non-analyte related). Noise can be difficult to remove from the sensor signal by calibration using standard calibration equations (e.g., because the background of the signal does not remain constant). Noise can significantly adversely affect the accuracy of the calibration of the analyte signal. Additionally noise, as described herein, can occur in the signal of conventional sensors with electrode configurations that are not particularly designed to measure noise substantially equally at both active and in-active electrodes (e.g., wherein the electrodes are spaced and/or non symmetrical, noise may not be equally measured and therefore not easily removed using conventional dual electrode designs).

There are a variety of ways noise can be recognized and/or analyzed. In preferred embodiments, the sensor data stream is monitored, signal artifacts are detected, and data processing is based at least in part on whether or not a signal artifact has been detected, such as described in U.S. Patent Publication No. US-2005-0043598-A1 and co-pending U.S. application Ser. No. 11/503,367 filed Aug. 10, 2006 and entitled "ANALYTE SENSOR," herein incorporated by reference in its entirety.

Accordingly, if a sensor is designed such that the signal contribution due to baseline and noise can be removed, then more accurate analyte concentration data can be provided to the host or a healthcare professional.

One embodiment provides an analyte sensor (e.g., glucose sensor) configured for insertion into a host for measuring an analyte (e.g., glucose) in the host. The sensor includes a first working electrode disposed beneath an active enzymatic portion of a membrane on the sensor; a second working electrode disposed beneath an inactive- or non-enzymatic portion of the membrane on the sensor; and electronics operably connected to the first and second working electrode and configured to process the first and second signals to generate an analyte (e.g., glucose) concentration substantially without signal contribution due to non-glucose related noise artifacts.

Referring now to FIG. 9B, in another embodiment, the sensor has a first working electrode E1 and a second working electrode E2. The sensor includes a membrane system (not shown) covering the electrodes, as described elsewhere herein. A portion of the membrane system on the first electrode contains active enzyme, which is depicted schematically as oval 904a (e.g., active GOx). A portion of the membrane system on the second electrode is non-enzymatic or contains inactivated enzyme, which is depicted schematically as oval 904b (e.g., heat- or chemically-inactivated GOx or optionally no GOx). A portion of the sensor includes electrical connectors 804. In some embodiments, the connectors 804 are located on an ex vivo portion of the sensor. Each electrode (e.g., E1, E2, etc.) is connected to sensor electronics (not shown) by a connector 804. Since the first electrode E1 includes active GOx, it produces a first signal that is related to the concentration of the analyte (in this case glucose) in the host as well as other species that have an oxidation potential that overlaps with the oxidation potential of the analyte or co-analyte (e.g., non-glucose related noise artifacts, noise-causing compounds, background). Since the second electrode E2 includes inactive GOx, it produces a second signal that is not substantially related to the analyte or co-analyte. Instead, the second signal is substantially related to noise-causing compounds and other background noise. The sensor electronics process the first and second signals to generate an analyte concentration that is substantially free of the non-analyte related noise artifacts. Elimination or reduction of noise (e.g., non-constant background) is attributed at least in part to the configuration of the electrodes in the preferred embodiments, e.g., the locality of first and second working electrode, the symmetrical or opposing design of the first and second working electrodes, and/or the overall sizing and configuration of the exposed electroactive portions. Accordingly, the host is provided with improved analyte concentration data, upon which he can make medical treatment decisions (e.g., if he should eat, if he should take medication or the amount of medication he should take). Advantageously, in the case of glucose sensors, since the sensor can provide improved quality of data, the host can be maintained under tighter glucose control (e.g., about 80 mg/dl to about 120 mg/dl) with a reduced risk of hypoglycemia and hypoglycemia's immediate complications (e.g., coma or death). Additionally, the reduced risk of hypoglycemia makes it possible to avoid the long-term complications of hyperglycemia (e.g., kidney and heart disease, neuropathy, poor healing, loss of eye sight) by consistently maintaining tight glucose control (e.g., about 80 mg/dl to about 120 mg/dl).

In one embodiment, the sensor is configured to substantially eliminate (e.g., subtract out) noise due to mechanical factors. Mechanical factors include macro-motion of the sensor, micro-motion of the sensor, pressure on the sensor, local tissue stress, and the like. Since both working electrodes are constructed substantially symmetrically and identically, and due to the sensor's small size, the working electrodes are substantially equally affected by mechanical factors impinging upon the sensor. For example, if a build-up of noise-causing compounds occurs (e.g., due to the host pressing upon and manipulating (e.g., fiddling with) the sensor, for example) both working electrodes will measure the resulting noise to substantially the same extend, while only one working electrode (the first working electrode, for example) will also measure signal due to the analyte concentration in the host's body. The sensor then calculates the analyte signal (e.g., glucose-only signal) by removing the noise that was measured by the second working electrode from the total signal that was measured by the first working electrode.

Non-analyte related noise can also be caused by biochemical and/or chemical factors (e.g., compounds with electroactive acidic, amine or sulfhydryl groups, urea, lactic acid, phosphates, citrates, peroxides, amino acids (e.g., L-arginine), amino acid precursors or break-down products, nitric oxide (NO), NO-donors, NO-precursors or other electroactive species or metabolites produced during cell metabolism and/or wound healing). As with noise due to mechanical factors, noise due to biochemical/chemical factors will impinge upon the two working electrodes of the preferred embodiments (e.g., with and without active GOx) about the same extent, because of the sensor's small size and symmetrical configuration. Accordingly, the sensor electronics can use these data to calculate the glucose-only signal, as described elsewhere herein.

In one exemplary embodiment, the analyte sensor is a glucose sensor that measures a first signal associated with both glucose and non-glucose related electroactive compounds having a first oxidation potential. For example, the oxidation potential of the non-glucose related electroactive compounds substantially overlaps with the oxidation potential of $H_2O_2$, which is produced according to the reaction of glucose with GOx and subsequently transfers electrons to the first working electrode (e.g., E1; FIG. 10). The glucose sensor also measures a second signal, which is associated with background noise of the glucose sensor. The background noise is composed of signal contribution due to noise-causing compounds (e.g., interferents), non-reaction-related hydrogen peroxide, or other electroactive species with an oxidation potential that substantially overlaps with the oxidation potential of $H_2O_2$ (the co-analyte). The first and second working electrodes integrally form at least a portion of the sensor, such as but not limited to the in vivo portion of the sensor, as discussed elsewhere herein. Additionally, each of the first working electrode, the second working electrode, and a non-conductive material/insulator are configured provide at least two functions (to the sensor), such as but not limited to electrical conductance, insulative properties, structural support, and diffusion barrier (described elsewhere herein). Furthermore, the sensor has a diffusion barrier that substantially blocks (e.g., attenuates) diffusion of glucose or $H_2O_2$ between the first and second working electrodes.

Diffusion Barrier

Another aspect of the sensor is a diffusion barrier, to prevent an undesired species, such as $H_2O_2$ or the analyte, from diffusing between active (with active enzyme) and inactive (without active enzyme) electrodes. In various embodiments, the sensor includes a diffusion barrier configured to be physical, spatial, and/or temporal.

FIG. 10 is a schematic illustrating one embodiment of a sensor (e.g., a portion of the in vivo portion of the sensor, such as but not limited to the sensor electroactive surfaces) having one or more components that act as a diffusion barrier (e.g., prevent diffusion of electroactive species from one electrode to another). The first working electrode E1 is coated with an enzyme layer 1000 comprising active enzyme. For example, in a glucose sensor, the first working electrode E1 is coated with glucose oxidase enzyme (GOx). A second working electrode E2 is separated from the first working electrode E1 by a diffusion barrier D, such as but not limited to a physical diffusion barrier (e.g., either a reference electrode or a layer of non-conductive material/insulator). The diffusion barrier can also be spatial or temporal, as discussed elsewhere herein.

Glucose and oxygen diffuse into the enzyme layer 1000, where they react with GOx, to produce gluconate and $H_2O_2$. At least a portion of the $H_2O_2$ diffuses to the first working electrode E1, where it is electrochemically oxidized to oxygen and transfers two electrons (e.g., 2e$^-$) to the first working electrode E1, which results in a glucose signal that is recorded by the sensor electronics (not shown). The remaining $H_2O_2$ can diffuse to other locations in the enzyme layer or out of the enzyme layer (illustrated by the wavy arrows). Without a diffusion barrier D, a portion of the $H_2O_2$ can diffuse to the second working electrode E2, which results in an aberrant signal that can be recorded by the sensor electronics as a non-glucose related signal (e.g., background).

Preferred embodiments provide for a substantial diffusion barrier D between the first and second working electrodes (E1, E2) such that the $H_2O_2$ cannot substantially diffuse from the first working electrode E1 to the second working electrode E2. Accordingly, the possibility of an aberrant signal produced by $H_2O_2$ from the first working electrode E1 (at the second working electrode E2) is reduced or avoided.

In some alternative embodiments, the sensor is provided with a spatial diffusion barrier between electrodes (e.g., the working electrodes). For example, a spatial diffusion barrier can be created by separating the first and second working electrodes by a distance that is too great for the $H_2O_2$ to substantially diffuse between the working electrodes. In some embodiments, the spatial diffusion barrier is about 0.01, 0.02, 0.03, 0.04, 0.05, 0.06, 0.07, or 0.08 inches to about 0.09, 0.10, 0.11, or 0.120 inches. In other embodiments, the spatial diffusion barrier is about 0.020 inches to about 0.050 inches. Still in other embodiments, the spatial diffusion barrier is about 0.055 inches to about 0.095 inches. A reference electrode R (e.g., a silver or silver/silver chloride electrode) or a non-conductive material I (e.g., a polymer structure or coating such as Parylene) can be configured to act as a spatial diffusion barrier.

FIGS. 9A and 9B illustrate two exemplary embodiments of sensors with spatial diffusion barriers. In each embodiment, the sensor has two working electrodes E1 and E2. Each working electrode includes an electroactive surface, represented schematically as windows 904a and 904b, respectively. The sensor includes a membrane system (not shown). Over one electroactive surface (e.g., 904a) the membrane includes active enzyme (e.g., GOx). Over the second electroactive surface (e.g., 904b) the membrane does not include active enzyme. In some embodiments, the portion of the membrane covering the second electroactive surface contains inactivated enzyme (e.g., heat- or chemically-inactivated GOx) while in other embodiments, this portion of the membrane does not contain any enzyme (e.g., non-enzymatic). The electroactive surfaces 904a and 904b are separated by a spatial diffusion barrier that is substantially wide such that $H_2O_2$ produced at the first electroactive surface 904a cannot substantially affect the second electroactive surface 904b. In some alternative embodiments, the diffusion barrier can be physical (e.g., a structure separating the electroactive surfaces) or temporal (e.g., oscillating activity between the electroactive surfaces).

In another embodiment, the sensor is an indwelling sensor, such as configured for insertion into the host's circulatory system via a vein or an artery. In some exemplary embodiments, an indwelling sensor includes at least two working electrodes that are inserted into the host's blood stream through a catheter. The sensor includes at least a reference electrode that can be disposed either with the working electrodes or remotely from the working electrodes. The sensor includes a spatial, a physical, or a temporal diffusion barrier. A spatial diffusion barrier can be configured as described elsewhere herein, with reference to FIG. 7A through FIG. 8A.

FIG. 9B provides one exemplary embodiment of an indwelling analyte sensor, such as but not limited to an intravascular glucose sensor to be used from a few hours to ten days or longer. Namely, the sensor includes two working electrodes. One working electrode detects the glucose-related signal (due to active GOx applied to the electroactive surface) as well as non-glucose related signal. The other working electrode detects only the non-glucose related signal (because no active GOx is applied to its electroactive surface). $H_2O_2$ is produced on the working electrode with active GOx. If the $H_2O_2$ diffuses to the other working electrode (the no GOx electrode) an aberrant signal will be detected at this electrode, resulting in reduced sensor activity. Accordingly, it is desirable to separate the electroactive surfaces with a diffusion barrier, such as but not limited to a spatial diffusion barrier. Indwelling sensors are described in more detail in copending U.S. patent application Ser. No. 11/543,396 filed on even date herewith and entitled "ANALYTE SENSOR," herein incorporated in its entirety by reference.

To configure a spatial diffusion barrier between the working electrodes, the location of the active enzyme (e.g., GOx) is dependent upon the orientation of the sensor after insertion into the host's artery or vein. For example, in an embodiment configured for insertion upstream in the host's blood flow (e.g., against the blood flow), active GOx would be applied to electroactive surface 904b and inactive GOX (or no GOx) would be applied to electroactive surface 904a (e.g., upstream from 904b, relative to the direction of blood flow). Due to this configuration, $H_2O_2$ produced at electroactive surface 904b would be carrier down stream (e.g., away from electroactive surface 904a) and thus not affect electrode E1.

Alternatively, the indwelling electrode can also be configured for insertion of the sensor into the host's vein or artery in the direction of the blood flow (e.g., pointing downstream). In this configuration, referred to as a spatial diffusion barrier, or as a flow path diffusion barrier, the active GOx can be advantageously applied to electroactive surface 904a on the first working electrode E1. The electroactive surface 904b on the second working electrode E2 has no active GOx. Accordingly, $H_2O_2$ produced at electroactive surface 904a is carried away by the blood flow, and has no substantial effect on the second working electrode E2.

In another embodiment of an indwelling analyte sensor, the reference electrode, which is generally configured of silver/silver chloride, can extend beyond the working electrodes, to provide a physical barrier around which the $H_2O_2$ generated at the electrode comprising active GOx cannot pass the other working electrode (that has active GOx). In some embodiments, the reference electrode has a surface area that is at least six times larger than the surface area of the working electrodes. In other embodiments, a 2-working electrode analyte sensor includes a counter electrode in addition to the reference electrode. As is generally know in the art, the inclusion of the counter electrode allows for a reduction in the reference electrode's surface area, and thereby allows for further miniaturization of the sensor (e.g., reduction in the sensor's diameter and/or length, etc.).

FIG. 7H provides one exemplary embodiment of a spatial diffusion barrier, wherein the reference electrode/non-conductive insulating material R/I is sized and shaped such that $H_2O_2$ produced at the first working electrode E1 (e.g., with enzyme) does not substantially diffuse around the reference electrode/non-conductive material R/I to the second working electrode E2 (e.g., without enzyme). In another example, shown in FIG. 7J, the X-shaped the reference electrode/non-conductive material R/I substantially prevents diffusion of electroactive species from the first working electrode E1 (e.g., with enzyme) to the second working electrode E2 (e.g., without enzyme). In another embodiment, such as the sensor shown in FIG. 7A, the layer of non-conductive material I (between the electrodes) is of a sufficient length that the $H_2O_2$ produced at one electrode cannot substantially diffuse to another electrode. (e.g., from E1 to either E2 or E3; or from E2 to either E1 or E3, etc.).

In some embodiments, a physical diffusion barrier is provided by a physical structure, such as an electrode, insulator, and/or membrane. For example, in the embodiments shown in FIGS. 7G to 7J, the insulator (I) or reference electrode (R) act as a diffusion barrier. As another example, the diffusion barrier can be a bioprotective membrane (e.g., a membrane that substantially resists, attenuates or blocks the transport of a species (e.g., hydrogen peroxide), such as a polyurethane. As yet another example, the diffusion barrier can be a resistance domain, as described in more detail elsewhere herein; namely, a semipermeable membrane that controls the flux of oxygen and an analyte (e.g., glucose) to the underlying enzyme domain. Numerous other structures and membranes can function as a physical diffusion barrier as is appreciated by one skilled in the art.

In other embodiments, a temporal diffusion barrier is provided (e.g., between the working electrodes). By temporal diffusion barrier is meant a period of time that substantially prevents an electroactive species (e.g., $H_2O_2$) from diffusing from a first working electrode to a second working electrode. For example, in some embodiments, the differential measurement can be obtained by switching the bias potential of each electrode between the measurement potential and a non-measurement potential. The bias potentials can be held at each respective setting (e.g., high and low bias settings) for as short as milliseconds to as long as minutes or hours. Pulsed amperometric detection (PED) is one method of quickly switching voltages, such as described in Bisenberger, M.; Brauchle, C.; Hampp, N. A triple-step potential waveform at enzyme multisensors with thick-film gold electrodes for detection of glucose and sucrose. Sensors and Actuators 1995, B, 181-189, which is incorporated herein by reference in its entirety. In some embodiments, bias potential settings are held long enough to allow equilibration.

One preferred embodiment provides a glucose sensor configured for insertion into a host for measuring glucose in the host. The sensor includes first and second working electrodes and an insulator located between the first and second working electrodes. The first working electrode is disposed beneath an active enzymatic portion of a membrane on the sensor and the second working electrode is disposed beneath an inactive- or non-enzymatic portion of the membrane on the sensor. The sensor also includes a diffusion barrier configured to substantially block (e.g., attenuate, restrict, suppress) diffusion of glucose or hydrogen peroxide between the first and second working electrodes.

In a further embodiment, the glucose sensor includes a reference electrode configured integrally with the first and second working electrodes. In some embodiments, the reference electrode can be located remotely from the sensor, as described elsewhere herein. In some embodiments, the surface area of the reference electrode is at least six times the surface area of the working electrodes. In some embodiments, the sensor includes a counter electrode that is integral to the sensor or is located remote from the sensor, as described elsewhere herein.

In a further embodiment, the glucose sensor detects a first signal associated with glucose and non-glucose related electroactive compounds having a first oxidation potential (e.g., the oxidation potential of $H_2O_2$). In some embodiments, the glucose sensor also detects a second signal is associated with background noise of the glucose sensor comprising signal contribution due to interfering species, non-reaction-related hydrogen peroxide, or other electroactive species with an oxidation potential that substantially overlaps with the oxidation potential of hydrogen peroxide; the first and second working electrodes integrally form at least a portion of the sensor; and each of the first working electrode, the second working electrode and the non-conductive material/insulator are configured provide at least two functions such as but not limited to electrical conductance, insulation, structural support, and a diffusion barrier In further embodiments, the glucose sensor includes electronics operably connected to the first and second working electrodes. The electronics are configured to calculate at least one analyte sensor data point using the first and second signals described above. In still another further embodiment, the electronics are operably connected to the first and second working electrode and are configured to process the first and second signals to generate a glucose concentration substantially without signal contribution due to non-glucose noise artifacts.

Membrane Configurations

Figure 3A:
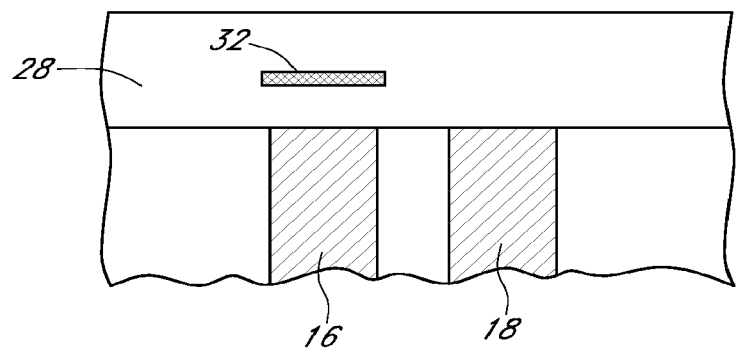
FIG. 3A which is a cross-sectional exploded schematic view of a sensing region of a continuous glucose sensor in one embodiment wherein an active enzyme of an enzyme domain is positioned only over the glucose-measuring working electrode.
Figure 3B:
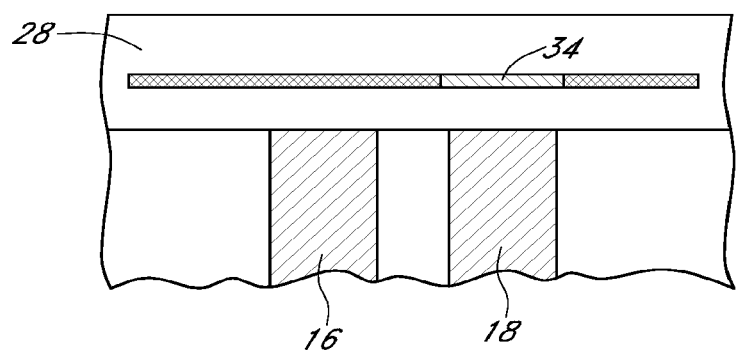
FIG. 3B is a cross-sectional exploded schematic view of a sensing region of a continuous glucose sensor in another embodiment, wherein an active portion of the enzyme within the enzyme domain positioned over the auxiliary working electrode has been deactivated.

FIGS. 3A to 3B are cross-sectional exploded schematic views of the sensing region of a glucose sensor 10, which show architectures of the membrane system 22 disposed over electroactive surfaces of glucose sensors in some embodiments. In the illustrated embodiments of FIGS. 3A and 3B, the membrane system 22 is positioned at least over the glucose-measuring working electrode 16 and the optional auxiliary working electrode 18; however the membrane system may be positioned over the reference and/or counter electrodes 20, 22 in some embodiments.

Reference is now made to FIG. 3A, which is a cross-sectional exploded schematic view of the sensing region in one embodiment wherein an active enzyme 32 of the enzyme domain is positioned only over the glucose-measuring working electrode 16. In this embodiment, the membrane system is formed such that the glucose oxidase 32 only exists above the glucose-measuring working electrode 16. In one embodiment, during the preparation of the membrane system 22, the enzyme domain coating solution can be applied as a circular region similar to the diameter of the glucose-measuring working electrode 16. This fabrication can be accomplished in a variety of ways such as screen-printing or pad printing. Preferably, the enzyme domain is pad printed during the enzyme domain fabrication with equipment as available from Pad Print Machinery of Vermont (Manchester, Vt.). This embodiment provides the active enzyme 32 above the glucose-measuring working electrode 16 only, so that the glucose-measuring working electrode 16 (and not the auxiliary working electrode 18) measures glucose concentration. Additionally, this embodiment provides an added advantage of eliminating the consumption of $O_2$ above the counter electrode (if applicable) by the oxidation of glucose with glucose oxidase.

FIG. 3B is a cross-sectional exploded schematic view of a sensing region of the preferred embodiments, and wherein the portion of the active enzyme within the membrane system 22 positioned over the auxiliary working electrode 18 has been deactivated 34. In one alternative embodiment, the enzyme of the membrane system 22 may be deactivated 34 everywhere except for the area covering the glucose-measuring working electrode 16 or may be selectively deactivated only over certain areas (for example, auxiliary working electrode 18, counter electrode 22, and/or reference electrode 20) by irradiation, heat, proteolysis, solvent, or the like. In such a case, a mask (for example, such as those used for photolithography) can be placed above the membrane that covers the glucose-measuring working electrode 16. In this way, exposure of the masked membrane to ultraviolet light deactivates the glucose oxidase in all regions except that covered by the mask.

In some alternative embodiments, the membrane system is disposed on the surface of the electrode(s) using known deposition techniques. The electrode-exposed surfaces can be inset within the sensor body, planar with the sensor body, or extending from the sensor body. Although some examples of membrane systems have been provided above, the concepts described herein can be applied to numerous known architectures not described herein.

Sensor Configurations for Equivalent Measurement of Noise Signals at the Two Working Electrodes In dual electrode biosensors (e.g., an analyte sensor having two working electrodes E1, E2), noise can be caused by a variety of sources, for example, located outside (e.g., by noise-causing species produced metabolically and/or consumed by the host) or within (e.g., crosstalk) the sensor. In some circumstances, biological and/or metabolic processes occurring in the host's body, such as in the locale of the implanted sensor, can cause noise. These metabolic processes, such as but not limited to wound healing, the body's response to illness and even daily cellular metabolic processes, can generate noise-causing metabolic species (e.g., compounds, substances) that impinge upon the sensor and cause noise on the signal. For example, some noise-causing species, the levels of which are relatively stable due to production during daily cellular metabolism, generally cause constant noise. In another example, some noise-causing species, the levels of which fluctuate due to production by intermittent metabolic process (e.g., wound healing or response to infection), generally cause non-constant noise. Noise-causing metabolic species include but are not limited to externally generated $H_2O_2$ (e.g., produced outside the sensor), compounds having electroactive acidic, amine or sulfhydryl groups, urea, lactic acid, phosphates, citrates, peroxides, amino acids (e.g., L-arginine), amino acid precursors or break-down products, nitric oxide (NO), NO-donors, NO-precursors, reactive oxygen species or other electroactive species or metabolites produced during cell metabolism and/or wound healing, for example. Noise-causing species, such as drugs, vitamins and the like, can also be consumed by the host. These noise causing species include but not limited to acetaminophen, ascorbic acid, dopamine, ephedrine, ibuprofen, L-dopa, methyldopa, salicylate, tetracycline, tolazamide, tolbutamide and triglycerides. Further discussion of noise and its sources can be found in U.S. Patent Publication No. US-2007-0027370-A1 and co-pending U.S. patent application Ser. No. 11/750,907, filed on May 18, 2007 and entitled "ANALYTE SENSORS HAVING AN OPTIMIZED SIGNAL-TO-NOISE RATIO", both of which are incorporated herein by reference in their entirety.

In dual-electrode sensors, noise can also be generated within the sensor, namely due to diffusion of a measured species (e.g., $H_2O_2$) from a first working electrode (e.g., the $H_2O_2$ is generated in an active enzymatic portion of the sensor membrane associated with the first working electrode) to a second working electrode and detection thereby (e.g., which is associated with a non-enzymatic portion of the sensor membrane). This type of noise is commonly referred to as "crosstalk." Crosstalk is undesirable as it causes sensor error, which can result in inaccurate reporting of sensor data. In conventional sensors, a common solution to the problem of crosstalk is to space the two working electrodes far enough apart that a measured species diffusing from one working electrode cannot reach the other working electrode; unfortunately, such spacing does not enable substantially equivalent measurement of noise-cause species, as discussed in more detail elsewhere herein. Unlike conventional sensors, the sensors of the preferred embodiments ensure accurate subtraction of noise signal by ensuring substantially equivalent measurement of the noise (e.g., noise component, constant and/or non-constant noise components) detected by the two working electrodes.

Depending upon the scale (e.g., point) of reference, noise has a dual nature. On a larger scale, with respect to the in vivo portion of the sensor and the surrounding tissue, noise occurs randomly (e.g., is scattered, intermittent, dispersed, unevenly distributed) in the local of an implanted sensor. Yet, on a smaller scale, such as that of a few cells (e.g., 100-300 microns), noise is a localized phenomenon because it creates hot spots of noise-causing species generation whose effects extend about a thousandths of an inch (e.g., localized nature, character). A "hot spot" of noise generation is referred to herein as a "point source." A point source (e.g., a localized hot spot for noise generation) can be a cell or a group of cells adjacent to the sensor membrane, or a noise-causing species (e.g., compound, substance, molecule) that diffused to the location of sensor implantation, such as by diffusion between cells (e.g., to the sensor). For example, in the circumstance of a single point source in contact with the sensor membrane's surface, noise is a local phenomenon, because the noise-causing species' ability to affect adjacent structures is limited by the maximum distance it can diffuse (e.g., through the membrane), which is generally very short (e.g., a few microns, such as between about 1-µm to about 500-µm). Due to the random yet localized nature of noise, the configuration of the electroactive surfaces (of the working electrodes) can substantially affect noise measurement. With respect to the configuration and arrangement (e.g., surface area) of the dual-electrode sensor's electroactive surfaces, the random yet localized nature of noise is discussed in greater detail below.

Figure 16:
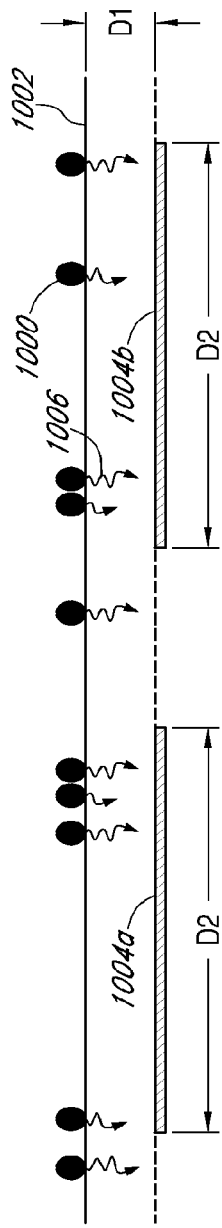
FIG. 16 is a two-dimensional schematic of a dual-electrode sensor in one embodiment, illustrating the sensor's first and second electroactive surfaces (of the first and second working electrodes, respectively) beneath a sensor membrane, wherein noise-causing species produced by a plurality of point sources can impinge upon an electroactive surface.

FIG. 16 is a two-dimensional schematic illustrating, on the scale of a sensor and the surrounding tissue (e.g., a generally larger scale), the random nature of noise relative to a dual-electrode sensor, in one exemplary embodiment. This figure is for illustrative purposes only, and should not be considered as a to-scale representation of a particular sensor configuration or of the events discussed herein. In the embodiment shown in FIG. 16, the dual electrode analyte sensor includes two electroactive surfaces 1004a, 1004b disposed beneath the sensor's membrane. While FIG. 16 illustrates only one dimension of the electroactive surfaces, in some embodiments, the electroactive surfaces (e.g., the surface area of each electroactive surface) can include both a length and a width. In some embodiments, the area can include additional dimensions, such as a circumference and/or a height. In some embodiments, the sensor can have a planar configuration. In some embodiments, the sensor can have a cylindrical, pyramidal, polygonal configuration. It should also be understood that the electroactive surfaces 1004a, 1004b are shown as boxes as a matter of illustrative convenience; however, electroactive surfaces can be thinner or thicker than illustrated in FIG. 16 or elsewhere herein. The membrane has a thickness D1 and a surface 1002. Depending upon the membrane configuration, fabrication methods and/or materials, D1 can vary in size, from less than about 0.001, 0.002, 0.003, 0.004, 0.005, 0.006, 0.007, 0.008, 0.009, or 0.010 inches to more than about 0.011, 0.012, 0.013, 0.014, 0.015, 0.015, 0.016, 0.017, 0.018, 0.019, 0.020, 0.025, 0.03, 0.035, or 0.050 inches. In some embodiments, a preferred membrane thickness is between about 0.001, 0.0012, 0.0014, 0.0016, or 0.0018 inches to about 0.002, 0.0022, 0.0024, 0.0026, 0.0028, or 0.003 inches. Noise-causing species (represented by squiggly arrows 1006) can be generated by and/or at point sources 1000 (e.g., noise hot spots) unevenly distributed relative the in vivo portion of the sensor. For example, some of the point sources 1000 (shown in FIG. 16) are concentrated at one end of electroactive surface 1004a, while some are distributed more evenly across electroactive surface 1004b. In some circumstances, the point source may be one or more cells (e.g., in contact with the membrane surface 1002) that release the noise-causing species during wound healing or another metabolic process, such as when a sensor is implanted in vivo. In some circumstances, the implanted sensor can be located within the diffusion distance of one or more noise-causing species produced during a nearby metabolic process. In some circumstances, the noise-causing species (e.g., a compound consumed by the host) can be carried to the local of the sensor via the circulatory and/or lymph system and diffuse to the sensor (e.g., between cells).

Random and/or unequally distributed noise can be generated in a variety of circumstances. For example, a peroxide-generating immune cell could be located adjacent to one electroactive surface but not the other. In general, a noise-causing species must be generated and/or occur close enough to the sensor membrane such that it can diffuse to (and through) the membrane, to the electroactive surfaces, and affect the sensor signal. If the noise-causing species is generated farther away from the membrane than the diffusion distance of the noise-causing species, then the noise-causing species may be unable to reach the electroactive surfaces, and therefore may have little effect on sensor signal. For example, $H_2O_2$ (produced by metabolic process when the sensor is implanted in a host) must be generated sufficiently close to the membrane for it to diffuse to the membrane and affect sensor function. The maximum distance that the noise-causing species can diffuse (e.g., from the cell to the membrane, from one working electrode to another working electrode) and still substantially affect sensor function is referred to herein as a "diffusion distance."

The sensor electronics are configured to mathematically correct for noise on the sensor signal (e.g., such as by subtraction of the noise signal, applying a filter, averaging, or other calculations), such that a substantially analyte-only signal can be presented to the user. The inventors have discovered that successful mathematical correction of noise on the sensor signal can be substantially affected by the equivalence (e.g., similarity) of the noise signals detected by the two working electrodes. If the detected noise signals are substantially equivalent (e.g., similar amounts, amplitudes, levels, relatively equal), then the calculations will be produce a more accurate resultant analyte signal. If, on the other hand, the detected noise signals are not substantially equal (e.g., have very different amplitudes and/or wave forms), then the calculations will have a greater degree of error. While not wishing to be bound by theory, it is believed that presentation of more accurate sensor data (e.g., to the host) will improve the host's management of his diabetes, which will prevent the immediate risks of hypoglycemia (e.g., loss of consciousness and death) and postpone and/or prevent long term diabetes complications (blindness, loss of limb, kidney dysfunction, and the like). Additionally, the increased accuracy afforded by the sensors of the preferred embodiment increases the feasibility of insulin dosing and/or an artificial pancreas system based on a continuous glucose sensor.

In order to compensate for the unevenly distributed nature of noise (e.g., the point sources are randomly and/or non-equally and/or non-equivalently distributed relative to the in vivo portion of the sensor) and thereby render the noise components equivalent, a continuous dual electrode glucose sensor having sufficiently large electroactive surfaces, such that the noise components can be substantially equalized (e.g., made and/or become equivalent) by integration there across, is provided in one embodiment. The first working electrode includes a first electroactive surface (1004a, FIG. 16) disposed beneath an active enzymatic portion (e.g., plus-GOx) of the sensor's membrane, as described elsewhere herein. The first electroactive surface includes a first area (e.g., first electroactive surface area) configured to detect a first signal (e.g., including an analyte-related component and a noise component) having a first noise component related to a noise-causing species. The sensor also includes a second working electrode having a second electroactive surface (1004b, FIG. 16) disposed beneath an inactive-enzymatic or a non-enzymatic portion of the sensor membrane, as described elsewhere herein. For example, an inactive-enzymatic portion of the membrane can include inactivated GOx or no GOx. The second electroactive surface includes a second area (e.g., second electroactive surface area) configured to generate a second signal having a second noise component related to the noise-causing species. In preferred embodiments, the first and second areas are dimensioned (e.g., sized) to be sufficiently large such that the first and second noise components integrated there across, such that the first and second integrated noise signals (e.g., from the first and second electroactive surfaces, respectively) are substantially equivalent. In some embodiments, the first and second integrated noise signals (e.g., noise components) are within 20% of each other (e.g., plus or minus 10%). In some embodiments, the first and second electroactive surfaces are dimensioned to integrate noise caused by a plurality of local point sources that produce noise-causing species in vivo.

Due to the random nature of noise, the configuration and/or arrangement of the first and second electroactive surfaces 1004a, 1004b can substantially affect the equivalence of the noise measured, the areas of the electroactive surfaces are dimensioned (e.g., sized, shaped) to be sufficiently large such that the noise detected at (e.g., across, along, and the like) each electroactive surface can be integrated. While not wishing to be bound by theory, it is believed that integration of noise across a sufficiently large area (e.g., surface area of an electroactive surface) ensures that, even though noise-causing species 1006 affect each electroactive surface unevenly (e.g., local hot spots 1000 for noise-causing species generation are intermittently distributed across the area of each electroactive surface), a sufficient amount of signal is detected at each electroactive surface, such that the first and second noise components caused by noise-causing species are substantially equivalent. Accordingly, in some embodiments, the first and second areas are each configured and arranged to integrate the signal caused by a plurality of local point sources 1000 that produce noise-causing species 1006, when the sensor is implanted in a host. In other words, each electroactive surface includes a sufficiently large area (e.g., in at least one dimension, such as but not limited to D2), such that the detected noise signals (e.g., noise components) can be integrated (e.g., averaged), such that the amount of the two noise components are substantially equivalent. In some embodiments, the areas are dimensioned such that noise signals integrated there across are equivalent by at least 40% (e.g., within plus or minus 20% of each other). In more preferred embodiment, the integrated signals are equivalent by at least 20% (e.g., within plus or minus 10% of each other). In a more preferred embodiment, the integrated signals are equivalent by at least 10% (e.g., within plus or minus 5% of each other).

In preferred embodiments, at least one dimension of each of the first and second areas is greater than the sum of the diameters of from about 10 to about 500 (or more) average human cells (e.g., the sum of the diameters of the cells). The diameter of an average human cell is about 20 μm to about 160 μm. Thus, in some embodiments, the at least one dimension (e.g., D2) of each of the first and second electroactive surface areas is greater than between about 200 μm to about 10,000 μm. In some embodiments, if an average human cell has a diameter of about 20 μm, the at least one dimension is greater than the sum of the diameters (e.g., total diameter) of about 15, 20, 25, 30, 35, 40, 45, 50, 55, 60, 65, 70, 75, 80, 85, 90, or 95 average human cells, such as greater than about 300-μm, 400-μm, 500-μm, 600-μm, 700-μm, 800-μm, 900-μm, 1000-μm, 1200-μm, 1300-μm, 1400-μm, 1500-μm, 1600-μm, 1700-μm, 1800-μm, or 1900-μm in at least one dimension. In some embodiments, if an average human cell has a diameter of about 160 μm, the at least one dimension is greater than the sum of the diameters (e.g., total diameter) of about 15, 20, 25, 30, 35, 40, 45, 50, 55, 60, 65, 70, 75, 80, 85, 90, or 95 average human cells, such as greater than about 2400-μm, 3200-μm, 4000-μm, 4800-μm, 5600-μm, 6400-μm, 7200-μm, 8000-μm, 8800-μm, 9600-μm, 10400-μm, 11200-μm, 12000-μm, 12800-μm, 13600-μm, or 14400-μm in at least one dimension. In some embodiments, the dimension is greater than the sum of the diameters of about 110 to 500 average human cells, or more.

In some embodiments, the first and second areas (e.g., of the electroactive surfaces) are also configured and arranged to integrate signals detected about a circumference of the sensor. For example, in some embodiments, the dual electrode sensor is fabricated of cylindrical wires, each of which includes a circumference. Accordingly, the electroactive surfaces can be disposed about a wire's circumference. In one exemplary embodiment, the two working electrodes can be twisted to share a common axis. As a result, in addition to extending along the sensor's length and/or width and/or about each wire's circumference, the electroactive surfaces extend around at least a portion of the sensor's circumference, and noise (e.g., from one or more point sources producing noise-causing species) can impinge upon the sensor about that circumference. Thus, noise impinging upon the sensor about a circumference can be integrated.

Figure 17:
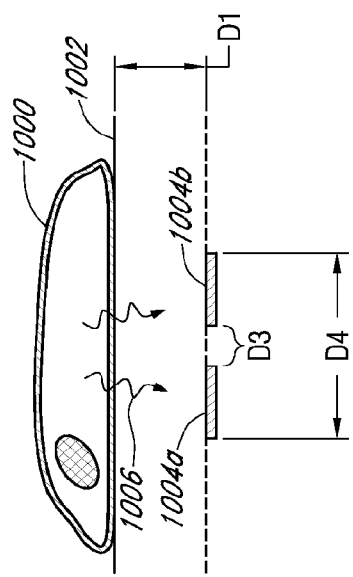
FIG. 17 is a two-dimensional schematic of a dual-electrode sensor in one embodiment, illustrating the sensor's first and second electroactive surfaces (of the first and second working electrodes, respectively) beneath a sensor membrane, wherein noise from a single point source (e.g., a cell) can impinge upon both electroactive surfaces.

FIG. 17 is a two-dimensional schematic illustrating the localized character of noise species (represented by squiggly arrows 1006) generated by a point source 1000, when examined from a cellular scale, as discussed elsewhere herein. FIG. 17 depicts a cross-section of a sensor, in one embodiment, wherein the sensor includes two working electrodes having electroactive surfaces 1004*a* and 1004*b*, and a membrane having surface 1002 and thickness D1. Distance D3 separates the electroactive surfaces; the distance between their outer edges is denoted by D4. Note that dimension D2, described above, is not shown in this figure. The sensor of this exemplary embodiment can have a variety of configurations, such as but not limited to planar, cylindrical or polygonal. Accordingly, the dimensions of an electroactive surface's surface area (referred to as "area" herein) can include but is not limited to length, width, height, and/or circumference. For example, in some embodiments, the area of each electroactive surface is defined by a length and a width. In some embodiments, the area includes a length or width and a circumference. In some embodiments, the area includes length, width and height. Additionally, it is know to one skilled in the art that, in some circumstances, differences in signal amplitude and/or sensitivity (e.g., from the two working electrodes), due to differences in electrode sizes (or some differences in compositions of membranes) can be corrected (adjusted, compensated for, calibrated out) mathematically. For example, if a first electroactive surface is two times as large as the second electroactive surface, then the signal from the second electroactive surface can be multiplied by two, such that the sensitivities are substantially similar.

Referring now to FIG. 17, in this exemplary circumstance the point source (e.g., noise hot spot) is an individual cell 1000 disposed adjacent to the membrane surface 1002 and generally above and/or over the sensor's electroactive surfaces 1004*a*, 1004*b*. The cell can produce noise-causing substances (e.g., 1006) that can diffuse to and affect its local environment. In general, the ability of a noise-causing substance to affect the local environment is limited by the maximum distance the substance can diffuse (e.g., the substance's diffusion distance). In some circumstances, some of the noise-causing substances can diffuse through the sensor membrane and affect the sensor's electroactive surfaces. While not wishing to be bound by theory, the inventors have found that in order for the two electroactive surfaces to be substantially equivalently affected by the noise 1006 from a point source, such as a cell, the electroactive surfaces must be affected by substantially the same microenvironment. In various circumstances, the electroactive surfaces will be affected by substantially the same microenvironment, if the electroactive surfaces are configured and arranged such that the electroactive surfaces are sufficiently close together and/or their external edges are sufficiently close together.

FIG. 17 shows that the sensor's electroactive surfaces 1004*a*, 1004*b* are separated by a distance D3 and their outer edges are spaced a distance D4 (e.g., in at least one dimension), in one exemplary embodiment. In this example, a point source 1000 (e.g., a cell) of noise-causing species 1006 is adjacent to the membrane's surface 1002. If the electroactive surfaces are configured and arranged such that D3 is sufficiently small, then the noise-causing species diffusing from the point source can impinge equivalently on both of the electroactive surfaces. Additionally or alternatively, if D4 is sufficiently small (e.g., the electroactive surfaces are sufficiently narrow in at least one dimension), then the noise-causing species diffusing from the point source can impinge equivalently on both of the electroactive surfaces. Accordingly, in preferred embodiments, the electroactive surfaces are spaced a distance (e.g., relative to each other, D3) such that the electroactive surfaces (e.g., at least a portion of each electroactive surface) detect substantially equivalent noise from a point source. In some embodiments, the electroactive surfaces are sufficiently close together (e.g., such that the noise components measured are substantially equal) when the distance between the electroactive surfaces (D3) is between about 0.5-times to about 10-times (or more) the membrane thickness (D1). In some preferred embodiments, the electroactive surfaces are sufficiently close together when D3 is about 2-, 3-, 4-, 5-, 6-, 7-, 8-, or 9-times the membrane thickness. In some embodiments, D3 is between about 5, 10, 15, 20, 25, 30, 35, 40, 45, or 50 microns or less to about 55, 60, 65, 70, 75, 80, 85, 90, 95, or 100 microns or more. In preferred embodiments, D3 is between about 20 to about 40 microns. In some embodiments, D4 is between about 25 microns or less to about 500 microns or more.

Depending upon the sensor's configuration, in some embodiments, D4 can be the distance between the outer edges of the electroactive surfaces, or D4 can be a distance equivalent to the maximum diameter of the bundles and/or twisted pair of working electrodes. For example, FIG. 17 illustrates a cross-section of a sensor (e.g., width and height), but doesn't illustrate any additional dimensions (e.g., length). The cross-section could be that of a planar sensor configuration, wherein the sensor also includes an additional dimension that has not been shown, such as but not limited to D2. In some circumstances, the sensor can have a non-planar configuration. For example, in the embodiment shown in FIG. 18, the working electrodes E1, E2 are fabricated from two wires. Since the wires are cylindrical, the electroactive surfaces do not include outer edges. In this exemplary circumstance, D4 is the total diameter of the bundled and/or twisted working electrodes. In both types of sensor configurations (e.g., planar and non-planar), if D4 is sufficiently small, then the two working electrodes can be equivalently affected by noise-causing species 1006 derived from a point source 1000.

As described above, dual electrode sensors can be affected by internally generated noise (e.g., generated by the sensor). The inventors have found that, in general, when D3 is sized to be sufficiently small such that the electroactive surfaces are equivalently affect by noise from an adjacent point source, the electroactive surfaces are also close enough together that crosstalk (an internally generated noise) can occur. In general, crosstalk is detection of an analyte signal generated at the plus-GOx working electrode (wherein the electrode includes the membrane portion thereon) by the minus-GOx working electrode (including the No GOx membrane portion thereon). For example, when the measured species is $H_2O_2$, crosstalk occurs when the $H_2O_2$ diffuses from the plus-GOx enzyme domain to the No GOx working electrode and is detected (e.g., a signal is generated on the No GOx electrode). In general, crosstalk is undesirable as it causes sensor error. However, in order for the two working electrodes to measure equivalent noise signals from a point source 1000, the electroactive surfaces must be spaced very close together. Accordingly, in preferred embodiments, this distance (D3) is less than a crosstalk diffusion distance of the measured species. In other words, D3 is shorter than the diffusion distance of $H_2O_2$ (e.g., the maximum distance $H_2O_2$ can diffuse from a first electrode to a second and still cause a signal on the second electrode).

In conventional dual-electrode sensors, spacing the electroactive surfaces within the crosstalk diffusion distance of the measured species is generally undesirable due to increased sensor error. However, in preferred embodiments, the sensor includes a physical diffusion barrier configured to attenuate crosstalk by physically blocking (e.g., suppressing, blocking, restricting) some of the crosstalk from the active enzymatic portion of the sensor membrane to the second electroactive surface. More preferably, the physical diffusion barrier is configured and arranged to attenuate and/or physically block a substantial amount of the measurable species (e.g., $H_2O_2$) diffusing from the active enzymatic portion of the membrane to the second electroactive surface, such that there is substantially no signal associated with crosstalk measured at the second working electrode.

Figure 18:
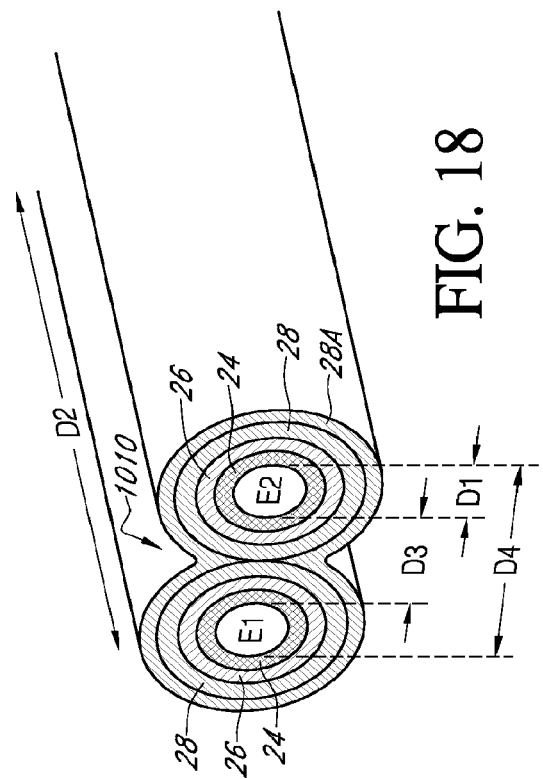
FIG. 18 is a cross-sectional schematic illustrating a dual electrode sensor, in one embodiment, including a physical diffusion barrier.

FIG. 18 is a schematic illustrating a perspective view of a cross-section of a dual electrode sensor that includes a physical diffusion barrier 1010, in one exemplary embodiment. In this embodiment, wires form the working electrodes E1, E2. The working electrodes each include a membrane, including an electrode domain 24, an enzyme domain 26 and a resistance domain 28. For example, E1 includes a first electrode domain, a first enzyme domain (Plus GOx) and a first resistance domain, and E2 includes a second electrode domain, a second enzyme domain (No GOx) and a second resistance domain. In this particular exemplary embodiment, the electrodes are placed together and coated with an additional resistance domain 28A (e.g., a third resistance domain). Depending upon the circumstances, the electrodes can be placed and/or held together using a variety of methods, such as bundling, twisting, wrapping, and the like, either alone or in combination. The distances shown are as follows; a thickness of the membrane D1, at least one dimension of the electroactive surface D2, a distance between the electroactive surfaces D3, and a distance between the outer edges of the electroactive surfaces D4. In the illustrated exemplary embodiment, the first and second electroactive surfaces extend about the circumferences of E1 and E2 (or portions thereof), respectively.

In preferred embodiments, the physical diffusion barrier 1010 is disposed between the electroactive surfaces of working electrodes E1 and E2. In some embodiments, the physical diffusion barrier is formed of one or more membrane materials, such as those used in formation of an interference domain and/or a resistance domain. Such materials include but are not limited to silicones, polyurethanes, cellulose derivatives (cellulose butyrates and cellulose acetates, and the like) and combinations thereof, as described elsewhere herein. In some embodiments, the physical diffusion barrier includes one or more membrane domains. For example, in the exemplary embodiment of FIG. 18, the physical diffusion barrier is a discontinuous portion of the membrane (e.g., separate, distinct or discontinuous membrane structures) disposed between the first and second electroactive surfaces, and can include one or more membrane portion(s) within distance D3 (e.g., interference and/or resistance domains). For example, in some embodiments, $H_2O_2$ diffusing from the Plus GOX working electrode to the No GOx working electrode must pass through two "sensor membranes" such as the first and second resistance domains disposed on E1 and E2 respectively, and optionally electrode, interference and/or enzyme domains disposed on E2. In some embodiments, the physical diffusion barrier includes first and second barrier layers formed independently on the first and second electrodes. In some embodiments the barrier layer is the resistance domain 28. In still other embodiments, the physical diffusion barrier can be a continuous membrane (and/or membrane domain(s)) disposed between the electroactive surfaces. In some embodiments, the physical diffusion barrier attenuates (e.g., suppresses, blocks, prevents) diffusion of the $H_2O_2$ (e.g., crosstalk) by at least 2-fold. In preferred embodiments, crosstalk is attenuated at least 5-fold. In a more preferred embodiment, crosstalk is attenuated at least 10-fold. In some embodiments, the physical diffusion barrier attenuates crosstalk at least about 50%. In a further embodiment, the physical diffusion barrier is configured and arranged to physically block an amount of the measured species diffusing from the active enzymatic portion of the membrane to the second electroactive surface, such that there is substantially no signal associated with crosstalk measured at the second working electrode.

In some embodiments, a dual electrode sensor having a physical barrier layer can be fabricated by initially preparing (e.g., fabricating, building) the first and second working electrodes E1, E2 independently (e.g., separately from each other), followed by joining and/or grouping and/or bundling the working electrodes and optionally applying one or more additional membrane domains fabrication. In this exemplary embodiment, to the first working electrode E1, an optional electrode domain 24, an enzyme domain 26 (e.g., plus-GOx), and at least one layer of the resistance domain material 28 (e.g., first resistance domain) are sequentially applied. Similarly, to the second working electrode E2, an optional electrode domain 24, an enzyme domain 26 (e.g., no-GOx), and at least one layer of the resistance domain material 28 (e.g., second resistance domain) are sequentially applied. The working electrodes are then held together, such as but not limited to by bundling and/or twisting them together, wrapping a material around them, or by any other method known in the art. In this embodiment, the physical diffusion barrier includes a discontinuous portion of a membrane (e.g., the initial layers of the resistance domain material applied independently to the two working electrodes) disposed between the first and second electroactive surfaces.

In an alternative exemplary sensor embodiment, the sensor includes working electrodes (including electroactive surfaces) disposed on a planar substrate and/or surface. The electroactive surfaces can be spaced a distance D3 that is sufficiently close together that the electroactive surfaces are equivalently affected by an adjacent noise hot spot (e.g., point source). In this configuration, D3 is also sufficiently small that crosstalk can occur between the Plus GOx working electrode (wherein the term "electrode" includes the membrane disposed thereon, for the purposes of this example) and the No GOx working electrode. However, in preferred embodiments, crosstalk is substantially attenuated by a physical diffusion barrier disposed between the working electrodes. Namely, the electrode domains (if present) and enzyme domains can be separately applied to the working electrodes and/or electroactive surfaces; followed by application of a continuous resistance domain applied thereon, such that a portion the resistance domain is deposited between the working electrodes. For example, a portion of resistance domain deposited on a planar substrate and between working electrodes can attenuate diffusion of the measured species (e.g., $H_2O_2$) from E1 to E2, such that the noise measured on E1 and E2 is equivalent.

In the context of glucose sensors, one skilled in the art recognizes that equivalent noise signals can have different amplitudes, but equivalent signal patterns (e.g., rises, falls, trends and the like) such that a noise component can be subtracted out (as described elsewhere herein) while compensating for any difference in signal amplitude (i.e., sensitivity of the first and second working electrodes), as described elsewhere herein. In some circumstances, the membrane portions associated with the working electrodes (e.g., of a dual electrode sensor) can possess different sensitivities (e.g., signal sensitivities), such that the amplitudes of the noise components measured by the working electrodes are not equivalent. In some circumstances, the areas of the electroactive surfaces may be different sizes, which can also result in non-equivalent signal amplitudes and/or sensitivities. While such differences in signal sensitivity can be corrected mathematically (e.g., by mathematical filters), mathematical correction of noise, in general, is improved when the signal sensitivities of the first and second working electrodes are closer. Accordingly, in a preferred embodiment, an additional resistance domain 28A (e.g., applied continuously over the discontinuous resistance domains 28 described elsewhere herein) is provided, such that the signal sensitivities are equivalent. In the exemplary embodiment shown in FIG. 18, the signal sensitivities are substantially equalized on a sensor including the combination of discontinuous resistance domains (e.g., resistance domains 28, applied independently to E1 and E2) and a continuous resistance domain 28A (e.g., applied over and/or adjacent to the discontinuous resistance domains). In other words, the noise signals detected on both E1 and E2 will have substantially the same amplitude (e.g., intensity, amount), as described with reference to Example 7, below. In a preferred embodiment, the sensitivities (of the working electrodes) are within 40% of each other (e.g., plus or minus 20%). In a preferred embodiment, the sensitivities (of the working electrodes) are within 20% of each other (e.g., plus or minus 10%). In a more preferred embodiment, the sensitivities (of the working electrodes) are within 10% of each other (e.g., plus or minus 5%).

In an alternative embodiment, the sensor electrodes can be disposed on a planar, cylindrical, pyramidal or otherwise shaped support. For example, the sensor's first and second working electrodes can be conductive traces deposited, such as by screen printing, sputtering or other thin film techniques known in the art, on a planar substrate. In this alternative embodiment, a physical diffusion barrier can be formed by layers of resistance domain material deposited separately (e.g., discontinuously) on each working electrode and/or between the electrodes, for example.

In the exemplary embodiments described above, diffusion of the $H_2O_2$ from the first working electrode E1 to the electroactive surface of the second working electrode E2 is first attenuated by the resistance domain 28 disposed over the first working electrode E1 (an independently formed first barrier layer), and then again by the resistance domain 28 disposed over the second working electrode E2 (an independently formed second barrier layer), such that only insubstantial amounts of $H_2O_2$ can reach the electroactive surface of the second working electrode. In preferred embodiments, the first and second resistance domains are configured and arranged to reduce diffusion of the measurable species (e.g., $H_2O_2$) from the first electroactive surface to the second electroactive surface by at least 2-fold. In more preferred embodiments, the physical diffusion barrier is configured and arranged to reduce diffusion of the measurable species by at least 10-fold. In some embodiments, the physical diffusion barrier is configured and arranged to reduce diffusion of the measurable species by at least 3-, 4-, 5-, 6-, 7-, 8-, or 9-fold. In some embodiments, the physical diffusion barrier is configured and arranged to reduce diffusion of the measurable species by at least 20-, 30-, 40- or 50-fold, or more. In some embodiments, the sensor's working electrodes E1, E2 are by an insulator I, which insulates the working electrodes from each other. In some embodiments, the insulator I is at least a portion of the sensor membrane.

In another exemplary embodiment, the membrane can be configured to function as an insulator I, and therefore block and/or attenuate crosstalk between the first and second working electrodes E1, E2. For example, as described herein in the section entitled "Exemplary Sensor Configurations," a physical diffusion barrier can be formed by integrally forming the first and second working electrodes E1, E2 either on a reference electrode R or an insulator I, such that the reference electrode R and/or insulator I physically blocks diffusion from one working electrode to the other, such that substantially no crosstalk affects the sensor signal. For example, if the insulator I is a planar polymer sheet or support, the working electrodes E1, E2 can be integrally formed on opposite sides to the polymer sheet and/or support, such $H_2O_2$ produced in the active enzymatic portion of the sensor membrane (e.g., disposed over E1) cannot diffuse around the sheet and/or support (e.g., and impinge upon E2).

In yet another exemplary embodiment, if the working electrodes are integrally formed on a substrate (planar, cylindrical, pyramidal, and the like) an insulative material can be deposited between the working electrodes (e.g., onto the substrate) to form a physical diffusion barrier. For example, the physical diffusion barrier can project a sufficient distance away from the substrate (e.g., similar to a wall-like structure) such that the measurable species cannot diffuse around it. Such a physical diffusion barrier can be formed from a variety of insulative materials (e.g., materials through which only insubstantial amounts of the measurable species can diffuse) can be integrally formed and/or deposited on the substrate. Additionally, any thin film deposition technique known to one skilled in the art (e.g., printing, sputtering, spin coating, and the like) can be employed to form the physical diffusion barrier on the substrate.

In some embodiments, a continuous glucose sensor configured for insertion into a host and detecting glucose in the host is provided. In general, the sensor includes first and second working electrodes, wherein each working electrode includes an electroactive surface (each including an area) disposed beneath a sensor membrane. The first electroactive surface (e.g., of the first working electrode) is disposed beneath an active enzymatic portion (plus-GOx) of the membrane while the second electroactive surface (of the second working electrode) is disposed beneath a non-enzymatic (no-GOx) portion of the membrane. The non-enzymatic portion of the membrane can include inactivated enzyme and/or no enzyme. Additionally, each working electrode is configured to generate a signal having a noise component related to a noise-causing species. In some circumstances, the noise-causing species is non-constant and related to a biological process. Preferably, the first and second areas are sufficiently large such that the noise components (e.g., first and second noise components detected by the first and second working electrodes) are substantially equivalent. In some embodiments, the first and second areas are each greater than the sum of the diameters of about 10 average human cells, in at least one dimension. In some embodiments, the first and second areas are each greater than about 500 µm, in at least one dimension. Preferably, the first and second areas (e.g., of the electroactive surfaces) are configured and arranged such that the signals caused by a plurality of local point sources (that produce noise-causing species when implanted in a host) can be integrated along each area (e.g., each area independently from the other). In some further embodiments, the first and second areas are configured and arranged to integrate signals detected about a circumference of the sensor. Preferably, the first and second electroactive surfaces are spaced a distance that is less than a crosstalk diffusion distance of a measured species, such as $H_2O_2$ produced in the active enzymatic portion of the membrane. In some embodiments, the sensor includes a physical diffusion barrier configured and arranged to physically block some crosstalk from the active enzymatic portion of the membrane to the second electroactive surface. In some further embodiments, the physical diffusion barrier is configured and arranged to physically block a substantial amount of the measurable species diffusing from the active enzymatic portion of the membrane to the second electroactive surface (e.g., crosstalk), such that there is substantially no signal associated with crosstalk measured at the second working electrode. In some embodiments, the physical diffusion barrier is a discontinuous portion of the membrane disposed between the first and second electroactive surfaces. In some further embodiments, the physical diffusion barrier includes a first barrier layer formed on the first working electrode and a second barrier layer formed on the second working electrode, wherein the first and second barrier layers are independently formed (e.g., formed separately on the two electroactive surfaces). In some further embodiments, the physical diffusion barrier includes a first resistance domain formed on the first working electrode and a second resistance domain formed on the second working electrode, and wherein the first and second resistance domains are configured and arranged to reduce diffusion of the measurable species (e.g., crosstalk) from the active enzymatic portion of the sensor to the second electroactive surface by at least 2-fold. In a preferred embodiment, the physical diffusion barrier can reduce the diffusion of the measurable species (e.g., crosstalk) by at least 10-fold.

In some embodiments, the continuous glucose sensor includes first and second working electrodes, each working electrode including an electroactive surface (each including an area) disposed beneath a sensor membrane. As described elsewhere herein, the first electroactive surface is disposed beneath an active enzymatic portion of the membrane and the second electroactive surface is disposed beneath a non-enzymatic portion of the membrane. Preferably, the sensor includes a physical diffusion barrier, and the first and second electroactive surfaces are disposed sufficiently close together that the first and second noise components (detected by the first and second working electrodes) are substantially equivalent. In some embodiments, the distance between the first and second electroactive surfaces is less than about twice the thickness of the membrane. In some embodiments, the first and second electroactive surfaces are spaced a distance that is less than or equal to about a crosstalk diffusion distance of a measurable species, such as the $H_2O_2$ produced in the active enzymatic portion of the sensor membrane. In some embodiments, the physical diffusion barrier is configured and arranged to physically block some diffusion of the measurable species from the active enzymatic portion of the membrane to the second electroactive surface (e.g., crosstalk). In preferred embodiments, the physical diffusion barrier blocks a substantial amount of the measurable species, such that there is substantially no signal associated with crosstalk measured at the second working electrode. In some embodiments, the physical diffusion barrier is a discontinuous portion of the membrane disposed between the first and second electroactive surfaces. In some embodiments, the physical diffusion barrier is a first barrier layer formed on the first electrode and a second barrier layer formed on the second electrode, wherein the first and second barrier layers are independently formed. In some embodiments, the physical diffusion barrier includes a first resistance domain formed on the first electrode and a second resistance domain formed on the second electrode. Preferably, the first and second resistance domains reduce diffusion of the measurable species (e.g., crosstalk) by at least 2-fold. In more preferred embodiments, the diffusion of the measurable species is reduced by at least 10-fold. In some embodiments, the membrane is an insulator that insulates the first working electrode from the second working electrodes. In some further embodiments, the first and second areas are sufficiently large that the first and second noise components are substantially equivalent.

Sensor Electronics

In some embodiments, the sensing region may include reference and/or electrodes associated with the glucose-measuring working electrode and separate reference and/or counter electrodes associated with the optional auxiliary working electrode(s). In yet another embodiment, the sensing region may include a glucose-measuring working electrode, an auxiliary working electrode, two counter electrodes (one for each working electrode), and one shared reference electrode. In yet another embodiment, the sensing region may include a glucose-measuring working electrode, an auxiliary working electrode, two reference electrodes, and one shared counter electrode. However, a variety of electrode materials and configurations can be used with the implantable analyte sensor of the preferred embodiments.

In some alternative embodiments, the working electrodes are interdigitated. In some alternative embodiments, the working electrodes each comprise multiple exposed electrode surfaces; one advantage of these architectures is to distribute the measurements across a greater surface area to overcome localized problems that may occur in vivo, for example, with the host's immune response at the biointerface. Preferably, the glucose-measuring and auxiliary working electrodes are provided within the same local environment, such as described in more detail elsewhere herein.

Figure 4:
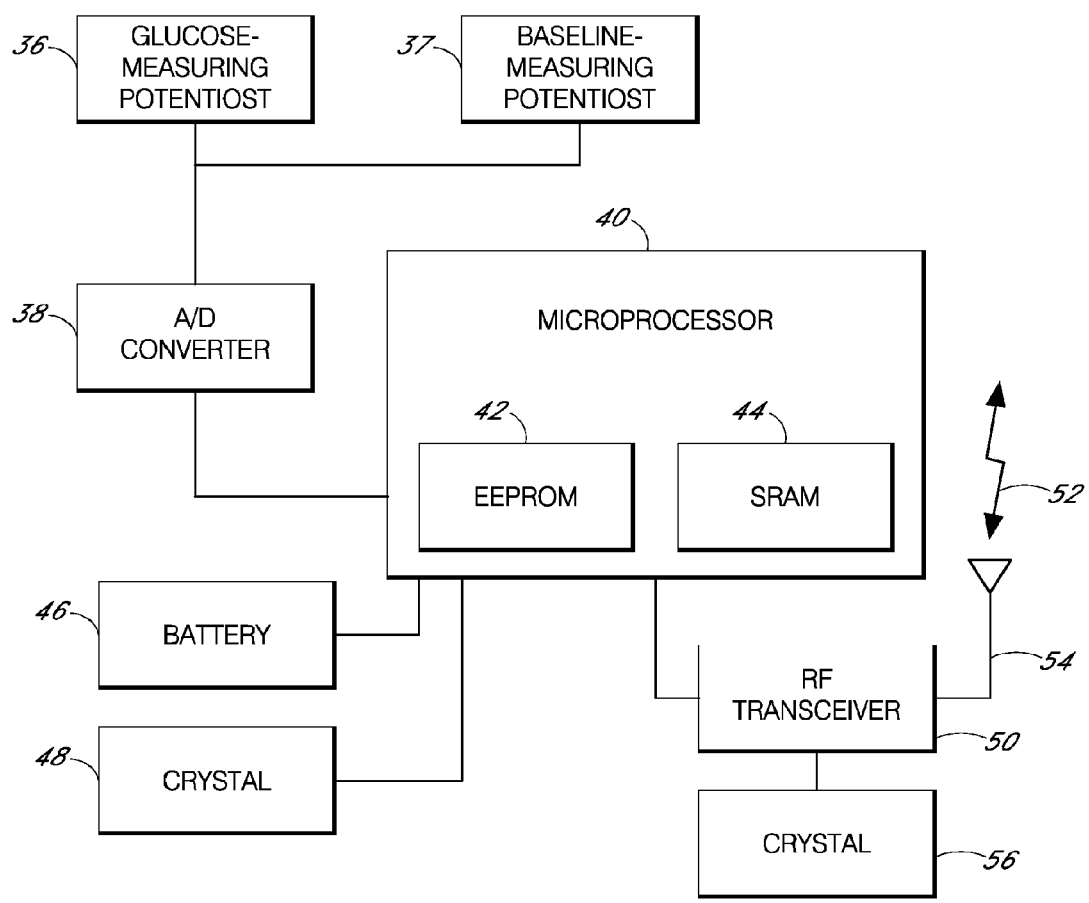
FIG. 4 is a block diagram that illustrates continuous glucose sensor electronics in one embodiment.

FIG. 4 is a block diagram that illustrates the continuous glucose sensor electronics in one embodiment. In this embodiment, a first potentiostat 36 is provided that is operatively associated with the glucose-measuring working electrode 16. The first potentiostat 36 measures a current value at the glucose-measuring working electrode and preferably includes a resistor (not shown) that translates the current into voltage. An optional second potentiostat 37 is provided that is operatively associated with the optional auxiliary working electrode 18. The second potentiostat 37 measures a current value at the auxiliary working electrode 18 and preferably includes a resistor (not shown) that translates the current into voltage. It is noted that in some embodiments, the optional auxiliary electrode can be configured to share the first potentiostat with the glucose-measuring working electrode. An A/D converter 38 digitizes the analog signals from the potentiostats 36, 37 into counts for processing. Accordingly, resulting raw data streams (in counts) can be provided that are directly related to the current measured by each of the potentiostats 36 and 37.

A microprocessor 40, also referred to as the processor module, is the central control unit that houses EEPROM 42 and SRAM 44, and controls the processing of the sensor electronics. It is noted that certain alternative embodiments can utilize a computer system other than a microprocessor to process data as described herein. In other alternative embodiments, an application-specific integrated circuit (ASIC) can be used for some or all the sensor's central processing. The EEPROM 42 provides semi-permanent storage of data, for example, storing data such as sensor identifier (ID) and programming to process data streams (for example, such as described in U.S. Patent Publication No. US-2005-0027463-A1, which is incorporated by reference herein in its entirety. The SRAM 44 can be used for the system's cache memory, for example for temporarily storing recent sensor data. In some alternative embodiments, memory storage components comparable to EEPROM and SRAM may be used instead of or in addition to the preferred hardware, such as dynamic RAM, non-static RAM, rewritable ROMs, flash memory, or the like.

A battery 46 is operably connected to the microprocessor 40 and provides the necessary power for the sensor 10a. In one embodiment, the battery is a Lithium Manganese Dioxide battery, however any appropriately sized and powered battery can be used (for example, AAA, Nickel-cadmium, Zinc-carbon, Alkaline, Lithium, Nickel-metal hydride, Lithium-ion, Zinc-air, Zinc-mercury oxide, Silver-zinc, and/or hermetically-sealed). In some embodiments the battery is rechargeable. In some embodiments, a plurality of batteries can be used to power the system. In some embodiments, one or more capacitors can be used to power the system. A Quartz Crystal 48 may be operably connected to the microprocessor 40 to maintain system time for the computer system as a whole.

An RF Transceiver 50 may be operably connected to the microprocessor 40 to transmit the sensor data from the sensor 10 to a receiver (see FIGS. 4 and 5) within a wireless transmission 52 via antenna 54. Although an RF transceiver is shown here, some other embodiments can include a wired rather than wireless connection to the receiver. In yet other embodiments, the receiver can be transcutaneously powered via an inductive coupling, for example. A second quartz crystal 56 can provide the system time for synchronizing the data transmissions from the RF transceiver. It is noted that the transceiver 50 can be substituted with a transmitter in other embodiments. In some alternative embodiments other mechanisms such as optical, infrared radiation (IR), ultrasonic, or the like may be used to transmit and/or receive data.

Receiver

Figure 5:
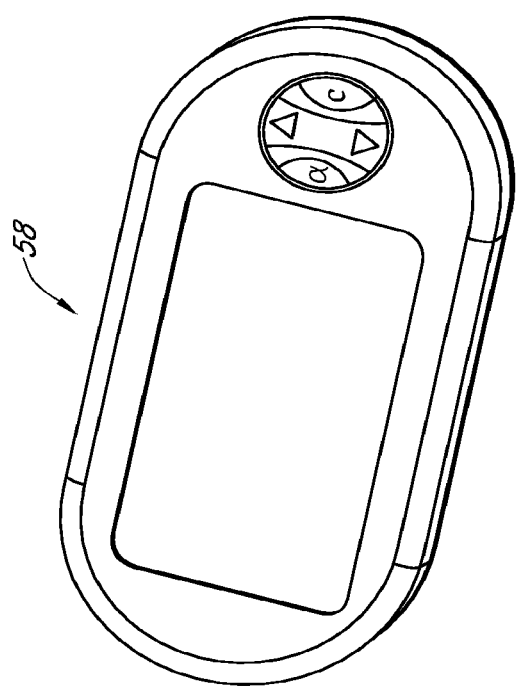
FIG. 5 is a drawing of a receiver for the continuous glucose sensor in one embodiment.

FIG. 5 is a schematic drawing of a receiver for the continuous glucose sensor in one embodiment. The receiver 58 comprises systems necessary to receive, process, and display sensor data from the analyte sensor, such as described in more detail elsewhere herein. Particularly, the receiver 58 may be a pager-sized device, for example, and house a user interface that has a plurality of buttons and/or keypad and a liquid crystal display (LCD) screen, and which may include a backlight. In some embodiments the user interface may also include a speaker, and a vibrator such as described with reference to FIG. 6.

Figure 6:
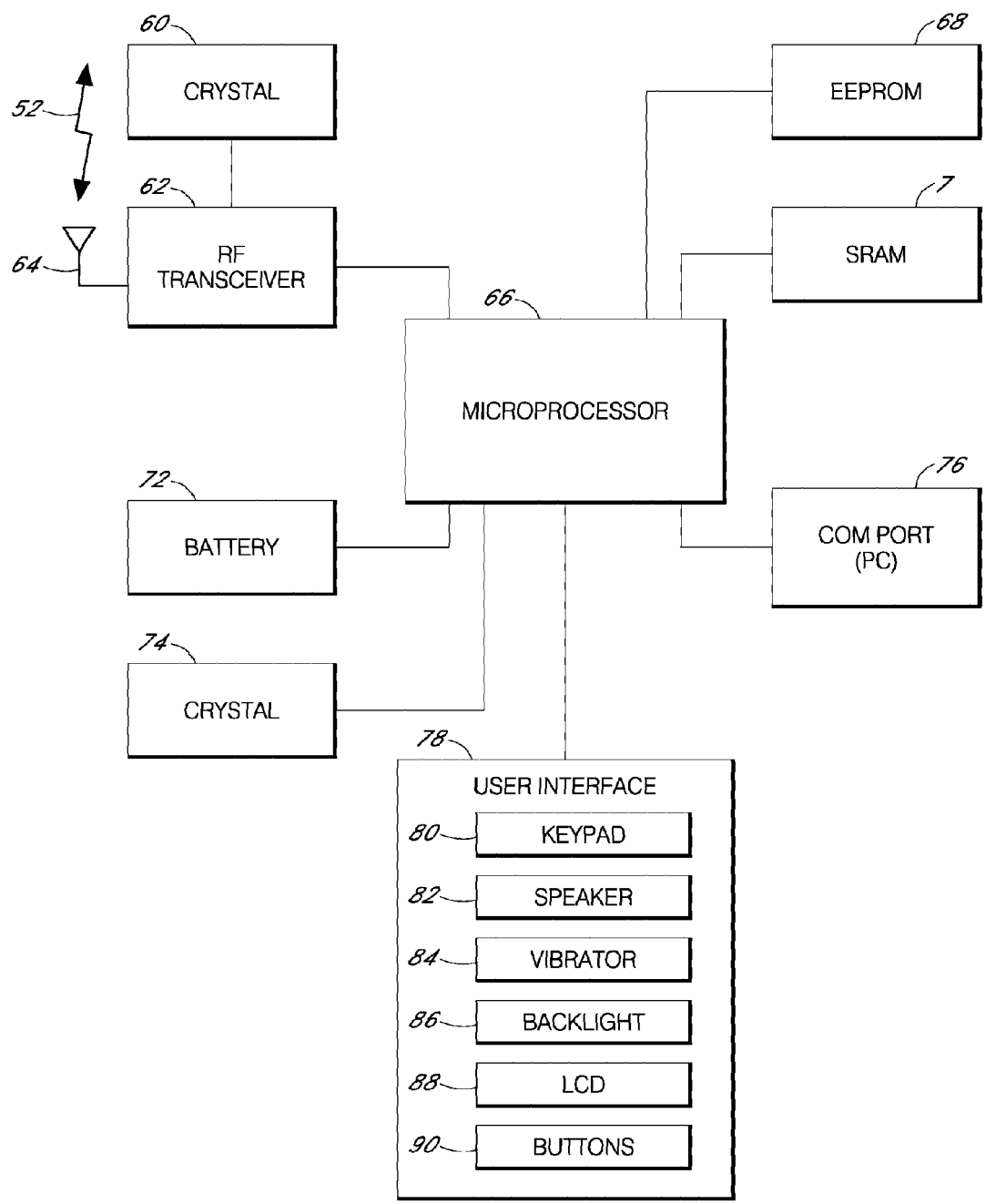
FIG. 6 is a block diagram of the receiver electronics in one embodiment.

FIG. 6 is a block diagram of the receiver electronics in one embodiment. In some embodiments, the receiver comprises a configuration such as described with reference to FIG. 5, above. However, the receiver may comprise any reasonable configuration, including a desktop computer, laptop computer, a personal digital assistant (PDA), a server (local or remote to the receiver), or the like. In some embodiments, a receiver may be adapted to connect (via wired or wireless connection) to a desktop computer, laptop computer, a PDA, a server (local or remote to the receiver), or the like in order to download data from the receiver. In some alternative embodiments, the receiver may be housed within or directly connected to the sensor in a manner that allows sensor and receiver electronics to work directly together and/or share data processing resources. Accordingly, the receiver, including its electronics, may be generally described as a "computer system."

A quartz crystal 60 may be operably connected to an RF transceiver 62 that together function to receive and synchronize data streams via an antenna 64 (for example, transmission 52 from the RF transceiver 50 shown in FIG. 4). Once received, a microprocessor 66 can process the signals, such as described below.

The microprocessor 66, also referred to as the processor module, is the central control unit that provides the processing, such as storing data, calibrating sensor data, downloading data, controlling the user interface by providing prompts, messages, warnings and alarms, or the like. The EEPROM 68 may be operably connected to the microprocessor 66 and provides semi-permanent storage of data, storing data such as receiver ID and programming to process data streams (for example, programming for performing calibration and other algorithms described elsewhere herein). SRAM 70 may be used for the system's cache memory and is helpful in data processing. For example, the SRAM stores information from the continuous glucose sensor for later recall by the patient or a doctor; a patient or doctor can transcribe the stored information at a later time to determine compliance with the medical regimen or a comparison of glucose concentration to medication administration (for example, this can be accomplished by downloading the information through the pc com port 76). In addition, the SRAM 70 can also store updated program instructions and/or patient specific information. In some alternative embodiments, memory storage components comparable to EEPROM and SRAM can be used instead of or in addition to the preferred hardware, such as dynamic RAM, non-static RAM, rewritable ROMs, flash memory, or the like.

A battery 72 may be operably connected to the microprocessor 66 and provides power for the receiver. In one embodiment, the battery is a standard AAA alkaline battery, however any appropriately sized and powered battery can be used. In some embodiments, a plurality of batteries can be used to power the system. In some embodiments, a power port (not shown) is provided permit recharging of rechargeable batteries. A quartz crystal 84 may be operably connected to the microprocessor 66 and maintains system time for the system as a whole.

A PC communication (com) port 76 can be provided to enable communication with systems, for example, a serial communications port, allows for communicating with another computer system (for example, PC, PDA, server, or the like). In one exemplary embodiment, the receiver is able to download historical data to a physician's PC for retrospective analysis by the physician. The PC communication port 76 can also be used to interface with other medical devices, for example pacemakers, implanted analyte sensor patches, infusion devices, telemetry devices, or the like.

A user interface 78 comprises a keypad 80, speaker 82, vibrator 84, backlight 86, liquid crystal display (LCD) 88, and one or more buttons 90. The components that comprise the user interface 78 provide controls to interact with the user. The keypad 80 can allow, for example, input of user information about himself/herself, such as mealtime, exercise, insulin administration, and reference glucose values. The speaker 82 can provide, for example, audible signals or alerts for conditions such as present and/or predicted hyper- and hypoglycemic conditions. The vibrator 84 can provide, for example, tactile signals or alerts for reasons such as described with reference to the speaker, above. The backlight 94 can be provided, for example, to aid the user in reading the LCD in low light conditions. The LCD 88 can be provided, for example, to provide the user with visual data output. In some embodiments, the LCD is a touch-activated screen. The buttons 90 can provide for toggle, menu selection, option selection, mode selection, and reset, for example. In some alternative embodiments, a microphone can be provided to allow for voice-activated control.

The user interface 78, which is operably connected to the microprocessor 70, serves to provide data input and output for the continuous analyte sensor. In some embodiments, prompts can be displayed to inform the user about necessary maintenance procedures, such as "Calibrate Sensor" or "Replace Battery." In some embodiments, prompts or messages can be displayed on the user interface to convey information to the user, such as malfunction, outlier values, missed data transmissions, or the like. Additionally, prompts can be displayed to guide the user through calibration of the continuous glucose sensor, for example when to obtain a reference glucose value.

Keypad, buttons, touch-screen, and microphone are all examples of mechanisms by which a user can input data directly into the receiver. A server, personal computer, personal digital assistant, insulin pump, and insulin pen are examples of external devices that can be connected to the receiver via PC com port 76 to provide useful information to the receiver. Other devices internal or external to the sensor that measure other aspects of a patient's body (for example, temperature sensor, accelerometer, heart rate monitor, oxygen monitor, or the like) can be used to provide input helpful in data processing. In one embodiment, the user interface can prompt the patient to select an activity most closely related to their present activity, which can be helpful in linking to an individual's physiological patterns, or other data processing. In another embodiment, a temperature sensor and/or heart rate monitor can provide information helpful in linking activity, metabolism, and glucose excursions of an individual. While a few examples of data input have been provided here, a variety of information can be input and can be helpful in data processing as will be understood by one skilled in the art.

Calibration Systems and Methods

As described above in the Overview Section, continuous analyte sensors define a relationship between sensor-generated measurements and a reference measurement that is meaningful to a user (for example, blood glucose in mg/dL). This defined relationship must be monitored to ensure that the continuous analyte sensor maintains a substantially accurate calibration and thereby continually provides meaningful values to a user. Unfortunately, both sensitivity m and baseline b of the calibration are subject to changes that occur in vivo over time (for example, hours to months), requiring updates to the calibration. Generally, any physical property that influences diffusion or transport of molecules through the membrane can alter the sensitivity (and/or baseline) of the calibration. Physical properties that can alter the transport of molecules include, but are not limited to, blockage of surface area due to foreign body giant cells and other barrier cells at the biointerface, distance of capillaries from the membrane, foreign body response/capsule, disease, tissue ingrowth, thickness of membrane system, or the like.

In one example of a change in transport of molecules, an implantable glucose sensor is implanted in the subcutaneous space of a human, which is at least partially covered with a biointerface membrane, such as described in U.S. Patent Publication No. US-2005-0112169-A1, which is incorporated by reference herein in its entirety. Although the body's natural response to a foreign object is to encapsulate the sensor, the architecture of this biointerface membrane encourages tissue ingrowth and neo-vascularization over time, providing transport of solutes (for example, glucose and oxygen) close to the membrane that covers the electrodes. While not wishing to be bound by theory, it is believed that ingrowth of vascularized tissue matures (changes) over time, beginning with a short period of high solute transport during the first few days after implantation, continuing through a time period of significant tissue ingrowth a few days to a week or more after implantation during which low solute transport to the membrane has been observed, and into a mature state of vascularized tissue during which the bed of vascularized tissue provides moderate to high solute transport, which can last for months and even longer after implantation. In some embodiments, this maturation process accounts for a substantial portion of the change in sensitivity and/or baseline of the calibration over time due to changes in solute transport to the membrane.

Accordingly, in one aspect of the preferred embodiments, systems and methods are provided for measuring changes in sensitivity, also referred to as changes in solute transport or biointerface changes, of an analyte sensor 10 implanted in a host over a time period. Preferably, the sensitivity measurement is a signal obtained by measuring a constant analyte other than the analyte being measured by the analyte sensor. For example, in a glucose sensor, a non-glucose constant analyte is measured, wherein the signal is measured beneath the membrane system 22 on the glucose sensor 10. While not wishing to be bound by theory, it is believed that by monitoring the sensitivity over a time period, a change associated with solute transport through the membrane system 22 can be measured and used as an indication of a sensitivity change in the analyte measurement. In other words, a biointerface monitor is provided, which is capable of monitoring changes in the biointerface surrounding an implantable device, thereby enabling the measurement of sensitivity changes of an analyte sensor over time.

In some embodiments, the analyte sensor 10 is provided with an auxiliary electrode 18 configured as a transport-measuring electrode disposed beneath the membrane system 22. The transport-measuring electrode can be configured to measure any of a number of substantially constant analytes or factors, such that a change measured by the transport-measuring electrode can be used to indicate a change in solute (for example, glucose) transport to the membrane system 22. Some examples of substantially constant analytes or factors that can be measured include, but are not limited to, oxygen, carboxylic acids (such as urea), amino acids, hydrogen, pH, chloride, baseline, or the like. Thus, the transport-measuring electrode provides an independent measure of changes in solute transport to the membrane, and thus sensitivity changes over time.

In some embodiments, the transport-measuring electrode measures analytes similar to the analyte being measured by the analyte sensor. For example, in some embodiments of a glucose sensor, water soluble analytes are believed to better represent the changes in sensitivity to glucose over time than non-water soluble analytes (due to the water-solubility of glucose), however relevant information may be ascertained from a variety of molecules. Although some specific examples are described herein, one skilled in the art appreciates a variety of implementations of sensitivity measurements that can be used as to qualify or quantify solute transport through the biointerface of the analyte sensor.

In one embodiment of a glucose sensor, the transport-measuring electrode is configured to measure urea, which is a water-soluble constant analyte that is known to react directly or indirectly at a hydrogen peroxide sensing electrode (similar to the working electrode of the glucose sensor example described in more detail above). In one exemplary implementation wherein urea is directly measured by the transport-measuring electrode, the glucose sensor comprises a membrane system as described in more detail above, however, does not include an active interference domain or active enzyme directly above the transport-measuring electrode, thereby allowing the urea to pass through the membrane system to the electroactive surface for measurement thereon. In one alternative exemplary implementation wherein urea is indirectly measured by the transport-measuring electrode, the glucose sensor comprises a membrane system as described in more detail above, and further includes an active uricase oxidase domain located directly above the transport-measuring electrode, thereby allowing the urea to react at the enzyme and produce hydrogen peroxide, which can be measured at the electroactive surface thereon.

In some embodiments, the change in sensitivity is measured by measuring a change in oxygen concentration, which can be used to provide an independent measurement of the maturation of the biointerface, and to indicate when recalibration of the system may be advantageous. In one alternative embodiment, oxygen is measured using pulsed amperometric detection on the glucose-measuring working electrode 16 (eliminating the need for a separate auxiliary electrode). In another embodiment, the auxiliary electrode is configured as an oxygen-measuring electrode. In another embodiment, an oxygen sensor (not shown) is added to the glucose sensor, as is appreciated by one skilled in the art, eliminating the need for an auxiliary electrode.

In some embodiments, a stability module is provided; wherein the sensitivity measurement changes can be quantified such that a co-analyte concentration threshold is determined. A co-analyte threshold is generally defined as a minimum amount of co-analyte required to fully react with the analyte in an enzyme-based analyte sensor in a non-limiting manner. The minimum co-analyte threshold is preferably expressed as a ratio (for example, a glucose-to-oxygen ratio) that defines a concentration of co-analyte required based on a concentration of analyte available to ensure that the enzyme reaction is limited only by the analyte. While not wishing to be bound by theory, it is believed that by determining a stability of the analyte sensor based on a co-analyte threshold, the processor module can be configured to compensate for instabilities in the glucose sensor accordingly, for example by filtering the unstable data, suspending calibration or display, or the like.

In one such embodiment, a data stream from an analyte signal is monitored and a co-analyte threshold set, whereby the co-analyte threshold is determined based on a signal-to-noise ratio exceeding a predetermined threshold. In one embodiment, the signal-to-noise threshold is based on measurements of variability and the sensor signal over a time period, however one skilled in the art appreciates the variety of systems and methods available for measuring signal-to-noise ratios. Accordingly, the stability module can be configured to set determine the stability of the analyte sensor based on the co-analyte threshold, or the like.

In some embodiments, the stability module is configured to prohibit calibration of the sensor responsive to the stability (or instability) of the sensor. In some embodiments, the stability module can be configured to trigger filtering of the glucose signal responsive to a stability (or instability) of the sensor.

In some embodiments, sensitivity changes can be used to trigger a request for one or more new reference glucose values from the host, which can be used to recalibrate the sensor. In some embodiments, the sensor is re-calibrated responsive to a sensitivity change exceeding a preselected threshold value. In some embodiments, the sensor is calibrated repeatedly at a frequency responsive to the measured sensitivity change. Using these techniques, patient inconvenience can be minimized because reference glucose values are generally only requested when timely and appropriate (namely, when a sensitivity or baseline shift is diagnosed).

In some alternative embodiments, sensitivity changes can be used to update calibration. For example, the measured change in transport can be used to update the sensitivity m in the calibration equation. While not wishing to be bound by theory, it is believed that in some embodiments, the sensitivity m of the calibration of the glucose sensor is substantially proportional to the change in solute transport measured by the transport-measuring electrode.

It should be appreciated by one skilled in the art that in some embodiments, the implementation of sensitivity measurements of the preferred embodiments typically necessitate an addition to, or modification of, the existing electronics (for example, potentiostat configuration or settings) of the glucose sensor and/or receiver.

In some embodiments, the signal from the oxygen measuring electrode may be digitally low-pass filtered (for example, with a passband of $0\text{-}10^{-5}$ Hz, dc-24 hour cycle lengths) to remove transient fluctuations in oxygen, due to local ischemia, postural effects, periods of apnea, or the like. Since oxygen delivery to tissues is held in tight homeostatic control, this filtered oxygen signal should oscillate about a relatively constant. In the interstitial fluid, it is thought that the levels are about equivalent with venous blood (40 mmHg). Once implanted, changes in the mean of the oxygen signal (for example, >5%) may be indicative of change in transport through the biointerface (change in sensor sensitivity and/or baseline due to changes in solute transport) and the need for system recalibration.

The oxygen signal may also be used in its unfiltered or a minimally filtered form to detect or predict oxygen deprivation-induced artifact in the glucose signal, and to control display of data to the user, or the method of smoothing, digital filtering, or otherwise replacement of glucose signal artifact. In some embodiments, the oxygen sensor may be implemented in conjunction with any signal artifact detection or prediction that may be performed on the counter electrode or working electrode voltage signals of the electrode system. U.S. Patent Publication No. US-2005-0043598-A1, which is incorporated by reference in its entirety herein, describes some methods of signal artifact detection and replacement that may be useful such as described herein.

Preferably, the transport-measuring electrode is located within the same local environment as the electrode system associated with the measurement of glucose, such that the transport properties at the transport-measuring electrode are substantially similar to the transport properties at the glucose-measuring electrode.

In a second aspect the preferred embodiments, systems and methods are provided for measuring changes baseline, namely non-glucose related electroactive compounds in the host. Preferably the auxiliary working electrode is configured to measure the baseline of the analyte sensor over time. In some embodiments, the glucose-measuring working electrode 16 is a hydrogen peroxide sensor coupled to a membrane system 22 containing an active enzyme 32 located above the electrode (such as described in more detail with reference to FIGS. 1 to 4, above). In some embodiments, the auxiliary working electrode 18 is another hydrogen peroxide sensor that is configured similar to the glucose-measuring working electrode however a portion 34 of the membrane system 22 above the base-measuring electrode does not have active enzyme therein, such as described in more detail with reference to FIGS. 3A and 3B. The auxiliary working electrode 18 provides a signal substantially comprising the baseline signal, b, which can be (for example, electronically or digitally) subtracted from the glucose signal obtained from the glucose-measuring working electrode to obtain the signal contribution due to glucose only according to the following equation:

$$\text{Signal}_{glucose\ only} = \text{Signal}_{glucose\text{-}measuring\ working\ electrode} - \text{Signal}_{baseline\text{-}measuring\ working\ electrode}$$

In some embodiments, electronic subtraction of the baseline signal from the glucose signal can be performed in the hardware of the sensor, for example using a differential amplifier. In some alternative embodiments, digital subtraction of the baseline signal from the glucose signal can be performed in the software or hardware of the sensor or an associated receiver, for example in the microprocessor.

One aspect the preferred embodiments provides for a simplified calibration technique, wherein the variability of the baseline has been eliminated (namely, subtracted). Namely, calibration of the resultant differential signal ($\text{Signal}_{glucose\ only}$) can be performed with a single matched data pair by solving the following equation:

$$y = mx$$

While not wishing to be bound by theory, it is believed that by calibrating using this simplified technique, the sensor is made less dependent on the range of values of the matched data pairs, which can be sensitive to human error in manual blood glucose measurements, for example. Additionally, by subtracting the baseline at the sensor (rather than solving for the baseline b as in conventional calibration schemes), accuracy of the sensor may increase by altering control of this variable (baseline b) from the user to the sensor. It is additionally believed that variability introduced by sensor calibration may be reduced.

In some embodiments, the glucose-measuring working electrode 16 is a hydrogen peroxide sensor coupled to a membrane system 22 containing an active enzyme 32 located above the electrode, such as described in more detail above; however the baseline signal is not subtracted from the glucose signal for calibration of the sensor. Rather, multiple matched data pairs are obtained in order to calibrate the sensor (for example using y=mx+b) in a conventional manner, and the auxiliary working electrode 18 is used as an indicator of baseline shifts in the sensor signal. Namely, the auxiliary working electrode 18 is monitored for changes above a certain threshold. When a significant change is detected, the system can trigger a request (for example, from the patient or caregiver) for a new reference glucose value (for example, SMBG), which can be used to recalibrate the sensor. By using the auxiliary working electrode signal as an indicator of baseline shifts, recalibration requiring user interaction (namely, new reference glucose values) can be minimized due to timeliness and appropriateness of the requests. In some embodiments, the sensor is re-calibrated responsive to a baseline shifts exceeding a preselected threshold value. In some embodiments, the sensor is calibrated repeatedly at a frequency responsive to the rate-of-change of the baseline.

In yet another alternative embodiment, the electrode system of the preferred embodiments is employed as described above, including determining the differential signal of glucose less baseline current in order to calibrate using the simplified equation (y=mx), and the auxiliary working electrode 18 is further utilized as an indicator of baseline shifts in the sensor signal. While not wishing to be bound by theory, it is believed that shifts in baseline may also correlate and/or be related to changes in the sensitivity m of the glucose signal. Consequently, a shift in baseline may be indicative of a change in sensitivity m. Therefore, the auxiliary working electrode 18 is monitored for changes above a certain threshold. When a significant change is detected, the system can trigger a request (for example, from the patient or caregiver) for a new reference glucose value (for example, SMBG), which can be used to recalibrate the sensor. By using the auxiliary signal as an indicator of possible sensitivity changes, recalibration requiring user interaction (new reference glucose values) can be minimized due to timeliness and appropriateness of the requests.

It is noted that infrequent new matching data pairs may be useful over time to recalibrate the sensor because the sensitivity m of the sensor may change over time (for example, due to maturation of the biointerface that may increase or decrease the glucose and/or oxygen availability to the sensor). However, the baseline shifts that have conventionally required numerous and/or regular blood glucose reference measurements for updating calibration (for example, due to interfering species, metabolism changes, or the like) can be consistently and accurately eliminated using the systems and methods of the preferred embodiments, allowing reduced interaction from the patient (for example, requesting less frequent reference glucose values such as daily or even as infrequently as monthly).

An additional advantage of the sensor of the preferred embodiments includes providing a method of eliminating signal effects of interfering species, which have conventionally been problematic in electrochemical glucose sensors. Namely, electrochemical sensors are subject to electrochemical reaction not only with the hydrogen peroxide (or other analyte to be measured), but additionally may react with other electroactive species that are not intentionally being measured (for example, interfering species), which cause an increase in signal strength due to this interference. In other words, interfering species are compounds with an oxidation potential that overlap with the analyte being measured. Interfering species such as acetaminophen, ascorbate, and urate, are notorious in the art of glucose sensors for producing inaccurate signal strength when they are not properly controlled. Some glucose sensors utilize a membrane system that blocks at least some interfering species, such as ascorbate and urate. Unfortunately, it is difficult to find membranes that are satisfactory or reliable in use, especially in vivo, which effectively block all interferants and/or interfering species (for example, see U.S. Pat. No. 4,776,944, U.S. Pat. No. 5,356,786, U.S. Pat. No. 5,593,852, U.S. Pat. No. 5,776,324B1, and U.S. Pat. No. 6,356,776).

The preferred embodiments are particularly advantageous in their inherent ability to eliminate the erroneous transient and non-transient signal effects normally caused by interfering species. For example, if an interferant such as acetaminophen is ingested by a host implanted with a conventional implantable electrochemical glucose sensor (namely, one without means for eliminating acetaminophen), a transient non-glucose related increase in signal output would occur. However, by utilizing the electrode system of the preferred embodiments, both working electrodes respond with substantially equivalent increased current generation due to oxidation of the acetaminophen, which would be eliminated by subtraction of the auxiliary electrode signal from the glucose-measuring electrode signal.

In summary, the system and methods of the preferred embodiments simplify the computation processes of calibration, decreases the susceptibility introduced by user error in calibration, and eliminates the effects of interfering species. Accordingly, the sensor requires less interaction by the patient (for example, less frequent calibration), increases patient convenience (for example, few reference glucose values), and improves accuracy (via simple and reliable calibration).

In another aspect of the preferred embodiments, the analyte sensor is configured to measure any combination of changes in baseline and/or in sensitivity, simultaneously and/or iteratively, using any of the above-described systems and methods. While not wishing to be bound by theory, the preferred embodiments provide for improved calibration of the sensor, increased patient convenience through less frequent patient interaction with the sensor, less dependence on the values/range of the paired measurements, less sensitivity to error normally found in manual reference glucose measurements, adaptation to the maturation of the biointerface over time, elimination of erroneous signal due to non-constant analyte-related signal so interfering species, and/or self-diagnosis of the calibration for more intelligent recalibration of the sensor.

EXAMPLES

Example 1

Dual-Electrode Sensor with Coiled Reference Electrode

Dual-electrode sensors (having a configuration similar to the embodiment shown in FIG. 9B) were constructed from two platinum wires, each coated with non-conductive material/insulator. Exposed electroactive windows were cut into the wires by removing a portion thereof. The platinum wires were laid next to each other such that the windows are offset (e.g., separated by a diffusion barrier). The bundle was then placed into a winding machine & silver wire was wrapped around the platinum electrodes. The silver wire was then chloridized to produce a silver/silver chloride reference electrode. The sensor was trimmed to length, and a glucose oxidase enzyme solution applied to both windows (e.g., enzyme applied to both sensors). To deactivate the enzyme in one window (e.g., window 904a, FIG. 9B) the window was dipped into dimethylacetamide (DMAC) and rinsed. After the sensor was dried, a resistance layer was sprayed onto the sensor and dried.

Figure 12:
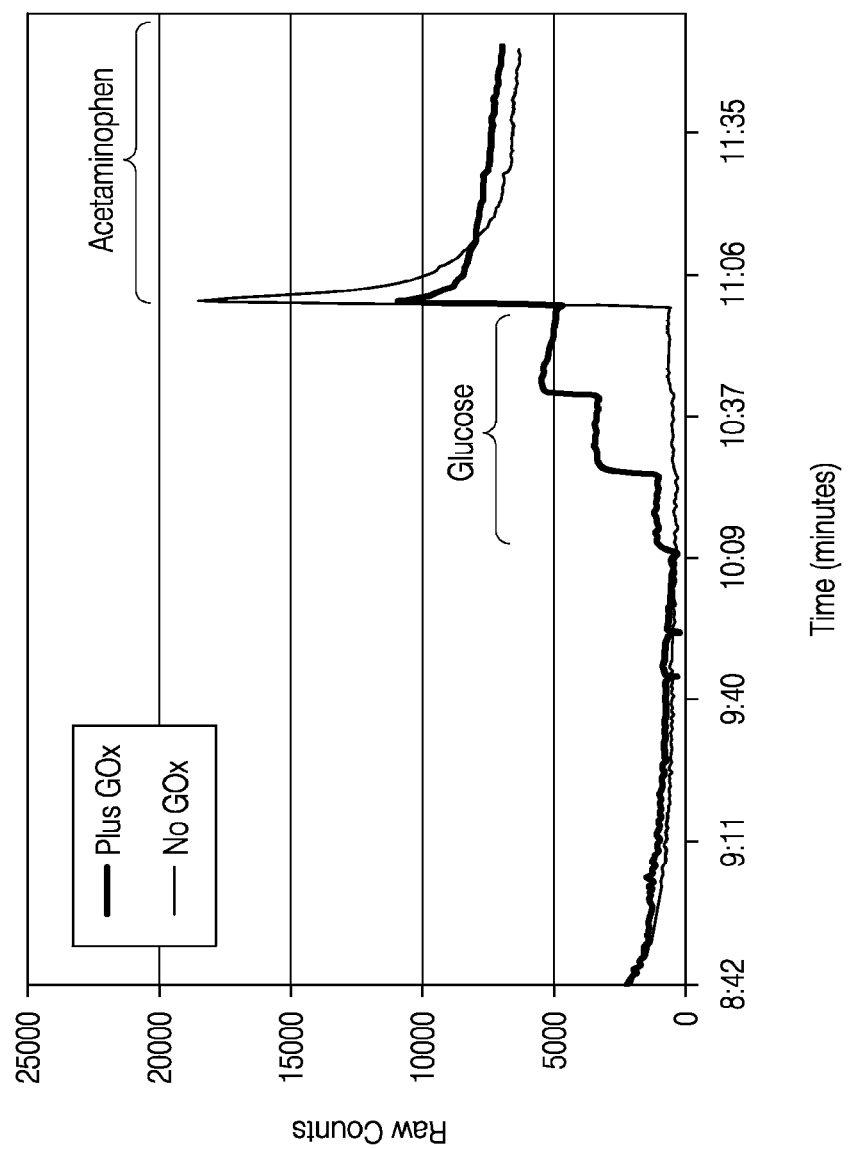
FIG. 12 is a graph that illustrates in vitro signal (raw counts) detected from a sensor having three bundled wire electrodes with staggered working electrodes. Plus GOx (thick line)=the electrode with active GOx. No GOx (thin line)=the electrode with inactive or no GOx.

FIG. 12 shows the results from one experiment, comparing the signals from the two electrodes of the dual-electrode sensor having a coiled silver/silver chloride wire reference electrode described above. The "Plus GOx" electrode included active GOx in its window. The "No GOx" electrode included DMAC-inactivated GOx in its window. To test, the sensor was incubated in room temperature phosphate buffered saline (PBS) for 30 minutes. During this time, the signals from the two electrodes were substantially equivalent. Then the sensor was moved to a 40-mg/dl solution of glucose in PBS. This increase in glucose concentration resulting in an expected rise in signal from the "Plus GOx" electrode but no significant increase in signal from the "No GOx" electrode. The sensor was then moved to a 200-mg/dl solution of glucose in PBS. Again, the "Plus GOx" electrode responded with a characteristic signal increase while no increase in signal was observed for the "No GOx" electrode. The sensor was then moved to a 400-mg/dl solution of glucose in PBS. The "Plus GOx" electrode signal increased to about 5000 counts while no increase in signal was observed for the "No GOx" electrode. As a final test, the sensor was moved to a solution of 400 mg/dl glucose plus 0.22 mM acetaminophen (a known interferant) in PBS. Both electrodes recorded similarly dramatic increases in signal (raw counts). These data indicate that the "No GOx" electrode is measuring sensor background (e.g., noise) that is substantially related to non-glucose factors.

Example 2

Dual-Electrode Sensor with X-Shaped Reference Electrode

This sensor was constructed similarly to the sensor of Example 1, except that the configuration was similar to the embodiment shown in FIG. 7J. Two platinum electrode wires were dipped into non-conductive material and then electroactive windows formed by removing portions of the nonconductive material. The two wires were then bundled with an X-shaped silver reference electrode therebetween. An additional layer of non-conductive material held the bundle together.

Figure 13:
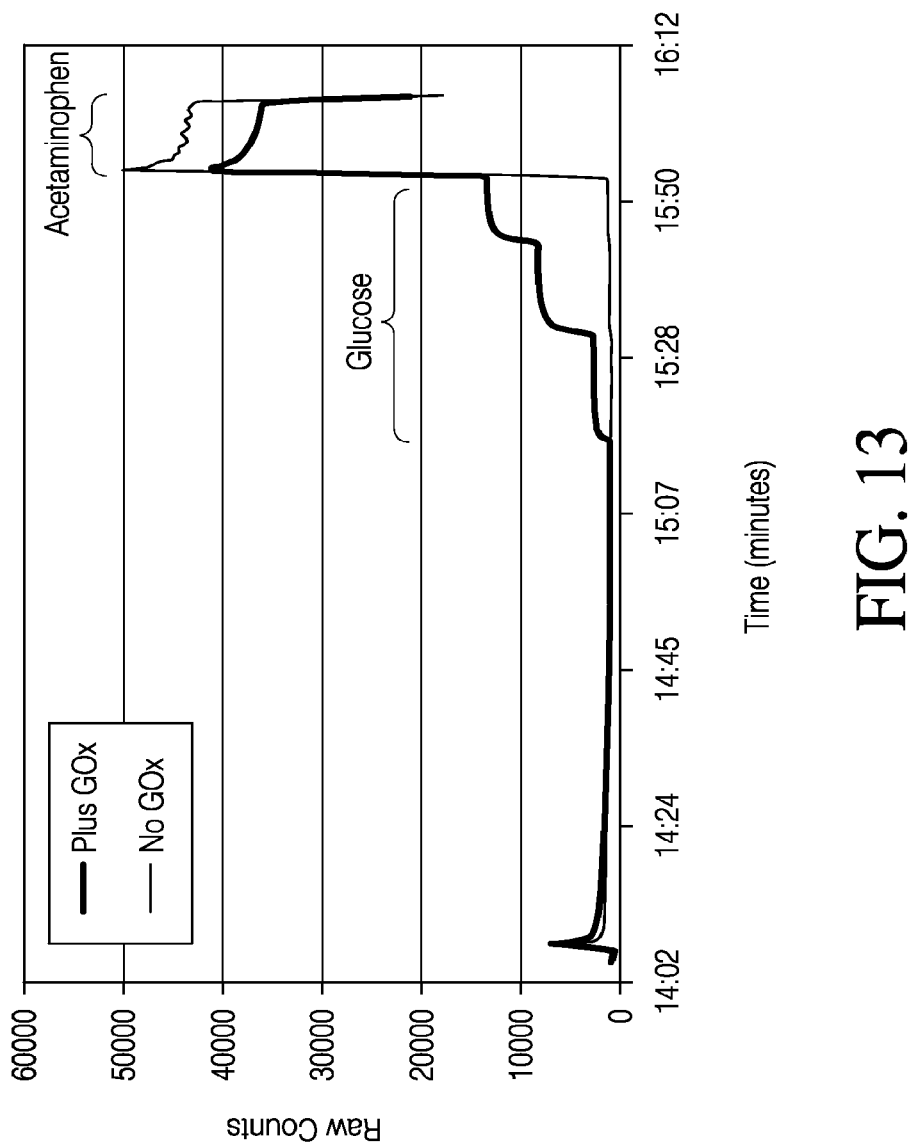
FIG. 13 is a graph that illustrates in vitro signal (counts) detected from a sensor having the configuration of the embodiment shown in FIG. 7J (silver/silver chloride X-wire reference electrode separating two platinum wire working electrodes). Plus GOx (thick line)=the electrode with active GOx. No GOx (thin line)=the electrode with inactive or no GOx.

FIG. 13 shows the results from one experiment, comparing the signals from the two electrodes of a dual-electrode sensor having an X-shaped reference electrode. The "Plus GOx" electrode has active GOx in its window. The "No GOx" electrode has DMAC-inactivated GOx in its window. The sensor was tested as was described for Experiment 1, above. Signal from the two electrodes were substantially equivalent until the sensor was transferred to the 40-mg/dl glucose solution. As this point, the "Plus GOx" electrode signal increased but the "No GOx" electrode signal did not. Similar increases were observed in the "Plus GOx" signal when the sensor was moved consecutively to 200-mg/dl and 400-mg/dl glucose solution, but still not increase in the "No GOx" signal was observed. When sensor was moved to a 400-mg/dl glucose solution containing 0.22 mM acetaminophen, both electrodes recorded a similar increase in signal (raw counts). These data indicate that the "No GOx" electrode measures sensor background (e.g., noise) signal that is substantially related to non-glucose factors.

Example 3

Dual-Electrode Challenge with Hydrogen Peroxide Glucose and Acetaminophen

A dual-electrode sensor was assembled similarly to the sensor of Example 1, with a bundled configuration similar to that shown in FIG. 7C (two platinum working electrodes and one silver/silver chloride reference electrode, not twisted). The electroactive windows were staggered by 0.085 inches, to create a diffusion barrier.

Figure 14:
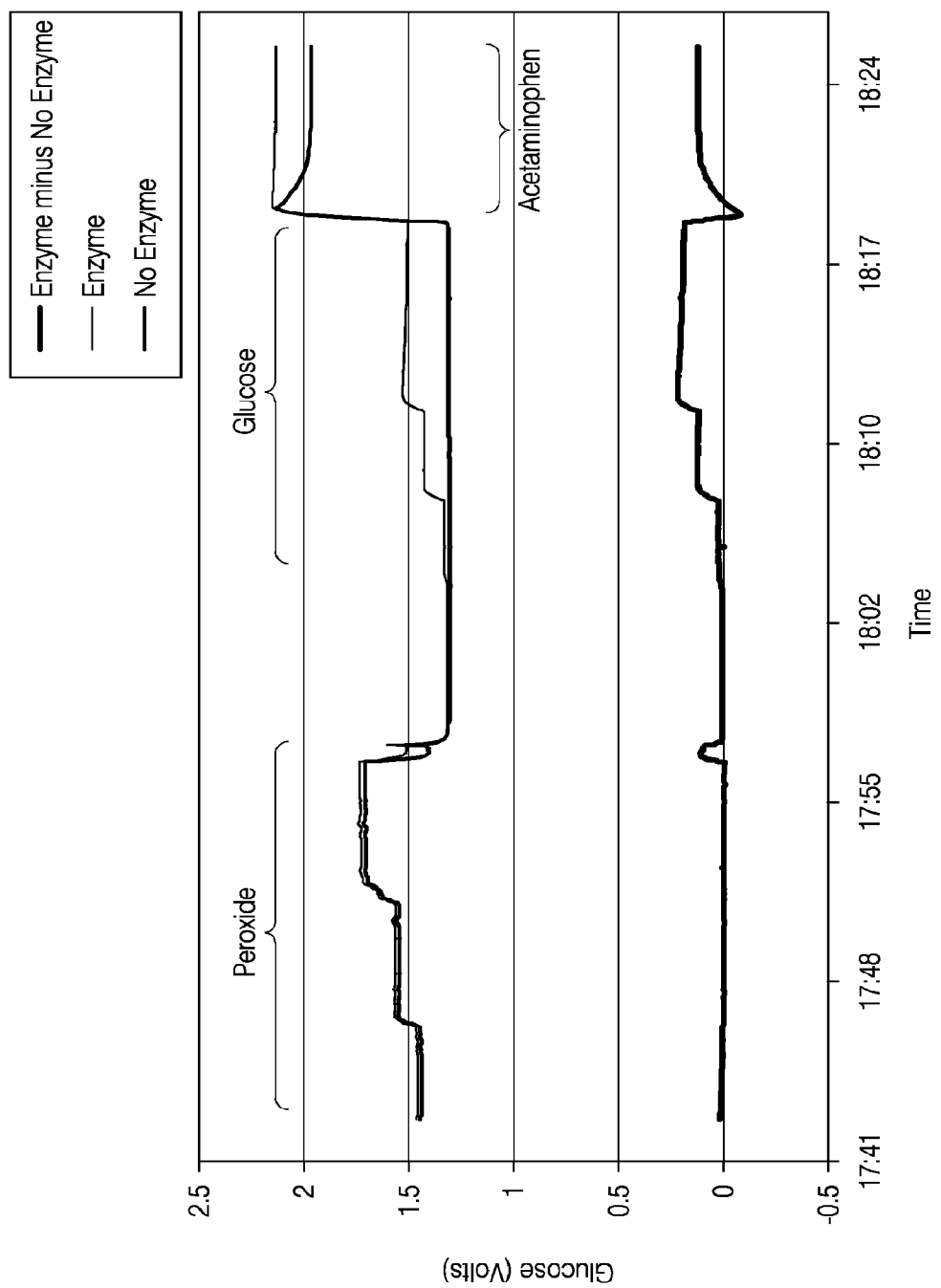
FIG. 14 is a graph that illustrates an in vitro signal (counts) detected from a dual-electrode sensor with a bundled configuration similar to that shown in FIG. 7C (two platinum working electrodes and one silver/silver chloride reference electrode, not twisted).

FIG. 14 shows the experimental results. The Y-axis shows the glucose signal (volts) and the X-axis shows time. The "Enzyme" electrode included active GOx. The "No Enzyme" electrode did not include active GOx. The "Enzyme minus No Enzyme" represents a simple subtraction of the "Enzyme" minus the "NO Enzyme." The "Enzyme" electrode measures the glucose-related signal and the non-glucose-related signal. The "No Enzyme" electrode measures only the non-glucose-related signal. The "Enzyme minus No Enzyme" graph illustrates the portion of the "Enzyme" signal related to only the glucose-related signal.

The sensor was challenged with increasing concentrations of hydrogen peroxide in PBS. As expected, both the "Enzyme" and "No Enzyme" electrodes responded substantially the same with increases in signal corresponding increased in $H_2O_2$ concentration (~50 µM, 100 µM and 250 µM $H_2O_2$). When the "No Enzyme" signal was subtracted from the "Enzyme" signal, the graph indicated that the signal was not related to glucose concentration.

The sensor was challenged with increasing concentrations of glucose (~20 mg/dl, 200 mg/dl, 400 mg/dl) in PBS. As glucose concentration increased, the "Enzyme" electrode registered a corresponding increase in signal. In contrast, the "No Enzyme" electrode did not record an increase in signal. Subtracting the "No Enzyme" signal from the "Enzyme" signal shows a step-wise increase in signal related to only glucose concentration.

The sensor was challenged with the addition of acetaminophen (~0.22 mM) to the highest glucose concentration. Acetaminophen is known to be an interferent (e.g., produces non-constant noise) of the sensors built as described above, e.g., due to a lack of acetaminophen-blocking membrane and/or mechanism formed thereon or provided therewith. Both the "Enzyme" and "No Enzyme" electrodes showed a substantial increase in signal. The "Enzyme minus No Enzyme" graph substantially shows the portion of the signal that was related to glucose concentration.

From these data, it is believed that a dual-electrode system can be used to determine the analyte-only portion of the signal.

Example 4

IV Dual-Electrode Sensor in Dogs

An intravascular dual-electrode sensor was built substantially as described in co-pending U.S. patent application Ser. No. 11/543,396 filed on even date herewith and entitled "ANALYTE SENSOR." Namely, the sensor was built by providing two platinum wires (e.g., dual working electrodes) and vapor-depositing the platinum wires with Parylene to form an insulating coating. A portion of the insulation on each wire was removed to expose the electroactive surfaces (e.g., 904a and 904b). The wires were bundled such that the windows were offset to provide a diffusion barrier, as described herein, cut to the desired length, to form an "assembly." A silver/silver chloride reference electrode was disposed remotely from the working electrodes (e.g., coiled inside the sensor's fluid connector).

An electrode domain was formed over the electroactive surface areas of the working electrodes by dip coating the assembly in an electrode solution (comprising BAYHYDROL® 123 with PVP and added EDC)) and drying.

An enzyme domain was formed over the electrode domain by subsequently dip coating the assembly in an enzyme domain solution (BAYHYDROL 140AQ mixed with glucose oxidase and glutaraldehyde) and drying. This dip coating process was repeated once more to form an enzyme domain having two layers and subsequently drying. Next an enzyme solution containing active GOx was applied to one window; and an enzyme solution without enzyme (e.g., No GOx) was applied to the other window.

A resistance domain was formed over the enzyme domain by subsequently spray coating the assembly with a resistance domain solution (Chronothane H and Chronothane 1020) and drying.

After the sensor was constructed, it was placed in a protective sheath and then threaded through and attached to a fluid coupler, as described in co-pending U.S. patent application Ser. No. 11/543,396 filed on even date herewith and entitled "ANALYTE SENSOR." Prior to use, the sensors were sterilized using electron beam radiation.

The forelimb of an anesthetized dog (2 years old, ~40 pounds) was cut down to the femoral artery and vein. An arterio-venous shunt was placed from the femoral artery to the femoral vein using 14 gauge catheters and ⅛-inch IV tubing. A pressurized arterial fluid line was connected to the sensor systems at all times. The test sensor system included a 20 gauge×1.25-inch catheter and took measurements every 30 seconds. The catheter was aseptically inserted into the shunt, followed by insertion of the sensor into the catheter. As controls, the dog's glucose was checked with an SMBG, as well as removing blood samples and measuring the glucose concentration with a Hemocue.

Figure 15:
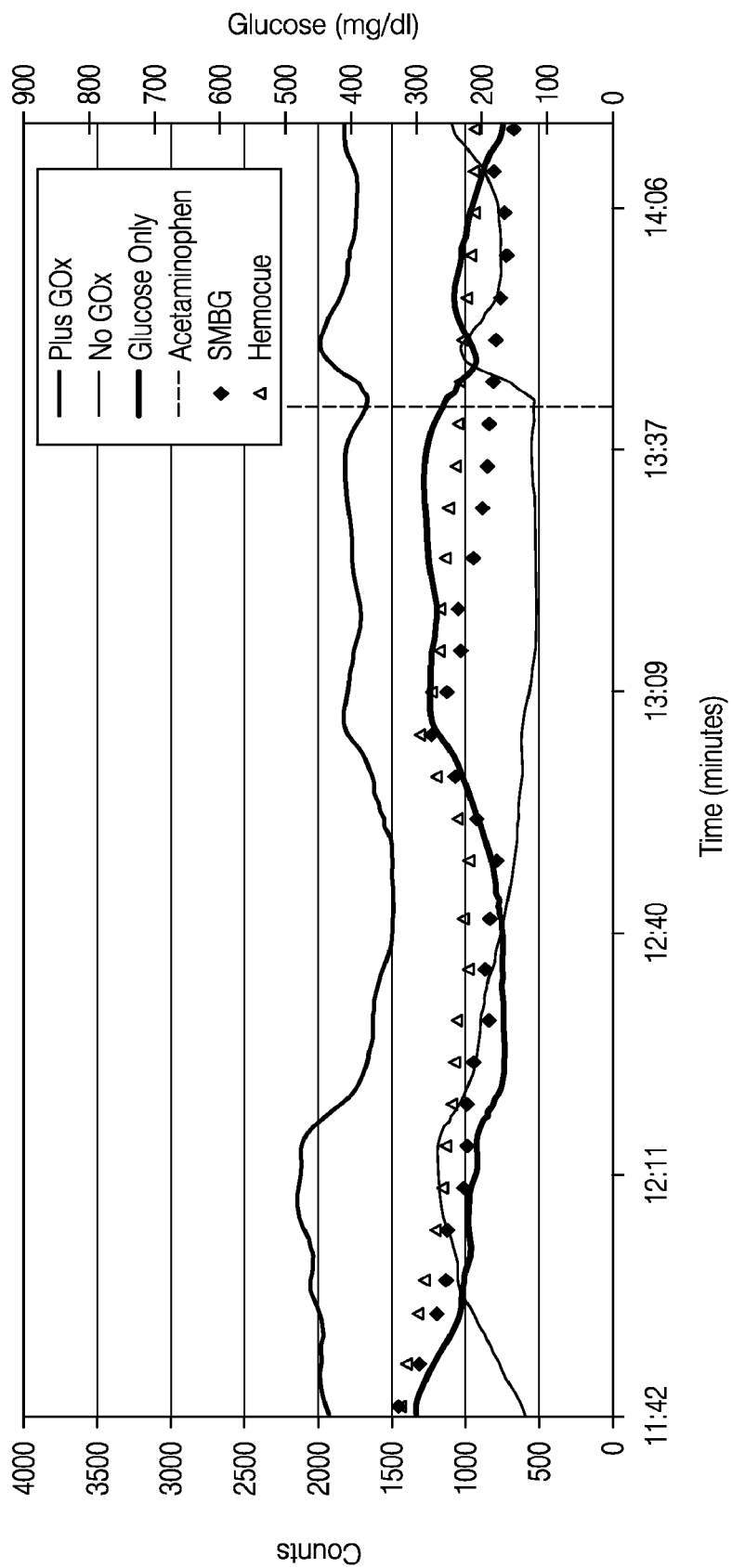
FIG. 15 is a graph that illustrates an in vivo signal (counts) detected from a dual-electrode sensor with a bundled configuration similar to that shown in FIG. 7C (two platinum working electrodes, not twisted, and one remotely disposed silver/silver chloride reference electrode).

FIG. 15 shows the experimental results. Glucose test data (counts) is shown on the left-hand Y-axis, glucose concentration for the controls (SMBG and Hemocue) are shown on the right-hand y-axis and time is shown on the X-axis. Each time interval on the X-axis represents 29-minutes (e.g., 12:11 to 12:40 equals 29 minutes). An acetaminophen challenge is shown as a vertical line on the graph.

The term "Plus GOx" refers to the signal from the electrode coated with active GOx, which represents signal due to both the glucose concentration and non-glucose-related electroactive compounds as described elsewhere herein (e.g., glucose signal and background signal, which includes both constant and non-constant noise). "No GOx" is signal from the electrode lacking GOx, which represents non-glucose related signal (e.g., background signal, which includes both constant and non-constant noise). The "Glucose Only" signal (e.g., related only to glucose concentration) is determined during data analysis (e.g., by sensor electronics). In this experiment, the "Glucose Only" signal was determined by a subtraction of the "No GOx" signal from the "Plus GOx" signal.

During the experiment, the "No GOx" signal (thin line) substantially paralleled the "Plus GOx" signal (medium line). The "Glucose Only" signal substantially paralleled the control tests (SMBG/Hemocue).

Acetaminophen is known to be an interferent (e.g., produces non-constant noise) of the sensors built as described above, e.g., due to a lack of acetaminophen-blocking membrane and/or mechanism formed thereon or provided therewith. The SMBG or Hemocue devices utilized in this experiment, however, do include mechanisms that substantially block acetaminophen from the signal (see FIG. 15). When the dog was challenged with acetaminophen, the signals from both working electrodes ("Plus GOx" and "No GOx") increased in a substantially similar manner. When the "Glucose Only" signal was determined, it substantially paralleled the signals of the control devices and was of a substantially similar magnitude.

From these experimental results, the inventors believe that an indwelling, dual-electrode glucose sensor system (as described herein) in contact with the circulatory system can provide substantially continuous glucose data that can be used to calculate a glucose concentration that is free from background components (e.g., constant and non-constant noise), in a clinical setting.

Example 5

Detection of Crosstalk In Vitro

In general, crosstalk in dual electrode sensors can be examined by recording the signal detected at each working electrode while placing them in a series of analyte solutions. This example describes one exemplary in vitro test for crosstalk on a dual electrode analyte sensor. A variety of dual electrode analyte sensors can be tested for crosstalk, using this method.

First, the sensor to be tested is placed in a phosphate buffered saline (PBS) for several minutes, such as until a stable signal is detected from both working electrodes. Next, the sensor is challenged with glucose solutions and optionally with one or more known noise-causing substances. For example, sensor can be placed sequentially in a series of glucose solutions (e.g., 40-mg/dl, 200-mg/dl and 400-mg/dl glucose in PBS) and the signals from the two working electrodes graphed.

If there is no crosstalk between the working electrodes, then, as the sensor is placed in solutions of increasingly higher glucose concentration, the graphed signal of the Plus GOx electrode should show corresponding signal increases, while the No GOx electrode signal should exhibit little or no change in signal. However, when the sensor is placed in a solution of a known noise-causing species (e.g., acetaminophen, ibuprofen, vitamin C, urea, and the like), both working electrodes (Plus GOx and No GOx) should exhibit an increase in signal. In some circumstances, this increase in signal is a dramatic spike in signal.

If there is crosstalk, then the signals from both electrodes should increase as the sensor is moved to solutions of increased glucose concentration. Similarly, when the sensor is placed in a solution of a known noise-causing species, both working electrodes should exhibit an increase in signal.

Example 6

Effect of Electroactive Surface Size in Dual Electrodes In Vivo

The effect of size of the electroactive surfaces (of the working electrodes) on noise measurement was examined in non-diabetic human hosts. Sensors having electroactive surfaces of different sizes, and lacking GOx in the enzyme layer were constructed as follows. Clean, insulated Pt/Ir wires were separated into two groups. For Group 1, 0.029" of the insulation was removed from each wire (e.g., about its entire circumference), to expose electroactive surfaces. For Group 2, the same procedure was performed, except that two sequential 0.029" portions of the insulation were removed; effectively doubling the size of the Group 2 electroactive surfaces relative to those of Group 1. After exposure of the electroactive surfaces, the two groups of wires were treated identically. On each wire, a portion of the sensor's membrane was fabricated by the sequential application (and curing thereof) of electrode domain, enzyme domain and resistance domain materials. The enzyme domain material contained no active GOx, so that the sensors would be able to detect only noise (no analyte). Next, pairs of wires (e.g., two Group 1 wires or two Group 2 wires) were aligned such that the electroactive surfaces were parallel to each other, and then twisted together. An Ag/AgCl ribbon was wrapped around a portion of the twisted wires (to form the reference electrode), and then additional resistance domain material was applied to the assembly. Each host consumed 1,000-mg of acetaminophen near the end of the trial, so that the affect of a known interferent could be examined.

Figure 19A:
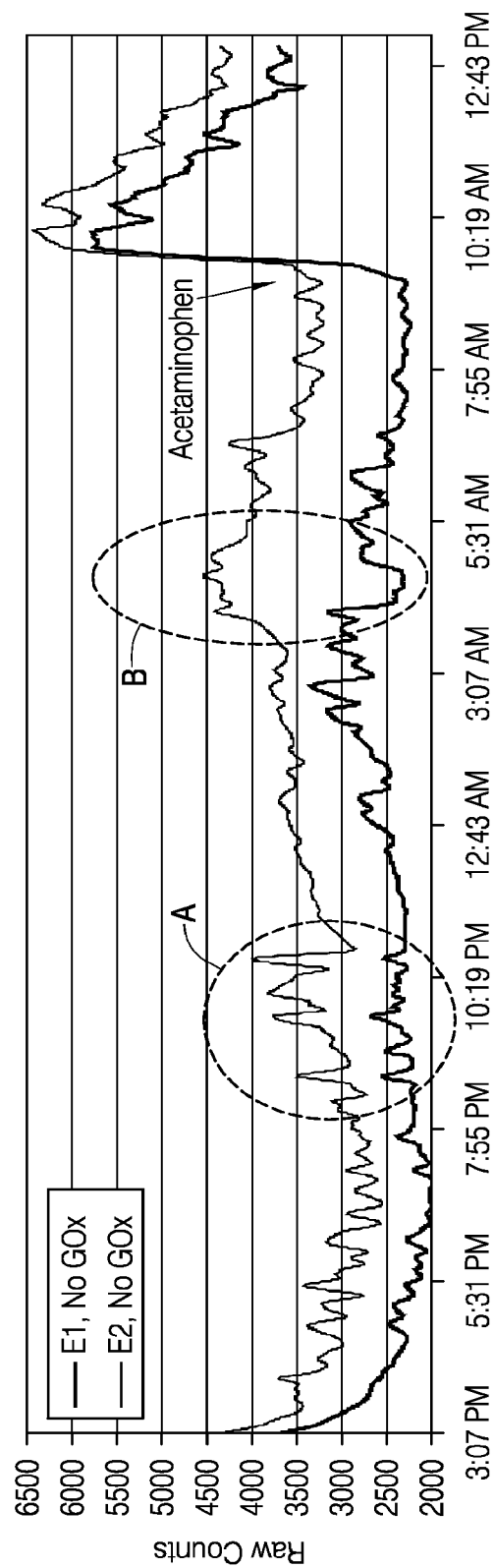
FIG. 19A is a graph that illustrates an in vivo signal (counts) detected from a dual-electrode sensor, in one embodiment, implanted in a non-diabetic human host.

FIG. 19A is a graph illustrating the in vivo experimental results from implantation of a Group 1 sensor (one 0.029" electroactive surface area per electrode). The Y-axis represents raw counts and the X-axis represents time. The data collected from each electroactive surface is shown as a line (E1, No GOx and E2, No GOx). Please note that the data represents only the noise component of the signal. No analyte component was detected, due to the lack of GOx in the portions of the membrane adjacent to the electroactive surfaces. Referring now to FIG. 19A, the noise signal detected by each of the working electrodes (E1, E2) fluctuated widely throughout the implantation time. The amplitude of the noise component detected by E2 was substantially greater than the noise component detected by E1. For example, referring to the data circled by oval A, the noise signal peaks detected by E2 were substantially greater than those detected by E1. Additionally, the noise fluctuations between the two working electrodes were not always in the same direction. For example, referring to the data circled by oval B, the E2 noise signal component increased while the E1 noise signal component decreased. When the sensor was challenged with acetaminophen (drug consumption indicated by the arrow), both electrodes registered a substantial increase in noise signal, wherein the shapes of the curves were substantially similar. However, E1 detected a substantially lower total amount of noise when compared with that detected by E2; this difference in signal amplitude (in response to a non-biologic interferent) indicates that the signals (e.g., on the two working electrodes) did not have substantially similar sensitivities.

Figure 19B:
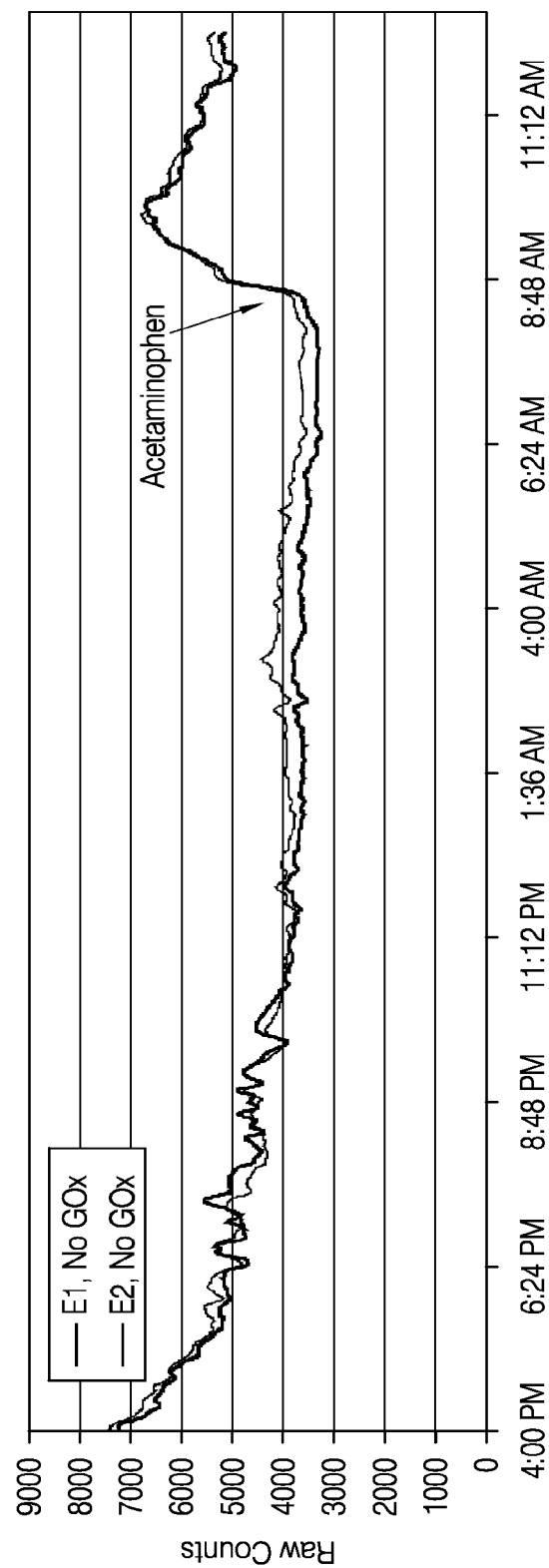
FIG. 19B is a graph that illustrates an in vivo signal (counts) detected from a dual-electrode, in another embodiment, implanted in a non-diabetic human host.

FIG. 19B is a graph illustrating the in vivo experimental results from implantation of a Group 2 sensor (two 0.029" electroactive surface areas per electrode). As described above, the Group 2 electroactive surfaces are about two-times as large as those of the Group 1 sensors. As before, the Y-axis represents raw counts and the X-axis represents time, and the data collected from each electroactive surface is shown as a line (E1, No GOx and E2, No GOx). As before, the data represents only the noise component of the signal. No analyte component was detected, due to the lack of GOx in the portions of the membrane adjacent to the electroactive surfaces. Referring now to FIG. 19B, the noise signal detected by each of the working electrodes (E1, E2). Throughout the course of the experiment (~20-hours), noise signals detected by E1 and E2 tracked very closely throughout the entire experiment. Namely, the noise signals detected by E1 and E2 were of substantially the same amplitude and followed substantially similar fluctuations, varying from about 7,000 counts (at 4:00 PM) to about 4500 counts (from about 6:30 AM to about 9:00 AM). Even when the Group 2 sensor was challenged with acetaminophen (a known non-biological interferent that should cause a false signal on the sensor), the working electrodes recorded substantially equal signal amplitudes (~6,900 counts) and followed substantially similar wave forms having substantially equivalent amplitudes; these data indicate that the two working electrodes had substantially equal sensitivities.

From these data, the inventors concluded that the electroactive surfaces of a dual electrode glucose sensor must be sufficiently large in order for the two electrodes to detect substantially equal noise signal components. For example, in this experiment, the electroactive surfaces of the Group 1 working electrodes, which did not measure noise equivalently, were 0.029" (e.g., along the electrode's length); while electroactive surfaces of the Group 2 working electrodes, which did measure noise substantially equivalently, were two times as large (e.g., 2×0.029"=0.058" along the electrode's length) as those of the Group 1 working electrodes.

Example 7

Effect of Electroactive Surface Spacing in Dual Electrodes In Vivo

The effect of the spacing of the electroactive surfaces (of the working electrodes) on noise measurement was examined in non-diabetic human hosts. Sensors having two different configurations were built and tested. Sensors of Configuration 1 (Config. 1) included Plus GOx and No GOx working electrodes with non-aligned (e.g., miss-aligned, skewed) electroactive surfaces. In other words, the electroactive surfaces were spaced such that, in the completed sensor, one electroactive surface would be more proximal to the sensor's tip than then other. Sensors of Configuration 2 (Config. 2) also included Plus GOx and No GOx working electrodes, except that the electroactive surfaces were closely aligned (e.g., parallel). In Config. 2, the membrane was the insulator between the two working electrodes, enabling the very close spacing (i.e., the thickness of the membrane determined the spacing between the two working electrodes, between about 0.001 inches to about 0.003 inches between the two working electrodes.)

Config. 1 sensors were fabricated as follow. For each sensor, two clean, insulated Pt/Ir wires were wound together (and an Ag/AgCl ribbon twisted there around), followed by removal of a portion of the insulating material from each wire to create the electroactive surfaces. The electroactive surfaces were offset (e.g., not next to each other) relative to the sensor's tip. The twisted wire pairs were then dipped in enzyme domain solution (including GOx) just far enough such that only the electroactive surface closest to the tip of the sensor was coated with the enzyme domain material (e.g., E1, Plus GOx). The electroactive surface farthest from the sensor tip was not coated with the enzyme domain material (e.g., E2, No GOx). After curing, resistance domain material was applied to the twisted pairs of wires.

Config. 2 sensors were fabricated as follow. Clean, insulated Pt/Ir wires were divided into two groups. Electrode and enzyme (Plus GOx) domain materials were sequentially applied to the E1, Plus GOx working electrode wires. Electrode and enzyme (No GOx) domain materials were sequentially applied to the E2, No GOx working electrode wires. Resistance domain material was applied to all wires individually (e.g., to form independent/discontinuous first and second resistance domains). After the resistance domain material was cured, one each of the E1, Plus GOx and E2, No GOx were placed together such that the wires' electroactive surfaces were aligned, and then twisted together to form a twisted pair. An Ag/AgCl ribbon was wrapped around each twisted pair (but not covering the electroactive surfaces), followed by application of a continuous resistance domain (e.g., a third resistance domain) over the sensor. The resulting sensors included a configuration similar to the example illustrated in FIG. 18.

Figure 20A:
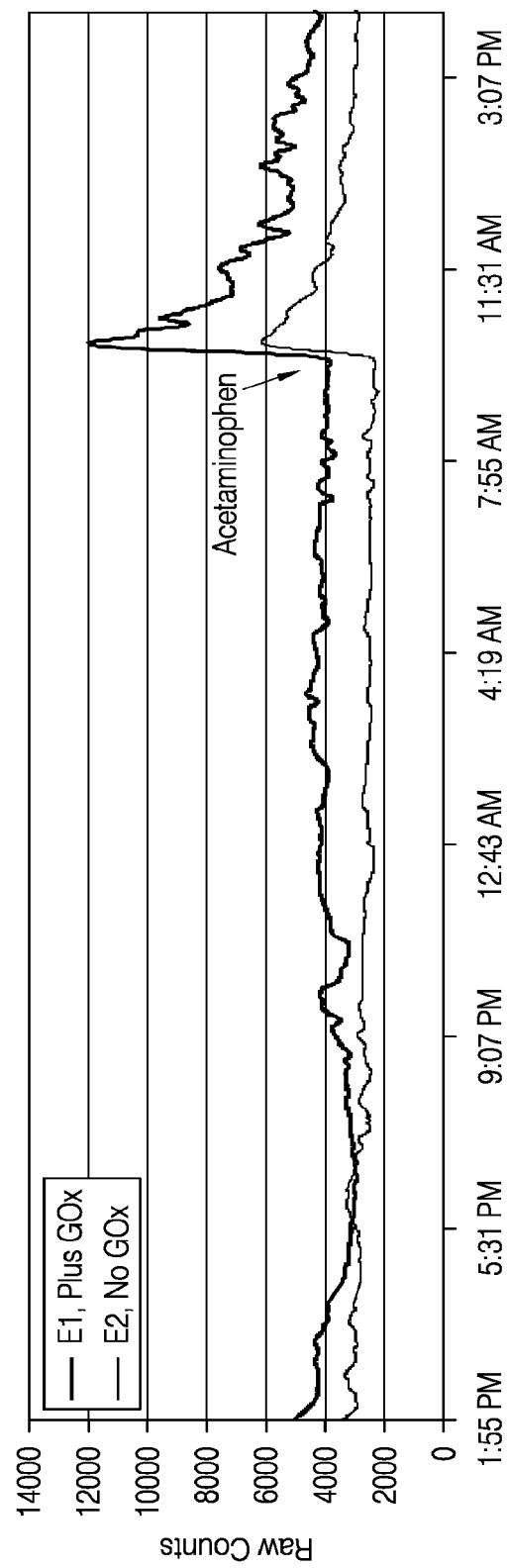
FIG. 20A is a graph that illustrates an in vivo signal (counts) detected from a dual-electrode, in one embodiment, implanted in a non-diabetic human host.

FIG. 20A is a graph illustrating the in vivo experimental results from implantation of a Config. 1 sensor (non-aligned electroactive surfaces). The Y-axis represents raw counts and the X-axis represents time. The E1, Plus GOx electrode detected both glucose and noise signal components while the E2, No GOx electrode detected only the noise signal component. Throughout most of the experiment's duration, the two working electrodes recorded signals having somewhat similar waveforms with the two lines being relatively flat with little fluctuation in amplitude (the volunteer was not diabetic, and thus would generally not have large fluctuations in glucose level). During the acetaminophen challenge, the E1, Plus GOx signal rapidly peaked at about 12,000 counts and then gradually declined, while the E2, No GOx signal peak was much lower in amplitude (6,000 counts).

Figure 20B:
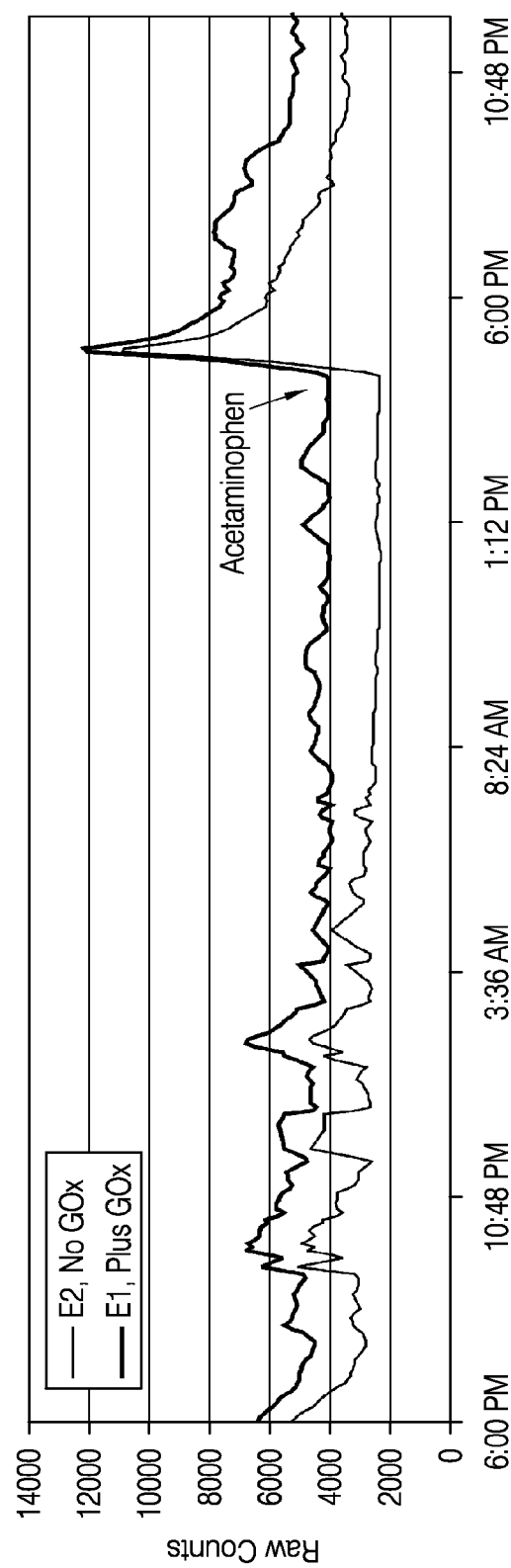
FIG. 20B is a graph that illustrates an in vivo signal (counts) detected from a dual-electrode, in another embodiment, implanted in a non-diabetic human host.

FIG. 20B is a graph illustrating the in vivo experimental results from implantation of a Config. 2 sensor (aligned electroactive surfaces). The Y-axis represents raw counts and the X-axis represents time. In general, the E1, Plus GOx electrode detected both glucose and noise signal components while the E2, No GOx electrode detected only the noise signal component. Throughout most of the experiment's duration, the two electrodes recorded signals having substantially similar waveforms; though the E1, Plus GOx electrode signal was generally higher in amplitude than that of the E2, No GOx electrode. When the sensor was challenged with acetaminophen, the signals of both working electrodes rapidly peaked at about 11,000-12,000 counts (e.g., the amplitudes of the two peaks were substantially equivalent/similar) and then gradually declined.

From these data, the inventors concluded that the electroactive surfaces of a dual electrode glucose sensor must be sufficiently close together in order for the two electrodes to detect substantially equivalent noise signal components. Additionally, the inventors concluded that for a dual electrode sensor including the combination of a continuous resistance domain disposed over discontinuous resistance domains (e.g., applied independently to the two working electrodes) the detected signal amplitudes more closely correspond to each other. This improves mathematical noise correction by enabling better noise signal subtraction.

Methods and devices that are suitable for use in conjunction with aspects of the preferred embodiments are disclosed in U.S. Pat. No. 4,994,167; U.S. Pat. No. 4,757,022; U.S. Pat. No. 6,001,067; U.S. Pat. No. 6,741,877; U.S. Pat. No. 6,702,857; U.S. Pat. No. 6,558,321; U.S. Pat. No. 6,931,327; U.S. Pat. No. 6,862,465; U.S. Pat. No. 7,074,307; U.S. Pat. No. 7,081,195; U.S. Pat. No. 7,108,778; U.S. Pat. No. 7,110,803; U.S. Pat. No. 7,192,450; U.S. Pat. No. 7,226,978; U.S. Pat. No. 7,236,890.

Methods and devices that are suitable for use in conjunction with aspects of the preferred embodiments are disclosed in U.S. Patent Publication No. US-2005-0176136-A1; U.S. Patent Publication No. US-2005-0251083-A1; U.S. Patent Publication No. US-2005-0143635-A1; U.S. Patent Publication No. US-2005-0181012-A1; U.S. Patent Publication No. US-2005-0177036-A1; U.S. Patent Publication No. US-2005-0124873-A1; U.S. Patent Publication No. US-2005-0115832-A1; U.S. Patent Publication No. US-2005-0245799-A1; U.S. Patent Publication No. US-2005-0245795-A1; U.S. Patent Publication No. US-2005-0242479-A1; U.S. Patent Publication No. US-2005-0182451-A1; U.S. Patent Publication No. US-2005-0056552-A1; U.S. Patent Publication No. US-2005-0192557-A1; U.S. Patent Publication No. US-2005-0154271-A1; U.S. Patent Publication No. US-2004-0199059-A1; U.S. Patent Publication No. US-2005-0054909-A1; U.S. Patent Publication No. US-2005-0051427-A1; U.S. Patent Publication No. US-2003-0032874-A1; U.S. Patent Publication No. US-2005-0103625-A1; U.S. Patent Publication No. US-2005-0203360-A1; U.S. Patent Publication No. US-2005-0090607-A1; U.S. Patent Publication No. US-2005-0187720-A1; U.S. Patent Publication No. US-2005-0161346-A1; U.S. Patent Publication No. US-2006-0015020-A1; U.S. Patent Publication No. US-2005-0043598-A1; U.S. Patent Publication No. US-2005-0033132-A1; U.S. Patent Publication No. US-2005-0031689-A1; U.S. Patent Publication No. US-2004-0186362-A1; U.S. Patent Publication No. US-2005-0027463-A1; U.S. Patent Publication No. US-2005-0027181-A1; U.S. Patent Publication No. US-2005-0027180-A1; U.S. Patent Publication No. US-2006-0020187-A1; U.S. Patent Publication No. US-2006-0036142-A1; U.S. Patent Publication No. US-2006-0020192-A1; U.S. Patent Publication No. US-2006-0036143-A1; U.S. Patent Publication No. US-2006-0036140-A1; U.S. Patent Publication No. US-2006-0019327-A1; U.S. Patent Publication No. US-2006-0020186-A1; U.S. Patent Publication No. US-2006-0020189-A1; U.S. Patent Publication No. US-2006-0036139-A1; U.S. Patent Publication No. US-2006-0020191-A1; U.S. Patent Publication No. US-2006-0020188-A1; U.S. Patent Publication No. US-2006-0036141-A1; U.S. Patent Publication No. US-2006-0020190-A1; U.S. Patent Publication No. US-2006-0036145-A1; U.S. Patent Publication No. US-2006-0036144-A1; U.S. Patent Publication No. US-2006-0016700-A1; U.S. Patent Publication No. US-2006-0142651-A1; U.S. Patent Publication No. US-2006-0086624-A1; U.S. Patent Publication No. US-2006-0068208-A1; U.S. Patent Publication No. US-2006-0040402-A1; U.S. Patent Publication No. US-2006-0036142-A1; U.S. Patent Publication No. US-2006-0036141-A1; U.S. Patent Publication No. US-2006-0036143-A1; U.S. Patent Publication No. US-2006-0036140-A1; U.S. Patent Publication No. US-2006-0036139-A1; U.S. Patent Publication No. US-2006-0142651-A1; U.S. Patent Publication No. US-2006-0036145-A1; U.S. Patent Publication No. US-2006-0036144-A1; U.S. Patent Publication No. US-2006-0200022-A1; U.S. Patent Publication No. US-2006-0198864-A1; U.S. Patent Publication No. US-2006-0200019-A1; U.S. Patent Publication No. US-2006-0189856-A1; U.S. Patent Publication No. US-2006-0200020-A1; U.S. Patent Publication No. US-2006-0200970-A1; U.S. Patent Publication No. US-2006-0183984-A1; U.S. Patent Publication No. US-2006-0183985-A1; U.S. Patent Publication No. US-2006-0195029-A1; U.S. Patent Publication No. US-2006-0229512-A1; U.S. Patent Publication No. US-2007-0032706-A1; U.S. Patent Publication No. US-2007-0016381-A1; U.S. Patent Publication No. US-2007-0027370-A1; U.S. Patent Publication No. US-2007-0027384-A1; U.S. Patent Publication No. US-2007-0032717-A1; U.S. Patent Publication No. US-2007-0032718 A1; U.S. Patent Publication No. US-2007-0059196-A1; U.S. Patent Publication No. US-2007-0066873-A1; U.S. Patent Publication No. US-2007-0093704-A1; U.S. Patent Publication No. US-2007-0197890-A1; U.S. Patent Publication No. US-2007-0173709-A1; U.S. Patent Publication No. US-2007-0173710-A1; U.S. Patent Publication No. US-2007-0197889-A1; U.S. Patent Publication No. US-2007-0163880-A1; U.S. Patent Publication No. US-2007-0203966-A1; U.S. Patent Publication No. US-2007-0208245-A1; U.S. Patent Publication No. US-2007-0208246-A1; U.S. Patent Publication No. US-2007-0208244-A1; and U.S. Patent Publication No. US-2007-0173708 A1.

Methods and devices that are suitable for use in conjunction with aspects of the preferred embodiments are disclosed in U.S. patent application Ser. No. 09/447,227 filed Nov. 22, 1999 and entitled "DEVICE AND METHOD FOR DETERMINING ANALYTE LEVELS"; U.S. patent application Ser. No. 11/675,063 filed Feb. 14, 2007 and entitled "ANALYTE SENSOR"; U.S. patent application Ser. No. 11/543,396 filed Oct. 4, 2006 and entitled "ANALYTE SENSOR"; U.S. patent application Ser. No. 11/543,490 filed Oct. 4, 2006 and entitled "ANALYTE SENSOR"; U.S. patent application Ser. No. 11/543,404 filed Oct. 4, 2006 and entitled "ANALYTE SENSOR"; U.S. patent application Ser. No. 11/691,426 filed Mar. 26, 2007 and entitled "ANALYTE SENSOR"; U.S. patent application Ser. No. 11/691,432 filed Mar. 26, 2007 and entitled "ANALYTE SENSOR"; U.S. patent application Ser. No. 11/691,424 filed Mar. 26, 2007 and entitled "ANALYTE SENSOR"; U.S. patent application Ser. No. 11/691,466 filed Mar. 26, 2007 and entitled "ANALYTE SENSOR"; U.S. patent application Ser. No. 11/692,154 filed Mar. 27, 2007 and entitled "DUAL ELECTRODE SYSTEM FOR A CONTINUOUS ANALYTE SENSOR"; U.S. patent application Ser. No. 11/797,520 filed May 3, 2007 and entitled "TRANSCUTANEOUS ANALYTE SENSOR"; U.S. patent application Ser. No. 11/797,521 filed May 3, 2007 and entitled "TRANSCUTANEOUS ANALYTE SENSOR"; and U.S. patent application Ser. No. 11/750,907 filed May 18, 2007 and entitled "ANALYTE SENSORS HAVING A SIGNAL-TO-NOISE RATIO SUBSTANTIALLY UNAFFECTED BY NON-CONSTANT NOISE"; U.S. patent application Ser. No. 11/762,638 filed Jun. 13, 2007 and entitled "SYSTEMS AND METHODS FOR REPLACING SIGNAL DATA ARTIFACTS IN A GLUCOSE SENSOR DATA STREAM"; U.S. patent application Ser. No. 11/763,215 filed Jun. 14, 2007 and entitled "SILICONE COMPOSITION FOR BIOCOMPATIBLE MEMBRANE"; U.S. patent application Ser. No. 11/842,148 filed Aug. 21, 2007 and entitled "TRANSCUTANEOUS ANALYTE SENSOR"; U.S. patent application Ser. No. 11/842,142 filed Aug. 21, 2007 and entitled "TRANSCUTANEOUS ANALYTE SENSOR"; U.S. patent application Ser. No. 11/842,154 filed Aug. 21, 2007 and entitled "TRANSCUTANEOUS ANALYTE SENSOR"; U.S. patent application Ser. No. 11/842,146 filed Aug. 21, 2007 and entitled "ANALYTE SENSOR"; U.S. patent application Ser. No. 11/842,151 filed Aug. 21, 2007 and entitled "ANALYTE SENSOR"; U.S. patent application Ser. No. 11/842,156 filed Aug. 21, 2007 and entitled "ANALYTE SENSORS HAVING A SIGNAL-TO-NOISE RATIO SUBSTANTIALLY UNAFFECTED BY NON-CONSTANT NOISE"; U.S. patent application Ser. No. 11/842,157 filed Aug. 21, 2007 and entitled "ANALYTE SENSOR"; U.S. patent application Ser. No. 11/842,143 filed Aug. 21, 2007 and entitled "TRANSCUTANEOUS ANALYTE SENSOR"; U.S. patent application Ser. No. 11/842,149 filed Aug. 21, 2007 and entitled "TRANSCUTANEOUS ANALYTE SENSOR"; and U.S. patent application Ser. No. 11/855,101 filed Sep. 13, 2007 and entitled "TRANSCUTANEOUS ANALYTE SENSOR".

All references cited herein, including but not limited to published and unpublished applications, patents, and literature references, are incorporated herein by reference in their entirety and are hereby made a part of this specification. To the extent publications and patents or patent applications incorporated by reference contradict the disclosure contained in the specification, the specification is intended to supersede and/or take precedence over any such contradictory material.

All numbers expressing quantities of ingredients, reaction conditions, and so forth used in the specification are to be understood as being modified in all instances by the term "about." Accordingly, unless indicated to the contrary, the numerical parameters set forth herein are approximations that may vary depending upon the desired properties sought to be obtained. At the very least, and not as an attempt to limit the application of the doctrine of equivalents to the scope of any claims in any application claiming priority to the present application, each numerical parameter should be construed in light of the number of significant digits and ordinary rounding approaches.

The term "comprising" as used herein is synonymous with "including," "containing," or "characterized by," and is inclusive or open-ended and does not exclude additional, unrecited elements or method steps.

The above description discloses several methods and materials of the present invention. This invention is susceptible to modifications in the methods and materials, as well as alterations in the fabrication methods and equipment. Such modifications will become apparent to those skilled in the art from a consideration of this disclosure or practice of the invention disclosed herein. Consequently, it is not intended that this invention be limited to the specific embodiments disclosed herein, but that it cover all modifications and alternatives coming within the true scope and spirit of the invention.

What is claimed is:

1. A continuous glucose sensor configured and arranged for insertion into a host for and detecting glucose in the host, the sensor comprising:
a first working electrode comprising a first electroactive surface, wherein the first working electrode is configured to generate a first signal, wherein the first working electrode is configured to switch from a first bias potential to a second bias potential, wherein the first bias potential is a glucose measurement potential and the second bias potential is a non-glucose-measurement potential;
a second working electrode comprising a second electro active surface wherein the second working electrode is configured to generate a second signal; and
sensor electronics configured to compare the first signal with the second signal and determine a level of glucose in the host based at least in part on the comparison of the first signal with the second signal.

2. The sensor of claim 1, wherein the sensor is configured to perform pulsed amperometric detection.

3. The sensor of claim 1, wherein the sensor is configured to perform a stepped potential waveform.

4. The sensor of claim 3, wherein the sensor further comprises a reference and a counter electrode.

5. The sensor of claim 4, wherein the sensor further comprises a reference and a counter electrode.

6. The sensor of claim 1, wherein the second working electrode is configured to switch from a third bias potential to a fourth bias potential.

7. The sensor of claim 1, wherein the first bias potential is held long enough to allow equilibration.

8. The sensor of claim 1, wherein the sensor electronics are configured to calculate at least one glucose sensor data point using the first and second signals.

9. The sensor of claim 1, wherein the sensor electronics are configured to process the first and second signals to generate a glucose concentration substantially without signal contribution due to non-glucose noise artifacts.

10. The sensor of claim 1, wherein the sensor is configured to oscillate potential between the first working electrode and the second working electrode.

11. A continuous glucose sensor configured and arranged for insertion into a host for and detecting glucose in the host, the sensor comprising:
  a first working electrode comprising a first resistance domain, wherein the first working electrode is configured to generate a first signal having a first noise component related to a noise-causing species;
  a second working electrode comprising a second resistance domain, wherein the second working electrode is configured to generate a second signal having a second noise component related to the noise-causing species;
  a third resistance domain disposed continuously over the first resistance domain and the second resistance domain;
  wherein each of the first resistance domain and the second resistance domain is independently formed on the first working electrode and the second working electrode, respectively.

12. The sensor of claim 11, wherein the noise-causing species comprises at least one member selected from the group consisting of externally produced H2O2, urea, lactic acid, phosphates, citrates, peroxides, amino acids, amino acid precursors, amino acid break-down products, nitric oxide, NO-donors, NO-precursors, reactive oxygen species, compounds having electroactive acidic, amine or sulfhydryl groups, acetaminophen, ascorbic acid, dopamine, ephedrine, ibuprofen, L-dopa, methyldopa, salicylate, tetracycline, tolazamide, tolbutamide, and triglycerides.

13. The sensor of claim 11, wherein the noise-causing species is non-constant.

14. The sensor of claim 11, wherein the first signal comprises a first sensitivity and the second signal comprises a second sensitivity, and wherein the third resistance domain is configured such that the first sensitivity and the second sensitivity are substantially equivalent.

15. The sensor of claim 14, wherein the first sensitivity and the second sensitivity are equivalent to ±10%.

16. The sensor of claim 11, wherein the first working electrode comprises a first electroactive surface and a first membrane portion disposed thereon, the first membrane portion comprising an active enzymatic enzyme domain and the first resistance domain, and wherein the second working electrode comprises a second electroactive surface and a second membrane portion disposed thereon, the second membrane portion comprising at least one of an inactive enzymatic portion or a non-enzymatic portion and the second resistance domain.

17. The sensor of claim 16, wherein the active enzymatic enzyme domain is configured to generate a measurable species.

18. The sensor of claim 17, wherein the measurable species comprises H2O2 produced in the active enzymatic portion of the sensor membrane.

19. The sensor of claim 17, wherein the crosstalk distance comprises a distance less than a maximum distance the measurable species can diffuse, and generate a signal associated with crosstalk.

20. The sensor of claim 17, wherein the first electroactive surface and the second electroactive surface are spaced a distance that allows noise caused by a local point source that produces noise-causing species to be measured equivalently at the first and second electroactive surfaces.

21. The sensor of claim 17, wherein each of the first electroactive surface and the second electroactive surface is configured and arranged to integrate the signal caused by a plurality of local point sources that produce noise-causing species in vivo, such that the first noise component and the second noise component are substantially equivalent.

22. The sensor of claim 17, wherein the first electroactive surface and the second electroactive surface are configured and arranged to integrate signals detected about a circumference of the sensor.

23. The sensor of claim 17, wherein the dimension of each of the first electroactive surface and the second electroactive surface is greater than a sum of diameters of about 10 average human cells.

24. The sensor of claim 23, wherein the dimension of each of the first electroactive surface and the second electroactive surface is greater than about 500 μm.

25. The sensor of claim 16, further comprising a physical diffusion barrier, wherein physical diffusion barrier comprises the first resistance domain and the second resistance domain.

26. The sensor of claim 25, wherein the physical diffusion barrier is configured and arranged to physically block some crosstalk from the active enzymatic enzyme domain to the second electroactive surface.

27. The sensor of claim 25, wherein the physical diffusion barrier is configured and arranged to physically block an amount of a measurable species diffusing from the active enzymatic enzyme domain to the second electroactive surface, such that there is substantially no signal associated with crosstalk measured at the second working electrode.

28. The sensor of claim 25, wherein the physical diffusion barrier comprises a first barrier layer formed on the first working electrode and a second barrier layer formed on the second working electrode, wherein each of the first barrier layer and the second barrier layer is independently formed.

29. A continuous glucose sensor configured and arranged for insertion into a host for and detecting glucose in the host, the sensor comprising:
  a first working electrode comprising a first resistance domain,
  wherein the first working electrode comprises a first electroactive surface and a first membrane portion disposed thereon, wherein the first membrane portion comprising an active enzymatic enzyme domain and the first resistance domain, wherein the first working electrode is configured to generate a first signal having a first noise component related to a noise-causing species;
  a second working electrode comprising a second resistance domain, wherein the second working electrode comprises a second electroactive surface and a second membrane portion disposed thereon, wherein the second membrane portion comprises at least one of an inactive enzymatic portion or a non-enzymatic portion and the second resistance domain, wherein the second working electrode is configured to generate a second signal having a second noise component related to the noise-causing species; and
  a third resistance domain disposed continuously over the first resistance domain and the second resistance domain;
  a physical diffusion barrier, wherein physical diffusion barrier comprises the first resistance domain and the second resistance domain;
  wherein the physical diffusion barrier is configured and arranged to attenuate diffusion of the measurable species from the active enzymatic enzyme domain to the second electroactive surface by at least 2-fold.

30. The sensor of claim 29, wherein the diffusion is attenuated by at least 10-fold.

31. The sensor of claim 29, wherein the noise-causing species comprises at least one member selected from the group consisting of externally produced H2O2, urea, lactic acid, phosphates, citrates, peroxides, amino acids, amino acid precursors, amino acid break-down products, nitric oxide, NO-donors, NO-precursors, reactive oxygen species, compounds having electroactive acidic, amine or sulfhydryl groups, acetaminophen, ascorbic acid, dopamine, ephedrine, ibuprofen, L-dopa, methyldopa, salicylate, tetracycline, tolazamide, tolbutamide, and triglycerides.

32. The sensor of claim 29, wherein the noise-causing species is non-constant.

33. The sensor of claim 29, wherein the first signal comprises a first sensitivity and the second signal comprises a second sensitivity, and wherein the third resistance domain is configured such that the first sensitivity and the second sensitivity are substantially equivalent.

34. A continuous glucose sensor configured and arranged for insertion into a host for and detecting glucose in the host, the sensor comprising:
- a first working electrode comprising a first resistance domain, wherein the first working electrode comprises a first electroactive surface and a first membrane portion disposed thereon, wherein the first membrane portion comprises an active enzymatic enzyme domain and the first resistance domain, wherein the active enzymatic enzyme domain is configured to generate a measurable species, wherein the first working electrode is configured to generate a first signal having a first noise component related to a noise-causing species;
- a second working electrode comprising a second resistance domain, wherein the second working electrode comprises a second electroactive surface and a second membrane portion disposed thereon, wherein the first electroactive surface and the second electroactive surface are spaced closer together than a crosstalk distance, wherein the second membrane portion comprises at least one of an inactive enzymatic portion or a non-enzymatic portion and the second resistance domain, wherein the second working electrode is configured to generate a second signal having a second noise component related to the noise-causing species;
- a third resistance domain disposed continuously over the first resistance domain and the second resistance domain.

35. The sensor of claim 34, wherein the noise-causing species comprises at least one member selected from the group consisting of externally produced H2O2, urea, lactic acid, phosphates, citrates, peroxides, amino acids, amino acid precursors, amino acid break-down products, nitric oxide, NO-donors, NO-precursors, reactive oxygen species, compounds having electroactive acidic, amine or sulfhydryl groups, acetaminophen, ascorbic acid, dopamine, ephedrine, ibuprofen, L-dopa, methyldopa, salicylate, tetracycline, tolazamide, tolbutamide, and triglycerides.

36. The sensor of claim 34, wherein the noise-causing species is non-constant.

37. The sensor of claim 34, wherein the first signal comprises a first sensitivity and the second signal comprises a second sensitivity, and wherein the third resistance domain is configured such that the first sensitivity and the second sensitivity are substantially equivalent.

38. A continuous glucose sensor configured and arranged for insertion into a host for and detecting glucose in the host, the sensor comprising:
- a first working electrode comprising a first resistance domain, wherein the first working electrode comprises a first electroactive surface and a first membrane portion disposed thereon, wherein the first membrane portion comprises an active enzymatic enzyme domain and the first resistance domain, wherein the active enzymatic enzyme domain is configured to generate a measurable species, wherein the first working electrode is configured to generate a first signal having a first noise component related to a noise-causing species;
- a second working electrode comprising a second resistance domain, wherein the second working electrode comprises a second electroactive surface and a second membrane portion disposed thereon, wherein the second membrane portion comprises at least one of an inactive enzymatic portion or a non-enzymatic portion and the second resistance domain, wherein the second working electrode is configured to generate a second signal having a second noise component related to the noise-causing species; and
- a third resistance domain disposed continuously over the first resistance domain and the second resistance domain;
- wherein the first electroactive surface and the second electroactive surface are each sized in at least one dimension such that the first noise component and the second noise component can be integrated across the dimension.

* * * * *

UNITED STATES PATENT AND TRADEMARK OFFICE
CERTIFICATE OF CORRECTION

| | | |
|---|---|---|
| PATENT NO. | : 9,504,413 B2 | Page 1 of 4 |
| APPLICATION NO. | : 13/863204 | |
| DATED | : November 29, 2016 | |
| INVENTOR(S) | : Peter C. Simpson | |

It is certified that error appears in the above-identified patent and that said Letters Patent is hereby corrected as shown below:

On the Title Page

In Column 2 (page 5, item (56)) at Line 72, Under Other Publications, change "Immoblized" to --Immobilized--.

In Column 1 (page 6, item (56)) at Line 8, Under Other Publications, change "hypoglycaemic" to --hypoglycemic--.

In Column 1 (page 6, item (56)) at Line 35, Under Other Publications, change "Thechnol." to --Technol.--.

In Column 1 (page 6, item (56)) at Line 38, Under Other Publications, change "Senso" to --Sensor--.

In Column 2 (page 6, item (56)) at Line 12, Under Other Publications, change "basedon" to --based--.

In Column 2 (page 6, item (56)) at Line 36, Under Other Publications, change "implntable," to --implantable,--.

In Column 2 (page 6, item (56)) at Line 39, Under Other Publications, change "reliablity" to --reliability--.

In Column 2 (page 6, item (56)) at Line 52, Under Other Publications, change "Enzymlology," to --Enzymology,--.

In Column 2 (page 6, item (56)) at Line 66, Under Other Publications, change "artifical" to --artificial--.

In Column 1 (page 7, item (56)) at Line 17, Under Other Publications, change "for your" to --for you--.

Signed and Sealed this
Eighteenth Day of April, 2017

Michelle K. Lee
*Director of the United States Patent and Trademark Office*

CERTIFICATE OF CORRECTION (continued)
U.S. Pat. No. 9,504,413 B2

In Column 1 (page 7, item (56)) at Line 38, Under Other Publications, change "glocuse" to --glucose--.

In Column 1 (page 7, item (56)) at Line 39, Under Other Publications, change "Diabetese" to --Diabetes--.

In Column 1 (page 7, item (56)) at Line 53, Under Other Publications, change "Hypoglycaemia" to --Hypoglycemia--.

In Column 1 (page 7, item (56)) at Line 66, Under Other Publications, change "Thechnol." to --Technol.--.

In Column 2 (page 7, item (56)) at Line 2, Under Other Publications, change "Diabetese" to --Diabetes--.

In Column 2 (page 7, item (56)) at Line 22, Under Other Publications, change "inactiviation" to --inactivation--.

In Column 2 (page 7, item (56)) at Line 36, Under Other Publications, change "patents" to --patients--.

In Column 1 (page 8, item (56)) at Line 41, Under Other Publications, change "biotelemeter" to --biotelemetry--.

In Column 2 (page 8, item (56)) at Line 18, Under Other Publications, change "activitiy," to --activity,--.

In Column 2 (page 8, item (56)) at Line 32, Under Other Publications, change "Biosensors& Beioelectronics," to --Biosensors & Bioelectronics,--.

In Column 2 (page 8, item (56)) at Line 33, Under Other Publications, change "glocuse" to --glucose--.

In Column 2 (page 8, item (56)) at Line 44, Under Other Publications, change "valication" to --validation--.

In Column 2 (page 8, item (56)) at Line 45, Under Other Publications, change "iunsulin interaaction in tyhpe" to --insulin interaction in type--.

In Column 2 (page 8, item (56)) at Line 60, Under Other Publications, change "Electronanalysis" to --Electroanalysis--.

In Column 1 (page 9, item (56)) at Line 8, Under Other Publications, change "artifical" to --artificial--.

CERTIFICATE OF CORRECTION (continued) Page 3 of 4
U.S. Pat. No. 9,504,413 B2

In Column 1 (page 9, item (56)) at Line 14, Under Other Publications, change "amperometeric" to --amperometric--.

In Column 1 (page 9, item (56)) at Line 63, Under Other Publications, change "Decarbozylase" to --Decarboxylase--.

In Column 2 (page 9, item (56)) at Line 20, Under Other Publications, change "Membran," to --Membrane,--.

In Column 2 (page 9, item (56)) at Line 71, Under Other Publications, change "form" to --from--.

In the Drawings

Sheet 4 of 26 (Reference Numeral 36, FIG. 4) at Line 3, Change "POTENTIOST" to --POTENTIOSTAT--.

Sheet 4 of 26 (Reference Numeral 37, FIG. 4) at Line 3, Change "POTENTIOST" to --POTENTIOSTAT--.

Sheet 7 of 26 (FIG. 7A$_1$) at Line 4, Change "FIG. 7A$_1$" to --FIG. 7A1--.

Sheet 7 of 26 (FIG. 7A$_2$) at Line 4, Change "FIG. 7A$_2$" to --FIG. 7A2--.

In the Specification

In Column 9 at Line 53, After "thereon" insert --.--.

In Column 12 at Line 27, Change "andrenostenedione;" to --androstenedione;--.

In Column 12 at Line 29, Change "biotimidase;" to --biotinidase;--.

In Column 12 at Line 38, Change "A,S,C,E," to --A, S, C, E,--.

In Column 12 at Line 42, Change "diptheria" to --diphtheria--.

In Column 12 at Line 49, Change "perioxidase;" to --peroxidase;--.

In Column 12 at Line 55, Change "phenyloin;" to --phenytoin;--.

In Column 12 at Line 62, Change "duodenalisa," to --duodenalis,--.

In Column 13 at Line 3, Change "Trepenoma pallidium," to --Treponema pallidum,--.

In Column 13 at Line 4, Change "stomatis" to --stomatitis--.

CERTIFICATE OF CORRECTION (continued)

U.S. Pat. No. 9,504,413 B2

In Column 13 at Lines 25-26, Change "(barbituates," to --(barbiturates,--.

In Column 21 at Line 11, Change "integrally" to --"integrally--.

In Column 26 at Line 16 (approx.), Change "can by" to --can be--.

In Column 26 at Line 63, Change "9B," to --9B),--.

In Column 27 at Line 24, Change "Bellafonte," to --Bellefonte,--.

In Column 31 at Line 8, Change "wt %" to --wt. %--.

In Column 31 at Line 10, Change "wt %" to --wt. %--.

In Column 33 at Line 67, Change "'Although" to --Although--.

In Column 35 at Line 27, Change "The" to --the--.

In Column 45 at Line 5, Change "RA" to --R/I--.

In Column 54 at Line 22, Change "the a" to --the--.

In Column 60 at Line 47, Change "705" to --(705--.

In Column 69 at Line 2, Change "know" to --known--.

In Column 69 at Line 9, Change "R/1" to --R/I--.

In Column 70 at Line 29, After "barrier" insert --.--.

In Column 76 at Line 24, Change "know" to --known--.

In Column 93 at Lines 51-52, Change "Peroxide Glucose" to --Peroxide, Glucose,--.

In Column 94 at Line 58, Change "EDC))" to --EDC)--.

In Column 99 at Line 7, Change "(6,000" to --(~6,000--.

In the Claims

In Column 103 at Line 11 (approx.), In Claim 11, after "species;" insert --and--.

In Column 105 at Line 42, In Claim 34, after "species;" insert --and--.